(12) United States Patent
Buschle et al.

(10) Patent No.: US 7,378,234 B2
(45) Date of Patent: May 27, 2008

(54) METHOD FOR ISOLATING HEPATITIS C VIRUS PEPTIDES

(75) Inventors: Michael Buschle, Perchtoldsdorf (AT); Andre Habel, Vienna (AT); Christoph Klade, Wr. Neustadt (AT); Frank Mattner, Vienna (AT); Alexander Otava, Vienna (AT); Oresta Vytvytska, Vienna (AT); Wolfgang Zauner, Vienna (AT); Sandra Zinke, Vienna (AT); Helen Kirlappos, Vienna (AT)

(73) Assignee: Intercell AG, Vienna (AT)

( * ) Notice: Subject to any disclaimer, the term of this patent is extended or adjusted under 35 U.S.C. 154(b) by 307 days.

(21) Appl. No.: 10/512,885

(22) PCT Filed: Aug. 27, 2003

(86) PCT No.: PCT/EP03/09482

§ 371 (c)(1),
(2), (4) Date: Oct. 28, 2004

(87) PCT Pub. No.: WO2004/024182

PCT Pub. Date: May 25, 2004

(65) Prior Publication Data

US 2006/0216691 A1    Sep. 28, 2006

(30) Foreign Application Priority Data

| Sep. 13, 2002 | (AT) | ............................. A 1376/2002 |
| Feb. 27, 2003 | (EP) | ..................... PCT/EP03/02005 |
| Jul. 11, 2003 | (EP) | ................................. 03450171 |

(51) Int. Cl.
| A61K 39/00 | (2006.01) |
| A61K 51/00 | (2006.01) |
| A61K 39/12 | (2006.01) |
| A61K 39/29 | (2006.01) |
| C12Q 1/70  | (2006.01) |

(52) U.S. Cl. .................... 435/5; 930/220; 930/223; 424/186.1; 424/189.1; 424/225.1; 424/228.1

(58) Field of Classification Search .................. None
See application file for complete search history.

(56) References Cited

U.S. PATENT DOCUMENTS

| 5,663,153 | A  | 9/1997  | Hutcherson et al. ........... 514/44 |
| 5,683,864 | A  | 11/1997 | Houghton et al. ............. 435/5 |
| 5,723,335 | A  | 3/1998  | Hutcherson et al. ....... 435/7.24 |
| 6,037,135 | A  | 3/2000  | Kubo et al. ................ 435/7.24 |
| 6,150,087 | A  | 11/2000 | Chien ............................ 435/5 |
| 6,413,517 | B1 | 7/2002  | Sette et al. .............. 424/185.1 |
| 2003/0162738 | A1 | 8/2003 | Egyed et al. ................. 514/44 |

FOREIGN PATENT DOCUMENTS

| AT | A 1973/2000 | 11/2000 |
| AT | A 805/2001  | 5/2001  |
| EP | 0 468 520   | 7/1991  |
| WO | WO 92/03458 | 3/1992  |
| WO | WO 93/00365 | 1/1993  |
| WO | WO 94/20127 | 9/1994  |
| WO | WO 94/25601 | 11/1994 |
| WO | WO 95/12766 | 5/1995  |
| WO | WO 95/22317 | 8/1995  |
| WO | WO 95/25122 | 9/1995  |
| WO | WO 95/27733 | 10/1995 |
| WO | WO 95/27901 | 10/1995 |
| WO | WO 96/02555 | 2/1996  |
| WO | WO 97/30721 | 8/1997  |
| WO | WO 98/15287 | 4/1998  |
| WO | WO 98/16247 | 4/1998  |
| WO | WO 98/18810 | 5/1998  |
| WO | WO 98/37919 | 9/1998  |
| WO | WO 98/40100 | 9/1998  |
| WO | WO 98/52581 | 11/1998 |
| WO | WO 98/52962 | 11/1998 |
| WO | WO 99/15259 | 4/1999  |
| WO | WO 99/33488 | 6/1999  |

(Continued)

OTHER PUBLICATIONS

Jung MC et al. T cell recognition of hepatitis B and C viral antigens. Eur J clin Invest. (Oct. 1994);24(10);641-50.*
Koziel MH et al. Hepatisis C Virus (HCV)-Specific Cytotoxic T Lymphocytes Recognize Epitopes in the Core and Envelope Proteins of HCV. J Virol. Dec. 1993;67(12):7522-7532.*
Koziel, et al. HCV-specific Cytotoxic T Lymphocytes Recognize Epitopes in the Core and Envelope Proteins of HCV. J Virol. 1993; 67(12):7522-7532.*
Betts, et al. Putative Immunodominant Human Immunodeficiency Virus-Specific CD8+ T-Cell Responses Cannot Be Predicted by Major Hiscompatibility Complex Class I Haplotype. J Virol. 2000; 74(19):9144-9151.*
Maecker, et al. Use of overlapping peptide mixtures as antigens for cytokine flow cytometry. J Immunol Meth. 2001; 255(1-2):27-40.*
"Aluminiumhydroxide," Röempp, $10^{th}$ Ed., pp. 139-140, 2006 (in German).

(Continued)

*Primary Examiner*—Mary E. Mosher
*Assistant Examiner*—Stuart W. Snyder
(74) *Attorney, Agent, or Firm*—Fulbright & Jaworski LLP

(57) ABSTRACT

Described is a method for isolating Hepatitis C Virus peptides (HPs) which have a binding capacity to a MHC/HLA molecule or a complex comprising said HCV-peptide and said MHC/HLA molecule characterized by the following steps: —providing a pool of HCV-peptide, said pool containing HCV-peptides which bind to said MHC/HLA molecule and HCV-peptides which do not bind to said MHC/HLA molecule, —contacting said MHC/HLA molecule with said pool of HCV-peptides whereby a HCV-peptide which has a binding capacity to said MHC/HLA molecule binds to said MHC/HLA molecule and a complex comprising said HCV-peptide and said MHC/HLA molecule is formed, —detecting and optionally separating said complex from the HCV-peptide which do not bind to said MHC/HLA molecule and optionally isolating and characterizing the HCV-peptide from said complex.

31 Claims, 10 Drawing Sheets

FOREIGN PATENT DOCUMENTS

| | | |
|---|---|---|
| WO | WO 99/38528 | 8/1999 |
| WO | WO 99/51259 | 10/1999 |
| WO | WO 99/56755 | 11/1999 |
| WO | WO 99/63941 | 12/1999 |
| WO | WO 00/11186 | 3/2000 |
| WO | WO 00/23105 | 4/2000 |
| WO | WO 00/31542 | 6/2000 |
| WO | WO 00/44775 | 8/2000 |
| WO | WO 01/17551 | 3/2001 |
| WO | WO 01/21189 | 3/2001 |
| WO | WO 01/24822 | 4/2001 |
| WO | WO 01/54719 | 8/2001 |
| WO | WO 01/72782 | 10/2001 |
| WO | WO 01/78767 | 10/2001 |
| WO | WO 01/93903 | 12/2001 |
| WO | WO 01/93905 | 12/2001 |
| WO | WO 02/13857 | 2/2002 |
| WO | WO 02/32451 | 4/2002 |
| WO | WO 02/33127 | 4/2002 |
| WO | WO 02/053185 | 7/2002 |
| WO | WO 02/095027 | 11/2002 |
| WO | WO 03/047602 | 6/2003 |
| WO | WO 03/073097 | 9/2003 |
| WO | WO 2004/014936 | 2/2004 |
| WO | WO 2004/024182 | 3/2004 |

OTHER PUBLICATIONS

Battegay et al., "Patients with chronic hepatitis C have circulating cytotoxic T cells which recognize hepatitis C virus-encoded peptides binding to HLA-A2.1 molecules," *J. Virol.*, 69(4):2462-2470, 1995.

Bellentani et al., "Epidemiology of hepatitis C virus infection in Italy: the slowly unraveling mystery," *Microbes Infect.*, 2(14):1757-63, 2000.

Blake et al., "Use of combinatorial peptide libraries to construct functional mimics of tumor epitopes recognized by MHC class I-restricted cytolytic T lymphocytes," *J. Exp. Med.*, 184:121-130, 1996.

Chang et al., "Identification of HLA-A3 and B7-restricted CTL response to hepatitis C virus in patients with acute and chronic hepatitis C," *J. Immunol.*, 162:1156-1164, 1999.

Cho et al., "Activation of human neutrophils by a synthetic antimicrobial peptide, KLKLLLLLK-NH2, via cell surface calreticulin," *Eur. J. Biochem.*, 266:878-885, 1999.

Diepolder et al., "Immunodominant CD4+ T-cell epitope within nonstructural protein 3 in acute hepatitis C virus infection," *J. Virol.*, 71(8):6011-6019, 1997.

Duenas-Carrera et al., "Enhancement of the immune response generated against hepatitis C virus envelope proteins after DNA vaccination with polyprotein-encoding plasmids," *Biotechnol. Appl. Biochem.*, 35:205-212, 2002.

Farci and Purcell, "Clinical significance of hepatitis C virus genotypes and quasispecies," *Semin Liver Dis.*, 20(1):103-26, 2000.

Gruener et al., "Sustained dysfunction of antiviral CD8+ T lymphocytes after infection with hepatitis C virus," *J. Virol.*, 75:5550-5558, 2001.

Heile et al., "Evaluation of hepatitis C virus glycoprotein E2 for vaccine design: an endoplasmic reticulum-retained recombinant protein is superior to secreted recombinant protein and DNA-based vaccine candidates," *J. Virol.*, 74(15):6885-6892, 2000.

Hemmer et al., "Predictable TCR antigen recognition based on peptide scans leads to the identification of agonist ligands with no sequence homology," *J. Immunol.*, 160:3631-3636, 1998.

Hemmer et al., "The use of soluble synthetic peptide combinatorial libraries to determine antigen recognition of T cells," *J. Peptide Res.*, 52:338-345, 1998.

HLA-prevalence studies, In: HLA 1998, (Gjertson and Terasaki, eds.) American Society for Histocompatibility and Immunogenetics, Lenexa, Kansas, pp. 103-263, 1998.

Hoffmann et al., "Mapping of Immunodominant CD4+ T Lymphocyte Epitopes of Hepatitis C Virus Antigens and Their Relevance During the Course if Chronic Infection," *Hepatology*, 21(3):632-638, 1995.

Ibe et al., "Identification and characterization of a cytotoxic T cell epitope of hepatitis C virus presented by HLA-B3501 in acute hepatitis," *J. Gen. Virol.*, 79:1735-1744, 1998.

Inchauspe and Feinstone, "Development of a heptatis C virus vaccine," *Clinics in Liver Disease*, 7:243-259, 2003.

Keilholz et al., "Immunologic monitoring of cancer vaccine therapy: results of a workshop sponsored by the Society for Biological Therapy," *J. Immunother.*, 25(2):97-138, 2002.

Koziel et al., "Hepatitis C virus (HCV)-specific cytotoxic T lymphocytes recognize epitopes in the core and envelope proteins of HCV," *J. Virol.*, 67:7522-7532, 1993.

Koziel et al., "HLA class I-restricted cytotoxic T lymphocytes specific for hepatitis C virus. Identification of multiple epitopes and characterization of patterns of cytokine release," *J. Clin. Invest.*, 96:2311-2321, 1995.

Kurokohchi et al., "A novel cytotoxic T-cell epitope presented by HLA-A24 molecule in hepatitis C virus infection," *J. Hepatology*, 34:930-935, 2001.

Lamonaca et al., "Conserved Hepatitis C Virus Sequences Are Highly Immunogenic for CD4+ T Cells: Implications for Vaccine Development," *Hepatology*, 30(4):1088-1098, 1999.

Lechmann and Liang, "Vaccine development for hepatitis C," *Seminars in Liver Disease*, 20:211-226, 2000.

Leroux-Roels et al., "Lymphoproliferative Responses to Hepatitis C Virus Coes, E1, E2, and NS3 in Patients With Chronic Hepatitis C Infection Treated With Interferon Alfa," *Hepatology*, 23(1):8-16, 1996.

Liang et al., "Pathogeneis, Natural History, Treatment, and Prevention of Hepatitis C," *Ann Intern Med.*, 132(4):296-305, 2000.

McCluskie et al., "Parenteral and mucosal prime-boost immunization strategies in mice with hepatitis B surface antigen and CpG DNA," *Fems Immunol and Medical Microbiol*, 32:179-185, 2002.

Nakajima et al., "Chemotherapeutic activity of synthetic antimicrobial peptides: correlation between chemotherapeutic activity and neutrophil-activating activity," *FEBS Lett.*, 415:64-66, 1997.

Rammensee et al., "SYFPEITHI: database for MHC ligands and peptide motifs," *Immunogenetics*, 50:213-219, 1999.

Rehermann et al., "Differential cytotoxic T-lymphocyte responsiveness to the hepatitis B and C viruses in chronically infected patients," *J. Virol.*, 70(10):7092-7102, 1996.

Rollier et al., "Control of heterologous hepatitis C virus infection in chimpanzees is associated with the quality of vaccine-induced peripheral T-helper immune response," *J. Virol.*, 78(1):187-196, 2004.

Sarobe et al., "Enhanced in vitro potency and in vivo immunogenicity of a CTL epitope from hepatitis C virus core protein following amino acid replacement at secondary HLA-A2.1 binding positions," *J. Clin. Invest.*, 102(6):1239-1248, 1998.

Shirai et al., "An epitope in hepatitis C virus core region recognized by cytotoxic T cells in mice and humans," *J. Virol.*, 68(5):3334-3342, 1994.

Sturniolo et al., "Generation of tissue-specific and promiscuous HLA ligand databases using DNA microarrays and virtual HLA class II matrices," *Nature Biotechnology*, 17:555-562, 1999.

Thursz et al., "Influence of MHC class II genotype on outcome of infection with hepatitis C virus. The HENCORE group. Hepatitis C European Network for Cooperative Research," *Lancet*, 354(9196):2119-24, 1999.

Vernacchio et al., "Effect of monophosphoryl lipid A (MPL) on T-helper cells when administered as an adjuvant pneumococcocal-CRM197 conjugate vaccine in healthy toddlers," *Vaccine*, 20(31-32):3658-67, 2002.

Ward et al., "Cellular immune responses against hepatitis C virus: the evidence base 2002," *Clin Exp Immunol.*, 128(2):195-203, 2002.

Weiner et al, "Persistent hepatitis C virus infection in a chimpanzee is associated with emergence of a cytotoxic T lymphocyte escape variant," *Proc Natl Acad Sci U. S. A.*, 92(7):2755-9, 1995.

Wentworth et al., "Identification of A2-restricted hepatitis C virus-specific cytotoxic T lymphocyte epitopes from conserved regions of the viral genome," *Int. Immunol.*, 8(5):651-659, 1996.

Wilson et al., "Immunogenicity. I. Use of peptide libraries to identify epitopes that activate clonotypic CD4+ T cells and induce T cell responses to native peptide ligands," *J. Immunol.*, 163:6424-6434, 1999.

Wong et al., "Liver-derived CTL in hepatitis C virus infection: breadth and specificity of responses in a cohort of persons with chronic infection," *J. Immunol.*, 160:1479-1488, 1998.

Aichinger et al., "Major histocompatibility complex class II-dependent unfolding, transport, and degradation of endogenous proteins," *J. Biol. Chem.*, 272:29127-29136, 1997.

Bihl et al., "Impact of HLA-B alleles, epitope binding affinity, functional avidity, and viral coinfection on the immunodominance of virus-specific CTL responses," *J. Immunol.*, 176:4094-4101, 2006.

Brooks et al., "HLA-B27 subtype polymorphism and CTL epitope choice: studies with EBV peptides link immunogenicity with stability of the B27:peptide complex," *J. Immunol.*, 161:5252-5259, 1998.

Field, "Human cytomegalovirus: challenges, opportunities and new drug development," *Antiviral Chem. Chemotherapy*, 10:219-232, 1999.

Fowler et al., "The outcome of congenital cytomegalovirus infection in relation to maternal antibody status," *New Engl. J. Med.*, 326:663-673, 1992.

Gallot et al., "Purification of Ag-specific T lymphocytes after direct peripheral blood mononuclear cell stimulation followed by CD25 selection. I. Application to CD4(+) or CD8(+) cytomegalovirus phosphoprotein pp65 epitope determination," *J. Immunol.*, 167:4196-4206, 2001.

Gavin et al., "Alkali hydrolysis of recombinant proteins allows for the rapid identification of class I MHC-restricted CTL epitopes," *J. Immunol.*, 151:3971-3980, 1993.

Gorga et al., "Purification and characterization of class II histocompatibility antigens from a homozygous human B cell line," *J. Biol. Chem.*, 262:16087-16094, 1987.

Greenberg and Riddell, "Deficient Cellular Immunity—Finding and Fixing the Defects," *Science*, 285:546-551, 1999.

Khattab et al., "Three T-cell epitopes within the C-terminal 265 amino acids of the matrix protein pp65 of human cytomegalovirus recognized by human lymphocytes," *J. Med. Virol.*, 52:68-76, 1997.

Kronenberg et al., "Conserved lipid and peptide presentation functions of nonclassical class I molecules," *Immunol. Today*, 20:515-521, 1999.

Kuzushima et al., "Efficient Identification of HLA-A2402-restricted cytomegalovirus-specific CD8+ T-cell epitopes by a computer algorithm and an enzyme-linked immunospot asay," *Blood*, 98:1872-1880, 2001.

Lalvani et al., "Rapid effector function in CD8+ memory T cells," *J. Exp. Med.*, 186:859-865, 1997.

Lamas et al., "Relationship between peptide binding and T cell epitope selection: a study with subtypes of HLA-B27," *Int. Immunol.*, 10:259-266, 1998.

Levitsky et al., "Supermotif Peptide Binding and Degeneracy of MHC: Peptide Recognition in an EBV Peptide-Specific CTL Response with Highly Restricted TCR Usage," *Human Immunol.*, 61:972-984, 2000.

Masuoka et al., "Identification of the HLA-A24 peptide epitope within cytomegalovirus protein pp65 recognized by CMV-specific cytotoxic T lymphocytes," *Viral Immunology*, 14:369-377, 2001.

McLaughlin-Taylor et al., "Identification of the major late human cytomegalovirus matrix protein pp65 as a target antigen for CD8+ virus-specific cytotoxic T lymphocytes," *J. Med. Virol.*, 43:103-110, 1994.

Nichols and Boeckh, "Recent advances in the therapy and prevention of CMV infections," *J. Clin. Virol.*, 16:25-40, 2000.

Nijman et al., "Identification of peptide sequences that potentially trigger HLA-A2.1-restricted cytotoxic T lymphocytes," *Eur. J. Immunol.*, 6:1215-1219, 1993.

Retriere et al., "Generation of cytomegalovirus-specific human T-lymphocyte clones by using autologous B-lymphoblastoid cells with stable expression of pp65 or IE1 proteins: a tool to study the fine specificity of the antiviral response," *J. Virol.*, 74:3948-3952, 2000.

Saulquin et al., "A global appraisal of immunodominant CD8 T cell responses to Epstein-Barr virus and cytomegalovirus by bulk screening," *Eur. J. Immunol.*, 30:2531-2539, 2000.

Sia and Patel, "New strategies for prevention and therapy of cytomegalovirus infection and disease in solid-organ transplant recipients," *Clin. Microbiol. Rev.*, 13:83-121, 2000.

Solache et al., "Identification of three HLA-A0201-restricted cytotoxic T cell epitopes in the cytomegalovirus protein pp65 that are conserved between eight strains of the virus," *J. Immunol.*, 163:5512-5518, 1999.

Tynan et al., "The immunogenicity of a viral cytotoxic T cell epitope is controlled by its MHC-bound conformation," *J. Exp. Med.*, 202:1249-1260, 2005.

Udaka et al., "Decrypting the structure of major histocompatibility complex class I-restricted cytotoxic T lymphocyte epitopes with complex peptide libraries," *J. Exp. Med.*, 181:2097-2108, 1995.

Valli et al., "Binding of myelin basic protein peptides to human histocompatibility leukocyte antigen class II molecules and their recognition by T cells from multiple sclerosis patients," *J. Clin. Invest.*, 91:616-628, 1993.

Von Son et al., "Overcoming the problem of cytomegalovirus infection after organ transplantation: calling for Heracles?," *Intervirology*, 42:285-290, 1999.

Anthony et al., "Comprehensive determinant mapping of the hepatitis C-specific CD8 cell repertoire reveals unpredicted immune hierarchy," *Clinical Immunology*, 103(3):264-276, 2002.

Chen et al., "Efficient class II major histocompatibility complex presentation of endogenously synthesized hepatitis C virus core protein by Epstein-Bar virus-transformed B-lymphoblastoid cell lines to $CD4^+$ T cells," *Journal of Virology*, 72(10):8301-8308, 1998.

Fleckenstein et al., "New ligands binding to the human leukocyte antigen class II molecule DRB+0101 based on the activity pattern of an undecappeptide library," *European Journal of Biochemistry*, 240:71-77, 1996.

Greten et al., "Development and use of multimeric major histocompatibility complex molecules," *Clinical and Diagnostic Laboratory Immunology*, 9(2):216-220, 2002.

Hammer et al., "Promiscuous and allel-specific anchors in HLA-DR-binding peptides," *Cell*, 74:197-203, 1993.

Hunziker et al., "In vitro studies of core peptide-bearing immunopotentiating reconstituted influenza virosomes as non-live prototype vaccine against hepatitis C virus," *International Immunology*, 14(6):615-626, 2002.

Kwok et al., "Rapid epitope identification from complex class-II-restricted T-cell antigens," *Trends in Immunology*, 22(11):583-588, 2001.

Lauer et al., "Comprehensive analysis of $CD8^+$ -T-cell responsces against hepatitis C virus reveals multiple unpredicted specificities," *Journal of Virology*, 76(12):6104-6113, 2002.

Novak et al., "Tetramer-guided epitope mapping: rapid identification and characterization of immunodominant $CD4^+$ T cell eiptopes from complex antigens," *The Journal of Immunology*, 166:6665-6670, 2001.

Smith et al., "Peptide sequences binding to MHC class II proteins," *Molecular Immunology*, 31:1431-1437, 1994.

Stevens et al., "Efficient generation of major histocompatibility complex class I-peptide complexes using synthetic peptide libraries," *Journal of Biological Chemistry*, 273:2874-2884, 1998.

Wong et al., "Detection of diverse hepatitis C virus (HCV)-specific cytotoxic T lymphocytes in peripheral blood of infected persons by screening for responses to all tranlated proteins of HCV," *Journal of Virology*, 75(3):1229-1235, 2001.

Bitmansour et al., "Clonotypic structure of the human CD4+ memory T cell response to cytomegalovirus," *J Immunol*, 167:1151-1163, 2001.

Britt and Alford, "Cytomegalovirus," In: *Fields Virology* by Fields et al. eds., Livincott-Raven, 2493-2523 1999.

Bullock et al. "Initiation codon scanthrough verses termination codon readthrough demonstrates strong potential for MHC class I restricted cryptic epitope expression," *Journal of Experimental Medicine*, 186:1051-1058, 1997.

Chen et al., "Efficient class II major histocompatibility complex presentation of endogenously synthesized hepatitis C virus core protein by Epstein-Bar virus-transformed B-lymphoblastoid cell lines to CD4+ T cells," *Journal of Virology*, 72(10):8301-8308, 1998.

Cox et al., "Identification of a peptide recognized by five melanoma-specific human cytotoxic t cell lines," *Science*, 264:716-719, 1994.

Di Bisceglie et al., "New therapeutic strategies for hepatitis C," *Hepatology*, 35:224-231, 2002.

Drew and Lalezari, "Cytomegalovirus: disease syndromes and treatment," *Curr Clin Top Infect Dis*, 19:16-29, 1999.

Elliot et al. "Recognition of out-of-frame major histocompatibility complex class I-restricted epitopes in vivo," *European Journal of Immunology*, 26:1175-1179, 1996.

Heemels et al., "Generation, translocation and presentation of mhc class I-restricted peptides," *Annu Rev Biochem*, 64:463-491, 1995.

Kern et al., "Analysis of cd8 t cell reactivity to cytomegalovirus using protein-spanning pools of overlapping pentadecapeptides," *Eur J Immun*, 30:1676-1682, 2000.

Kern et al., "Target structures of the cd8+-t-cell response to human cytomegalovirus: the 72-kilodalton major immediate-early protein revisited," *J Virol*, 73:8179-8184, 1999.

Klein, *Natural History of the MHC*, John Wiley and Sons, 1986.

Komanduri et al., "Restoration of cytomegalovirus-specific cd4+ t-lymphocyte responses after ganciclovir and highly active antiretroviral therapy in individuals infected with HIV-1," *Nat Med*, 4:953-956, 1998.

Maecker, "Use of overlapping peptide mixtures as antigens for cytokine flow cytometry," *J Immunol Methods*, 255:27-40, 2001.

Malarkannan et al., "Presentation of out-of-frame peptide/MHC class I complexes by a novel translation initiation mechanism," *Immunity*, 10:681-690, 1999.

Maynard et al., "An alternative translation reading frame encodes an immunodominant retroviral CTL determinant expressed by an immunodeficiency-causing retrovirus," *J. of Immunology*, 160:39-50, 1998.

Maynard et al. "Non-traditionally derived CTL epitopes: exceptions that prove the rules?" *Immunology Today*, 19:551-556, 1998.

Morgan et al., "The influence of exogenous peptide on beta2-microglobulin exchange in the HLA complex: analysis in real time," *Immunogenetics*, 48:98-107, 1998.

Parker et al., "Scheme for ranking potential HLA-A2 binding peptides based on independent binding of individual peptide side-chains," *J. Immunol.*, 152:163, 1994.

Plotkin et al., "Vaccination against cytomegalovirus, the changeling demon," *Pediatr Infect Dis J*, 18:313-325, 1999.

Reddehase, "The immunogenicity of human and murine cytomegaloviruses," *Curr Opin Immunol*, 12:390-396, 2000.

Shastri et al., "Major histocompatibility class I molecules can present cryptic translation products to T-cells.," *J. Biol. Chem.* 270:1088-1091, 1995.

Stern and Wiley, "Antigenic peptide binding by class I and class II histocompatibility proteins," *Structure*, 2:245-251, 1994.

Tana et al., "An HLA-binding-motif-aided peptide epitope library: a novel library design for the screening of HLA-DR4-restricted antigenic peptides recognized by CD4+ T cells," *J Hum Genet*, 43:14-21, 1998.

Tobery, "A simple and efficient method for the monitoring of antigen-specific T cell responses using peptide pool arrays in a modified elispot assay," *J Immunol Methods*, 254:59-66, 2001.

Tourdot et al., "A general strategy to enhance immunogenicity of low-affinity HLA-A2. 1-associated peptides: implication in the identification of cryptic tumor epitopes," *Eur. J. Immunol.* 30:3411-3421, 2000.

Van den Eynde and van der Bruggen, "T cell defined tumor antigens," *Curr Opin Immunol*, 5:684-693, 1997.

Varaklioti et al., "Alternative translation occurs within the core coding region of the hepatitis C viral menome," *The Journal of Biological Chemistry*, 227:17713-17721, 2002.

Villadangos, "Proteolysis in mhc class II antigen presentation: who's in charge," *Immunity*, 12:233-239, 2000.

Waldrop et al., "Normal human cd4+ memory t cells display broad heterogeneity in their activation threshold for cytokine synthesis," *J Immunol*, 161:5284, 1998.

Walewski et al., "Evidence for a new hepatitis C virus antigen encoded in an overlapping reading frame," *RNA*, 7:710-721, 2001.

Wang et al., "Sequence variation in the gene encoding the nonstructural 3 protein of hepatitis C virus: evidence for immune selection," *J. Mol. Evol.*, 54:456-473, 2002.

Weekes et al., "Human CD28-CD28+ T cells contain greatly expanded functional virus-specific memory CTL clones," *J. Immunol*, 162:7569-7577, 1999.

Weekes et al., "The memory cytotoxic T-lymphocyte (CTL) response to human cytomegalovirus infection contains individual peptide-specific CTL clones that have undergone extensive expansion in vivo," *J. Virol.*, 73(3):2099-2108, 1999.

Wolfel et al., "Isolation of naturally processed peptides recognized by cytolytic t lymphocytes(ctl) on human emlanoma cells in association with hla-a2.1," *Int. J. Cancer*, 57:413-419, 1994.

Xu et al., "Synthesis of a novel hepatitis C virus protein by ribosomal frameshift," *The EMBO Journal*, 20:3840-3848, 2001.

Zaia et al., "Cytomegalovirus prevention and treatment in 2000," *Hematology*, 339-355, 2000.

\* cited by examiner

Figure 1. HCV peptide array

| | M1 | M2 | M3 | M4 | M5 | M6 | M7 | M8 | M9 | M10 | M11 | M12 | M13 | M14 | M15 | M16 | M17 | M18 | M19 | M20 |
|---|---|---|---|---|---|---|---|---|---|---|---|---|---|---|---|---|---|---|---|---|
| M21 | A2 | A4 | A6 | A8 | A10 | A12 | A14 | A16 | A18 | A20 | A22 | A24 | A26 | A28 | A30 | A32 | A34 | A36 | 1631 | 1632 |
| M22 | A38 | A40 | A42 | A44 | A46 | A48 | A50 | A52 | A54 | A56 | A58 | A60 | A62 | A64 | A66 | A68 | A70 | A72 | 1624 | 1625 |
| M23 | A74 | A76 | A78 | A80 | A82 | A84 | A86 | A88 | A90 | A92* | A94 | A96 | A98 | A100 | A102 | A104 | A106 | A108 | 1577 | 1578 |
| M24 | A110 | A112 | A114 | A116 | A118 | A120 | A122 | A124 | A126 | A128 | A130 | A132 | A134 | A136 | A138 | A140 | A142 | A144 | 1579 | 1580 |
| M25 | A146 | A148 | A150 | A152 | A154 | A156 | A158 | A160 | A162 | A164 | A166 | A168 | A170 | A172 | A174 | A176 | A178 | A180 | 1547 | 1623 |
| M26 | A182 | A184 | A186 | A188 | A190 | A192 | A194 | A196 | A198 | A200 | A202 | A204 | A206 | A208 | A210 | A212 | A214 | A216 | 1606 | 1607 |
| M27 | A218 | A220 | A222 | A224 | A226 | A228 | A230 | A232 | A234 | A236 | A238 | A240 | A242 | A244 | A246 | A248 | A250 | A252 | 1626 | 1613 |
| M28 | A254 | A256 | A258 | A260 | A262 | A264 | A266* | A268 | A270 | A272 | A274 | A276 | B2 | B4 | B6 | B8 | B10 | B12 | 1604 | 1605 |
| M29 | B14 | B16 | B18 | B20 | B22 | B24 | B26 | B28 | B30 | B32* | B34 | B36 | B38 | B40 | B42 | B44 | B46 | B48 | 1618 | 1619 |
| M30 | B50 | B52 | B54 | B56 | B58 | B60 | B62 | B64 | B66 | B68 | B70 | B72* | B74 | B76 | B78 | B80 | B82 | B84 | 1559 | 1560 |
| M31 | B86 | B88 | B90 | B92 | B94 | B96 | B98 | B100 | B102 | B104 | B106 | B108 | B110 | B112 | B114 | B116 | B118 | B120 | B122 | B124 |
| M32 | C2 | C4 | C6 | C8 | C10 | C12 | C14 | C16 | C18 | C20 | C22 | C24 | C26 | C28 | C30 | C32 | C34 | C36 | 1614 | 1615 |
| M33 | C38 | C40 | C42 | C44 | C46 | C47 | C50 | C52 | C54 | C56 | C58 | C60 | C62 | C64 | C66 | C68 | C70 | C72 | 1616 | 1617 |
| M34 | C74 | C76 | C78 | C80 | C82 | C84 | C85 | C88 | C90 | C91 | C92 | C93 | C94 | C95 | C96 | C97 | C98 | C99 | C100 | C101 |
| M35 | C102 | C103 | C104 | C105 | C106 | C107 | C108 | C109 | C110 | C111 | C112 | C113 | C114 | C115 | C116 | C117 | C118 | C119 | C120 | PBS |
| M36 | C121 | C122 | C123 | C124 | C125 | C126 | C127 | C128 | C129 | C130 | C131 | C132 | C133 | C134 | C135 | C136 | C137 | C138 | 1620 | 1621 |
| M37 | C139 | C140 | C141 | C142 | C143 | C144 | C145 | C146 | C147 | C148 | C149 | C150 | C151 | C152 | C153 | C154 | C155 | C156 | PBS | PBS |
| M38 | C157 | C158 | C159 | C160 | C161 | C162 | C163 | C164 | C165 | C166 | C167 | C168 | C169 | C170 | C171 | C172 | C173 | C174 | PBS | PBS |
| M39 | C175 | C176 | C177 | C178 | C179 | C180 | C181 | C182 | C183 | C184 | C185 | C186 | C187 | C188 | C189 | C190 | C191 | C192 | PBS | PBS |
| M40 | 1629 | 1628 | 1630 | 1545 | 1581 | 1546 | 1622 | 1603 | 1557 | 1558 | 1556 | 1627 | PBS | PBS | PBS | C193 | C195 | C197 | PBS | PBS |

Figure 2. Peptide pools that bind to DRB1*0401

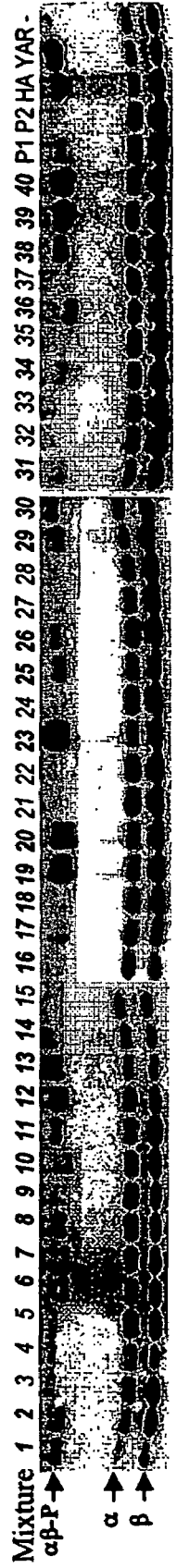

| | M1 | M2 | M3 | M4 | M5 | M6 | M7 | M8 | M9 | M10 | M11 | M12 | M13 | M14 | M15 | M16 | M17 | M18 | M19 | M20 |
|---|---|---|---|---|---|---|---|---|---|---|---|---|---|---|---|---|---|---|---|---|
| M21 | A2 | A4 | A6 | A8 | A10 | A12 | A14 | A16 | A18 | A20 | A22 | A24 | A26 | A28 | A30 | A32 | A34 | A36 | 1631 | 1632 |
| M22 | A38 | A40 | A42 | A44 | A46 | A48 | A50 | A52 | A54 | A56 | A58 | A60 | A62 | A64 | A66 | A68 | A70 | A72 | 1624 | 1625 |
| M23 | A74 | A76 | A78 | A80 | A82 | A84 | A86 | A88 | A90 | A92* | A94 | A96 | A98 | A100 | A102 | A104 | A106 | A108 | 1577 | 1578 |
| M24 | A110 | A112 | A114 | A116 | A118 | A120 | A122 | A124 | A126 | A128 | A130 | A132 | A134 | A136 | A138 | A140 | A142 | A144 | 1579 | 1580 |
| M25 | A146 | A148 | A150 | A152 | A154 | A156 | A158 | A160 | A162 | A164 | A166 | A168 | A170 | A172 | A174 | A176 | A178 | A180 | 1547 | 1623 |
| M26 | A182 | A184 | A186 | A188 | A190 | A192 | A194 | A196 | A198 | A200 | A202 | A204 | A206 | A208 | A210 | A212 | A214 | A216 | 1606 | 1607 |
| M27 | A218 | A220 | A222 | A224 | A226 | A228 | A230 | A232 | A234 | A236 | A238 | A240 | A242 | A244 | A246 | A248 | A250 | A252 | 1626 | 1613 |
| M28 | A254 | A256 | A258 | A260 | A262 | A264 | A266* | A268 | A270 | A272 | A274 | A276 | B2 | B4 | B6 | B8 | B10 | B12 | 1604 | 1605 |
| M29 | B14 | B16 | B18 | B20 | B22 | B24 | B26 | B28 | B30 | B32* | B34 | B36 | B38 | B40 | B42 | B44 | B46 | B48 | 1618 | 1619 |
| M30 | B50 | B52 | B54 | B56 | B58 | B60 | B62 | B64 | B66 | B68 | B70 | B72* | B74 | B76 | B78 | B80 | B82 | B84 | 1559 | 1560 |
| M31 | B86 | B88 | B90 | B92 | B94 | B96 | B98 | B100 | B102 | B104 | B106 | B108 | B110 | B112 | B114 | B116 | B118 | B120 | B122 | B124 |
| M32 | C2 | C4 | C6 | C8 | C10 | C12 | C14 | C16 | C18 | C20 | C22 | C24 | C26 | C28 | C30 | C32 | C34 | C36 | 1614 | 1615 |
| M33 | C38 | C40 | C42 | C44 | C46 | C47 | C50 | C52 | C54 | C56 | C58 | C60 | C62 | C64 | C66 | C68 | C70 | C72 | 1616 | 1617 |
| M34 | C74 | C76 | C78 | C80 | C82 | C84 | C85 | C88 | C90 | C91 | C92 | C93 | C94 | C95 | C96 | C97 | C98 | C99 | C100 | C101 |
| M35 | C102 | C103 | C104 | C105 | C106 | C107 | C108 | C109 | C110 | C111 | C112 | C113 | C114 | C115 | C116 | C117 | C118 | C119 | C120 | PBS |
| M36 | C121 | C122 | C123 | C124 | C125 | C126 | C127 | C128 | C129 | C130 | C131 | C132 | C133 | C134 | C135 | C136 | C137 | C138 | 1620 | 1621 |
| M37 | C139 | C140 | C141 | C142 | C143 | C144 | C145 | C146 | C147 | C148 | C149 | C150 | C151 | C152 | C153 | C154 | C155 | C156 | PBS | PBS |
| M38 | C157 | C158 | C159 | C160 | C161 | C162 | C163 | C164 | C165 | C166 | C167 | C168 | C169 | C170 | C171 | C172 | C173 | C174 | PBS | PBS |
| M39 | C175 | C176 | C177 | C178 | C179 | C180 | C181 | C182 | C183 | C184 | C185 | C186 | C187 | C188 | C189 | C190 | C191 | C192 | PBS | PBS |
| M40 | 1629 | 1628 | 1630 | 1545 | 1581 | 1546 | 1622 | 1603 | 1557 | 1558 | 1556 | 1627 | PBS | PBS | PBS | C193 | C195 | C197 | PBS | PBS |

Figure 3. Peptide pools that bind to DRB1*0404

| | M1 | M2 | M3 | M4 | M5 | M6 | M7 | M8 | M9 | M10 | M11 | M12 | M13 | M14 | M15 | M16 | M17 | M18 | M19 | M20 |
|---|---|---|---|---|---|---|---|---|---|---|---|---|---|---|---|---|---|---|---|---|
| M21 | A2 | A4 | A6 | A8 | A10 | A12 | A14 | A16 | A18 | A20 | A22 | A24 | A26 | A28 | A30 | A32 | A34 | A36 | 1631 | 1632 |
| M22 | A38 | A40 | A42 | A44 | A46 | A48 | A50 | A52 | A54 | A56 | A58 | A60 | A62 | A64 | A66 | A68 | A70 | A72 | 1624 | 1625 |
| M23 | A74 | A76 | A78 | A80 | A82 | A84 | A86 | A88 | A90 | A92* | A94 | A96 | A98 | A100 | A102 | A104 | A106 | A108 | 1577 | 1578 |
| M24 | A110 | A112 | A114 | A116 | A118 | A120 | A122 | A124 | A126 | A128 | A130 | A132 | A134 | A136 | A138 | A140 | A142 | A144 | 1579 | 1580 |
| M25 | A146 | A148 | A150 | A152 | A154 | A156 | A158 | A160 | A162 | A164 | A166 | A168 | A170 | A172 | A174 | A176 | A178 | A180 | 1547 | 1623 |
| M26 | A182 | A184 | A186 | A188 | A190 | A192 | A194 | A196 | A198 | A200 | A202 | A204 | A206 | A208 | A210 | A212 | A214 | A216 | 1606 | 1607 |
| M27 | A218 | A220 | A222 | A224 | A226 | A228 | A230 | A232 | A234 | A236 | A238 | A240 | A242 | A244 | A246 | A248 | A250 | A252 | 1626 | 1613 |
| M28 | A254 | A256 | A258 | A260 | A262 | A254 | A256* | A268 | A270 | A272 | A274 | A276 | B2 | B4 | B6 | B8 | B10 | B12 | 1604 | 1605 |
| M29 | B14 | B16 | B18 | B20 | B22 | B24 | B26 | B28 | B30 | B32* | B34 | B36 | B38 | B40 | B42 | B44 | B46 | B48 | 1618 | 1619 |
| M30 | B50 | B52 | B54 | B56 | B58 | B60 | B62 | B64 | B66 | B68 | B70 | B72* | B74 | B76 | B78 | B80 | B82 | B84 | 1559 | 1560 |
| M31 | B86 | B88 | B90 | B92 | B94 | B96 | B98 | B100 | B102 | B104 | B106 | B108 | B110 | B112 | B114 | B116 | B118 | B120 | B122 | B124 |
| M32 | C2 | C4 | C6 | C8 | C10 | C12 | C14 | C16 | C18 | C20 | C22 | C24 | C26 | C28 | C30 | C32 | C34 | C36 | 1614 | 1615 |
| M33 | C38 | C40 | C42 | C44 | C46 | C47 | C50 | C52 | C54 | C56 | C58 | C60 | C62 | C64 | C66 | C68 | C70 | C72 | 1616 | 1617 |
| M34 | C74 | C76 | C78 | C80 | C82 | C84 | C85 | C88 | C90 | C91 | C92 | C93 | C94 | C95 | C96 | C97 | C98 | C99 | C100 | C101 |
| M35 | C102 | C103 | C104 | C105 | C106 | C107 | C108 | C109 | C110 | C111 | C112 | C113 | C114 | C115 | C116 | C117 | C118 | C119 | C120 | PBS |
| M36 | C121 | C122 | C123 | C124 | C125 | C126 | C127 | C128 | C129 | C130 | C131 | C132 | C133 | C134 | C135 | C136 | C137 | C138 | 1620 | 1621 |
| M37 | C139 | C140 | C141 | C142 | C143 | C144 | C145 | C146 | C147 | C148 | C149 | C150 | C151 | C152 | C153 | C154 | C155 | C156 | PBS | PBS |
| M38 | C157 | C158 | C159 | C160 | C161 | C162 | C163 | C164 | C165 | C166 | C167 | C168 | C169 | C170 | C171 | C172 | C173 | C174 | PBS | PBS |
| M39 | C175 | C176 | C177 | C178 | C179 | C180 | C181 | C182 | C183 | C184 | C185 | C186 | C187 | C188 | C189 | C190 | C191 | C192 | PBS | PBS |
| M40 | 1629 | 1628 | 1630 | 1545 | 1581 | 1546 | 1622 | 1603 | 1557 | 1558 | 1556 | 1627 | PBS | PBS | PBS | C193 | C195 | C197 | PBS | PBS |

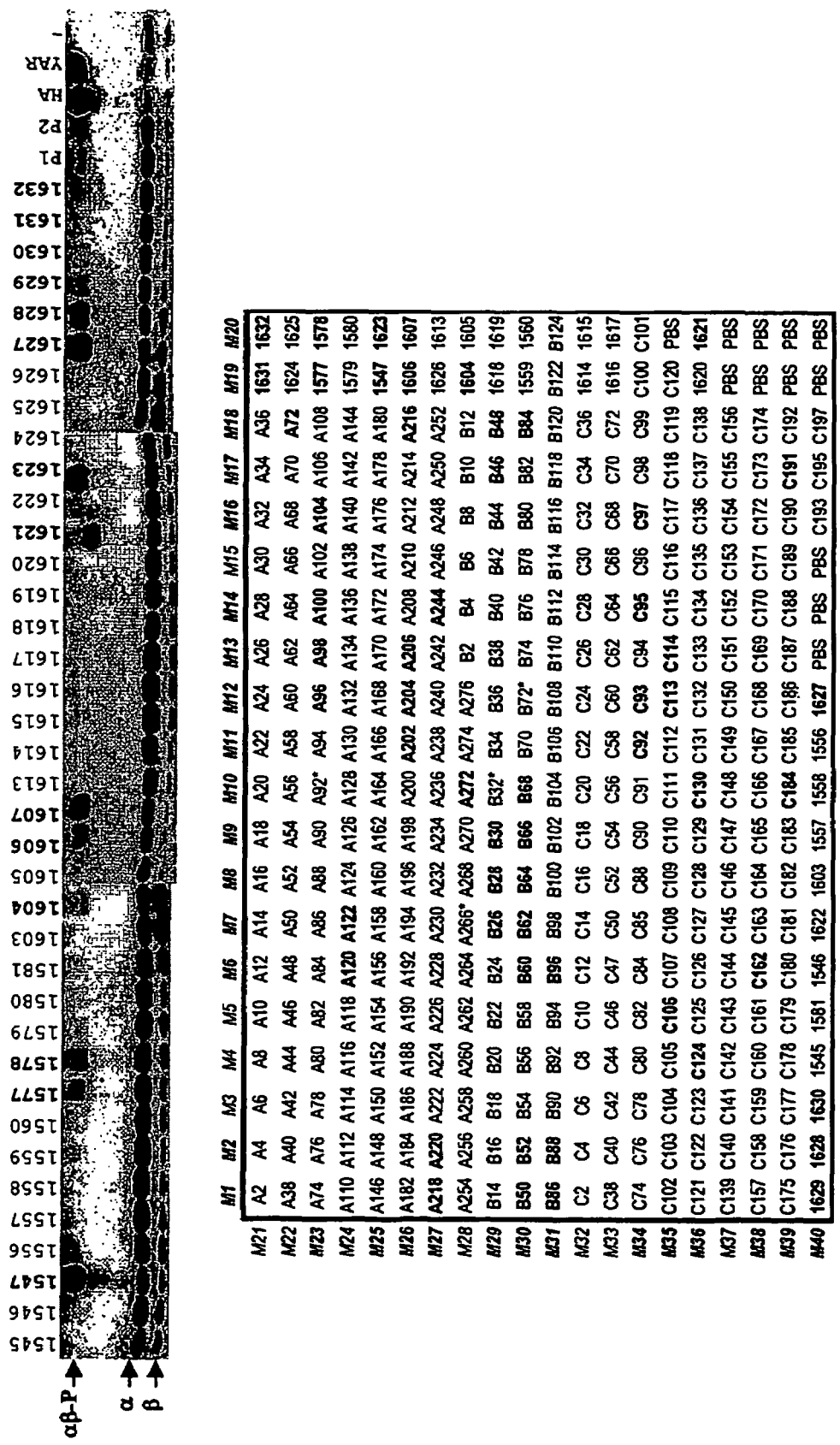
Figure 4. Individual peptides that bind to DRB1*0401

Figure 5. Individual peptides that bind to DRB1*0404

| | M1 | M2 | M3 | M4 | M5 | M6 | M7 | M8 | M9 | M10 | M11 | M12 | M13 | M14 | M15 | M16 | M17 | M18 | M19 | M20 |
|---|---|---|---|---|---|---|---|---|---|---|---|---|---|---|---|---|---|---|---|---|
| M21 | A2 | A4 | A6 | A8 | A10 | A12 | A14 | A16 | A18 | A20 | A22 | A24 | A26 | A28 | A30 | A32 | A34 | A36 | 1631 | 1632 |
| M22 | A38 | A40 | A42 | A44 | A46 | A48 | A50 | A52 | A54 | A56 | A58 | A60 | A62 | A64 | A66 | A68 | A70 | A72 | 1624 | 1625* |
| M23 | A74 | A76 | A78 | A80 | A82 | A84 | A86 | A88 | A90 | A92* | A94 | A96 | A98 | A100 | A102 | A104 | A106 | A108 | 1577 | 1578 |
| M24 | A110 | A112 | A114 | A116 | A118 | A120 | A122 | A124 | A126 | A128 | A130 | A132 | A134 | A136 | A138 | A140 | A142 | A144 | 1579 | 1580 |
| M25 | A146 | A148 | A150 | A152 | A154 | A156 | A158 | A160 | A162 | A164 | A166 | A168 | A170 | A172 | A174 | A176 | A178 | A180 | 1547 | 1623 |
| M26 | A182 | A184 | A186 | A188 | A190 | A192 | A194 | A196 | A198 | A200 | A202 | A204 | A206 | A208 | A210 | A212 | A214 | A216 | 1606 | 1607 |
| M27 | A218 | A220 | A222 | A224 | A226 | A228 | A230 | A232 | A234 | A236 | A238 | A240 | A242 | A244 | A246 | A248 | A250 | A252 | 1626 | 1613 |
| M28 | A254 | A256 | A258 | A260 | A262 | A264 | A266* | A268 | A270 | A272 | A274 | A276 | B2 | B4 | B6 | B8 | B10 | B12 | 1604 | 1605 |
| M29 | B14 | B16 | B18 | B20 | B22 | B24 | B26 | B28 | B30 | B32* | B34 | B36 | B38 | B40 | B42 | B44 | B46 | B48 | 1618 | 1619 |
| M30 | B50 | B52 | B54 | B56 | B58 | B60 | B62 | B64 | B66 | B68 | B70 | B72* | B74 | B76 | B78 | B80 | B82 | B84 | 1559 | 1560 |
| M31 | B86 | B88 | B90 | B92 | B94 | B96 | B98 | B100 | B102 | B104 | B106 | B108 | B110 | B112 | B114 | B116 | B118 | B120 | B122 | B124 |
| M32 | C2 | C4 | C6 | C8 | C10 | C12 | C14 | C16 | C18 | C20 | C22 | C24 | C26 | C28 | C30 | C32 | C34 | C36 | 1614 | 1615 |
| M33 | C38 | C40 | C42 | C44 | C46 | C47 | C50 | C52 | C54 | C56 | C58 | C60 | C62 | C64 | C66 | C68 | C70 | C72 | 1616 | 1617 |
| M34 | C74 | C76 | C78 | C80 | C82 | C84 | C85 | C88 | C90 | C91 | C92 | C93 | C94 | C95 | C96 | C97 | C98 | C99 | C100 | C101 |
| M35 | C102 | C103 | C104 | C105 | C106 | C107 | C108 | C109 | C110 | C111 | C112 | C113 | C114 | C115 | C116 | C117 | C118 | C119 | C120 | PBS |
| M36 | C121 | C122 | C123 | C124 | C125 | C126 | C127 | C128 | C129 | C130 | C131 | C132 | C133 | C134 | C135 | C136 | C137 | C138 | 1620 | 1621 |
| M37 | C139 | C140 | C141 | C142 | C143 | C144 | C145 | C146 | C147 | C148 | C149 | C150 | C151 | C152 | C153 | C154 | C155 | C156 | PBS | PBS |
| M38 | C157 | C158 | C159 | C160 | C161 | C162 | C163 | C164 | C165 | C166 | C167 | C168 | C169 | C170 | C171 | C172 | C173 | C174 | PBS | PBS |
| M39 | C175 | C176 | C177 | C178 | C179 | C180 | C181 | C182 | C183 | C184 | C185 | C186 | C187 | C188 | C189 | C190 | C191 | C192 | PBS | PBS |
| M40 | 1629 | 1628 | 1630 | 1545 | 1581 | 1546 | 1622 | 1603 | 1557 | 1558 | 1556 | 1627 | PBS | PBS | PBS | PBS | C193 | C195 | C197 | PBS |

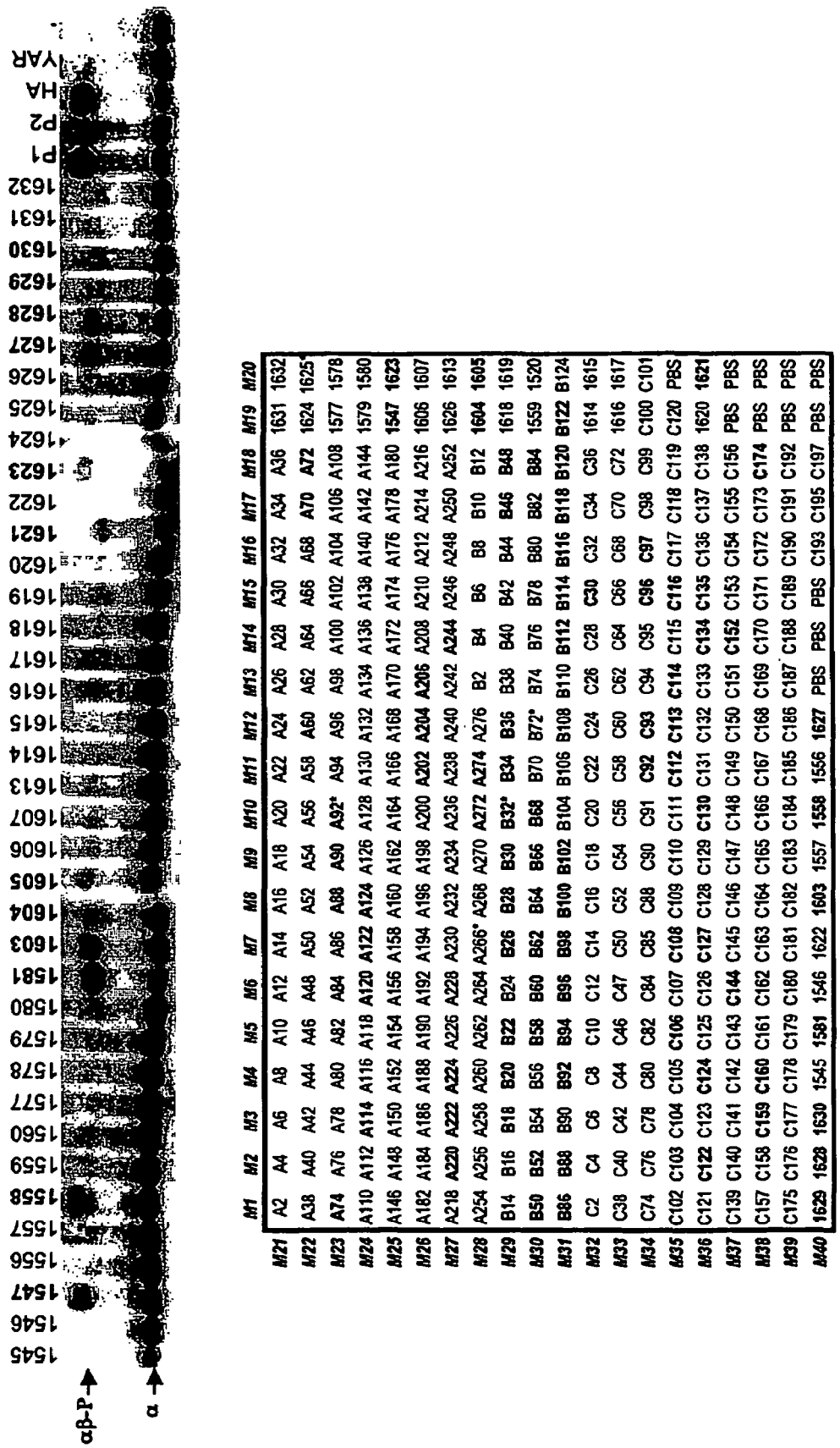
Figure 6. Individual peptides that bind to DRB1*0101

Figure 7. Individual peptides that bind to DRB1*0701

| | M1 | M2 | M3 | M4 | M5 | M6 | M7 | M8 | M9 | M10 | M11 | M12 | M13 | M14 | M15 | M16 | M17 | M18 | M19 | M20 |
|---|---|---|---|---|---|---|---|---|---|---|---|---|---|---|---|---|---|---|---|---|
| M21 | A2 | A4 | A6 | A8 | A10 | A12 | A14 | A16 | A18 | A20 | A22 | A24 | A26 | A28 | A30 | A32 | A34 | A36 | 1631 | 1632 |
| M22 | A38 | A40 | A42 | A44 | A46 | A48 | A50 | A52 | A54 | A56 | A58 | A60 | A62 | A64 | A66 | A68 | A70 | A72 | 1624 | 1625 |
| M23 | A74 | A76 | A78 | A80 | A82 | A84 | A86 | A88 | A90 | A92* | A94 | A96 | A98 | A100 | A102 | A104 | A106 | A108 | 1577 | 1578 |
| M24 | A110 | A112 | A114 | A116 | A118 | A120 | A122 | A124 | A126 | A128 | A130 | A132 | A134 | A136 | A138 | A140 | A142 | A144 | 1579 | 1580 |
| M25 | A146 | A148 | A150 | A152 | A154 | A156 | A158 | A160 | A162 | A164 | A166 | A168 | A170 | A172 | A174 | A176 | A178 | A180 | 1547 | 1623 |
| M26 | A182 | A184 | A186 | A188 | A190 | A192 | A194 | A196 | A198 | A200 | A202 | A204 | A206 | A208 | A210 | A212 | A214 | A216 | 1606 | 1607 |
| M27 | A218 | A220 | A222 | A224 | A226 | A228 | A230 | A232 | A234 | A236 | A238 | A240 | A242 | A244 | A246 | A248 | A250 | A252 | 1626 | 1613 |
| M28 | A254 | A256 | A258 | A260 | A262 | A264 | A266* | A268 | A270 | A272 | A274 | A276 | B2 | B4 | B6 | B8 | B10 | B12 | 1604 | 1605 |
| M29 | B14 | B16 | B18 | B20 | B22 | B24 | B26 | B28 | B30 | B32* | B34 | B36 | B38 | B40 | B42 | B44 | B46 | B48 | 1618 | 1619 |
| M30 | B50 | B52 | B54 | B56 | B58 | B60 | B62 | B64 | B66 | B68 | B70 | B72* | B74 | B76 | B78 | B80 | B82 | B84 | 1559 | 1560 |
| M31 | B86 | B88 | B90 | B92 | B94 | B96 | B98 | B100 | B102 | B104 | B106 | B108 | B110 | B112 | B114 | B116 | B118 | B120 | B122 | B124 |
| M32 | C2 | C4 | C6 | C8 | C10 | C12 | C14 | C16 | C18 | C20 | C22 | C24 | C26 | C28 | C30 | C32 | C34 | C36 | 1614 | 1615 |
| M33 | C38 | C40 | C42 | C44 | C46 | C47 | C50 | C52 | C54 | C56 | C58 | C60 | C62 | C64 | C66 | C68 | C70 | C72 | 1616 | 1617 |
| M34 | C74 | C76 | C78 | C80 | C82 | C84 | C85 | C88 | C90 | C91 | C92 | C93 | C94 | C95 | C96 | C97 | C98 | C99 | C100 | C101 |
| M35 | C102 | C103 | C104 | C105 | C106 | C107 | C108 | C109 | C110 | C111 | C112 | C113 | C114 | C115 | C116 | C117 | C118 | C119 | C120 | PBS |
| M36 | C121 | C122 | C123 | C124 | C125 | C126 | C127 | C128 | C129 | C130 | C131 | C132 | C133 | C134 | C135 | C136 | C137 | C138 | 1620 | 1621 |
| M37 | C139 | C140 | C141 | C142 | C143 | C144 | C145 | C146 | C147 | C148 | C149 | C150 | C151 | C152 | C153 | C154 | C155 | C156 | PBS | PBS |
| M38 | C157 | C158 | C159 | C160 | C161 | C162 | C163 | C164 | C165 | C166 | C167 | C168 | C169 | C170 | C171 | C172 | C173 | C174 | PBS | PBS |
| M39 | C175 | C176 | C177 | C178 | C179 | C180 | C181 | C182 | C183 | C184 | C185 | C186 | C187 | C188 | C189 | C190 | C191 | C192 | PBS | PBS |
| M40 | 1629 | 1628 | 1630 | 1545 | 1581 | 1546 | 1622 | 1603 | 1557 | 1558 | 1556 | 1627 | PBS | PBS | PBS | PBS | PBS | C193 | C195 | C197 |

SEQUENCE LISTING

```
<160> NUMBER OF SEQ ID NOS: 1172

<210> SEQ ID NO 1
<211> LENGTH: 15
<212> TYPE: PRT
<213> ORGANISM: Hepatitis C virus

<400> SEQUENCE: 1

Asn Thr Asn Gly Ser Trp His Ile Asn Arg Thr Ala Leu Asn Cys
1               5                   10                  15

<210> SEQ ID NO 2
<211> LENGTH: 15
<212> TYPE: PRT
<213> ORGANISM: Hepatitis C virus
```

```
<400> SEQUENCE: 2

Thr Asn Gly Ser Trp His Ile Asn Arg Thr Ala Leu Asn Cys Asn
1               5                   10                  15

<210> SEQ ID NO 3
<211> LENGTH: 15
<212> TYPE: PRT
<213> ORGANISM: Hepatitis C virus

<400> SEQUENCE: 3

Asn Gly Ser Trp His Ile Asn Arg Thr Ala Leu Asn Cys Asn Asp
1               5                   10                  15

<210> SEQ ID NO 4
<211> LENGTH: 15
<212> TYPE: PRT
<213> ORGANISM: Hepatitis C virus

<400> SEQUENCE: 4

Gly Ser Trp His Ile Asn Arg Thr Ala Leu Asn Cys Asn Asp Ser
1               5                   10                  15

<210> SEQ ID NO 5
<211> LENGTH: 15
<212> TYPE: PRT
<213> ORGANISM: Hepatitis C virus

<400> SEQUENCE: 5

Ser Trp His Ile Asn Arg Thr Ala Leu Asn Cys Asn Asp Ser Leu
1               5                   10                  15

<210> SEQ ID NO 6
<211> LENGTH: 15
<212> TYPE: PRT
<213> ORGANISM: Hepatitis C virus

<400> SEQUENCE: 6

Asp Ala Gly Cys Ala Trp Tyr Glu Leu Thr Pro Ala Glu Thr Ser
1               5                   10                  15

<210> SEQ ID NO 7
<211> LENGTH: 15
<212> TYPE: PRT
<213> ORGANISM: Hepatitis C virus

<400> SEQUENCE: 7

Ala Gly Cys Ala Trp Tyr Glu Leu Thr Pro Ala Glu Thr Ser Val
1               5                   10                  15

<210> SEQ ID NO 8
<211> LENGTH: 15
<212> TYPE: PRT
<213> ORGANISM: Hepatitis C virus

<400> SEQUENCE: 8

Gly Cys Ala Trp Tyr Glu Leu Thr Pro Ala Glu Thr Ser Val Arg
1               5                   10                  15

<210> SEQ ID NO 9
<211> LENGTH: 15
<212> TYPE: PRT
<213> ORGANISM: Hepatitis C virus

<400> SEQUENCE: 9
```

```
Cys Ala Trp Tyr Glu Leu Thr Pro Ala Glu Thr Ser Val Arg Leu
1               5                  10                  15

<210> SEQ ID NO 10
<211> LENGTH: 15
<212> TYPE: PRT
<213> ORGANISM: Hepatitis C virus

<400> SEQUENCE: 10

Ala Trp Tyr Glu Leu Thr Pro Ala Glu Thr Ser Val Arg Leu Arg
1               5                  10                  15

<210> SEQ ID NO 11
<211> LENGTH: 15
<212> TYPE: PRT
<213> ORGANISM: Hepatitis C virus

<400> SEQUENCE: 11

Trp Tyr Glu Leu Thr Pro Ala Glu Thr Ser Val Arg Leu Arg Ala
1               5                  10                  15

<210> SEQ ID NO 12
<211> LENGTH: 15
<212> TYPE: PRT
<213> ORGANISM: Hepatitis C virus

<400> SEQUENCE: 12

Ala Gly Ala Ala Trp Tyr Glu Leu Thr Pro Ala Glu Thr Thr Val
1               5                  10                  15

<210> SEQ ID NO 13
<211> LENGTH: 15
<212> TYPE: PRT
<213> ORGANISM: Hepatitis C virus

<400> SEQUENCE: 13

Gly Ala Ala Trp Tyr Glu Leu Thr Pro Ala Glu Thr Thr Val Arg
1               5                  10                  15

<210> SEQ ID NO 14
<211> LENGTH: 15
<212> TYPE: PRT
<213> ORGANISM: Hepatitis C virus

<400> SEQUENCE: 14

Ala Ala Trp Tyr Glu Leu Thr Pro Ala Glu Thr Thr Val Arg Leu
1               5                  10                  15

<210> SEQ ID NO 15
<211> LENGTH: 15
<212> TYPE: PRT
<213> ORGANISM: Hepatitis C virus

<400> SEQUENCE: 15

Gly Ser Ile Gly Leu Gly Lys Val Leu Val Asp Ile Leu Ala Gly
1               5                  10                  15

<210> SEQ ID NO 16
<211> LENGTH: 15
<212> TYPE: PRT
<213> ORGANISM: Hepatitis C virus

<400> SEQUENCE: 16

Ser Ile Gly Leu Gly Lys Val Leu Val Asp Ile Leu Ala Gly Tyr
1               5                  10                  15
```

```
<210> SEQ ID NO 17
<211> LENGTH: 15
<212> TYPE: PRT
<213> ORGANISM: Hepatitis C virus

<400> SEQUENCE: 17

Ile Gly Leu Gly Lys Val Leu Val Asp Ile Leu Ala Gly Tyr Gly
1               5                   10                  15

<210> SEQ ID NO 18
<211> LENGTH: 15
<212> TYPE: PRT
<213> ORGANISM: Hepatitis C virus

<400> SEQUENCE: 18

Gly Leu Gly Lys Val Leu Val Asp Ile Leu Ala Gly Tyr Gly Ala
1               5                   10                  15

<210> SEQ ID NO 19
<211> LENGTH: 15
<212> TYPE: PRT
<213> ORGANISM: Hepatitis C virus

<400> SEQUENCE: 19

Leu Gly Lys Val Leu Val Asp Ile Leu Ala Gly Tyr Gly Ala Gly
1               5                   10                  15

<210> SEQ ID NO 20
<211> LENGTH: 15
<212> TYPE: PRT
<213> ORGANISM: Hepatitis C virus

<400> SEQUENCE: 20

Gly Lys Val Leu Val Asp Ile Leu Ala Gly Tyr Gly Ala Gly Val
1               5                   10                  15

<210> SEQ ID NO 21
<211> LENGTH: 15
<212> TYPE: PRT
<213> ORGANISM: Hepatitis C virus

<400> SEQUENCE: 21

Lys Val Leu Val Asp Ile Leu Ala Gly Tyr Gly Ala Gly Val Ala
1               5                   10                  15

<210> SEQ ID NO 22
<211> LENGTH: 15
<212> TYPE: PRT
<213> ORGANISM: Hepatitis C virus

<400> SEQUENCE: 22

Val Leu Val Asp Ile Leu Ala Gly Tyr Gly Ala Gly Val Ala Gly
1               5                   10                  15

<210> SEQ ID NO 23
<211> LENGTH: 15
<212> TYPE: PRT
<213> ORGANISM: Hepatitis C virus

<400> SEQUENCE: 23

Leu Val Asp Ile Leu Ala Gly Tyr Gly Ala Gly Val Ala Gly Ala
1               5                   10                  15
```

<210> SEQ ID NO 24
<211> LENGTH: 15
<212> TYPE: PRT
<213> ORGANISM: Hepatitis C virus

<400> SEQUENCE: 24

Ala Gly Val Ala Gly Ala Leu Val Ala Phe Lys Val Met Ser Gly
1               5                   10                  15

<210> SEQ ID NO 25
<211> LENGTH: 15
<212> TYPE: PRT
<213> ORGANISM: Hepatitis C virus

<400> SEQUENCE: 25

Asp Ile Leu Ala Gly Tyr Gly Ala Gly Ile Ser Gly Ala Leu Val
1               5                   10                  15

<210> SEQ ID NO 26
<211> LENGTH: 15
<212> TYPE: PRT
<213> ORGANISM: Hepatitis C virus

<400> SEQUENCE: 26

Ile Leu Ala Gly Tyr Gly Ala Gly Ile Ser Gly Ala Leu Val Ala
1               5                   10                  15

<210> SEQ ID NO 27
<211> LENGTH: 18
<212> TYPE: PRT
<213> ORGANISM: Hepatitis C virus

<400> SEQUENCE: 27

Pro Glu Tyr Asp Leu Glu Leu Ile Thr Ser Cys Ser Ser Asn Val Ser
1               5                   10                  15

Val Ala

<210> SEQ ID NO 28
<211> LENGTH: 20
<212> TYPE: PRT
<213> ORGANISM: Hepatitis C virus

<400> SEQUENCE: 28

Val Cys Gly Pro Val Tyr Cys Phe Thr Pro Ser Pro Val Val Val Gly
1               5                   10                  15

Thr Thr Asp Arg
            20

<210> SEQ ID NO 29
<211> LENGTH: 18
<212> TYPE: PRT
<213> ORGANISM: Hepatitis C virus

<400> SEQUENCE: 29

Gly Trp Ala Gly Trp Leu Leu Ser Pro Arg Gly Ser Arg Pro Ser Trp
1               5                   10                  15

Gly Pro

<210> SEQ ID NO 30
<211> LENGTH: 18
<212> TYPE: PRT
<213> ORGANISM: Hepatitis C virus

<400> SEQUENCE: 30

```
Val Val Cys Cys Ser Met Ser Tyr Thr Trp Thr Gly Ala Leu Ile Thr
1               5                   10                  15

Pro Cys
```

<210> SEQ ID NO 31
<211> LENGTH: 17
<212> TYPE: PRT
<213> ORGANISM: Hepatitis C virus

<400> SEQUENCE: 31

```
Leu Leu Phe Leu Leu Leu Ala Asp Ala Arg Val Cys Ala Cys Leu Trp
1               5                   10                  15

Met
```

<210> SEQ ID NO 32
<211> LENGTH: 15
<212> TYPE: PRT
<213> ORGANISM: Hepatitis C virus

<400> SEQUENCE: 32

```
Gly Val Leu Phe Gly Leu Ala Tyr Phe Ser Met Val Gly Asn Trp
1               5                   10                  15
```

<210> SEQ ID NO 33
<211> LENGTH: 21
<212> TYPE: PRT
<213> ORGANISM: Hepatitis C virus

<400> SEQUENCE: 33

```
Tyr Leu Val Ala Tyr Gln Ala Thr Val Cys Ala Arg Ala Gln Ala Pro
1               5                   10                  15

Pro Pro Ser Trp Asp
                20
```

<210> SEQ ID NO 34
<211> LENGTH: 15
<212> TYPE: PRT
<213> ORGANISM: Hepatitis C virus

<400> SEQUENCE: 34

```
Asp Ile Leu Ala Gly Tyr Gly Ala Gly Val Ala Gly Ala Leu Val
1               5                   10                  15
```

<210> SEQ ID NO 35
<211> LENGTH: 15
<212> TYPE: PRT
<213> ORGANISM: Hepatitis C virus

<400> SEQUENCE: 35

```
Ile Leu Ala Gly Tyr Gly Ala Gly Val Ala Gly Ala Leu Val Ala
1               5                   10                  15
```

<210> SEQ ID NO 36
<211> LENGTH: 15
<212> TYPE: PRT
<213> ORGANISM: Hepatitis C virus

<400> SEQUENCE: 36

```
Leu Ala Gly Tyr Gly Ala Gly Val Ala Gly Ala Leu Val Ala Phe
1               5                   10                  15
```

<210> SEQ ID NO 37

```
<211> LENGTH: 15
<212> TYPE: PRT
<213> ORGANISM: Hepatitis C virus

<400> SEQUENCE: 37

Ala Gly Tyr Gly Ala Gly Val Ala Gly Ala Leu Val Ala Phe Lys
1               5                   10                  15

<210> SEQ ID NO 38
<211> LENGTH: 15
<212> TYPE: PRT
<213> ORGANISM: Hepatitis C virus

<400> SEQUENCE: 38

Gly Tyr Gly Ala Gly Val Ala Gly Ala Leu Val Ala Phe Lys Ile
1               5                   10                  15

<210> SEQ ID NO 39
<211> LENGTH: 15
<212> TYPE: PRT
<213> ORGANISM: Hepatitis C virus

<400> SEQUENCE: 39

Glu Thr Ala Gly Val Arg Leu Thr Val Leu Ala Thr Ala Thr Pro
1               5                   10                  15

<210> SEQ ID NO 40
<211> LENGTH: 15
<212> TYPE: PRT
<213> ORGANISM: Hepatitis C virus

<400> SEQUENCE: 40

Thr Ala Gly Val Arg Leu Thr Val Leu Ala Thr Ala Thr Pro Pro
1               5                   10                  15

<210> SEQ ID NO 41
<211> LENGTH: 15
<212> TYPE: PRT
<213> ORGANISM: Hepatitis C virus

<400> SEQUENCE: 41

Ala Gly Val Arg Leu Thr Val Leu Ala Thr Ala Thr Pro Pro Gly
1               5                   10                  15

<210> SEQ ID NO 42
<211> LENGTH: 15
<212> TYPE: PRT
<213> ORGANISM: Hepatitis C virus

<400> SEQUENCE: 42

Gly Val Arg Leu Thr Val Leu Ala Thr Ala Thr Pro Pro Gly Ser
1               5                   10                  15

<210> SEQ ID NO 43
<211> LENGTH: 15
<212> TYPE: PRT
<213> ORGANISM: Hepatitis C virus

<400> SEQUENCE: 43

Val Arg Leu Thr Val Leu Ala Thr Ala Thr Pro Pro Gly Ser Val
1               5                   10                  15

<210> SEQ ID NO 44
<211> LENGTH: 15
<212> TYPE: PRT
```

```
<213> ORGANISM: Hepatitis C virus

<400> SEQUENCE: 44

Ala Gly Ile Ser Gly Ala Leu Val Ala Phe Lys Ile Met Ser Gly
1               5                   10                  15

<210> SEQ ID NO 45
<211> LENGTH: 15
<212> TYPE: PRT
<213> ORGANISM: Hepatitis C virus

<400> SEQUENCE: 45

Val Asn Leu Leu Pro Ala Ile Leu Ser Pro Gly Ala Leu Val Val
1               5                   10                  15

<210> SEQ ID NO 46
<211> LENGTH: 15
<212> TYPE: PRT
<213> ORGANISM: Hepatitis C virus

<400> SEQUENCE: 46

His Ala Gly Leu Arg Asp Leu Ala Val Ala Val Glu Pro Val Val
1               5                   10                  15

<210> SEQ ID NO 47
<211> LENGTH: 15
<212> TYPE: PRT
<213> ORGANISM: Hepatitis C virus

<400> SEQUENCE: 47

Thr Thr Leu Leu Phe Asn Ile Leu Gly Gly Trp Val Ala Ala Gln
1               5                   10                  15

<210> SEQ ID NO 48
<211> LENGTH: 15
<212> TYPE: PRT
<213> ORGANISM: Hepatitis C virus

<400> SEQUENCE: 48

Val Met Gly Ser Ser Tyr Gly Phe Gln Tyr Ser Pro Gly Gln Arg
1               5                   10                  15

<210> SEQ ID NO 49
<211> LENGTH: 17
<212> TYPE: PRT
<213> ORGANISM: Hepatitis C virus

<400> SEQUENCE: 49

Val Leu Thr Ser Met Leu Thr Asp Pro Ser His Ile Thr Ala Glu Thr
1               5                   10                  15

Ala

<210> SEQ ID NO 50
<211> LENGTH: 17
<212> TYPE: PRT
<213> ORGANISM: Hepatitis C virus

<400> SEQUENCE: 50

Val Leu Thr Ser Met Leu Thr Asp Pro Ser His Ile Thr Ala Glu Ala
1               5                   10                  15

Ala

<210> SEQ ID NO 51
```

```
<211> LENGTH: 16
<212> TYPE: PRT
<213> ORGANISM: Hepatitis C virus

<400> SEQUENCE: 51

Gly Glu Val Gln Val Val Ser Thr Ala Thr Gln Ser Phe Leu Ala Thr
1               5                   10                  15

<210> SEQ ID NO 52
<211> LENGTH: 16
<212> TYPE: PRT
<213> ORGANISM: Hepatitis C virus

<400> SEQUENCE: 52

Gly Glu Val Gln Val Leu Ser Thr Val Thr Gln Ser Phe Leu Gly Thr
1               5                   10                  15

<210> SEQ ID NO 53
<211> LENGTH: 15
<212> TYPE: PRT
<213> ORGANISM: Hepatitis C virus

<400> SEQUENCE: 53

Ala Gly Ala Ala Trp Tyr Glu Leu Thr Pro Ala Glu Thr Ser Val
1               5                   10                  15

<210> SEQ ID NO 54
<211> LENGTH: 15
<212> TYPE: PRT
<213> ORGANISM: Hepatitis C virus

<400> SEQUENCE: 54

Gly Ala Ala Trp Tyr Glu Leu Thr Pro Ala Glu Thr Ser Val Arg
1               5                   10                  15

<210> SEQ ID NO 55
<211> LENGTH: 15
<212> TYPE: PRT
<213> ORGANISM: Hepatitis C virus

<400> SEQUENCE: 55

Ala Ala Trp Tyr Glu Leu Thr Pro Ala Glu Thr Ser Val Arg Leu
1               5                   10                  15

<210> SEQ ID NO 56
<211> LENGTH: 21
<212> TYPE: PRT
<213> ORGANISM: Hepatitis C virus

<400> SEQUENCE: 56

Tyr Leu Val Ala Tyr Gln Ala Thr Val Cys Ala Arg Ala Lys Ala Pro
1               5                   10                  15

Pro Pro Ser Trp Asp
            20

<210> SEQ ID NO 57
<211> LENGTH: 15
<212> TYPE: PRT
<213> ORGANISM: Hepatitis C virus

<400> SEQUENCE: 57

Gln Thr Val Asp Phe Ser Leu Asp Pro Thr Phe Thr Ile Glu Thr
1               5                   10                  15
```

```
<210> SEQ ID NO 58
<211> LENGTH: 18
<212> TYPE: PRT
<213> ORGANISM: Hepatitis C virus

<400> SEQUENCE: 58

Val Phe Thr Gly Leu Thr His Ile Asp Ala His Phe Leu Ser Gln Thr
1               5                   10                  15

Lys Gln

<210> SEQ ID NO 59
<211> LENGTH: 15
<212> TYPE: PRT
<213> ORGANISM: Hepatitis C virus

<400> SEQUENCE: 59

Gly Val Leu Ala Gly Leu Ala Tyr Tyr Ser Met Val Gly Asn Trp
1               5                   10                  15

<210> SEQ ID NO 60
<211> LENGTH: 15
<212> TYPE: PRT
<213> ORGANISM: Hepatitis C virus

<400> SEQUENCE: 60

Tyr Tyr Leu Thr Arg Asp Pro Thr Thr Pro Leu Ala Arg Ala Ala
1               5                   10                  15

<210> SEQ ID NO 61
<211> LENGTH: 15
<212> TYPE: PRT
<213> ORGANISM: Hepatitis C virus

<400> SEQUENCE: 61

Ser Gly Lys Ser Thr Lys Val Pro Val Ala Tyr Ala Ala Gln Gly
1               5                   10                  15

<210> SEQ ID NO 62
<211> LENGTH: 15
<212> TYPE: PRT
<213> ORGANISM: Hepatitis C virus

<400> SEQUENCE: 62

Gly Lys Ser Thr Lys Val Pro Val Ala Tyr Ala Ala Gln Gly Tyr
1               5                   10                  15

<210> SEQ ID NO 63
<211> LENGTH: 15
<212> TYPE: PRT
<213> ORGANISM: Hepatitis C virus

<400> SEQUENCE: 63

Lys Ser Thr Lys Val Pro Val Ala Tyr Ala Ala Gln Gly Tyr Lys
1               5                   10                  15

<210> SEQ ID NO 64
<211> LENGTH: 15
<212> TYPE: PRT
<213> ORGANISM: Hepatitis C virus

<400> SEQUENCE: 64

Ser Thr Lys Val Pro Val Ala Tyr Ala Ala Gln Gly Tyr Lys Val
1               5                   10                  15
```

<210> SEQ ID NO 65
<211> LENGTH: 15
<212> TYPE: PRT
<213> ORGANISM: Hepatitis C virus

<400> SEQUENCE: 65

Thr Lys Val Pro Val Ala Tyr Ala Ala Gln Gly Tyr Lys Val Leu
1               5                   10                  15

<210> SEQ ID NO 66
<211> LENGTH: 15
<212> TYPE: PRT
<213> ORGANISM: Hepatitis C virus

<400> SEQUENCE: 66

Lys Val Pro Val Ala Tyr Ala Ala Gln Gly Tyr Lys Val Leu Val
1               5                   10                  15

<210> SEQ ID NO 67
<211> LENGTH: 15
<212> TYPE: PRT
<213> ORGANISM: Hepatitis C virus

<400> SEQUENCE: 67

Val Pro Val Ala Tyr Ala Ala Gln Gly Tyr Lys Val Leu Val Leu
1               5                   10                  15

<210> SEQ ID NO 68
<211> LENGTH: 15
<212> TYPE: PRT
<213> ORGANISM: Hepatitis C virus

<400> SEQUENCE: 68

Pro Val Ala Tyr Ala Ala Gln Gly Tyr Lys Val Leu Val Leu Asn
1               5                   10                  15

<210> SEQ ID NO 69
<211> LENGTH: 15
<212> TYPE: PRT
<213> ORGANISM: Hepatitis C virus

<400> SEQUENCE: 69

Val Ala Tyr Ala Ala Gln Gly Tyr Lys Val Leu Val Leu Asn Pro
1               5                   10                  15

<210> SEQ ID NO 70
<211> LENGTH: 15
<212> TYPE: PRT
<213> ORGANISM: Hepatitis C virus

<400> SEQUENCE: 70

Thr Ile Leu Gly Ile Gly Thr Val Leu Asp Gln Ala Glu Thr Ala
1               5                   10                  15

<210> SEQ ID NO 71
<211> LENGTH: 15
<212> TYPE: PRT
<213> ORGANISM: Hepatitis C virus

<400> SEQUENCE: 71

Ile Leu Gly Ile Gly Thr Val Leu Asp Gln Ala Glu Thr Ala Gly
1               5                   10                  15

<210> SEQ ID NO 72
<211> LENGTH: 15

<212> TYPE: PRT
<213> ORGANISM: Hepatitis C virus

<400> SEQUENCE: 72

Leu Gly Ile Gly Thr Val Leu Asp Gln Ala Glu Thr Ala Gly Ala
1               5                   10                  15

<210> SEQ ID NO 73
<211> LENGTH: 15
<212> TYPE: PRT
<213> ORGANISM: Hepatitis C virus

<400> SEQUENCE: 73

Ala Phe Cys Ser Ala Met Tyr Val Gly Asp Leu Cys Gly Ser Val
1               5                   10                  15

<210> SEQ ID NO 74
<211> LENGTH: 15
<212> TYPE: PRT
<213> ORGANISM: Hepatitis C virus

<400> SEQUENCE: 74

Ala Phe Cys Ser Ala Leu Tyr Val Gly Asp Leu Cys Gly Ser Val
1               5                   10                  15

<210> SEQ ID NO 75
<211> LENGTH: 15
<212> TYPE: PRT
<213> ORGANISM: Hepatitis C virus

<400> SEQUENCE: 75

Pro Ala Leu Ser Thr Gly Leu Leu His Leu His Gln Asn Ile Val
1               5                   10                  15

<210> SEQ ID NO 76
<211> LENGTH: 15
<212> TYPE: PRT
<213> ORGANISM: Hepatitis C virus

<400> SEQUENCE: 76

Ser Gly Met Phe Asp Ser Val Val Leu Cys Glu Cys Tyr Asp Ala
1               5                   10                  15

<210> SEQ ID NO 77
<211> LENGTH: 15
<212> TYPE: PRT
<213> ORGANISM: Hepatitis C virus

<400> SEQUENCE: 77

Gly Met Phe Asp Ser Val Val Leu Cys Glu Cys Tyr Asp Ala Gly
1               5                   10                  15

<210> SEQ ID NO 78
<211> LENGTH: 15
<212> TYPE: PRT
<213> ORGANISM: Hepatitis C virus

<400> SEQUENCE: 78

Met Phe Asp Ser Val Val Leu Cys Glu Cys Tyr Asp Ala Gly Ala
1               5                   10                  15

<210> SEQ ID NO 79
<211> LENGTH: 15
<212> TYPE: PRT

<400> SEQUENCE: 79

Phe Asp Ser Val Val Leu Cys Glu Cys Tyr Asp Ala Gly Ala Ala
1               5                   10                  15

<210> SEQ ID NO 80
<211> LENGTH: 15
<212> TYPE: PRT
<213> ORGANISM: Hepatitis C virus

<400> SEQUENCE: 80

Asp Ser Val Val Leu Cys Glu Cys Tyr Asp Ala Gly Ala Ala Trp
1               5                   10                  15

<210> SEQ ID NO 81
<211> LENGTH: 15
<212> TYPE: PRT
<213> ORGANISM: Hepatitis C virus

<400> SEQUENCE: 81

Ser Val Val Leu Cys Glu Cys Tyr Asp Ala Gly Ala Ala Trp Tyr
1               5                   10                  15

<210> SEQ ID NO 82
<211> LENGTH: 15
<212> TYPE: PRT
<213> ORGANISM: Hepatitis C virus

<400> SEQUENCE: 82

Val Val Leu Cys Glu Cys Tyr Asp Ala Gly Ala Ala Trp Tyr Glu
1               5                   10                  15

<210> SEQ ID NO 83
<211> LENGTH: 15
<212> TYPE: PRT
<213> ORGANISM: Hepatitis C virus

<400> SEQUENCE: 83

Gly Ala Gly Val Ala Gly Ala Leu Val Ala Phe Lys Ile Met Ser
1               5                   10                  15

<210> SEQ ID NO 84
<211> LENGTH: 15
<212> TYPE: PRT
<213> ORGANISM: Hepatitis C virus

<400> SEQUENCE: 84

Ala Gly Val Ala Gly Ala Leu Val Ala Phe Lys Ile Met Ser Gly
1               5                   10                  15

<210> SEQ ID NO 85
<211> LENGTH: 15
<212> TYPE: PRT
<213> ORGANISM: Hepatitis C virus

<400> SEQUENCE: 85

Gly Val Ala Gly Ala Leu Val Ala Phe Lys Ile Met Ser Gly Glu
1               5                   10                  15

<210> SEQ ID NO 86
<211> LENGTH: 15
<212> TYPE: PRT
<213> ORGANISM: Hepatitis C virus

<400> SEQUENCE: 86

```
Thr Thr Leu Leu Leu Asn Ile Leu Gly Gly Trp Leu Ala Ala Gln
1               5                   10                  15

<210> SEQ ID NO 87
<211> LENGTH: 15
<212> TYPE: PRT
<213> ORGANISM: Hepatitis C virus

<400> SEQUENCE: 87

Ala Val Arg Thr Lys Leu Lys Leu Thr Pro Leu Pro Ala Ala Ser
1               5                   10                  15

<210> SEQ ID NO 88
<211> LENGTH: 17
<212> TYPE: PRT
<213> ORGANISM: Hepatitis C virus

<400> SEQUENCE: 88

Pro Met Gly Phe Ser Tyr Asp Thr Arg Cys Phe Asp Ser Thr Val Thr
1               5                   10                  15

Glu

<210> SEQ ID NO 89
<211> LENGTH: 16
<212> TYPE: PRT
<213> ORGANISM: Hepatitis C virus

<400> SEQUENCE: 89

Asn Thr Pro Gly Leu Pro Val Cys Gln Asp His Leu Glu Phe Trp Glu
1               5                   10                  15

<210> SEQ ID NO 90
<211> LENGTH: 19
<212> TYPE: PRT
<213> ORGANISM: Hepatitis C virus

<400> SEQUENCE: 90

Leu Glu Asp Arg Asp Arg Ser Glu Leu Ser Pro Leu Leu Leu Ser Thr
1               5                   10                  15

Thr Glu Trp

<210> SEQ ID NO 91
<211> LENGTH: 20
<212> TYPE: PRT
<213> ORGANISM: Hepatitis C virus

<400> SEQUENCE: 91

Thr Val Pro Gln Asp Ala Val Ser Arg Ser Gln Arg Arg Gly Arg Thr
1               5                   10                  15

Gly Arg Gly Arg
            20

<210> SEQ ID NO 92
<211> LENGTH: 16
<212> TYPE: PRT
<213> ORGANISM: Hepatitis C virus

<400> SEQUENCE: 92

Phe Thr Glu Ala Met Thr Arg Tyr Ser Ala Pro Pro Gly Asp Pro Pro
1               5                   10                  15

<210> SEQ ID NO 93
```

```
<211> LENGTH: 15
<212> TYPE: PRT
<213> ORGANISM: Hepatitis C virus

<400> SEQUENCE: 93

Leu Pro Gly Cys Ser Phe Ser Ile Phe Leu Leu Ala Leu Leu Ser
1               5                   10                  15

<210> SEQ ID NO 94
<211> LENGTH: 15
<212> TYPE: PRT
<213> ORGANISM: Hepatitis C virus

<400> SEQUENCE: 94

Met Trp Asn Phe Ile Ser Gly Ile Gln Tyr Leu Ala Gly Leu Ser
1               5                   10                  15

<210> SEQ ID NO 95
<211> LENGTH: 15
<212> TYPE: PRT
<213> ORGANISM: Hepatitis C virus

<400> SEQUENCE: 95

Val Asp Ile Leu Ala Gly Tyr Gly Ala Gly Ile Ser Gly Ala Leu
1               5                   10                  15

<210> SEQ ID NO 96
<211> LENGTH: 15
<212> TYPE: PRT
<213> ORGANISM: Hepatitis C virus

<400> SEQUENCE: 96

Asp Ile Leu Ala Gly Tyr Gly Ala Gly Ile Ser Gly Ala Leu Val
1               5                   10                  15

<210> SEQ ID NO 97
<211> LENGTH: 15
<212> TYPE: PRT
<213> ORGANISM: Hepatitis C virus

<400> SEQUENCE: 97

Ile Leu Ala Gly Tyr Gly Ala Gly Ile Ser Gly Ala Leu Val Ala
1               5                   10                  15

<210> SEQ ID NO 98
<211> LENGTH: 15
<212> TYPE: PRT
<213> ORGANISM: Hepatitis C virus

<400> SEQUENCE: 98

Leu Ala Gly Tyr Gly Ala Gly Ile Ser Gly Ala Leu Val Ala Phe
1               5                   10                  15

<210> SEQ ID NO 99
<211> LENGTH: 15
<212> TYPE: PRT
<213> ORGANISM: Hepatitis C virus

<400> SEQUENCE: 99

Ala Gly Tyr Gly Ala Gly Ile Ser Gly Ala Leu Val Ala Phe Lys
1               5                   10                  15

<210> SEQ ID NO 100
<211> LENGTH: 15
<212> TYPE: PRT
```

<213> ORGANISM: Hepatitis C virus

<400> SEQUENCE: 100

Gly Tyr Gly Ala Gly Ile Ser Gly Ala Leu Val Ala Phe Lys Ile
1 5 10 15

<210> SEQ ID NO 101
<211> LENGTH: 15
<212> TYPE: PRT
<213> ORGANISM: Hepatitis C virus

<400> SEQUENCE: 101

Tyr Gly Ala Gly Ile Ser Gly Ala Leu Val Ala Phe Lys Ile Met
1 5 10 15

<210> SEQ ID NO 102
<211> LENGTH: 15
<212> TYPE: PRT
<213> ORGANISM: Hepatitis C virus

<400> SEQUENCE: 102

Asp Ala Gly Cys Ala Trp Tyr Glu Leu Thr Pro Ala Glu Thr Thr
1 5 10 15

<210> SEQ ID NO 103
<211> LENGTH: 15
<212> TYPE: PRT
<213> ORGANISM: Hepatitis C virus

<400> SEQUENCE: 103

Ala Gly Cys Ala Trp Tyr Glu Leu Thr Pro Ala Glu Thr Thr Val
1 5 10 15

<210> SEQ ID NO 104
<211> LENGTH: 15
<212> TYPE: PRT
<213> ORGANISM: Hepatitis C virus

<400> SEQUENCE: 104

Gly Cys Ala Trp Tyr Glu Leu Thr Pro Ala Glu Thr Thr Val Arg
1 5 10 15

<210> SEQ ID NO 105
<211> LENGTH: 15
<212> TYPE: PRT
<213> ORGANISM: Hepatitis C virus

<400> SEQUENCE: 105

Cys Ala Trp Tyr Glu Leu Thr Pro Ala Glu Thr Thr Val Arg Leu
1 5 10 15

<210> SEQ ID NO 106
<211> LENGTH: 15
<212> TYPE: PRT
<213> ORGANISM: Hepatitis C virus

<400> SEQUENCE: 106

Ala Trp Tyr Glu Leu Thr Pro Ala Glu Thr Thr Val Arg Leu Arg
1 5 10 15

<210> SEQ ID NO 107
<211> LENGTH: 15
<212> TYPE: PRT
<213> ORGANISM: Hepatitis C virus

```
<400> SEQUENCE: 107

Gly Gln Gly Trp Arg Leu Leu Ala Pro Ile Thr Ala Tyr Ser Gln
1               5                   10                  15

<210> SEQ ID NO 108
<211> LENGTH: 15
<212> TYPE: PRT
<213> ORGANISM: Hepatitis C virus

<400> SEQUENCE: 108

Gly Cys Ile Val Val Ser Met Thr Gly Arg Asp Lys Thr Gln Val
1               5                   10                  15

<210> SEQ ID NO 109
<211> LENGTH: 15
<212> TYPE: PRT
<213> ORGANISM: Hepatitis C virus

<400> SEQUENCE: 109

Ser Tyr Leu Lys Gly Ser Ser Gly Gly Pro Leu Leu Cys Pro Ser
1               5                   10                  15

<210> SEQ ID NO 110
<211> LENGTH: 15
<212> TYPE: PRT
<213> ORGANISM: Hepatitis C virus

<400> SEQUENCE: 110

Thr Gly Glu Ile Pro Phe Tyr Gly Lys Ala Ile Pro Ile Glu Val
1               5                   10                  15

<210> SEQ ID NO 111
<211> LENGTH: 15
<212> TYPE: PRT
<213> ORGANISM: Hepatitis C virus

<400> SEQUENCE: 111

Phe Phe Thr Trp Leu Asp Gly Val Gln Ile His Arg Tyr Ala Pro
1               5                   10                  15

<210> SEQ ID NO 112
<211> LENGTH: 15
<212> TYPE: PRT
<213> ORGANISM: Hepatitis C virus

<400> SEQUENCE: 112

Asp Leu Pro Gln Ile Ile Glu Arg Leu His Gly Leu Ser Ala Phe
1               5                   10                  15

<210> SEQ ID NO 113
<211> LENGTH: 15
<212> TYPE: PRT
<213> ORGANISM: Hepatitis C virus

<400> SEQUENCE: 113

Asp Leu Pro Gln Ile Ile Gln Arg Leu His Gly Leu Ser Ala Phe
1               5                   10                  15

<210> SEQ ID NO 114
<211> LENGTH: 15
<212> TYPE: PRT
<213> ORGANISM: Hepatitis C virus

<400> SEQUENCE: 114
```

```
Gly Leu Pro Val Ser Ala Leu Arg Gly Arg Glu Ile Leu Leu Gly
1               5                   10                  15
```

<210> SEQ ID NO 115
<211> LENGTH: 15
<212> TYPE: PRT
<213> ORGANISM: Hepatitis C virus

<400> SEQUENCE: 115

```
Cys Gly Tyr Arg Arg Cys Arg Ala Ser Gly Val Leu Thr Thr Ser
1               5                   10                  15
```

<210> SEQ ID NO 116
<211> LENGTH: 16
<212> TYPE: PRT
<213> ORGANISM: Hepatitis C virus

<400> SEQUENCE: 116

```
Asn Ala Val Ala Tyr Tyr Arg Gly Leu Asp Val Ser Val Ile Pro Thr
1               5                   10                  15
```

<210> SEQ ID NO 117
<211> LENGTH: 15
<212> TYPE: PRT
<213> ORGANISM: Hepatitis C virus

<400> SEQUENCE: 117

```
Glu Phe Val Gln Asp Cys Asn Cys Ser Ile Tyr Pro Gly His Val
1               5                   10                  15
```

<210> SEQ ID NO 118
<211> LENGTH: 15
<212> TYPE: PRT
<213> ORGANISM: Hepatitis C virus

<400> SEQUENCE: 118

```
Pro Thr Ser Gly Asp Val Val Val Ala Thr Asp Ala Leu Met
1               5                   10                  15
```

<210> SEQ ID NO 119
<211> LENGTH: 15
<212> TYPE: PRT
<213> ORGANISM: Hepatitis C virus

<400> SEQUENCE: 119

```
Leu Trp Ala Arg Met Ile Leu Met Thr His Phe Phe Ser Ile Leu
1               5                   10                  15
```

<210> SEQ ID NO 120
<211> LENGTH: 15
<212> TYPE: PRT
<213> ORGANISM: Hepatitis C virus

<400> SEQUENCE: 120

```
Leu Trp Val Arg Met Val Leu Met Thr His Phe Phe Ser Ile Leu
1               5                   10                  15
```

<210> SEQ ID NO 121
<211> LENGTH: 15
<212> TYPE: PRT
<213> ORGANISM: Hepatitis C virus

<400> SEQUENCE: 121

```
Glu Thr Ala Gly Ala Arg Leu Val Val Leu Ala Thr Ala Thr Pro
1               5                   10                  15
```

```
<210> SEQ ID NO 122
<211> LENGTH: 15
<212> TYPE: PRT
<213> ORGANISM: Hepatitis C virus

<400> SEQUENCE: 122

Thr Ala Gly Ala Arg Leu Val Val Leu Ala Thr Ala Thr Pro Pro
1               5                   10                  15

<210> SEQ ID NO 123
<211> LENGTH: 15
<212> TYPE: PRT
<213> ORGANISM: Hepatitis C virus

<400> SEQUENCE: 123

Ala Gly Ala Arg Leu Val Val Leu Ala Thr Ala Thr Pro Pro Gly
1               5                   10                  15

<210> SEQ ID NO 124
<211> LENGTH: 15
<212> TYPE: PRT
<213> ORGANISM: Hepatitis C virus

<400> SEQUENCE: 124

Gly Ala Arg Leu Val Val Leu Ala Thr Ala Thr Pro Pro Gly Ser
1               5                   10                  15

<210> SEQ ID NO 125
<211> LENGTH: 15
<212> TYPE: PRT
<213> ORGANISM: Hepatitis C virus

<400> SEQUENCE: 125

Ala Arg Leu Val Val Leu Ala Thr Ala Thr Pro Pro Gly Ser Val
1               5                   10                  15

<210> SEQ ID NO 126
<211> LENGTH: 18
<212> TYPE: PRT
<213> ORGANISM: Hepatitis C virus

<400> SEQUENCE: 126

Val Val Cys Cys Ser Met Ser Tyr Ser Trp Thr Gly Ala Leu Ile Thr
1               5                   10                  15

Pro Cys

<210> SEQ ID NO 127
<211> LENGTH: 15
<212> TYPE: PRT
<213> ORGANISM: Hepatitis C virus

<400> SEQUENCE: 127

Ala Ala Gly Leu Arg Asp Leu Ala Val Ala Val Glu Pro Ile Val
1               5                   10                  15

<210> SEQ ID NO 128
<211> LENGTH: 15
<212> TYPE: PRT
<213> ORGANISM: Hepatitis C virus

<400> SEQUENCE: 128

Ala Val Arg Thr Lys Leu Lys Leu Thr Pro Ile Pro Ala Ala Ser
1               5                   10                  15
```

<210> SEQ ID NO 129
<211> LENGTH: 37
<212> TYPE: PRT
<213> ORGANISM: Hepatitis C virus

<400> SEQUENCE: 129

Gly Ala Ala Val Gly Ser Ile Gly Leu Gly Lys Val Leu Val Asp Ile
1               5                   10                  15

Leu Ala Gly Tyr Gly Ala Gly Ile Ser Gly Ala Leu Val Ala Phe Lys
                20                  25                  30

Ile Met Ser Gly Glu
        35

<210> SEQ ID NO 130
<211> LENGTH: 15
<212> TYPE: PRT
<213> ORGANISM: Hepatitis C virus

<400> SEQUENCE: 130

Pro Val Asn Ser Trp Leu Gly Asn Ile Ile Met Tyr Ala Pro Thr
1               5                   10                  15

<210> SEQ ID NO 131
<211> LENGTH: 15
<212> TYPE: PRT
<213> ORGANISM: Hepatitis C virus

<400> SEQUENCE: 131

Pro Val Asn Ser Trp Leu Gly Asn Ile Ile Gln Tyr Ala Pro Thr
1               5                   10                  15

<210> SEQ ID NO 132
<211> LENGTH: 34
<212> TYPE: PRT
<213> ORGANISM: Hepatitis C virus

<400> SEQUENCE: 132

Ser Gly Met Phe Asp Ser Val Val Leu Cys Glu Cys Tyr Asp Ala Gly
1               5                   10                  15

Ala Ala Trp Tyr Glu Leu Thr Pro Ala Glu Thr Thr Val Arg Leu Arg
                20                  25                  30

Ala Tyr

<210> SEQ ID NO 133
<211> LENGTH: 34
<212> TYPE: PRT
<213> ORGANISM: Hepatitis C virus

<400> SEQUENCE: 133

Phe Trp Ala Lys His Met Trp Asn Phe Ile Ser Gly Ile Gln Tyr Leu
1               5                   10                  15

Ala Gly Leu Ser Thr Leu Pro Gly Asn Pro Ala Val Ala Ser Met Met
                20                  25                  30

Ala Phe

<210> SEQ ID NO 134
<211> LENGTH: 19
<212> TYPE: PRT
<213> ORGANISM: Hepatitis C virus

<400> SEQUENCE: 134

-continued

Leu Thr Pro Pro His Ser Ala Lys Ser Lys Tyr Gly Tyr Gly Ala Lys
1               5                   10                  15

Glu Val Arg

<210> SEQ ID NO 135
<211> LENGTH: 16
<212> TYPE: PRT
<213> ORGANISM: Hepatitis C virus

<400> SEQUENCE: 135

Thr Gly Asp Phe Asp Ser Val Ile Asp Cys Asn Val Ala Val Thr Gln
1               5                   10                  15

<210> SEQ ID NO 136
<211> LENGTH: 19
<212> TYPE: PRT
<213> ORGANISM: Hepatitis C virus

<400> SEQUENCE: 136

Leu Glu Asp Arg Asp Arg Ser Gln Leu Ser Pro Leu Leu His Ser Thr
1               5                   10                  15

Thr Glu Trp

<210> SEQ ID NO 137
<211> LENGTH: 36
<212> TYPE: PRT
<213> ORGANISM: Hepatitis C virus

<400> SEQUENCE: 137

Asp Pro Arg His Arg Ser Arg Asn Val Gly Lys Val Ile Asp Thr Leu
1               5                   10                  15

Thr Cys Gly Phe Ala Asp Leu Met Gly Tyr Ile Pro Val Val Gly Ala
                20                  25                  30

Pro Leu Gly Gly
            35

<210> SEQ ID NO 138
<211> LENGTH: 32
<212> TYPE: PRT
<213> ORGANISM: Hepatitis C virus

<400> SEQUENCE: 138

Val Asp Tyr Pro Tyr Arg Leu Trp His Tyr Pro Cys Thr Val Asn Phe
1               5                   10                  15

Thr Ile Phe Lys Val Arg Met Tyr Val Gly Gly Val Glu His Arg Leu
                20                  25                  30

<210> SEQ ID NO 139
<211> LENGTH: 32
<212> TYPE: PRT
<213> ORGANISM: Hepatitis C virus

<400> SEQUENCE: 139

Val Asp Tyr Pro Tyr Arg Leu Trp His Tyr Pro Cys Thr Val Asn Tyr
1               5                   10                  15

Thr Ile Phe Lys Ile Arg Met Tyr Val Gly Gly Val Glu His Arg Leu
                20                  25                  30

<210> SEQ ID NO 140
<211> LENGTH: 28
<212> TYPE: PRT

<213> ORGANISM: Hepatitis C virus

<400> SEQUENCE: 140

Lys Gly Gly Arg Lys Pro Ala Arg Le

Ala Ala Thr Leu Gly Phe Gly Ala Tyr
         35                  40

<210> SEQ ID NO 146
<211> LENGTH: 15
<212> TYPE: PRT
<213> ORGANISM: Hepatitis C virus

<400> SEQUENCE: 146

Ser Ser Met Pro Pro Leu Glu Gly Glu Pro Gly Asp Pro Asp Leu
1               5                   10                  15

<210> SEQ ID NO 147
<211> LENGTH: 19
<212> TYPE: PRT
<213> ORGANISM: Hepatitis C virus

<400> SEQUENCE: 147

Leu Thr Pro Pro His Ser Ala Lys Ser Lys Phe Gly Tyr Gly Ala Lys
1               5                   10                  15

Asp Val Arg

<210> SEQ ID NO 148
<211> LENGTH: 19
<212> TYPE: PRT
<213> ORGANISM: Hepatitis C virus

<400> SEQUENCE: 148

Leu Thr Pro Pro His Ser Ala Arg Ser Lys Tyr Gly Tyr Gly Ala Lys
1               5                   10                  15

Glu Val Arg

<210> SEQ ID NO 149
<211> LENGTH: 16
<212> TYPE: PRT
<213> ORGANISM: Hepatitis C virus

<400> SEQUENCE: 149

Ser Gly His Arg Met Ala Trp Asp Met Met Asn Trp Ser Pro Thr
1               5                   10                  15

<210> SEQ ID NO 150
<211> LENGTH: 16
<212> TYPE: PRT
<213> ORGANISM: Hepatitis C virus

<400> SEQUENCE: 150

Thr Gly His Arg Met Ala Trp Asp Met Met Asn Trp Ser Pro Thr
1               5                   10                  15

<210> SEQ ID NO 151
<211> LENGTH: 30
<212> TYPE: PRT
<213> ORGANISM: Hepatitis C virus

<400> SEQUENCE: 151

Ile Thr Tyr Ser Thr Tyr Gly Lys Phe Leu Ala Asp Gly Gly Cys Ser
1               5                   10                  15

Gly Gly Ala Tyr Asp Ile Ile Ile Cys Asp Glu Cys His Ser
            20                  25                  30

<210> SEQ ID NO 152

```
<211> LENGTH: 37
<212> TYPE: PRT
<213> ORGANISM: Hepatitis C virus

<400> SEQUENCE: 152

Ala Arg Ala Leu Ala His Gly Val Arg Val Leu Glu Asp Gly Val Asn
1               5                   10                  15

Tyr Ala Thr Gly Asn Leu Pro Gly Cys Ser Phe Ser Ile Phe Leu Leu
            20                  25                  30

Ala Leu Leu Ser Cys
            35

<210> SEQ ID NO 153
<211> LENGTH: 28
<212> TYPE: PRT
<213> ORGANISM: Hepatitis C virus

<400> SEQUENCE: 153

Lys Gly Gly Lys Lys Ala Ala Arg Leu Ile Val Tyr Pro Asp Leu Gly
1               5                   10                  15

Val Arg Val Cys Glu Lys Met Ala Leu Tyr Asp Val
            20                  25

<210> SEQ ID NO 154
<211> LENGTH: 15
<212> TYPE: PRT
<213> ORGANISM: Hepatitis C virus

<400> SEQUENCE: 154

Thr Val Asn Phe Thr Ile Phe Lys Val Arg Met Tyr Val Gly Gly
1               5                   10                  15

<210> SEQ ID NO 155
<211> LENGTH: 23
<212> TYPE: PRT
<213> ORGANISM: Hepatitis C virus

<400> SEQUENCE: 155

His Met Trp Asn Phe Ile Ser Gly Ile Gln Tyr Leu Ala Gly Leu Ser
1               5                   10                  15

Thr Leu Pro Gly Asn Pro Ala
            20

<210> SEQ ID NO 156
<211> LENGTH: 67
<212> TYPE: PRT
<213> ORGANISM: Hepatitis C virus

<400> SEQUENCE: 156

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Gly Arg Arg Gln Pro
        50                  55                  60

Ile Pro Lys
65

<210> SEQ ID NO 157
```

```
<211> LENGTH: 56
<212> TYPE: PRT
<213> ORGANISM: Hepatitis C virus

<400> SEQUENCE: 157

Val Asn Leu Leu Pro Ala Ile Leu Ser Pro Gly Ala Leu Val Val Gly
1               5                   10                  15

Val Val Cys Ala Ala Ile Leu Arg Arg His Val Gly Pro Gly Glu Gly
            20                  25                  30

Ala Val Gln Trp Met Asn Arg Leu Ile Ala Phe Ala Ser Arg Gly Asn
        35                  40                  45

His Val Ser Pro Thr His Tyr Val
    50                  55

<210> SEQ ID NO 158
<211> LENGTH: 37
<212> TYPE: PRT
<213> ORGANISM: Hepatitis C virus

<400> SEQUENCE: 158

Gly Ala Ala Val Gly Ser Ile Gly Leu Gly Lys Val Leu Val Asp Ile
1               5                   10                  15

Leu Ala Gly Tyr Gly Ala Gly Val Ala Gly Ala Leu Val Ala Phe Lys
            20                  25                  30

Ile Met Ser Gly Glu
        35

<210> SEQ ID NO 159
<211> LENGTH: 34
<212> TYPE: PRT
<213> ORGANISM: Hepatitis C virus

<400> SEQUENCE: 159

Ser Gly Met Phe Asp Ser Ser Val Leu Cys Glu Cys Tyr Asp Ala Gly
1               5                   10                  15

Cys Ala Trp Tyr Glu Leu Thr Pro Ala Glu Thr Ser Val Arg Leu Arg
            20                  25                  30

Ala Tyr

<210> SEQ ID NO 160
<211> LENGTH: 34
<212> TYPE: PRT
<213> ORGANISM: Hepatitis C virus

<400> SEQUENCE: 160

Phe Trp Ala Lys His Met Trp Asn Phe Ile Ser Gly Ile Gln Tyr Leu
1               5                   10                  15

Ala Gly Leu Ser Thr Leu Pro Gly Asn Pro Ala Ile Ala Ser Leu Met
            20                  25                  30

Ala Phe

<210> SEQ ID NO 161
<211> LENGTH: 16
<212> TYPE: PRT
<213> ORGANISM: Hepatitis C virus

<400> SEQUENCE: 161

Phe Ser Asp Asn Ser Thr Pro Pro Ala Val Pro Gln Thr Tyr Gln Val
1               5                   10                  15
```

<210> SEQ ID NO 162
<211> LENGTH: 56
<212> TYPE: PRT
<213> ORGANISM: Hepatitis C virus

<400> SEQUENCE: 162

Val Asn Leu Leu Pro Gly Ile Leu Ser Pro Gly Ala Leu Val Val Gly
1               5                   10                  15

Val Ile Cys Ala Ala Ile Leu Arg Arg His Val Gly Pro Gly Glu Gly
            20                  25                  30

Ala Val Gln Trp Met Asn Arg Leu Ile Ala Phe Ala Ser Arg Gly Asn
        35                  40                  45

His Val Ala Pro Thr His Tyr Val
    50                  55

<210> SEQ ID NO 163
<211> LENGTH: 8
<212> TYPE: PRT
<213> ORGANISM: Hepatitis C virus

<400> SEQUENCE: 163

Leu Pro Arg Arg Gly Pro Arg Leu
1               5

<210> SEQ ID NO 164
<211> LENGTH: 10
<212> TYPE: PRT
<213> ORGANISM: Hepatitis C virus

<400> SEQUENCE: 164

Ser Pro Gly Ala Leu Val Val Gly Val Ile
1               5                   10

<210> SEQ ID NO 165
<211> LENGTH: 9
<212> TYPE: PRT
<213> ORGANISM: Hepatitis C virus

<400> SEQUENCE: 165

Gln Arg Lys Thr Lys Arg Asn Thr Asn
1               5

<210> SEQ ID NO 166
<211> LENGTH: 8
<212> TYPE: PRT
<213> ORGANISM: Hepatitis C virus

<400> SEQUENCE: 166

Gln Arg Lys Thr Lys Arg Asn Thr
1               5

<210> SEQ ID NO 167
<211> LENGTH: 9
<212> TYPE: PRT
<213> ORGANISM: Hepatitis C virus

<400> SEQUENCE: 167

Gln Arg Lys Thr Lys Arg Asn Thr Asn
1               5

<210> SEQ ID NO 168
<211> LENGTH: 9
<212> TYPE: PRT
<213> ORGANISM: Hepatitis C virus

```
<400> SEQUENCE: 168

Ser Ala Lys Ser Lys Tyr Gly Tyr Gly
1               5

<210> SEQ ID NO 169
<211> LENGTH: 9
<212> TYPE: PRT
<213> ORGANISM: Hepatitis C virus

<400> SEQUENCE: 169

Ser Ala Arg Ser Lys Tyr Gly Tyr Gly
1               5

<210> SEQ ID NO 170
<211> LENGTH: 9
<212> TYPE: PRT
<213> ORGANISM: Hepatitis C virus

<400> SEQUENCE: 170

Arg Lys Thr Lys Arg Asn Thr Asn Arg
1               5

<210> SEQ ID NO 171
<211> LENGTH: 29
<212> TYPE: PRT
<213> ORGANISM: Hepatitis C virus

<400> SEQUENCE: 171

Lys Phe Pro Gly Gly Gly Gln Ile Val Gly Gly Val Tyr Leu Leu Pro
1               5                   10                  15

Arg Arg Gly Pro Arg Leu Gly Val Arg Ala Thr Arg Lys
            20                  25

<210> SEQ ID NO 172
<211> LENGTH: 19
<212> TYPE: PRT
<213> ORGANISM: Hepatitis C virus

<400> SEQUENCE: 172

Ala Tyr Ala Ala Gln Gly Tyr Lys Val Leu Val Leu Asn Pro Ser Val
1               5                   10                  15

Ala Ala Thr

<210> SEQ ID NO 173
<211> LENGTH: 13
<212> TYPE: PRT
<213> ORGANISM: Hepatitis C virus

<400> SEQUENCE: 173

Asp Leu Met Gly Tyr Ile Pro Leu Val Gly Ala Pro Leu
1               5                   10

<210> SEQ ID NO 174
<211> LENGTH: 25
<212> TYPE: PRT
<213> ORGANISM: Hepatitis C virus

<400> SEQUENCE: 174

Gly Glu Val Gln Val Val Ser Thr Ala Thr Gln Ser Phe Leu Ala Thr
1               5                   10                  15

Cys Ile Asn Gly Val Cys Trp Thr Val
            20                  25
```

```
<210> SEQ ID NO 175
<211> LENGTH: 20
<212> TYPE: PRT
<213> ORGANISM: Hepatitis C virus

<400> SEQUENCE: 175

Asp Tyr Pro Tyr Arg Leu Trp His Tyr Pro Cys Thr Val Asn Phe Thr
1               5                   10                  15

Ile Phe Lys Ile
            20

<210> SEQ ID NO 176
<211> LENGTH: 20
<212> TYPE: PRT
<213> ORGANISM: Hepatitis C virus

<400> SEQUENCE: 176

Asp Tyr Pro Tyr Arg Leu Trp His Tyr Pro Cys Thr Val Asn Phe Thr
1               5                   10                  15

Ile Phe Lys Val
            20

<210> SEQ ID NO 177
<211> LENGTH: 20
<212> TYPE: PRT
<213> ORGANISM: Hepatitis C virus

<400> SEQUENCE: 177

Asp Tyr Pro Tyr Arg Leu Trp His Tyr Pro Cys Thr Val Asn Tyr Thr
1               5                   10                  15

Ile Phe Lys Ile
            20

<210> SEQ ID NO 178
<211> LENGTH: 16
<212> TYPE: PRT
<213> ORGANISM: Hepatitis C virus

<400> SEQUENCE: 178

Ala Ala Trp Tyr Glu Leu Thr Pro Ala Glu Thr Thr Val Arg Leu Arg
1               5                   10                  15

<210> SEQ ID NO 179
<211> LENGTH: 12
<212> TYPE: PRT
<213> ORGANISM: Hepatitis C virus

<400> SEQUENCE: 179

Thr Ala Tyr Ser Gln Gln Thr Arg Gly Leu Leu Gly
1               5                   10

<210> SEQ ID NO 180
<211> LENGTH: 25
<212> TYPE: PRT
<213> ORGANISM: Hepatitis C virus

<400> SEQUENCE: 180

Gly Gln Gly Trp Arg Leu Leu Ala Pro Ile Thr Ala Tyr Ser Gln Gln
1               5                   10                  15

Thr Arg Gly Leu Leu Gly Cys Ile Val
            20                  25
```

<210> SEQ ID NO 181
<211> LENGTH: 23
<212> TYPE: PRT
<213> ORGANISM: Hepatitis C virus

<400> SEQUENCE: 181

Gly Trp Arg Leu Leu Ala Pro Ile Thr Ala Tyr Ser Gln Gln Thr Arg
1               5                   10                  15

Gly Leu Leu Gly Cys Ile Val
            20

<210> SEQ ID NO 182
<211> LENGTH: 26
<212> TYPE: PRT
<213> ORGANISM: Hepatitis C virus

<400> SEQUENCE: 182

Ile Gly Leu Gly Lys Val Leu Val Asp Ile Leu Ala Gly Tyr Gly Ala
1               5                   10                  15

Gly Val Ala Gly Ala Leu Val Ala Phe Lys
            20                  25

<210> SEQ ID NO 183
<211> LENGTH: 13
<212> TYPE: PRT
<213> ORGANISM: Hepatitis C virus

<400> SEQUENCE: 183

Ser Met Ser Tyr Thr Trp Thr Gly Ala Leu Ile Thr Pro
1               5                   10

<210> SEQ ID NO 184
<211> LENGTH: 16
<212> TYPE: PRT
<213> ORGANISM: Hepatitis C virus

<400> SEQUENCE: 184

Phe Thr Asp Asn Ser Ser Pro Pro Ala Val Pro Gln Thr Phe Gln Val
1               5                   10                  15

<210> SEQ ID NO 185
<211> LENGTH: 16
<212> TYPE: PRT
<213> ORGANISM: Hepatitis C virus

<400> SEQUENCE: 185

Leu Glu Asp Arg Asp Arg Ser Glu Leu Ser Pro Leu Leu Leu Ser Thr
1               5                   10                  15

<210> SEQ ID NO 186
<211> LENGTH: 17
<212> TYPE: PRT
<213> ORGANISM: Hepatitis C virus

<400> SEQUENCE: 186

Met Ser Thr Asn Pro Lys Pro Gln Arg Lys Thr Lys Arg Asn Thr Asn
1               5                   10                  15

Arg

<210> SEQ ID NO 187
<211> LENGTH: 21
<212> TYPE: PRT
<213> ORGANISM: Hepatitis C virus -continued

```
<400> SEQUENCE: 187

Leu Ile Asn Thr Asn Gly Ser Trp His Ile Asn Arg Thr Ala Leu Asn
1               5                   10                  15

Cys Asn Asp Ser Leu
            20

<210> SEQ ID NO 188
<211> LENGTH: 16
<212> TYPE: PRT
<213> ORGANISM: Hepatitis C virus

<400> SEQUENCE: 188

Leu Ile Asn Thr Asn Gly Ser Trp His Ile Asn Arg Thr Ala Leu Asn
1               5                   10                  15

<210> SEQ ID NO 189
<211> LENGTH: 15
<212> TYPE: PRT
<213> ORGANISM: Hepatitis C virus

<400> SEQUENCE: 189

Thr Thr Ile Leu Gly Ile Gly Thr Val Leu Asp Gln Ala Glu Thr
1               5                   10                  15

<210> SEQ ID NO 190
<211> LENGTH: 18
<212> TYPE: PRT
<213> ORGANISM: Hepatitis C virus

<400> SEQUENCE: 190

Phe Asp Ser Ser Val Leu Cys Glu Cys Tyr Asp Ala Gly Ala Ala Trp
1               5                   10                  15

Tyr Glu

<210> SEQ ID NO 191
<211> LENGTH: 20
<212> TYPE: PRT
<213> ORGANISM: Hepatitis C virus

<400> SEQUENCE: 191

Ala Arg Leu Ile Val Phe Pro Asp Leu Gly Val Arg Val Cys Glu Lys
1               5                   10                  15

Met Ala Leu Tyr
            20

<210> SEQ ID NO 192
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 192

Ser Thr Lys Val Pro Ala Ala Tyr Ala Ala Gln Gly Tyr Lys Val
  1               5                   10                  15

<210> SEQ ID NO 193
<211> LENGTH: 15
<212> TYPE: PRT
<213> ORGANISM: Artificial Sequence
<220> FEATURE:
<223> OTHER INFORMATION: Description of Artificial Sequence: Synthetic
```

Peptides

<400> SEQUENCE: 193

Thr Lys Val Pro Ala Ala Tyr Ala Ala Gln Gly Tyr Lys Val Leu
 1               5                  10                  15

START WITH NUMBERING OF 194

<210> SEQ ID NO 194
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 194

Lys Val Pro Ala Ala Tyr Ala Ala Gln Gly Tyr Lys Val Leu Val
 1               5                  10                  15

<210> SEQ ID NO 195
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 195

Val Pro Ala Ala Tyr Ala Ala Gln Gly Tyr Lys Val Leu Val Leu
 1               5                  10                  15

<210> SEQ ID NO 196
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 196

Pro Ala Ala Tyr Ala Ala Gln Gly Tyr Lys Val Leu Val Leu Asn
 1               5                  10                  15

<210> SEQ ID NO 197
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 197

Ala Ala Tyr Ala Ala Gln Gly Tyr Lys Val Leu Val Leu Asn Pro
 1               5                  10                  15

<210> SEQ ID NO 198
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 198

Ala Tyr Ala Ala Gln Gly Tyr Lys Val Leu Val Leu Asn Pro Ser
 1               5                  10                  15

-continued

```
<210> SEQ ID NO 199
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 199

Tyr Ala Ala Gln Gly Tyr Lys Val Leu Val Leu Asn Pro Ser Val
 1               5                  10                  15

<210> SEQ ID NO 200
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 200

Ala Ala Gln Gly Tyr Lys Val Leu Val Leu Asn Pro Ser Val Ala
 1               5                  10                  15

<210> SEQ ID NO 201
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 201

Ala Gln Gly Tyr Lys Val Leu Val Leu Asn Pro Ser Val Ala Ala
 1               5                  10                  15

<210> SEQ ID NO 202
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 202

Gln Gly Tyr Lys Val Leu Val Leu Asn Pro Ser Val Ala Ala Thr
 1               5                  10                  15

<210> SEQ ID NO 203
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 203

Met Ser Thr Asn Pro Lys Pro Gln Arg Lys Thr Lys Arg Asn Thr
 1               5                  10                  15

<210> SEQ ID NO 204
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides
```

```
<400> SEQUENCE: 204

Ser Thr Asn Pro Lys Pro Gln Arg Lys Thr Lys Arg Asn Thr Asn
 1               5                  10                  15

<210> SEQ ID NO 205
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 205

Thr Asn Pro Lys Pro Gln Arg Lys Thr Lys Arg Asn Thr Asn Arg
 1               5                  10                  15

<210> SEQ ID NO 206
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 206

Asn Pro Lys Pro Gln Arg Lys Thr Lys Arg Asn Thr Asn Arg Arg
 1               5                  10                  15

<210> SEQ ID NO 207
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 207

Pro Lys Pro Gln Arg Lys Thr Lys Arg Asn Thr Asn Arg Arg Pro
 1               5                  10                  15

<210> SEQ ID NO 208
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 208

Lys Pro Gln Arg Lys Thr Lys Arg Asn Thr Asn Arg Arg Pro Gln
 1               5                  10                  15

<210> SEQ ID NO 209
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 209

Pro Gln Arg Lys Thr Lys Arg Asn Thr Asn Arg Arg Pro Gln Asp
 1               5                  10                  15

<210> SEQ ID NO 210
<211> LENGTH: 15
<212> TYPE: PRT
```

<213> ORGANISM: Artificial Sequence
<220> FEATURE:
<223> OTHER INFORMATION: Description of Artificial Sequence: Synthetic
      Peptides

<400> SEQUENCE: 210

Gln Arg Lys Thr Lys Arg Asn Thr Asn Arg Arg Pro Gln Asp Val
 1               5                  10                  15

<210> SEQ ID NO 211
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 211

Arg Lys Thr Lys Arg Asn Thr Asn Arg Arg Pro Gln Asp Val Lys
 1               5                  10                  15

<210> SEQ ID NO 212
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 212

Lys Thr Lys Arg Asn Thr Asn Arg Arg Pro Gln Asp Val Lys Phe
 1               5                  10                  15

<210> SEQ ID NO 213
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 213

Thr Lys Arg Asn Thr Asn Arg Arg Pro Gln Asp Val Lys Phe Pro
 1               5                  10                  15

<210> SEQ ID NO 214
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 214

Lys Arg Asn Thr Asn Arg Arg Pro Gln Asp Val Lys Phe Pro Gly
 1               5                  10                  15

<210> SEQ ID NO 215
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 215

Arg Asn Thr Asn Arg Arg Pro Gln Asp Val Lys Phe Pro Gly Gly
 1               5                  10                  15

<210> SEQ ID NO 216
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 216

Asn Thr Asn Arg Arg Pro Gln Asp Val Lys Phe Pro Gly Gly Gly
 1               5                  10                  15

<210> SEQ ID NO 217
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 217

Thr Asn Arg Arg Pro Gln Asp Val Lys Phe Pro Gly Gly Gly Gln
 1               5                  10                  15

<210> SEQ ID NO 218
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 218

Asn Arg Arg Pro Gln Asp Val Lys Phe Pro Gly Gly Gly Gln Ile
 1               5                  10                  15

<210> SEQ ID NO 219
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 219

Arg Arg Pro Gln Asp Val Lys Phe Pro Gly Gly Gly Gln Ile Val
 1               5                  10                  15

<210> SEQ ID NO 220
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 220

Arg Pro Gln Asp Val Lys Phe Pro Gly Gly Gly Gln Ile Val Gly
 1               5                  10                  15

<210> SEQ ID NO 221
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides -continued

<400> SEQUENCE: 221

Pro Gln Asp Val Lys Phe Pro Gly Gly Gly Gln Ile Val Gly Gly
1               5                   10                  15

<210> SEQ ID NO 222
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 222

Gln Asp Val Lys Phe Pro Gly Gly Gly Gln Ile Val Gly Gly Val
1               5                   10                  15

<210> SEQ ID NO 223
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 223

Asp Val Lys Phe Pro Gly Gly Gly Gln Ile Val Gly Gly Val Tyr
1               5                   10                  15

<210> SEQ ID NO 224
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 224

Val Lys Phe Pro Gly Gly Gly Gln Ile Val Gly Gly Val Tyr Leu
1               5                   10                  15

<210> SEQ ID NO 225
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 225

Lys Phe Pro Gly Gly Gly Gln Ile Val Gly Gly Val Tyr Leu Leu
1               5                   10                  15

<210> SEQ ID NO 226
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 226

Phe Pro Gly Gly Gly Gln Ile Val Gly Gly Val Tyr Leu Leu Pro
1               5                   10                  15

<210> SEQ ID NO 227
<211> LENGTH: 15

```
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 227

Pro Gly Gly Gly Gln Ile Val Gly Gly Val Tyr Leu Leu Pro Arg
 1               5                  10                  15

<210> SEQ ID NO 228
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 228

Gly Gly Gly Gln Ile Val Gly Gly Val Tyr Leu Leu Pro Arg Arg
 1               5                  10                  15

<210> SEQ ID NO 229
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 229

Gly Gly Gln Ile Val Gly Gly Val Tyr Leu Leu Pro Arg Arg Gly
 1               5                  10                  15

<210> SEQ ID NO 230
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 230

Gly Gln Ile Val Gly Gly Val Tyr Leu Leu Pro Arg Arg Gly Pro
 1               5                  10                  15

<210> SEQ ID NO 231
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 231

Gln Ile Val Gly Gly Val Tyr Leu Leu Pro Arg Arg Gly Pro Arg
 1               5                  10                  15

<210> SEQ ID NO 232
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 232

Ile Val Gly Gly Val Tyr Leu Leu Pro Arg Arg Gly Pro Arg Leu
```

<210> SEQ ID NO 233
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 233

Val Gly Gly Val Tyr Leu Leu Pro Arg Arg Gly Pro Arg Leu Gly
 1               5                  10                  15

<210> SEQ ID NO 234
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 234

Gly Gly Val Tyr Leu Leu Pro Arg Arg Gly Pro Arg Leu Gly Val
 1               5                  10                  15

<210> SEQ ID NO 235
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 235

Gly Val Tyr Leu Leu Pro Arg Arg Gly Pro Arg Leu Gly Val Arg
 1               5                  10                  15

<210> SEQ ID NO 236
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 236

Val Tyr Leu Leu Pro Arg Arg Gly Pro Arg Leu Gly Val Arg Ala
 1               5                  10                  15

<210> SEQ ID NO 237
<211> LENGTH: 14
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 237

Tyr Leu Pro Arg Arg Gly Pro Arg Leu Gly Val Arg Ala Thr
 1               5                  10

<210> SEQ ID NO 238
<211> LENGTH: 14
<212> TYPE: PRT
<213> ORGANISM: Artificial Sequence
<220> FEATURE:
<223> OTHER INFORMATION: Description of Artificial Sequence: Synthetic

```
                         Peptides

<400> SEQUENCE: 238

Leu Leu Pro Arg Arg Gly Pro Arg Leu Gly Val Arg Ala Thr
 1               5                  10

<210> SEQ ID NO 239
<211> LENGTH: 14
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 239

Leu Pro Arg Arg Gly Pro Arg Leu Gly Val Arg Ala Thr Arg
 1               5                  10

<210> SEQ ID NO 240
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 240

Pro Arg Arg Gly Pro Arg Leu Gly Val Arg Ala Thr Arg Lys Thr
 1               5                  10                  15

<210> SEQ ID NO 241
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 241

Arg Arg Gly Pro Arg Leu Gly Val Arg Ala Thr Arg Lys Thr Ser
 1               5                  10                  15

<210> SEQ ID NO 242
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 242

Arg Gly Pro Arg Leu Gly Val Arg Ala Thr Arg Lys Thr Ser Glu
 1               5                  10                  15

<210> SEQ ID NO 243
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 243

Gly Pro Arg Leu Gly Val Arg Ala Thr Arg Lys Thr Ser Glu Arg
 1               5                  10                  15

<210> SEQ ID NO 244
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 244

Pro Arg Leu Gly Val Arg Ala Thr Arg Lys Thr Ser Glu Arg Ser
 1               5                  10                  15

<210> SEQ ID NO 245
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 245

Arg Leu Gly Val Arg Ala Thr Arg Lys Thr Ser Glu Arg Ser Gln
 1               5                  10                  15

<210> SEQ ID NO 246
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 246

Leu Gly Val Arg Ala Thr Arg Lys Thr Ser Glu Arg Ser Gln Pro
 1               5                  10                  15

<210> SEQ ID NO 247
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 247

Gly Val Arg Ala Thr Arg Lys Thr Ser Glu Arg Ser Gln Pro Arg
 1               5                  10                  15

<210> SEQ ID NO 248
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 248

Val Arg Ala Thr Arg Lys Thr Ser Glu Arg Ser Gln Pro Arg Gly
 1               5                  10                  15

<210> SEQ ID NO 249
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 249
```

Arg Ala Thr Arg Lys Thr Ser Glu Arg Ser Gln Pro Arg Gly Arg
1               5                   10                  15

<210> SEQ ID NO 250
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 250

Ala Thr Arg Lys Thr Ser Glu Arg Ser Gln Pro Arg Gly Arg Arg
1               5                   10                  15

<210> SEQ ID NO 251
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 251

Thr Arg Lys Thr Ser Glu Arg Ser Gln Pro Arg Gly Arg Arg Gln
1               5                   10                  15

<210> SEQ ID NO 252
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 252

Arg Lys Thr Ser Glu Arg Ser Gln Pro Arg Gly Arg Arg Gln Pro
1               5                   10                  15

<210> SEQ ID NO 253
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 253

Lys Thr Ser Glu Arg Ser Gln Pro Arg Gly Arg Arg Gln Pro Ile
1               5                   10                  15

<210> SEQ ID NO 254
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 254

Thr Ser Glu Arg Ser Gln Pro Arg Gly Arg Arg Gln Pro Ile Pro
1               5                   10                  15

<210> SEQ ID NO 255
<211> LENGTH: 15
<212> TYPE: PRT
<213> ORGANISM: Artificial Sequence
<220> FEATURE:

```
<223> OTHER INFORMATION: Description of Artificial Sequence: Synthetic
      Peptides

<400> SEQUENCE: 255

Ser Glu Arg Ser Gln Pro Arg Gly Arg Arg Gln Pro Ile Pro Lys
  1               5                  10                  15

<210> SEQ ID NO 256
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 256

Asp Pro Arg Arg Arg Ser Arg Asn Leu Gly Lys Val Ile Asp Thr
  1               5                  10                  15

<210> SEQ ID NO 257
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 257

Pro Arg Arg Arg Ser Arg Asn Leu Gly Lys Val Ile Asp Thr Leu
  1               5                  10                  15

<210> SEQ ID NO 258
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 258

Arg Arg Arg Ser Arg Asn Leu Gly Lys Val Ile Asp Thr Leu Thr
  1               5                  10                  15

<210> SEQ ID NO 259
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 259

Arg Arg Ser Arg Asn Leu Gly Lys Val Ile Asp Thr Leu Thr Cys
  1               5                  10                  15

<210> SEQ ID NO 260
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 260

Arg Ser Arg Asn Leu Gly Lys Val Ile Asp Thr Leu Thr Cys Gly
  1               5                  10                  15
```

```
<210> SEQ ID NO 261
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 261

Ser Arg Asn Leu Gly Lys Val Ile Asp Thr Leu Thr Cys Gly Phe
 1               5                  10                  15

<210> SEQ ID NO 262
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 262

Ser Arg Asn Leu Gly Lys Val Ile Asp Thr Leu Thr Cys Gly Phe
 1               5                  10                  15

<210> SEQ ID NO 263
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 263

Asn Leu Gly Lys Val Ile Asp Thr Leu Thr Cys Gly Phe Ala Asp
 1               5                  10                  15

<210> SEQ ID NO 264
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 264

Leu Gly Lys Val Ile Asp Thr Leu Thr Cys Gly Phe Ala Asp Leu
 1               5                  10                  15

<210> SEQ ID NO 265
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 265

Gly Lys Val Ile Asp Thr Leu Thr Cys Gly Phe Ala Asp Leu Met
 1               5                  10                  15

<210> SEQ ID NO 266
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 266
```

```
Lys Val Ile Asp Thr Leu Thr Cys Gly Phe Ala Asp Leu Met Gly
 1               5                   10                  15
```

<210> SEQ ID NO 267
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 267

```
Val Ile Asp Thr Leu Thr Cys Gly Phe Ala Asp Leu Met Gly Tyr
 1               5                   10                  15
```

<210> SEQ ID NO 268
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 268

```
Ile Asp Thr Leu Thr Cys Gly Phe Ala Asp Leu Met Gly Tyr Ile
 1               5                   10                  15
```

<210> SEQ ID NO 269
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 269

```
Asp Thr Leu Thr Cys Gly Phe Ala Asp Leu Met Gly Tyr Ile Pro
 1               5                   10                  15
```

<210> SEQ ID NO 270
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 270

```
Thr Leu Thr Cys Gly Phe Ala Asp Leu Met Gly Tyr Ile Pro Leu
 1               5                   10                  15
```

<210> SEQ ID NO 271
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 271

```
Leu Thr Cys Gly Phe Ala Asp Leu Met Gly Tyr Ile Pro Leu Val
 1               5                   10                  15
```

<210> SEQ ID NO 272
<211> LENGTH: 15
<212> TYPE: PRT
<213> ORGANISM: Artificial Sequence

```
<220> FEATURE:
<223> OTHER INFORMATION: Description of Artificial Sequence: Synthetic
      Peptides

<400> SEQUENCE: 272

Thr Cys Gly Phe Ala Asp Leu Met Gly Tyr Ile Pro Leu Val Gly
1               5                   10                  15

<210> SEQ ID NO 273
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 273

Cys Gly Phe Ala Asp Leu Met Gly Tyr Ile Pro Leu Val Gly Ala
1               5                   10                  15

<210> SEQ ID NO 274
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 274

Gly Phe Ala Asp Leu Met Gly Tyr Ile Pro Leu Val Gly Ala Pro
1               5                   10                  15

<210> SEQ ID NO 275
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 275

Phe Ala Asp Leu Met Gly Tyr Ile Pro Leu Val Gly Ala Pro Leu
1               5                   10                  15

<210> SEQ ID NO 276
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 276

Ala Asp Leu Met Gly Tyr Ile Pro Leu Val Gly Ala Pro Leu Gly
1               5                   10                  15

<210> SEQ ID NO 277
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 277

Asp Leu Met Gly Tyr Ile Pro Leu Val Gly Ala Pro Leu Gly Gly
1               5                   10                  15
```

```
<210> SEQ ID NO 278
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 278

Asp Pro Arg His Arg Ser Arg Asn Val Gly Lys Val Ile Asp Thr
 1               5                  10                  15

<210> SEQ ID NO 279
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 279

Pro Arg His Arg Ser Arg Asn Val Gly Lys Val Ile Asp Thr Leu
 1               5                  10                  15

<210> SEQ ID NO 280
<211> LENGTH: 14
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 280

Arg His Arg Ser Arg Asn Val Gly Lys Ile Asp Thr Leu Thr
 1               5                  10

<210> SEQ ID NO 281
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 281

His Arg Ser Arg Asn Val Gly Lys Val Ile Asp Thr Leu Thr Cys
 1               5                  10                  15

<210> SEQ ID NO 282
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 282

Arg Ser Arg Asn Val Gly Lys Val Ile Asp Thr Leu Thr Cys Gly
 1               5                  10                  15

<210> SEQ ID NO 283
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides
```

```
<400> SEQUENCE: 283

Ser Arg Asn Val Gly Lys Val Ile Asp Thr Leu Thr Cys Gly Phe
  1               5                  10                  15

<210> SEQ ID NO 284
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 284

Arg Asn Val Gly Lys Val Ile Asp Thr Leu Thr Cys Gly Phe Ala
  1               5                  10                  15

<210> SEQ ID NO 285
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 285

Asn Val Gly Lys Val Ile Asp Thr Leu Thr Cys Gly Phe Ala Asp
  1               5                  10                  15

<210> SEQ ID NO 286
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 286

Val Gly Lys Val Ile Asp Thr Leu Thr Cys Gly Phe Ala Asp Leu
  1               5                  10                  15

<210> SEQ ID NO 287
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 287

Thr Leu Thr Cys Gly Phe Ala Asp Leu Met Gly Tyr Ile Pro Val
  1               5                  10                  15

<210> SEQ ID NO 288
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 288

Leu Thr Cys Gly Phe Ala Asp Leu Met Gly Tyr Ile Pro Val Val
  1               5                  10                  15

<210> SEQ ID NO 289
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      Peptides

<400> SEQUENCE: 289

Thr Cys Gly Phe Ala Asp Leu Met Gly Tyr Ile Pro Val Val Gly
 1               5                  10                  15

<210> SEQ ID NO 290
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 290

Cys Gly Phe Ala Asp Leu Met Gly Tyr Ile Pro Val Val Gly Ala
 1               5                  10                  15

<210> SEQ ID NO 291
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 291

Gly Phe Ala Asp Leu Met Gly Tyr Ile Pro Val Val Gly Ala Pro
 1               5                  10                  15

<210> SEQ ID NO 292
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 292

Phe Ala Asp Leu Met Gly Tyr Ile Pro Val Val Gly Ala Pro Leu
 1               5                  10                  15

<210> SEQ ID NO 293
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 293

Ala Asp Leu Met Gly Tyr Ile Pro Val Val Gly Ala Pro Leu Gly
 1               5                  10                  15

<210> SEQ ID NO 294
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 294

Asp Leu Met Gly Tyr Ile Pro Val Val Gly Ala Pro Leu Gly Gly
 1               5                  10                  15
```

-continued

<210> SEQ ID NO 295
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 295

Ala Arg Ala Leu Ala His Gly Val Arg Val Leu Glu Asp Gly Val
 1               5                  10                  15

<210> SEQ ID NO 296
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 296

Arg Ala Leu Ala His Gly Val Arg Val Leu Glu Asp Gly Val Asn
 1               5                  10                  15

<210> SEQ ID NO 297
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 297

Ala Leu Ala His Gly Val Arg Val Leu Glu Asp Gly Val Asn Tyr
 1               5                  10                  15

<210> SEQ ID NO 298
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 298

Leu Ala His Gly Val Arg Val Leu Glu Asp Gly Val Asn Tyr Ala
 1               5                  10                  15

<210> SEQ ID NO 299
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 299

Ala His Gly Val Arg Val Leu Glu Asp Gly Val Asn Tyr Ala Thr
 1               5                  10                  15

<210> SEQ ID NO 300
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides -continued

```
<400> SEQUENCE: 300

His Gly Val Arg Val Leu Glu Asp Gly Val Asn Tyr Ala Thr Gly
 1               5                  10                  15

<210> SEQ ID NO 301
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 301

Gly Val Arg Val Leu Glu Asp Gly Val Asn Tyr Ala Thr Gly Asn
 1               5                  10                  15

<210> SEQ ID NO 302
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 302

Val Arg Val Leu Glu Asp Gly Val Asn Tyr Ala Thr Gly Asn Leu
 1               5                  10                  15

<210> SEQ ID NO 303
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 303

Arg Val Leu Glu Asp Gly Val Asn Tyr Ala Thr Gly Asn Leu Pro
 1               5                  10                  15

<210> SEQ ID NO 304
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 304

Val Leu Glu Asp Gly Val Asn Tyr Ala Thr Gly Asn Leu Pro Gly
 1               5                  10                  15

<210> SEQ ID NO 305
<211> LENGTH: 16
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 305

Leu Glu Asp Gly Gly Val Asn Tyr Ala Thr Gly Asn Leu Pro Gly Cys
 1               5                  10                  15

<210> SEQ ID NO 306
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 306

Glu Asp Gly Val Asn Tyr Ala Thr Gly Asn Leu Pro Gly Cys Ser
 1               5                  10                  15

<210> SEQ ID NO 307
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 307

Asp Gly Val Asn Tyr Ala Thr Gly Asn Leu Pro Gly Cys Ser Phe
 1               5                  10                  15

<210> SEQ ID NO 308
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 308

Gly Val Asn Tyr Ala Thr Gly Asn Leu Pro Gly Cys Ser Phe Ser
 1               5                  10                  15

<210> SEQ ID NO 309
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 309

Val Asn Tyr Ala Thr Gly Asn Leu Pro Gly Cys Ser Phe Ser Ile
 1               5                  10                  15

<210> SEQ ID NO 310
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 310

Asn Tyr Ala Thr Gly Asn Leu Pro Gly Cys Ser Phe Ser Ile Phe
 1               5                  10                  15

<210> SEQ ID NO 311
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 311

Tyr Ala Thr Gly Asn Leu Pro Gly Cys Ser Phe Ser Ile Phe Leu
```

-continued

<210> SEQ ID NO 312
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 312

Ala Thr Gly Asn Leu Pro Gly Cys Ser Phe Ser Ile Phe Leu Leu
 1               5                  10                  15

<210> SEQ ID NO 313
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 313

Thr Gly Asn Leu Pro Gly Cys Ser Phe Ser Ile Phe Leu Leu Ala
 1               5                  10                  15

<210> SEQ ID NO 314
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 314

Gly Asn Leu Pro Gly Cys Ser Phe Ser Ile Phe Leu Leu Ala Leu
 1               5                  10                  15

<210> SEQ ID NO 315
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 315

Asn Leu Pro Gly Cys Ser Phe Ser Ile Phe Leu Leu Ala Leu Leu
 1               5                  10                  15

<210> SEQ ID NO 316
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 316

Leu Pro Gly Cys Ser Phe Ser Ile Phe Leu Leu Ala Leu Leu Ser
 1               5                  10                  15

<210> SEQ ID NO 317
<211> LENGTH: 15
<212> TYPE: PRT
<213> ORGANISM: Artificial Sequence
<220> FEATURE:
<223> OTHER INFORMATION: Description of Artificial Sequence: Synthetic -continued

```
      Peptides

<400> SEQUENCE: 317

Pro Gly Cys Ser Phe Ser Ile Phe Leu Leu Ala Leu Leu Ser Cys
  1               5                  10                  15

<210> SEQ ID NO 318
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 318

Ile Gln Leu Ile Asn Thr Asn Gly Ser Trp His Ile Asn Arg Thr
  1               5                  10                  15

<210> SEQ ID NO 319
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 319

Gln Leu Ile Asn Thr Asn Gly Ser Trp His Ile Asn Arg Thr Ala
  1               5                  10                  15

<210> SEQ ID NO 320
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 320

Leu Ile Asn Thr Asn Gly Ser Trp His Ile Asn Arg Thr Ala Leu
  1               5                  10                  15

<210> SEQ ID NO 321
<211> LENGTH: 14
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 321

Ile Asn Thr Asn Gly Ser Trp Ile Asn Arg Thr Ala Leu Asn
  1               5                  10

<210> SEQ ID NO 322
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 322

Asn Thr Asn Gly Ser Trp His Ile Asn Arg Thr Ala Leu Asn Cys
  1               5                  10                  15

<210> SEQ ID NO 323
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 323

Thr Asn Gly Ser Trp His Ile Asn Arg Thr Ala Leu Asn Cys Asn
 1               5                  10                  15

<210> SEQ ID NO 324
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 324

Asn Gly Ser Trp His Ile Asn Arg Thr Ala Leu Asn Cys Asn Asp
 1               5                  10                  15

<210> SEQ ID NO 325
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 325

Gly Ser Trp His Ile Asn Arg Thr Ala Leu Asn Cys Asn Asp Ser
 1               5                  10                  15

<210> SEQ ID NO 326
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 326

Ser Trp His Ile Asn Arg Thr Ala Leu Asn Cys Asn Asp Ser Leu
 1               5                  10                  15

<210> SEQ ID NO 327
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 327

Ile Gln Leu Val Asn Thr Asn Gly Ser Trp His Ile Asn Arg Thr
 1               5                  10                  15

<210> SEQ ID NO 328
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 328
```

```
Gln Leu Val Asn Thr Asn Gly Ser Trp His Ile Asn Arg Thr Ala
  1               5                  10                  15

<210> SEQ ID NO 329
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 329

Leu Val Asn Thr Asn Gly Ser Trp His Ile Asn Arg Thr Ala Leu
  1               5                  10                  15

<210> SEQ ID NO 330
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 330

Val Asn Thr Asn Gly Ser Trp His Ile Asn Arg Thr Ala Leu Asn
  1               5                  10                  15

<210> SEQ ID NO 331
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 331

Val Asp Tyr Pro Tyr Arg Leu Trp His Tyr Pro Cys Thr Val Asn
  1               5                  10                  15

<210> SEQ ID NO 332
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 332

Asp Tyr Pro Tyr Arg Leu Trp His Tyr Pro Cys Thr Val Asn Phe
  1               5                  10                  15

<210> SEQ ID NO 333
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 333

Tyr Pro Tyr Arg Leu Trp His Tyr Pro Cys Thr Val Asn Phe Thr
  1               5                  10                  15

<210> SEQ ID NO 334
<211> LENGTH: 15
<212> TYPE: PRT
<213> ORGANISM: Artificial Sequence
<220> FEATURE:
```

<223> OTHER INFORMATION: Description of Artificial Sequence: Synthetic
      Peptides

<400> SEQUENCE: 334

Pro Tyr Arg Leu Trp His Tyr Pro Cys Thr Val Asn Phe Thr Ile
 1               5                   10                  15

<210> SEQ ID NO 335
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 335

Tyr Arg Leu Trp His Tyr Pro Cys Thr Val Asn Phe Thr Ile Phe
 1               5                   10                  15

<210> SEQ ID NO 336
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 336

Arg Leu Trp His Tyr Pro Cys Thr Val Asn Phe Thr Ile Phe Lys
 1               5                   10                  15

<210> SEQ ID NO 337
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 337

Leu Trp His Tyr Pro Cys Thr Val Asn Phe Thr Ile Phe Lys Val
 1               5                   10                  15

<210> SEQ ID NO 338
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 338

Trp His Tyr Pro Cys Thr Val Asn Phe Thr Ile Phe Lys Val Arg
 1               5                   10                  15

<210> SEQ ID NO 339
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 339

His Tyr Pro Cys Thr Val Asn Phe Thr Ile Phe Lys Val Arg Met
 1               5                   10                  15

<210> SEQ ID NO 340
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 340

Tyr Pro Cys Thr Val Asn Phe Thr Ile Phe Lys Val Arg Met Tyr
 1               5                  10                  15

<210> SEQ ID NO 341
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 341

Pro Cys Thr Val Asn Phe Thr Ile Phe Lys Val Arg Met Tyr Val
 1               5                  10                  15

<210> SEQ ID NO 342
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 342

Cys Thr Val Asn Phe Thr Ile Phe Lys Val Arg Met Tyr Val Gly
 1               5                  10                  15

<210> SEQ ID NO 343
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 343

Thr Val Asn Phe Thr Ile Phe Lys Val Arg Met Tyr Val Gly Gly
 1               5                  10                  15

<210> SEQ ID NO 344
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 344

Val Asn Phe Thr Ile Phe Lys Val Arg Met Tyr Val Gly Gly Val
 1               5                  10                  15

<210> SEQ ID NO 345
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 345

```
Asn Phe Thr Ile Phe Lys Val Arg Met Tyr Val Gly Gly Val Glu
  1               5                  10                  15

<210> SEQ ID NO 346
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 346

Phe Thr Ile Phe Lys Val Arg Met Tyr Val Gly Gly Val Glu His
  1               5                  10                  15

<210> SEQ ID NO 347
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 347

Thr Ile Phe Lys Val Arg Met Tyr Val Gly Gly Val Glu His Arg
  1               5                  10                  15

<210> SEQ ID NO 348
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 348

Ile Phe Lys Val Arg Met Tyr Val Gly Gly Val Glu His Arg Leu
  1               5                  10                  15

<210> SEQ ID NO 349
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 349

Asp Tyr Pro Tyr Arg Leu Trp His Tyr Pro Cys Thr Val Asn Tyr
  1               5                  10                  15

<210> SEQ ID NO 350
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 350

Tyr Pro Tyr Arg Leu Trp His Tyr Pro Cys Thr Val Asn Tyr Thr
  1               5                  10                  15

<210> SEQ ID NO 351
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      Peptides

<400> SEQUENCE: 351

Pro Tyr Arg Leu Trp His Tyr Pro Cys Thr Val Asn Tyr Thr Ile
 1               5                  10                  15

<210> SEQ ID NO 352
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 352

Tyr Arg Leu Trp His Tyr Pro Cys Thr Val Asn Tyr Thr Ile Phe
 1               5                  10                  15

<210> SEQ ID NO 353
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 353

Arg Leu Trp His Tyr Pro Cys Thr Val Asn Tyr Thr Ile Phe Lys
 1               5                  10                  15

<210> SEQ ID NO 354
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 354

Leu Trp His Tyr Pro Cys Thr Val Asn Tyr Thr Ile Phe Lys Ile
 1               5                  10                  15

<210> SEQ ID NO 355
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 355

Trp His Tyr Pro Cys Thr Val Asn Tyr Thr Ile Phe Lys Ile Arg
 1               5                  10                  15

<210> SEQ ID NO 356
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 356

His Tyr Pro Cys Thr Val Asn Tyr Thr Ile Phe Lys Ile Arg Met
 1               5                  10                  15
```

```
<210> SEQ ID NO 357
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 357

Tyr Pro Cys Thr Val Asn Tyr Thr Ile Phe Lys Ile Arg Met Tyr
 1               5                  10                  15

<210> SEQ ID NO 358
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 358

Pro Cys Thr Val Asn Tyr Thr Ile Phe Lys Ile Arg Met Tyr Val
 1               5                  10                  15

<210> SEQ ID NO 359
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 359

Cys Thr Val Asn Tyr Thr Ile Phe Lys Ile Arg Met Tyr Val Gly
 1               5                  10                  15

<210> SEQ ID NO 360
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 360

Thr Val Asn Tyr Thr Ile Phe Lys Ile Arg Met Tyr Val Gly Gly
 1               5                  10                  15

<210> SEQ ID NO 361
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 361

Val Asn Tyr Thr Ile Phe Lys Ile Arg Met Tyr Val Gly Gly Val
 1               5                  10                  15

<210> SEQ ID NO 362
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides
```

-continued

```
<400> SEQUENCE: 362

Asn Tyr Thr Ile Phe Lys Ile Arg Met Tyr Val Gly Gly Val Glu
 1               5                  10                  15

<210> SEQ ID NO 363
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 363

Tyr Thr Ile Phe Lys Ile Arg Met Tyr Val Gly Gly Val Glu His
 1               5                  10                  15

<210> SEQ ID NO 364
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 364

Thr Ile Phe Lys Ile Arg Met Tyr Val Gly Gly Val Glu His Arg
 1               5                  10                  15

<210> SEQ ID NO 365
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 365

Ile Phe Lys Ile Arg Met Tyr Val Gly Gly Val Glu His Arg Leu
 1               5                  10                  15

<210> SEQ ID NO 366
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 366

Leu Pro Ala Leu Ser Thr Gly Leu Ile His Leu His Gln Asn Ile
 1               5                  10                  15

<210> SEQ ID NO 367
<211> LENGTH: 14
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 367

Pro Ala Leu Ser Thr Gly Ile His Leu His Gln Asn Ile Val
 1               5                  10

<210> SEQ ID NO 368
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      Peptides

<400> SEQUENCE: 368

Ala Leu Ser Thr Gly Leu Ile His Leu His Gln Asn Ile Val Asp
 1               5                  10                  15

<210> SEQ ID NO 369
<211> LENGTH: 14
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 369

Leu Ser Thr Gly Ile His Leu His Gln Asn Ile Val Asp Val
 1               5                  10

<210> SEQ ID NO 370
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 370

Ser Thr Gly Leu Ile His Leu His Gln Asn Ile Val Asp Val Gln
 1               5                  10                  15

<210> SEQ ID NO 371
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 371

Thr Gly Leu Ile His Leu His Gln Asn Ile Val Asp Val Gln Tyr
 1               5                  10                  15

<210> SEQ ID NO 372
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 372

Gly Leu Ile His Leu His Gln Asn Ile Val Asp Val Gln Tyr Leu
 1               5                  10                  15

<210> SEQ ID NO 373
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 373

Leu Ile His Leu His Gln Asn Ile Val Asp Val Gln Tyr Leu Tyr
 1               5                  10                  15
```

-continued

<210> SEQ ID NO 374
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 374

Ile His Leu His Gln Asn Ile Val Asp Val Gln Tyr Leu Tyr Gly
 1               5                  10                  15

<210> SEQ ID NO 375
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 375

Leu Pro Ala Leu Ser Thr Gly Leu Leu His Leu His Gln Asn Ile
 1               5                  10                  15

<210> SEQ ID NO 376
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 376

Pro Ala Leu Ser Thr Gly Leu Leu His Leu His Gln Asn Ile Val
 1               5                  10                  15

<210> SEQ ID NO 377
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 377

Ala Leu Ser Thr Gly Leu Leu His Leu His Gln Asn Ile Val Asp
 1               5                  10                  15

<210> SEQ ID NO 378
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 378

Leu Ser Thr Gly Leu Leu His Leu His Gln Asn Ile Val Asp Val
 1               5                  10                  15

<210> SEQ ID NO 379
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides -continued

```
<400> SEQUENCE: 379

Ser Thr Gly Leu Leu His Leu His Gln Asn Ile Val Asp Val Gln
 1               5                  10                  15

<210> SEQ ID NO 380
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 380

Thr Gly Leu Leu His Leu His Gln Asn Ile Val Asp Val Gln Tyr
 1               5                  10                  15

<210> SEQ ID NO 381
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 381

Gly Leu Leu His Leu His Gln Asn Ile Val Asp Val Gln Tyr Met
 1               5                  10                  15

<210> SEQ ID NO 382
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 382

Leu Leu His Leu His Gln Asn Ile Val Asp Val Gln Tyr Met Tyr
 1               5                  10                  15

<210> SEQ ID NO 383
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 383

Leu His Leu His Gln Asn Ile Val Asp Val Gln Tyr Met Tyr Gly
 1               5                  10                  15

<210> SEQ ID NO 384
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 384

His Leu His Ala Pro Thr Gly Ser Gly Lys Ser Thr Lys Val Pro
 1               5                  10                  15

<210> SEQ ID NO 385
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 385

Leu His Ala Pro Thr Gly Ser Gly Lys Ser Thr Lys Val Pro Ala
 1               5                  10                  15

<210> SEQ ID NO 386
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 386

His Ala Pro Thr Gly Ser Gly Lys Ser Thr Lys Val Pro Ala Ala
 1               5                  10                  15

<210> SEQ ID NO 387
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 387

Ala Pro Thr Gly Ser Gly Lys Ser Thr Lys Val Pro Ala Ala Tyr
 1               5                  10                  15

<210> SEQ ID NO 388
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 388

Pro Thr Gly Ser Gly Lys Ser Thr Lys Val Pro Ala Ala Tyr Ala
 1               5                  10                  15

<210> SEQ ID NO 389
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 389

Thr Gly Ser Gly Lys Ser Thr Lys Val Pro Ala Ala Tyr Ala Ala
 1               5                  10                  15

<210> SEQ ID NO 390
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 390

Gly Ser Gly Lys Ser Thr Lys Val Pro Ala Ala Tyr Ala Ala Gln
```

<210> SEQ ID NO 391
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 391

Ser Gly Lys Ser Thr Lys Val Pro Ala Ala Tyr Ala Ala Gln Gly
 1               5                  10                  15

<210> SEQ ID NO 392
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 392

Gly Lys Ser Thr Lys Val Pro Ala Ala Tyr Ala Ala Gln Gly Tyr
 1               5                  10                  15

<210> SEQ ID NO 393
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 393

Lys Ser Thr Lys Val Pro Ala Ala Tyr Ala Ala Gln Gly Tyr Lys
 1               5                  10                  15

<210> SEQ ID NO 394
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 394

Ser Thr Lys Val Pro Ala Ala Tyr Ala Ala Gln Gly Tyr Lys Val
 1               5                  10                  15

<210> SEQ ID NO 395
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 395

Thr Lys Val Pro Ala Ala Tyr Ala Ala Gln Gly Tyr Lys Val Leu
 1               5                  10                  15

<210> SEQ ID NO 396
<211> LENGTH: 15
<212> TYPE: PRT
<213> ORGANISM: Artificial Sequence
<220> FEATURE:
<223> OTHER INFORMATION: Description of Artificial Sequence: Synthetic

```
                         Peptides

<400> SEQUENCE: 396

Lys Val Pro Ala Ala Tyr Ala Ala Gln Gly Tyr Lys Val Leu Val
  1               5                  10                  15

<210> SEQ ID NO 397
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 397

Val Pro Ala Ala Tyr Ala Ala Gln Gly Tyr Lys Val Leu Val Leu
  1               5                  10                  15

<210> SEQ ID NO 398
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 398

Pro Ala Ala Tyr Ala Ala Gln Gly Tyr Lys Val Leu Val Leu Asn
  1               5                  10                  15

<210> SEQ ID NO 399
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 399

Ala Ala Tyr Ala Ala Gln Gly Tyr Lys Val Leu Val Leu Asn Pro
  1               5                  10                  15

<210> SEQ ID NO 400
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 400

Ala Tyr Ala Ala Gln Gly Tyr Lys Val Leu Val Leu Asn Pro Ser
  1               5                  10                  15

<210> SEQ ID NO 401
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 401

Tyr Ala Ala Gln Gly Tyr Lys Val Leu Val Leu Asn Pro Ser Val
  1               5                  10                  15

<210> SEQ ID NO 402
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 402

Ala Ala Gln Gly Tyr Lys Val Leu Val Leu Asn Pro Ser Val Ala
 1               5                  10                  15

<210> SEQ ID NO 403
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 403

Ala Gln Gly Tyr Lys Val Leu Val Leu Asn Pro Ser Val Ala Ala
 1               5                  10                  15

<210> SEQ ID NO 404
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 404

Gln Gly Tyr Lys Val Leu Val Leu Asn Pro Ser Val Ala Ala Thr
 1               5                  10                  15

<210> SEQ ID NO 405
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 405

Gly Tyr Lys Val Leu Val Leu Asn Pro Ser Val Ala Ala Thr Leu
 1               5                  10                  15

<210> SEQ ID NO 406
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 406

Tyr Lys Val Leu Val Leu Asn Pro Ser Val Ala Ala Thr Leu Gly
 1               5                  10                  15

<210> SEQ ID NO 407
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 407
```

-continued

```
Lys Val Leu Val Leu Asn Pro Ser Val Ala Ala Thr Leu Gly Phe
 1               5                  10                  15

<210> SEQ ID NO 408
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 408

Val Leu Val Leu Asn Pro Ser Val Ala Ala Thr Leu Gly Phe Gly
 1               5                  10                  15

<210> SEQ ID NO 409
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 409

Leu Val Leu Asn Pro Ser Val Ala Ala Thr Leu Gly Phe Gly Ala
 1               5                  10                  15

<210> SEQ ID NO 410
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 410

Val Leu Asn Pro Ser Val Ala Ala Thr Leu Gly Phe Gly Ala Tyr
 1               5                  10                  15

<210> SEQ ID NO 411
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 411

Tyr Leu His Ala Pro Thr Gly Ser Gly Lys Ser Thr Lys Val Pro
 1               5                  10                  15

<210> SEQ ID NO 412
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 412

Leu His Ala Pro Thr Gly Ser Gly Lys Ser Thr Lys Val Pro Val
 1               5                  10                  15

<210> SEQ ID NO 413
<211> LENGTH: 15
<212> TYPE: PRT
<213> ORGANISM: Artificial Sequence
<220> FEATURE:
```

```
<223> OTHER INFORMATION: Description of Artificial Sequence: Synthetic
      Peptides

<400> SEQUENCE: 413

His Ala Pro Thr Gly Ser Gly Lys Ser Thr Lys Val Pro Val Ala
 1               5                  10                  15

<210> SEQ ID NO 414
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 414

Ala Pro Thr Gly Ser Gly Lys Ser Thr Lys Val Pro Val Ala Tyr
 1               5                  10                  15

<210> SEQ ID NO 415
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 415

Pro Thr Gly Ser Gly Lys Ser Thr Lys Val Pro Val Ala Tyr Ala
 1               5                  10                  15

<210> SEQ ID NO 416
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 416

Thr Gly Ser Gly Lys Ser Thr Lys Val Pro Val Ala Tyr Ala Ala
 1               5                  10                  15

<210> SEQ ID NO 417
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 417

Gly Ser Gly Lys Ser Thr Lys Val Pro Val Ala Tyr Ala Ala Gln
 1               5                  10                  15

<210> SEQ ID NO 418
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 418

Ser Gly Lys Ser Thr Lys Val Pro Val Ala Tyr Ala Ala Gln Gly
 1               5                  10                  15
```

<210> SEQ ID NO 419
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 419

Gly Lys Ser Thr Lys Val Pro Val Ala Tyr Ala Ala Gln Gly Tyr
1               5                   10                  15

<210> SEQ ID NO 420
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 420

Lys Ser Thr Lys Val Pro Val Ala Tyr Ala Ala Gln Gly Tyr Lys
1               5                   10                  15

<210> SEQ ID NO 421
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 421

Ser Thr Lys Val Pro Val Ala Tyr Ala Ala Gln Gly Thr Lys Val
1               5                   10                  15

<210> SEQ ID NO 422
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 422

Thr Lys Val Pro Val Ala Tyr Ala Ala Gln Gly Tyr Lys Val Leu
1               5                   10                  15

<210> SEQ ID NO 423
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 423

Lys Val Pro Val Ala Tyr Ala Ala Gln Gly Tyr Lys Val Leu Val
1               5                   10                  15

<210> SEQ ID NO 424
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 424

```
Val Pro Val Ala Tyr Ala Ala Gln Gly Tyr Lys Val Leu Val Leu
  1               5                  10                  15
```

<210> SEQ ID NO 425
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 425

```
Pro Val Ala Tyr Ala Ala Gln Gly Tyr Lys Val Leu Val Leu Asn
  1               5                  10                  15
```

<210> SEQ ID NO 426
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 426

```
Val Ala Tyr Ala Ala Gln Gly Tyr Lys Val Leu Val Leu Asn Pro
  1               5                  10                  15
```

<210> SEQ ID NO 427
<211> LENGTH: 14
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 427

```
Ile Thr Ser Thr Tyr Gly Lys Phe Leu Ala Asp Gly Gly Cys
  1               5                  10
```

<210> SEQ ID NO 428
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 428

```
Thr Tyr Ser Thr Tyr Gly Lys Phe Leu Ala Asp Gly Gly Cys Ser
  1               5                  10                  15
```

<210> SEQ ID NO 429
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 429

```
Tyr Ser Thr Tyr Gly Lys Phe Leu Ala Asp Gly Gly Cys Ser Gly
  1               5                  10                  15
```

<210> SEQ ID NO 430
<211> LENGTH: 15
<212> TYPE: PRT
<213> ORGANISM: Artificial Sequence

```
<220> FEATURE:
<223> OTHER INFORMATION: Description of Artificial Sequence: Synthetic
      Peptides

<400> SEQUENCE: 430

Ser Thr Tyr Gly Lys Phe Leu Ala Asp Gly Gly Cys Ser Gly Gly
 1               5                  10                  15

<210> SEQ ID NO 431
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 431

Thr Tyr Gly Lys Phe Leu Ala Asp Gly Gly Cys Ser Gly Gly Ala
 1               5                  10                  15

<210> SEQ ID NO 432
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 432

Tyr Gly Lys Phe Leu Ala Asp Gly Gly Cys Ser Gly Gly Ala Tyr
 1               5                  10                  15

<210> SEQ ID NO 433
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 433

Gly Lys Phe Leu Ala Asp Gly Gly Cys Ser Gly Gly Ala Tyr Asp
 1               5                  10                  15

<210> SEQ ID NO 434
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 434

Lys Phe Leu Ala Asp Gly Gly Cys Ser Gly Gly Ala Tyr Asp Ile
 1               5                  10                  15

<210> SEQ ID NO 435
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 435

Phe Leu Ala Asp Gly Gly Cys Ser Gly Gly Ala Tyr Asp Ile Ile
 1               5                  10                  15
```

```
<210> SEQ ID NO 436
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 436

Leu Ala Asp Gly Gly Cys Ser Gly Gly Ala Tyr Asp Ile Ile Ile
 1               5                  10                  15

<210> SEQ ID NO 437
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 437

Ala Asp Gly Gly Cys Ser Gly Gly Ala Tyr Asp Ile Ile Ile Cys
 1               5                  10                  15

<210> SEQ ID NO 438
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 438

Asp Gly Gly Cys Ser Gly Gly Ala Tyr Asp Ile Ile Ile Cys Asp
 1               5                  10                  15

<210> SEQ ID NO 439
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 439

Gly Gly Cys Ser Gly Gly Ala Tyr Asp Ile Ile Ile Cys Asp Glu
 1               5                  10                  15

<210> SEQ ID NO 440
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 440

Gly Cys Ser Gly Gly Ala Tyr Asp Ile Ile Ile Cys Asp Glu Cys
 1               5                  10                  15

<210> SEQ ID NO 441
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides
```

<400> SEQUENCE: 441

Cys Ser Gly Gly Ala Tyr Asp Ile Ile Ile Cys Asp Glu Cys His
 1               5                  10                  15

<210> SEQ ID NO 442
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 442

Ser Gly Gly Ala Tyr Asp Ile Ile Ile Cys Asp Glu Cys His Ser
 1               5                  10                  15

<210> SEQ ID NO 443
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 443

Thr Thr Ile Leu Gly Ile Gly Thr Val Leu Asp Gln Ala Glu Thr
 1               5                  10                  15

<210> SEQ ID NO 444
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 444

Thr Ile Leu Gly Ile Gly Thr Val Leu Asp Gln Ala Glu Thr Ala
 1               5                  10                  15

<210> SEQ ID NO 445
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 445

Ile Leu Gly Ile Gly Thr Val Leu Asp Gln Ala Glu Thr Ala Gly
 1               5                  10                  15

<210> SEQ ID NO 446
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 446

Leu Gly Ile Gly Thr Val Leu Asp Gln Ala Glu Thr Ala Gly Ala
 1               5                  10                  15

<210> SEQ ID NO 447
<211> LENGTH: 15
<212> TYPE: PRT

<213> ORGANISM: Artificial Sequence
<220> FEATURE:
<223> OTHER INFORMATION: Description of Artificial Sequence: Synthetic
      Peptides

<400> SEQUENCE: 447

Gly Ile Gly Thr Val Leu Asp Gln Ala Glu Thr Ala Gly Ala Arg
1               5                   10                  15

<210> SEQ ID NO 448
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 448

Ile Gly Thr Val Leu Asp Gln Ala Glu Thr Ala Gly Ala Arg Leu
1               5                   10                  15

<210> SEQ ID NO 449
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 449

Gly Thr Val Leu Asp Gln Ala Glu Thr Ala Gly Ala Arg Leu Val
1               5                   10                  15

<210> SEQ ID NO 450
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 450

Thr Val Leu Asp Gln Ala Glu Thr Ala Gly Ala Arg Leu Val Val
1               5                   10                  15

<210> SEQ ID NO 451
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 451

Val Leu Asp Gln Ala Glu Thr Ala Gly Ala Arg Leu Val Val Leu
1               5                   10                  15

<210> SEQ ID NO 452
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 452

Leu Asp Gln Ala Glu Thr Ala Gly Ala Arg Leu Val Val Leu Ala
1               5                   10                  15

<210> SEQ ID NO 453
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 453

Asp Gln Ala Glu Thr Ala Gly Ala Arg Leu Val Val Leu Ala Thr
 1               5                  10                  15

<210> SEQ ID NO 454
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 454

Gln Ala Glu Thr Ala Gly Ala Arg Leu Val Val Leu Ala Thr Ala
 1               5                  10                  15

<210> SEQ ID NO 455
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 455

Ala Glu Thr Ala Gly Ala Arg Leu Val Val Leu Ala Thr Ala Thr
 1               5                  10                  15

<210> SEQ ID NO 456
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 456

Glu Thr Ala Gly Ala Arg Leu Val Val Leu Ala Thr Ala Thr Pro
 1               5                  10                  15

<210> SEQ ID NO 457
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 457

Thr Ala Gly Ala Arg Leu Val Val Leu Ala Thr Ala Thr Pro Pro
 1               5                  10                  15

<210> SEQ ID NO 458
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

```
<400> SEQUENCE: 458

Ala Gly Ala Arg Leu Val Val Leu Ala Thr Ala Thr Pro Pro Gly
 1               5                  10                  15

<210> SEQ ID NO 459
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 459

Gly Ala Arg Leu Val Val Leu Ala Thr Ala Thr Pro Pro Gly Ser
 1               5                  10                  15

<210> SEQ ID NO 460
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 460

Ala Arg Leu Val Val Leu Ala Thr Ala Thr Pro Pro Gly Ser Val
 1               5                  10                  15

<210> SEQ ID NO 461
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 461

Arg Leu Val Val Leu Ala Thr Ala Thr Pro Pro Gly Ser Val Thr
 1               5                  10                  15

<210> SEQ ID NO 462
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 462

Thr Ser Ile Leu Gly Ile Gly Thr Val Leu Asp Gln Ala Glu Thr
 1               5                  10                  15

<210> SEQ ID NO 463
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 463

Ser Ile Leu Gly Ile Gly Thr Val Leu Asp Gln Ala Glu Thr Ala
 1               5                  10                  15

<210> SEQ ID NO 464
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 464

Leu Gly Ile Gly Thr Val Leu Asp Gln Ala Glu Thr Ala Gly Val
 1               5                  10                  15

<210> SEQ ID NO 465
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 465

Gly Ile Gly Thr Val Leu Asp Gln Ala Glu Thr Ala Gly Val Arg
 1               5                  10                  15

<210> SEQ ID NO 466
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 466

Ile Gly Thr Val Leu Asp Gln Ala Glu Thr Ala Gly Val Arg Leu
 1               5                  10                  15

<210> SEQ ID NO 467
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 467

Gly Thr Val Leu Asp Gln Ala Glu Thr Ala Gly Val Arg Leu Thr
 1               5                  10                  15

<210> SEQ ID NO 468
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 468

Thr Val Leu Asp Gln Ala Glu Thr Ala Gly Val Arg Leu Thr Val
 1               5                  10                  15

<210> SEQ ID NO 469
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 469

Val Leu Asp Gln Ala Glu Thr Ala Gly Val Arg Leu Thr Val Leu
```

```
                1               5                  10                  15

<210> SEQ ID NO 470
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 470

Leu Asp Gln Ala Glu Thr Ala Gly Val Arg Leu Thr Val Leu Ala
  1               5                  10                  15

<210> SEQ ID NO 471
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 471

Asp Gln Ala Glu Thr Ala Gly Val Arg Leu Thr Val Leu Ala Thr
  1               5                  10                  15

<210> SEQ ID NO 472
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 472

Gln Ala Glu Thr Ala Gly Val Arg Leu Thr Val Leu Ala Thr Ala
  1               5                  10                  15

<210> SEQ ID NO 473
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 473

Ala Glu Thr Ala Gly Val Arg Leu Thr Val Leu Ala Thr Ala Thr
  1               5                  10                  15

<210> SEQ ID NO 474
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 474

Glu Thr Ala Gly Val Arg Leu Thr Val Leu Ala Thr Ala Thr Pro
  1               5                  10                  15

<210> SEQ ID NO 475
<211> LENGTH: 15
<212> TYPE: PRT
<213> ORGANISM: Artificial Sequence
<220> FEATURE:
<223> OTHER INFORMATION: Description of Artificial Sequence:  Synthetic
```

Peptides

<400> SEQUENCE: 475

Thr Ala Gly Val Arg Leu Thr Val Leu Ala Thr Ala Thr Pro Pro
1               5                   10                  15

<210> SEQ ID NO 476
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 476

Ala Gly Val Arg Leu Thr Val Leu Ala Thr Ala Thr Pro Pro Gly
1               5                   10                  15

<210> SEQ ID NO 477
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 477

Gly Val Arg Leu Thr Val Leu Ala Thr Ala Thr Pro Pro Gly Ser
1               5                   10                  15

<210> SEQ ID NO 478
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 478

Val Arg Leu Thr Val Leu Ala Thr Ala Thr Pro Pro Gly Ser Val
1               5                   10                  15

<210> SEQ ID NO 479
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 479

Ser Gly Met Phe Asp Ser Ser Val Leu Cys Glu Cys Tyr Asp Ala
1               5                   10                  15

<210> SEQ ID NO 480
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 480

Gly Met Phe Asp Ser Ser Val Leu Cys Glu Cys Tyr Asp Ala Gly
1               5                   10                  15

<210> SEQ ID NO 481

```
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 481

Met Phe Asp Ser Ser Val Leu Cys Glu Cys Tyr Asp Ala Gly Cys
 1               5                  10                  15

<210> SEQ ID NO 482
<211> LENGTH: 14
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 482

Phe Asp Ser Ser Val Leu Cys Glu Cys Asp Ala Gly Cys Ala
 1               5                  10

<210> SEQ ID NO 483
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 483

Asp Ser Ser Val Leu Cys Glu Cys Tyr Asp Ala Gly Cys Ala Trp
 1               5                  10                  15

<210> SEQ ID NO 484
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 484

Ser Ser Val Leu Cys Glu Cys Tyr Asp Ala Gly Cys Ala Trp Tyr
 1               5                  10                  15

<210> SEQ ID NO 485
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 485

Ser Val Leu Cys Glu Cys Tyr Asp Ala Gly Cys Ala Trp Tyr Glu
 1               5                  10                  15

<210> SEQ ID NO 486
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 486
```

-continued

Val Leu Cys Glu Cys Tyr Asp Ala Gly Cys Ala Trp Tyr Glu Leu
1               5                   10                  15

<210> SEQ ID NO 487
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 487

Leu Cys Glu Cys Tyr Asp Ala Gly Cys Ala Trp Tyr Glu Leu Thr
1               5                   10                  15

<210> SEQ ID NO 488
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 488

Cys Glu Cys Tyr Asp Ala Gly Cys Ala Trp Tyr Glu Leu Thr Pro
1               5                   10                  15

<210> SEQ ID NO 489
<211> LENGTH: 14
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 489

Glu Cys Tyr Asp Ala Gly Cys Ala Trp Tyr Glu Leu Thr Ala
1               5                   10

<210> SEQ ID NO 490
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 490

Cys Tyr Asp Ala Gly Cys Ala Trp Tyr Glu Leu Thr Pro Ala Glu
1               5                   10                  15

<210> SEQ ID NO 491
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 491

Tyr Asp Ala Gly Cys Ala Trp Tyr Glu Leu Thr Pro Ala Glu Thr
1               5                   10                  15

<210> SEQ ID NO 492
<211> LENGTH: 15
<212> TYPE: PRT
<213> ORGANISM: Artificial Sequence
<220> FEATURE:

```
<223> OTHER INFORMATION: Description of Artificial Sequence: Synthetic
      Peptides

<400> SEQUENCE: 492

Asp Ala Gly Cys Ala Trp Tyr Glu Leu Thr Pro Ala Glu Thr Thr
 1               5                  10                  15

<210> SEQ ID NO 493
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 493

Ala Gly Cys Ala Trp Tyr Glu Leu Thr Pro Ala Glu Thr Thr Val
 1               5                  10                  15

<210> SEQ ID NO 494
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 494

Gly Cys Ala Trp Tyr Glu Leu Thr Pro Ala Glu Thr Thr Val Arg
 1               5                  10                  15

<210> SEQ ID NO 495
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 495

Cys Ala Trp Tyr Glu Leu Thr Pro Ala Glu Thr Thr Val Arg Leu
 1               5                  10                  15

<210> SEQ ID NO 496
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 496

Ala Trp Tyr Glu Leu Thr Pro Ala Glu Thr Thr Val Arg Leu Arg
 1               5                  10                  15

<210> SEQ ID NO 497
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 497

Trp Tyr Glu Leu Thr Pro Ala Glu Thr Thr Val Arg Leu Arg Ala
 1               5                  10                  15
```

<210> SEQ ID NO 498
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 498

Tyr Glu Leu Thr Pro Ala Glu Thr Thr Val Arg Leu Arg Ala Tyr
 1               5                  10                  15

<210> SEQ ID NO 499
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 499

Asp Ala Gly Cys Ala Trp Tyr Glu Leu Thr Pro Ala Glu Thr Ser
 1               5                  10                  15

<210> SEQ ID NO 500
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 500

Ala Gly Cys Ala Trp Tyr Glu Leu Thr Pro Ala Glu Thr Ser Val
 1               5                  10                  15

<210> SEQ ID NO 501
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 501

Gly Cys Ala Trp Tyr Glu Leu Thr Pro Ala Glu Thr Ser Val Arg
 1               5                  10                  15

<210> SEQ ID NO 502
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 502

Cys Ala Trp Tyr Glu Leu Thr Pro Ala Glu Thr Ser Val Arg Leu
 1               5                  10                  15

<210> SEQ ID NO 503
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 503

```
Ala Trp Tyr Glu Leu Thr Pro Ala Glu Thr Ser Val Arg Leu Arg
 1               5                  10                  15

<210> SEQ ID NO 504
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 504

Trp Tyr Glu Leu Thr Pro Ala Glu Thr Ser Val Arg Leu Arg Ala
 1               5                  10                  15

<210> SEQ ID NO 505
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 505

Gly Met Phe Asp Ser Val Val Leu Cys Glu Cys Tyr Asp Ala Gly
 1               5                  10                  15

<210> SEQ ID NO 506
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 506

Ser Gly Met Phe Asp Ser Val Val Leu Cys Glu Cys Tyr Asp Ala
 1               5                  10                  15

<210> SEQ ID NO 507
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 507

Gly Met Phe Asp Ser Val Val Leu Cys Glu Cys Tyr Asp Ala Gly
 1               5                  10                  15

<210> SEQ ID NO 508
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 508

Met Phe Asp Ser Val Val Leu Cys Glu Cys Tyr Asp Ala Gly Ala
 1               5                  10                  15

<210> SEQ ID NO 509
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      Peptides

<400> SEQUENCE: 509

Phe Asp Ser Val Val Leu Cys Glu Cys Tyr Asp Ala Gly Ala Ala
 1               5                  10                  15

<210> SEQ ID NO 510
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 510

Asp Ser Val Val Leu Cys Glu Cys Tyr Asp Ala Gly Ala Ala Trp
 1               5                  10                  15

<210> SEQ ID NO 511
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 511

Ser Val Val Leu Cys Glu Cys Tyr Asp Ala Gly Ala Ala Trp Tyr
 1               5                  10                  15

<210> SEQ ID NO 512
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 512

Val Val Leu Cys Glu Cys Tyr Asp Ala Gly Ala Ala Trp Tyr Glu
 1               5                  10                  15

<210> SEQ ID NO 513
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 513

Val Leu Cys Glu Cys Tyr Asp Ala Gly Ala Ala Trp Tyr Glu Leu
 1               5                  10                  15

<210> SEQ ID NO 514
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 514

Leu Cys Glu Cys Tyr Asp Ala Gly Ala Ala Trp Tyr Glu Leu Thr
 1               5                  10                  15
```

<210> SEQ ID NO 515
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 515

Cys Glu Cys Tyr Asp Ala Gly Ala Ala Trp Tyr Glu Leu Thr Pro
 1               5                  10                  15

<210> SEQ ID NO 516
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 516

Glu Cys Tyr Asp Ala Gly Ala Ala Trp Tyr Glu Leu Thr Pro Ala
 1               5                  10                  15

<210> SEQ ID NO 517
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 517

Cys Tyr Asp Ala Gly Ala Ala Trp Tyr Glu Leu Thr Pro Ala Glu
 1               5                  10                  15

<210> SEQ ID NO 518
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 518

Tyr Asp Ala Gly Ala Ala Trp Tyr Glu Leu Thr Pro Ala Glu Thr
 1               5                  10                  15

<210> SEQ ID NO 519
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 519

Asp Ala Gly Ala Ala Trp Tyr Glu Leu Thr Pro Ala Glu Thr Thr
 1               5                  10                  15

<210> SEQ ID NO 520
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides -continued

```
<400> SEQUENCE: 520

Ala Gly Ala Ala Trp Tyr Glu Leu Thr Pro Ala Glu Thr Thr Val
 1               5                  10                  15

<210> SEQ ID NO 521
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 521

Gly Ala Ala Trp Tyr Glu Leu Thr Ile Pro Ala Glu Thr Thr Val
 1               5                  10                  15

<210> SEQ ID NO 522
<211> LENGTH: 14
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 522

Ala Ala Trp Tyr Glu Leu Thr Pro Ala Glu Thr Thr Val Arg
 1               5                  10

<210> SEQ ID NO 523
<211> LENGTH: 14
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 523

Asp Ala Gly Ala Ala Trp Tyr Glu Leu Thr Pro Ala Glu Thr
 1               5                  10

<210> SEQ ID NO 524
<211> LENGTH: 14
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 524

Ala Gly Ala Ala Trp Tyr Glu Leu Thr Pro Ala Glu Thr Ser
 1               5                  10

<210> SEQ ID NO 525
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 525

Gly Ala Ala Trp Tyr Glu Leu Thr Pro Ala Glu Thr Ser Val Arg
 1               5                  10                  15

<210> SEQ ID NO 526
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      Peptides

<400> SEQUENCE: 526

Ala Ala Trp Tyr Glu Leu Thr Pro Ala Glu Thr Ser Val Arg Leu
 1               5                  10                  15

<210> SEQ ID NO 527
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 527

Phe Trp Ala Lys His Met Trp Asn Phe Ile Ser Gly Ile Gln Tyr
 1               5                  10                  15

<210> SEQ ID NO 528
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 528

Trp Ala Lys His Met Trp Asn Phe Ile Ser Gly Ile Gln Tyr Leu
 1               5                  10                  15

<210> SEQ ID NO 529
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 529

Ala Lys His Met Trp Asn Phe Ile Ser Gly Ile Gln Tyr Leu Ala
 1               5                  10                  15

<210> SEQ ID NO 530
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 530

Lys His Met Trp Asn Phe Ile Ser Gly Ile Gln Tyr Leu Ala Gly
 1               5                  10                  15

<210> SEQ ID NO 531
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 531

His Met Trp Asn Phe Ile Ser Gly Ile Gln Tyr Leu Ala Gly Leu
 1               5                  10                  15
```

<210> SEQ ID NO 532
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 532

Met Trp Asn Phe Ile Ser Gly Ile Gln Tyr Leu Ala Gly Leu Ser
 1               5                  10                  15

<210> SEQ ID NO 533
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 533

Trp Asn Phe Ile Ser Gly Ile Gln Tyr Leu Ala Gly Leu Ser Thr
 1               5                  10                  15

<210> SEQ ID NO 534
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 534

Asn Phe Ile Ser Gly Ile Gln Tyr Leu Ala Gly Leu Ser Thr Leu
 1               5                  10                  15

<210> SEQ ID NO 535
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 535

Phe Ile Ser Gly Ile Gln Tyr Leu Ala Gly Leu Ser Thr Leu Pro
 1               5                  10                  15

<210> SEQ ID NO 536
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 536

Ile Ser Gly Ile Gln Tyr Leu Ala Gly Leu Ser Thr Leu Pro Gly
 1               5                  10                  15

<210> SEQ ID NO 537
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides -continued

<400> SEQUENCE: 537

Ser Gly Ile Gln Tyr Leu Ala Gly Leu Ser Thr Leu Pro Gly Asn
1               5                   10                  15

<210> SEQ ID NO 538
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 538

Gly Ile Gln Tyr Leu Ala Gly Leu Ser Thr Leu Pro Gly Asn Pro
1               5                   10                  15

<210> SEQ ID NO 539
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 539

Ile Gln Tyr Leu Ala Gly Leu Ser Thr Leu Pro Gly Asn Pro Ala
1               5                   10                  15

<210> SEQ ID NO 540
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 540

Gln Tyr Leu Ala Gly Leu Ser Thr Leu Pro Gly Asn Pro Ala Ile
1               5                   10                  15

<210> SEQ ID NO 541
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 541

Tyr Leu Ala Gly Leu Ser Thr Leu Pro Gly Asn Pro Ala Ile Ala
1               5                   10                  15

<210> SEQ ID NO 542
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 542

Leu Ala Gly Leu Ser Thr Leu Pro Gly Asn Pro Ala Ile Ala Ser
1               5                   10                  15

<210> SEQ ID NO 543
<211> LENGTH: 15

```
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 543

Ala Gly Leu Ser Thr Leu Pro Gly Asn Pro Ala Ile Ala Ser Ile
 1               5                  10                  15

<210> SEQ ID NO 544
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 544

Gly Leu Ser Thr Leu Pro Gly Asn Pro Ala Ile Ala Ser Leu Met
 1               5                  10                  15

<210> SEQ ID NO 545
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 545

Leu Ser Thr Leu Pro Gly Asn Pro Ala Ile Ala Ser Leu Met Ala
 1               5                  10                  15

<210> SEQ ID NO 546
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 546

Ser Thr Leu Pro Gly Asn Pro Ala Ile Ala Ser Leu Met Ala Phe
 1               5                  10                  15

<210> SEQ ID NO 547
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 547

Gln Tyr Leu Ala Gly Leu Ser Thr Leu Pro Gly Asn Pro Ala Val
 1               5                  10                  15

<210> SEQ ID NO 548
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 548

Tyr Leu Ala Gly Leu Ser Thr Leu Pro Gly Asn Pro Ala Val Ala
```

-continued

<210> SEQ ID NO 549
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 549

Leu Ala Gly Leu Ser Thr Leu Pro Gly Asn Pro Ala Val Ala Ser
1               5                   10                  15

<210> SEQ ID NO 550
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 550

Ala Gly Leu Ser Thr Leu Pro Gly Asn Pro Ala Val Ala Ser Met
1               5                   10                  15

<210> SEQ ID NO 551
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 551

Gly Leu Ser Thr Leu Pro Gly Asn Pro Ala Val Ala Ser Met Met
1               5                   10                  15

<210> SEQ ID NO 552
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 552

Leu Ser Thr Leu Pro Gly Asn Pro Ala Val Ala Ser Met Met Ala
1               5                   10                  15

<210> SEQ ID NO 553
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 553

Ser Thr Leu Pro Gly Asn Pro Ala Val Ala Ser Met Met Ala Phe
1               5                   10                  15

<210> SEQ ID NO 554
<211> LENGTH: 15
<212> TYPE: PRT
<213> ORGANISM: Artificial Sequence
<220> FEATURE:
<223> OTHER INFORMATION: Description of Artificial Sequence: Synthetic -continued

```
      Peptides

<400> SEQUENCE: 554

Gly Ala Ala Val Gly Ser Ile Gly Leu Gly Lys Val Leu Val Asp
 1               5                  10                  15

<210> SEQ ID NO 555
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 555

Ala Ala Val Gly Ser Ile Gly Leu Gly Lys Val Leu Val Asp Ile
 1               5                  10                  15

<210> SEQ ID NO 556
<211> LENGTH: 14
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 556

Ala Val Gly Ser Ile Gly Leu Gly Lys Val Leu Asp Ile Leu
 1               5                  10

<210> SEQ ID NO 557
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 557

Val Gly Ser Ile Gly Leu Gly Lys Val Leu Val Asp Ile Leu Ala
 1               5                  10                  15

<210> SEQ ID NO 558
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 558

Gly Ser Ile Gly Leu Gly Lys Val Leu Val Asp Ile Leu Ala Gly
 1               5                  10                  15

<210> SEQ ID NO 559
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 559

Ser Ile Gly Leu Gly Lys Val Leu Val Asp Ile Leu Ala Gly Tyr
 1               5                  10                  15

<210> SEQ ID NO 560
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 560

Ile Gly Leu Gly Lys Val Leu Val Asp Ile Leu Ala Gly Tyr Gly
 1               5                  10                  15

<210> SEQ ID NO 561
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 561

Gly Leu Gly Lys Val Leu Val Asp Ile Leu Ala Gly Tyr Gly Ala
 1               5                  10                  15

<210> SEQ ID NO 562
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 562

Leu Gly Lys Val Leu Val Asp Ile Leu Ala Gly Tyr Gly Ala Gly
 1               5                  10                  15

<210> SEQ ID NO 563
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 563

Gly Lys Val Leu Val Asp Ile Leu Ala Gly Tyr Gly Ala Gly Val
 1               5                  10                  15

<210> SEQ ID NO 564
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 564

Lys Val Leu Val Asp Ile Leu Ala Gly Tyr Gly Ala Gly Val Ala
 1               5                  10                  15

<210> SEQ ID NO 565
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 565
```

-continued

Val Leu Val Asp Ile Leu Ala Gly Tyr Gly Ala Gly Val Ala Gly
 1               5                  10                  15

<210> SEQ ID NO 566
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 566

Leu Val Asp Ile Leu Ala Gly Tyr Gly Ala Gly Val Ala Gly Ala
 1               5                  10                  15

<210> SEQ ID NO 567
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 567

Val Asp Ile Leu Ala Gly Tyr Gly Ala Gly Val Ala Gly Ala Leu
 1               5                  10                  15

<210> SEQ ID NO 568
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 568

Asp Ile Leu Ala Gly Tyr Gly Ala Gly Val Ala Gly Ala Leu Val
 1               5                  10                  15

<210> SEQ ID NO 569
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 569

Ile Leu Ala Gly Tyr Gly Ala Gly Val Ala Gly Ala Leu Val Ala
 1               5                  10                  15

<210> SEQ ID NO 570
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 570

Leu Ala Gly Tyr Gly Ala Gly Val Ala Gly Ala Leu Val Ala Phe
 1               5                  10                  15

<210> SEQ ID NO 571
<211> LENGTH: 15
<212> TYPE: PRT
<213> ORGANISM: Artificial Sequence
<220> FEATURE:

```
<223> OTHER INFORMATION: Description of Artificial Sequence: Synthetic
      Peptides

<400> SEQUENCE: 571

Ala Gly Tyr Gly Ala Gly Val Ala Gly Ala Leu Val Ala Phe Lys
 1               5                  10                  15

<210> SEQ ID NO 572
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 572

Gly Tyr Gly Ala Gly Val Ala Gly Ala Leu Val Ala Phe Lys Ile
 1               5                  10                  15

<210> SEQ ID NO 573
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 573

Tyr Gly Ala Gly Val Ala Gly Ala Leu Val Ala Phe Lys Ile Met
 1               5                  10                  15

<210> SEQ ID NO 574
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 574

Gly Ala Gly Val Ala Gly Ala Leu Val Ala Phe Lys Ile Met Ser
 1               5                  10                  15

<210> SEQ ID NO 575
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 575

Ala Gly Val Ala Gly Ala Leu Val Ala Phe Lys Ile Met Ser Gly
 1               5                  10                  15

<210> SEQ ID NO 576
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 576

Gly Val Ala Gly Ala Leu Val Ala Phe Lys Ile Met Ser Gly Glu
 1               5                  10                  15
```

<210> SEQ ID NO 577
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 577

Gly Tyr Gly Ala Gly Val Ala Gly Ala Leu Val Ala Phe Lys Val
 1               5                  10                  15

<210> SEQ ID NO 578
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 578

Tyr Gly Ala Gly Val Ala Gly Ala Leu Val Ala Phe Lys Val Met
 1               5                  10                  15

<210> SEQ ID NO 579
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 579

Gly Ala Gly Val Ala Gly Ala Leu Val Ala Phe Lys Val Met Ser
 1               5                  10                  15

<210> SEQ ID NO 580
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 580

Ala Gly Val Ala Gly Ala Leu Val Ala Phe Lys Val Met Ser Gly
 1               5                  10                  15

<210> SEQ ID NO 581
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 581

Gly Val Ala Gly Ala Leu Val Ala Phe Lys Val Met Ser Gly Glu
 1               5                  10                  15

<210> SEQ ID NO 582
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 582

Gly Lys Val Leu Val Asp Ile Leu Ala Gly Tyr Gly Ala Gly Ile
1               5                   10                  15

<210> SEQ ID NO 583
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 583

Lys Val Leu Val Asp Ile Leu Ala Gly Tyr Gly Ala Gly Ile Ser
1               5                   10                  15

<210> SEQ ID NO 584
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 584

Val Leu Val Asp Ile Leu Ala Gly Tyr Gly Ala Gly Ile Ser Gly
1               5                   10                  15

<210> SEQ ID NO 585
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 585

Leu Val Asp Ile Leu Ala Gly Tyr Gly Ala Gly Ile Ser Gly Ala
1               5                   10                  15

<210> SEQ ID NO 586
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 586

Val Asp Ile Leu Ala Gly Tyr Gly Ala Gly Ile Ser Gly Ala Leu
1               5                   10                  15

<210> SEQ ID NO 587
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 587

Asp Ile Leu Ala Gly Tyr Gly Ala Gly Ile Ser Gly Ala Leu Val
1               5                   10                  15

<210> SEQ ID NO 588
<211> LENGTH: 15
<212> TYPE: PRT
<213> ORGANISM: Artificial Sequence

```
<220> FEATURE:
<223> OTHER INFORMATION: Description of Artificial Sequence: Synthetic
      Peptides

<400> SEQUENCE: 588

Ile Leu Ala Gly Tyr Gly Ala Gly Ile Ser Gly Ala Leu Val Ala
 1               5                  10                  15

<210> SEQ ID NO 589
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 589

Leu Ala Gly Tyr Gly Ala Gly Ile Ser Gly Ala Leu Val Ala Phe
 1               5                  10                  15

<210> SEQ ID NO 590
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 590

Ala Gly Tyr Gly Ala Gly Ile Ser Gly Ala Leu Val Ala Phe Lys
 1               5                  10                  15

<210> SEQ ID NO 591
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 591

Gly Tyr Gly Ala Gly Ile Ser Gly Ala Leu Val Ala Phe Lys Ile
 1               5                  10                  15

<210> SEQ ID NO 592
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 592

Tyr Gly Ala Gly Ile Ser Gly Ala Leu Val Ala Phe Lys Ile Met
 1               5                  10                  15

<210> SEQ ID NO 593
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 593

Gly Ala Gly Ile Ser Gly Ala Leu Val Ala Phe Lys Ile Met Ser
 1               5                  10                  15
```

```
<210> SEQ ID NO 594
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 594

Ala Gly Ile Ser Gly Ala Leu Val Ala Phe Lys Ile Met Ser Gly
  1               5                  10                  15

<210> SEQ ID NO 595
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 595

Gly Ile Ser Gly Ala Leu Val Ala Phe Lys Ile Met Ser Gly Glu
  1               5                  10                  15

<210> SEQ ID NO 596
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 596

Val Asn Leu Leu Pro Ala Ile Leu Ser Pro Gly Ala Leu Val Val
  1               5                  10                  15

<210> SEQ ID NO 597
<211> LENGTH: 14
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 597

Asn Leu Leu Pro Ala Ile Leu Ser Pro Gly Ala Leu Trp Gly
  1               5                  10

<210> SEQ ID NO 598
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 598

Leu Leu Pro Ala Ile Leu Ser Pro Gly Ala Leu Val Val Gly Val
  1               5                  10                  15

<210> SEQ ID NO 599
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides
```

```
<400> SEQUENCE: 599

Leu Pro Ala Ile Leu Ser Pro Gly Ala Leu Val Val Gly Val Val
 1               5                  10                  15

<210> SEQ ID NO 600
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 600

Pro Ala Ile Leu Ser Pro Gly Ala Leu Val Val Gly Val Val Cys
 1               5                  10                  15

<210> SEQ ID NO 601
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 601

Ala Ile Leu Ser Pro Gly Ala Leu Val Val Gly Val Val Cys Ala
 1               5                  10                  15

<210> SEQ ID NO 602
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 602

Ile Leu Ser Pro Gly Ala Leu Val Val Gly Val Val Cys Ala Ala
 1               5                  10                  15

<210> SEQ ID NO 603
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 603

Leu Ser Pro Gly Ala Leu Val Val Gly Val Val Cys Ala Ala Ile
 1               5                  10                  15

<210> SEQ ID NO 604
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 604

Ser Pro Gly Ala Leu Val Val Gly Val Val Cys Ala Ala Ile Leu
 1               5                  10                  15

<210> SEQ ID NO 605
<211> LENGTH: 15
<212> TYPE: PRT
```

<213> ORGANISM: Artificial Sequence
<220> FEATURE:
<223> OTHER INFORMATION: Description of Artificial Sequence: Synthetic
      Peptides

<400> SEQUENCE: 605

Pro Gly Ala Leu Val Val Gly Val Val Cys Ala Ala Ile Leu Arg
 1               5                  10                  15

<210> SEQ ID NO 606
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 606

Gly Ala Leu Val Val Gly Val Val Cys Ala Ala Ile Leu Arg Arg
 1               5                  10                  15

<210> SEQ ID NO 607
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 607

Ala Leu Val Val Gly Val Val Cys Ala Ala Ile Leu Arg Arg His
 1               5                  10                  15

<210> SEQ ID NO 608
<211> LENGTH: 14
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 608

Leu Val Val Gly Trp Cys Ala Ala Ile Leu Arg Arg His Val
 1               5                  10

<210> SEQ ID NO 609
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 609

Val Val Gly Val Val Cys Ala Ala Ile Leu Arg Arg His Val Gly
 1               5                  10                  15

<210> SEQ ID NO 610
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 610

Val Gly Val Val Cys Ala Ala Ile Leu Arg Arg His Val Gly Pro
 1               5                  10                  15

-continued

<210> SEQ ID NO 611
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 611

Gly Val Val Cys Ala Ala Ile Leu Arg Arg His Val Gly Pro Gly
 1               5                  10                  15

<210> SEQ ID NO 612
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 612

Val Val Cys Ala Ala Ile Leu Arg Arg His Val Gly Pro Gly Glu
 1               5                  10                  15

<210> SEQ ID NO 613
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 613

Val Cys Ala Ala Ile Leu Arg Arg His Val Gly Pro Gly Glu Gly
 1               5                  10                  15

<210> SEQ ID NO 614
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 614

Cys Ala Ala Ile Leu Arg Arg His Val Gly Pro Gly Glu Gly Ala
 1               5                  10                  15

<210> SEQ ID NO 615
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 615

Ala Ala Ile Leu Arg Arg His Val Gly Pro Gly Glu Gly Ala Val
 1               5                  10                  15

<210> SEQ ID NO 616
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides -continued

```
<400> SEQUENCE: 616

Ala Ile Leu Arg Arg His Val Gly Pro Gly Glu Gly Ala Val Gln
 1               5                  10                  15

<210> SEQ ID NO 617
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 617

Ile Leu Arg Arg His Val Gly Pro Gly Glu Gly Ala Val Gln Trp
 1               5                  10                  15

<210> SEQ ID NO 618
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 618

Leu Arg Arg His Val Gly Pro Gly Glu Gly Ala Val Gln Trp Met
 1               5                  10                  15

<210> SEQ ID NO 619
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 619

Arg Arg His Val Gly Pro Gly Glu Gly Ala Val Gln Trp Met Asn
 1               5                  10                  15

<210> SEQ ID NO 620
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 620

Arg His Val Gly Pro Gly Glu Gly Ala Val Gln Trp Met Asn Arg
 1               5                  10                  15

<210> SEQ ID NO 621
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 621

His Val Gly Pro Gly Glu Gly Ala Val Gln Trp Met Asn Arg Leu
 1               5                  10                  15

<210> SEQ ID NO 622
<211> LENGTH: 15
```

<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 622

Val Gly Pro Gly Glu Gly Ala Val Gln Trp Met Asn Arg Leu Ile
 1               5                  10                  15

<210> SEQ ID NO 623
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 623

Gly Pro Gly Glu Gly Ala Val Gln Trp Met Asn Arg Leu Ile Ala
 1               5                  10                  15

<210> SEQ ID NO 624
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 624

Pro Gly Glu Gly Ala Val Gln Trp Met Asn Arg Leu Ile Ala Phe
 1               5                  10                  15

<210> SEQ ID NO 625
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 625

Gly Glu Gly Ala Val Gln Trp Met Asn Arg Leu Ile Ala Phe Ala
 1               5                  10                  15

<210> SEQ ID NO 626
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 626

Glu Gly Ala Val Gln Trp Met Asn Arg Leu Ile Ala Phe Ala Ser
 1               5                  10                  15

<210> SEQ ID NO 627
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 627

Gly Ala Val Gln Trp Met Asn Arg Leu Ile Ala Phe Ala Ser Arg

```
                1               5                  10                  15

<210> SEQ ID NO 628
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 628

Ala Val Gln Trp Met Asn Arg Leu Ile Ala Phe Ala Ser Arg Gly
 1               5                  10                  15

<210> SEQ ID NO 629
<211> LENGTH: 16
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 629

Val Gln Trp Met Asn Arg Leu Ile Ala Phe Ala Ser Arg Asn Gly Asn
 1               5                  10                  15

<210> SEQ ID NO 630
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 630

Gln Trp Met Asn Arg Leu Ile Ala Phe Ala Ser Arg Gly Asn His
 1               5                  10                  15

<210> SEQ ID NO 631
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 631

Trp Met Asn Arg Leu Ile Ala Phe Ala Ser Arg Gly Asn His Val
 1               5                  10                  15

<210> SEQ ID NO 632
<211> LENGTH: 14
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 632

Met Asn Arg Leu Ala Phe Ala Ser Arg Gly Asn His Val Ser
 1               5                  10

<210> SEQ ID NO 633
<211> LENGTH: 15
<212> TYPE: PRT
<213> ORGANISM: Artificial Sequence
<220> FEATURE:
<223> OTHER INFORMATION: Description of Artificial Sequence:  Synthetic
```

```
                       Peptides

<400> SEQUENCE: 633

Asn Arg Leu Ile Ala Phe Ala Ser Arg Gly Asn His Val Ser Pro
 1               5                  10                  15

<210> SEQ ID NO 634
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 634

Arg Leu Ile Ala Phe Ala Ser Arg Gly Asn His Val Ser Pro Thr
 1               5                  10                  15

<210> SEQ ID NO 635
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 635

Leu Ile Ala Phe Ala Ser Arg Gly Asn His Val Ser Pro Thr His
 1               5                  10                  15

<210> SEQ ID NO 636
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 636

Ile Ala Phe Ala Ser Arg Gly Asn His Val Ser Pro Thr His Tyr
 1               5                  10                  15

<210> SEQ ID NO 637
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 637

Ala Phe Ala Ser Arg Gly Asn His Val Ser Pro Thr His Tyr Val
 1               5                  10                  15

<210> SEQ ID NO 638
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 638

Val Asn Leu Leu Pro Gly Ile Leu Ser Pro Gly Ala Leu Val Val
 1               5                  10                  15

<210> SEQ ID NO 639
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 639

Asn Leu Leu Pro Gly Ile Leu Ser Pro Gly Ala Leu Val Val Gly
 1               5                  10                  15

<210> SEQ ID NO 640
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 640

Leu Leu Pro Gly Ile Leu Ser Pro Gly Ala Leu Val Val Gly Val
 1               5                  10                  15

<210> SEQ ID NO 641
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 641

Leu Pro Gly Ile Leu Ser Pro Gly Ala Leu Val Val Gly Val Ile
 1               5                  10                  15

<210> SEQ ID NO 642
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 642

Pro Gly Ile Leu Ser Pro Gly Ala Leu Val Val Gly Val Ile Cys
 1               5                  10                  15

<210> SEQ ID NO 643
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 643

Gly Ile Leu Ser Pro Gly Ala Leu Val Val Gly Val Ile Cys Ala
 1               5                  10                  15

<210> SEQ ID NO 644
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 644
```

```
Ile Leu Ser Pro Gly Ala Leu Val Val Gly Val Ile Cys Ala Ala
 1               5                  10                  15

<210> SEQ ID NO 645
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 645

Leu Ser Pro Gly Ala Leu Val Val Gly Val Ile Cys Ala Ala Ile
 1               5                  10                  15

<210> SEQ ID NO 646
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 646

Ser Pro Gly Ala Leu Val Val Gly Val Ile Cys Ala Ala Ile Leu
 1               5                  10                  15

<210> SEQ ID NO 647
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 647

Pro Gly Ala Leu Val Val Gly Val Ile Cys Ala Ala Ile Leu Arg
 1               5                  10                  15

<210> SEQ ID NO 648
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 648

Gly Ala Leu Val Val Gly Val Ile Cys Ala Ala Ile Leu Arg Arg
 1               5                  10                  15

<210> SEQ ID NO 649
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 649

Ala Leu Val Val Gly Val Ile Cys Ala Ala Ile Leu Arg Arg His
 1               5                  10                  15

<210> SEQ ID NO 650
<211> LENGTH: 15
<212> TYPE: PRT
<213> ORGANISM: Artificial Sequence
<220> FEATURE:
```

```
<223> OTHER INFORMATION: Description of Artificial Sequence:  Synthetic
      Peptides

<400> SEQUENCE: 650

Leu Val Val Gly Val Ile Cys Ala Ala Ile Leu Arg Arg His Val
 1               5                  10                  15

<210> SEQ ID NO 651
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 651

Val Val Gly Val Ile Cys Ala Ala Ile Leu Arg Arg His Val Gly
 1               5                  10                  15

<210> SEQ ID NO 652
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 652

Val Gly Val Ile Cys Ala Ala Ile Leu Arg Arg His Val Gly Pro
 1               5                  10                  15

<210> SEQ ID NO 653
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 653

Gly Val Ile Cys Ala Ala Ile Leu Arg Arg His Val Gly Pro Gly
 1               5                  10                  15

<210> SEQ ID NO 654
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 654

Val Ile Cys Ala Ala Ile Leu Arg Arg His Val Gly Pro Gly Glu
 1               5                  10                  15

<210> SEQ ID NO 655
<211> LENGTH: 14
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 655

Cys Ala Ala Ile Leu Arg Arg His Val Gly Pro Gly Glu Gly
 1               5                  10
```

```
<210> SEQ ID NO 656
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 656

Met Asn Arg Leu Ile Ala Phe Ala Ser Arg Gly Asn His Val Ala
 1               5                  10                  15

<210> SEQ ID NO 657
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 657

Asn Arg Leu Ile Ala Phe Ala Ser Arg Gly Asn His Val Ala Pro
 1               5                  10                  15

<210> SEQ ID NO 658
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 658

Arg Leu Ile Ala Phe Ala Ser Arg Gly Asn His Val Ala Pro Thr
 1               5                  10                  15

<210> SEQ ID NO 659
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 659

Leu Ile Ala Phe Ala Ser Arg Gly Asn His Val Ala Pro Thr His
 1               5                  10                  15

<210> SEQ ID NO 660
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 660

Ile Ala Phe Ala Ser Arg Gly Asn His Val Ala Pro Thr His Tyr
 1               5                  10                  15

<210> SEQ ID NO 661
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 661
```

Ala Phe Ala Ser Arg Gly Asn His Val Ala Pro Thr His Tyr Val
1               5                   10                  15

<210> SEQ ID NO 662
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 662

Lys Gly Gly Arg Lys Pro Ala Arg Leu Ile Val Phe Pro Asp Leu
1               5                   10                  15

<210> SEQ ID NO 663
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 663

Gly Gly Arg Lys Pro Ala Arg Leu Ile Val Phe Pro Asp Leu Gly
1               5                   10                  15

<210> SEQ ID NO 664
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 664

Gly Arg Lys Pro Ala Arg Leu Ile Val Phe Pro Asp Leu Gly Val
1               5                   10                  15

<210> SEQ ID NO 665
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 665

Arg Lys Pro Ala Arg Leu Ile Val Phe Pro Asp Leu Gly Val Arg
1               5                   10                  15

<210> SEQ ID NO 666
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 666

Lys Pro Ala Arg Leu Ile Val Phe Pro Asp Leu Gly Val Arg Val
1               5                   10                  15

<210> SEQ ID NO 667
<211> LENGTH: 15
<212> TYPE: PRT
<213> ORGANISM: Artificial Sequence

```
<220> FEATURE:
<223> OTHER INFORMATION: Description of Artificial Sequence: Synthetic
      Peptides

<400> SEQUENCE: 667

Pro Ala Arg Leu Ile Val Phe Pro Asp Leu Gly Val Arg Val Cys
1               5                   10                  15

<210> SEQ ID NO 668
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 668

Ala Arg Leu Ile Val Phe Pro Asp Leu Gly Val Arg Val Cys Glu
1               5                   10                  15

<210> SEQ ID NO 669
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 669

Arg Leu Ile Val Phe Pro Asp Leu Gly Val Arg Val Cys Glu Lys
1               5                   10                  15

<210> SEQ ID NO 670
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 670

Leu Ile Val Phe Pro Asp Leu Gly Val Arg Val Cys Glu Lys Met
1               5                   10                  15

<210> SEQ ID NO 671
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 671

Ile Val Phe Pro Asp Leu Gly Val Arg Val Cys Glu Lys Met Ala
1               5                   10                  15

<210> SEQ ID NO 672
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 672

Val Phe Pro Asp Leu Gly Val Arg Val Cys Glu Lys Met Ala Leu
1               5                   10                  15
```

```
<210> SEQ ID NO 673
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 673

Phe Pro Asp Leu Gly Val Arg Val Cys Glu Lys Met Ala Leu Tyr
 1               5                  10                  15

<210> SEQ ID NO 674
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 674

Pro Asp Leu Gly Val Arg Val Cys Glu Lys Met Ala Leu Tyr Asp
 1               5                  10                  15

<210> SEQ ID NO 675
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 675

Asp Leu Gly Val Arg Val Cys Glu Lys Met Ala Leu Tyr Asp Val
 1               5                  10                  15

<210> SEQ ID NO 676
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 676

Lys Gly Gly Lys Lys Ala Ala Arg Leu Ile Val Tyr Pro Asp Leu
 1               5                  10                  15

<210> SEQ ID NO 677
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 677

Gly Gly Lys Lys Ala Ala Arg Leu Ile Val Tyr Pro Asp Leu Gly
 1               5                  10                  15

<210> SEQ ID NO 678
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides
```

-continued

```
<400> SEQUENCE: 678

Gly Lys Lys Ala Ala Arg Leu Ile Val Tyr Pro Asp Leu Gly Val
 1               5                  10                  15

<210> SEQ ID NO 679
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 679

Lys Lys Ala Ala Arg Leu Ile Val Tyr Pro Asp Leu Gly Val Arg
 1               5                  10                  15

<210> SEQ ID NO 680
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 680

Lys Ala Ala Arg Leu Ile Val Tyr Pro Asp Leu Gly Val Arg Val
 1               5                  10                  15

<210> SEQ ID NO 681
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 681

Ala Ala Arg Leu Ile Val Tyr Pro Asp Leu Gly Val Arg Val Cys
 1               5                  10                  15

<210> SEQ ID NO 682
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 682

Ala Arg Leu Ile Val Tyr Pro Asp Leu Gly Val Arg Val Cys Glu
 1               5                  10                  15

<210> SEQ ID NO 683
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 683

Arg Leu Ile Val Tyr Pro Asp Leu Gly Val Arg Val Cys Glu Lys
 1               5                  10                  15

<210> SEQ ID NO 684
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      Peptides

<400> SEQUENCE: 684

Leu Ile Val Tyr Pro Asp Leu Gly Val Arg Val Cys Glu Lys Met
 1               5                  10                  15

<210> SEQ ID NO 685
<211> LENGTH: 14
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 685

Ile Val Pro Asp Leu Gly Val Arg Val Cys Glu Lys Met Ala
 1               5                  10

<210> SEQ ID NO 686
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 686

Val Tyr Pro Asp Leu Gly Val Arg Val Cys Glu Lys Met Ala Leu
 1               5                  10                  15

<210> SEQ ID NO 687
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 687

Tyr Pro Asp Leu Gly Val Arg Val Cys Glu Lys Met Ala Leu Tyr
 1               5                  10                  15

<210> SEQ ID NO 688
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 688

Ala Gln Pro Gly Tyr Pro Trp Pro Leu Tyr Gly Asn Glu Gly Leu
 1               5                  10                  15

<210> SEQ ID NO 689
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 689

Gly Gln Pro Gly Tyr Pro Trp Pro Leu Tyr Gly Asn Glu Gly Leu
 1               5                  10                  15
```

<210> SEQ ID NO 690
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 690

Ala Phe Cys Ser Ala Met Tyr Val Gly Asp Leu Cys Gly Ser Val
 1               5                  10                  15

<210> SEQ ID NO 691
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 691

Ala Phe Cys Ser Ala Leu Tyr Val Gly Asp Leu Cys Gly Ser Val
 1               5                  10                  15

<210> SEQ ID NO 692
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 692

Glu Thr Val Gln Asp Cys Asn Cys Ser Ile Tyr Pro Gly His Val
 1               5                  10                  15

<210> SEQ ID NO 693
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 693

Glu Phe Val Gln Asp Cys Asn Cys Ser Ile Tyr Pro Gly His Val
 1               5                  10                  15

<210> SEQ ID NO 694
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 694

Gly Val Leu Ala Gly Leu Ala Tyr Tyr Ser Met Val Gly Asn Trp
 1               5                  10                  15

<210> SEQ ID NO 695
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides -continued

<400> SEQUENCE: 695

Gly Val Leu Phe Gly Leu Ala Tyr Phe Ser Met Val Gly Asn Trp
1               5                   10                  15

<210> SEQ ID NO 696
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 696

Asp Gln Arg Pro Tyr Cys Trp His Tyr Ala Pro Arg Pro Cys Gly
1               5                   10                  15

<210> SEQ ID NO 697
<211> LENGTH: 14
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 697

Asp Gln Arg Pro Tyr Cys Trp Tyr Pro Pro Arg Pro Cys Gly
1               5                   10

<210> SEQ ID NO 698
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 698

Thr Cys Pro Thr Asp Cys Phe Arg Lys His Pro Glu Ala Thr Tyr
1               5                   10                  15

<210> SEQ ID NO 699
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 699

Tyr Thr Lys Cys Gly Ser Gly Pro Trp Leu Thr Pro Arg Cys Leu
1               5                   10                  15

<210> SEQ ID NO 700
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 700

Leu Asn Ala Ala Cys Asn Trp Thr Arg Gly Glu Arg Cys Asp Leu
1               5                   10                  15

<210> SEQ ID NO 701
<211> LENGTH: 15

-continued

```
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 701

Leu Asn Ala Ala Cys Asn Phe Thr Arg Gly Glu Arg Cys Asp Leu
 1               5                  10                  15

<210> SEQ ID NO 702
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 702

Ile Ala Gln Ala Glu Ala Ala Leu Glu Asn Leu Val Val Leu Asn
 1               5                  10                  15

<210> SEQ ID NO 703
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 703

Ile Ala Gln Ala Glu Ala Ala Leu Glu Lys Leu Val Val Leu His
 1               5                  10                  15

<210> SEQ ID NO 704
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 704

Thr Arg Val Pro Tyr Phe Val Arg Ala Gln Gly Leu Ile Arg Ala
 1               5                  10                  15

<210> SEQ ID NO 705
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 705

Thr Arg Val Pro Tyr Phe Val Arg Ala His Gly Leu Ile Arg Ala
 1               5                  10                  15

<210> SEQ ID NO 706
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 706

His Ala Gly Leu Arg Asp Leu Ala Val Ala Val Glu Pro Val Val
```

```
                1               5                  10                  15
```

<210> SEQ ID NO 707
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 707

```
Ala Ala Gly Leu Arg Asp Leu Ala Val Ala Val Glu Pro Ile Val
  1               5                  10                  15
```

<210> SEQ ID NO 708
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 708

```
Ile Thr Trp Gly Ala Asp Thr Ala Ala Cys Gly Asp Ile Ile Leu
  1               5                  10                  15
```

<210> SEQ ID NO 709
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 709

```
Ile Thr Trp Gly Ala Glu Thr Ala Ala Cys Gly Asp Ile Ile Leu
  1               5                  10                  15
```

<210> SEQ ID NO 710
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 710

```
Gly Gln Gly Trp Arg Leu Leu Ala Pro Ile Thr Ala Tyr Ser Gln
  1               5                  10                  15
```

<210> SEQ ID NO 711
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 711

```
Thr Ala Tyr Ser Gln Gln Thr Arg Gly Leu Leu Gly Cys Ile Ile
  1               5                  10                  15
```

<210> SEQ ID NO 712
<211> LENGTH: 15
<212> TYPE: PRT
<213> ORGANISM: Artificial Sequence
<220> FEATURE:
<223> OTHER INFORMATION: Description of Artificial Sequence: Synthetic -continued

```
      Peptides

<400> SEQUENCE: 712

Thr Ala Tyr Ser Gln Gln Thr Arg Gly Leu Leu Gly Cys Ile Val
 1               5                  10                  15

<210> SEQ ID NO 713
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 713

Gly Cys Ile Ile Thr Ser Leu Thr Gly Arg Asp Lys Asn Gln Val
 1               5                  10                  15

<210> SEQ ID NO 714
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 714

Gly Cys Ile Val Val Ser Met Thr Gly Arg Asp Lys Thr Gln Val
 1               5                  10                  15

<210> SEQ ID NO 715
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 715

Val Asn Gly Val Cys Trp Thr Val Tyr His Gly Ala Gly Ser Lys
 1               5                  10                  15

<210> SEQ ID NO 716
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 716

Lys Gly Pro Ile Thr Gln Met Tyr Thr Asn Val Asp Gln Asp Leu
 1               5                  10                  15

<210> SEQ ID NO 717
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 717

Lys Gly Pro Ile Thr Gln Met Tyr Ser Ser Ala Glu Gln Asp Leu
 1               5                  10                  15

<210> SEQ ID NO 718
```

```
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 718

Gly Asp Ser Arg Gly Ser Leu Leu Ser Pro Arg Pro Val Ser Tyr
 1               5                  10                  15

<210> SEQ ID NO 719
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 719

Gly Asp Ser Arg Gly Ala Leu Leu Ser Pro Arg Pro Val Ser Tyr
 1               5                  10                  15

<210> SEQ ID NO 720
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 720

Ser Tyr Leu Lys Gly Ser Ser Gly Gly Pro Leu Leu Cys Pro Ser
 1               5                  10                  15

<210> SEQ ID NO 721
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 721

Ser Tyr Leu Lys Gly Ser Ser Gly Gly Pro Val Leu Cys Pro Ser
 1               5                  10                  15

<210> SEQ ID NO 722
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 722

Gly His Ala Val Gly Ile Phe Arg Ala Ala Val Cys Thr Arg Gly
 1               5                  10                  15

<210> SEQ ID NO 723
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 723
```

-continued

Gly Val Asp Pro Asn Ile Arg Thr Gly Val Arg Thr Ile Thr Thr
1               5                   10                  15

<210> SEQ ID NO 724
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 724

Val Pro His Pro Asn Ile Glu Glu Val Ala Leu Ser Asn Thr Gly
1               5                   10                  15

<210> SEQ ID NO 725
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 725

Thr Gly Glu Ile Pro Phe Tyr Gly Lys Ala Ile Pro Ile Glu Val
1               5                   10                  15

<210> SEQ ID NO 726
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 726

Thr Gly Glu Ile Pro Phe Tyr Gly Lys Ala Ile Pro Leu Glu Val
1               5                   10                  15

<210> SEQ ID NO 727
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 727

Pro Thr Ser Gly Asp Val Val Val Ala Thr Asp Ala Leu Met
1               5                   10                  15

<210> SEQ ID NO 728
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 728

Gln Thr Val Asp Phe Ser Leu Asp Pro Thr Phe Thr Ile Glu Thr
1               5                   10                  15

<210> SEQ ID NO 729
<211> LENGTH: 15
<212> TYPE: PRT
<213> ORGANISM: Artificial Sequence
<220> FEATURE:

<223> OTHER INFORMATION: Description of Artificial Sequence: Synthetic
      Peptides

<400> SEQUENCE: 729

Thr Leu His Gly Pro Thr Pro Leu Leu Tyr Arg Leu Gly Ala Val
 1               5                  10                  15

<210> SEQ ID NO 730
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 730

Val Gln Asn Glu Val Thr Leu Thr His Pro Ile Thr Lys Tyr Ile
 1               5                  10                  15

<210> SEQ ID NO 731
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 731

Leu Tyr Arg Glu Phe Asp Glu Met Glu Glu Cys Ala Ser His Leu
 1               5                  10                  15

<210> SEQ ID NO 732
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 732

Thr Thr Leu Leu Phe Asn Ile Leu Gly Gly Trp Val Ala Ala Gln
 1               5                  10                  15

<210> SEQ ID NO 733
<211> LENGTH: 14
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 733

Thr Thr Leu Leu Asn Ile Leu Gly Gly Trp Leu Ala Ala Gln
 1               5                  10

<210> SEQ ID NO 734
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 734

Pro Ser Ala Ala Ser Ala Phe Val Gly Ala Gly Ile Ala Gly Ala
 1               5                  10                  15

```
<210> SEQ ID NO 735
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 735

Pro Ser Ala Ala Thr Gly Phe Val Val Ser Gly Leu Ala Gly Ala
  1               5                  10                  15

<210> SEQ ID NO 736
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 736

Thr Pro Cys Ser Gly Ser Trp Leu Arg Asp Val Trp Asp Trp Ile
  1               5                  10                  15

<210> SEQ ID NO 737
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 737

Val Ala Ala Glu Glu Tyr Val Glu Val Thr Arg Val Gly Asp Phe
  1               5                  10                  15

<210> SEQ ID NO 738
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 738

Val Ala Ala Glu Glu Tyr Ala Glu Val Thr Arg His Gly Asp Phe
  1               5                  10                  15

<210> SEQ ID NO 739
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 739

Phe Phe Thr Glu Val Asp Gly Val Arg Leu His Arg Tyr Ala Pro
  1               5                  10                  15

<210> SEQ ID NO 740
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 740
```

Phe Phe Thr Glu Leu Asp Gly Val Arg Leu His Arg Tyr Ala Pro
 1               5                   10                  15

<210> SEQ ID NO 741
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 741

Phe Phe Thr Trp Val Asp Gly Val Gln Ile His Arg Tyr Ala Pro
 1               5                   10                  15

<210> SEQ ID NO 742
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 742

Phe Phe Thr Trp Leu Asp Gly Val Gln Ile His Arg Tyr Ala Pro
 1               5                   10                  15

<210> SEQ ID NO 743
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 743

Tyr Leu Val Gly Ser Gln Leu Pro Cys Glu Pro Glu Pro Asp Val
 1               5                   10                  15

<210> SEQ ID NO 744
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 744

Tyr Leu Val Gly Ser Gln Leu Pro Cys Asp Pro Glu Pro Asp Val
 1               5                   10                  15

<210> SEQ ID NO 745
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 745

Leu Pro Thr Trp Ala Arg Pro Asp Tyr Asn Pro Pro Leu Leu Glu
 1               5                   10                  15

<210> SEQ ID NO 746
<211> LENGTH: 15
<212> TYPE: PRT
<213> ORGANISM: Artificial Sequence

```
<220> FEATURE:
<223> OTHER INFORMATION: Description of Artificial Sequence:  Synthetic
      Peptides

<400> SEQUENCE: 746

Ala Ser Leu Arg Gln Lys Lys Val Thr Phe Asp Arg Leu Gln Val
 1               5                  10                  15

<210> SEQ ID NO 747
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 747

Ala Ser Leu Arg Ala Lys Lys Val Thr Phe Asp Arg Leu Gln Val
 1               5                  10                  15

<210> SEQ ID NO 748
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 748

His Ile Arg Ser Val Trp Lys Asp Leu Leu Glu Asp Thr Glu Thr
 1               5                  10                  15

<210> SEQ ID NO 749
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 749

Ile Asp Thr Thr Ile Met Ala Lys Asn Glu Val Phe Cys Val Gln
 1               5                  10                  15

<210> SEQ ID NO 750
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 750

Val Met Gly Ser Ser Tyr Gly Phe Gln Tyr Ser Pro Gly Gln Arg
 1               5                  10                  15

<210> SEQ ID NO 751
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 751

Asp Cys Thr Met Leu Val Cys Gly Asp Asp Leu Val Val Ile Cys
 1               5                  10                  15
```

```
<210> SEQ ID NO 752
<211> LENGTH: 14
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 752

Asp Cys Thr Met Leu Val Asn Gly Asp Asp Leu Trp Ile Cys
 1               5                  10

<210> SEQ ID NO 753
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 753

Asp Pro Thr Met Leu Val Cys Gly Asp Asp Leu Val Val Ile Cys
 1               5                  10                  15

<210> SEQ ID NO 754
<211> LENGTH: 14
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 754

Asp Pro Thr Met Leu Val Asn Gly Asp Asp Leu Trp Ile Cys
 1               5                  10

<210> SEQ ID NO 755
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 755

Leu Trp Ala Arg Met Ile Leu Met Thr His Phe Phe Ser Ile Leu
 1               5                  10                  15

<210> SEQ ID NO 756
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 756

Leu Trp Val Arg Met Val Leu Met Thr His Phe Phe Ser Ile Leu
 1               5                  10                  15

<210> SEQ ID NO 757
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides
```

-continued

```
<400> SEQUENCE: 757

Asp Leu Pro Gln Ile Ile Glu Arg Leu His Gly Leu Ser Ala Phe
 1               5                  10                  15

<210> SEQ ID NO 758
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 758

Asp Leu Pro Gln Ile Ile Gln Arg Leu His Gly Leu Ser Ala Phe
 1               5                  10                  15

<210> SEQ ID NO 759
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 759

Ala Val Arg Thr Lys Leu Lys Leu Thr Pro Ile Pro Ala Ala Ser
 1               5                  10                  15

<210> SEQ ID NO 760
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 760

Ala Val Arg Thr Lys Leu Lys Leu Thr Pro Leu Pro Ala Ala Ser
 1               5                  10                  15

<210> SEQ ID NO 761
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 761

Ser Gly Gly Asp Ile Tyr His Ser Leu Ser Arg Ala Arg Pro Arg
 1               5                  10                  15

<210> SEQ ID NO 762
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 762

Ser Gly Gly Asp Ile Tyr His Ser Val Ser Arg Ala Arg Pro Arg
 1               5                  10                  15

<210> SEQ ID NO 763
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      Peptides

<400> SEQUENCE: 763

Trp Gly Glu Asn Glu Thr Asp Val Leu Leu Leu Asn Asn Thr Arg
 1               5                  10                  15

<210> SEQ ID NO 764
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 764

Gly Glu Asn Glu Thr Asp Val Leu Leu Leu Asn Asn Thr Arg Pro
 1               5                  10                  15

<210> SEQ ID NO 765
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 765

Trp Phe Gly Cys Thr Trp Met Asn Ser Thr Gly Phe Thr Lys Thr
 1               5                  10                  15

<210> SEQ ID NO 766
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 766

Phe Gly Cys Thr Trp Met Asn Ser Thr Gly Phe Thr Lys Thr Cys
 1               5                  10                  15

<210> SEQ ID NO 767
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 767

Gly Cys Thr Trp Met Asn Ser Thr Gly Phe Thr Lys Thr Cys Gly
 1               5                  10                  15

<210> SEQ ID NO 768
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 768

Gly Leu Pro Val Ser Ala Arg Arg Gly Arg Glu Ile Leu Leu Gly
 1               5                  10                  15
```

```
<210> SEQ ID NO 769
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 769

Leu Pro Val Ser Ala Arg Arg Gly Arg Glu Ile Leu Leu Gly Pro
 1               5                  10                  15

<210> SEQ ID NO 770
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 770

Pro Val Ser Ala Arg Arg Gly Arg Glu Ile Leu Leu Gly Pro Ala
 1               5                  10                  15

<210> SEQ ID NO 771
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 771

Val Ser Ala Arg Arg Gly Arg Glu Ile Leu Leu Gly Pro Ala Asp
 1               5                  10                  15

<210> SEQ ID NO 772
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 772

Gly Leu Pro Val Ser Ala Leu Arg Gly Arg Glu Ile Leu Leu Gly
 1               5                  10                  15

<210> SEQ ID NO 773
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 773

Leu Pro Val Ser Ala Leu Arg Gly Arg Glu Ile Leu Leu Gly Pro
 1               5                  10                  15

<210> SEQ ID NO 774
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides
```

-continued

```
<400> SEQUENCE: 774

Pro Val Ser Ala Leu Arg Gly Arg Glu Ile Leu Leu Gly Pro Ala
1               5                   10                  15

<210> SEQ ID NO 775
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 775

Val Ser Ala Leu Arg Gly Arg Glu Ile Leu Leu Gly Pro Ala Asp
1               5                   10                  15

<210> SEQ ID NO 776
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 776

Pro Asp Arg Glu Val Leu Tyr Arg Glu Phe Asp Glu Met Glu Glu
1               5                   10                  15

<210> SEQ ID NO 777
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 777

Asp Arg Glu Val Leu Tyr Arg Glu Phe Asp Glu Met Glu Glu Cys
1               5                   10                  15

<210> SEQ ID NO 778
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 778

Arg Glu Val Leu Tyr Arg Glu Phe Asp Glu Met Glu Glu Cys Ala
1               5                   10                  15

<210> SEQ ID NO 779
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 779

Glu Val Leu Tyr Arg Glu Phe Asp Glu Met Glu Glu Cys Ala Ser
1               5                   10                  15

<210> SEQ ID NO 780
<211> LENGTH: 15
```

-continued

```
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 780

Val Leu Tyr Arg Glu Phe Asp Glu Met Glu Glu Cys Ala Ser His
 1               5                  10                  15

<210> SEQ ID NO 781
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 781

Leu Tyr Arg Glu Phe Asp Glu Met Glu Glu Cys Ala Ser His Leu
 1               5                  10                  15

<210> SEQ ID NO 782
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 782

Tyr Tyr Leu Thr Arg Asp Pro Thr Thr Pro Leu Ala Arg Ala Ala
 1               5                  10                  15

<210> SEQ ID NO 783
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 783

Tyr Leu Thr Arg Asp Pro Thr Thr Pro Leu Ala Arg Ala Ala Trp
 1               5                  10                  15

<210> SEQ ID NO 784
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 784

Leu Thr Arg Asp Pro Thr Thr Pro Leu Ala Arg Ala Ala Trp Glu
 1               5                  10                  15

<210> SEQ ID NO 785
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 785

Thr Arg Asp Pro Thr Thr Pro Leu Ala Arg Ala Ala Trp Glu Thr
```

-continued

```
                1               5                  10                  15
```

<210> SEQ ID NO 786
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 786

Arg Asp Pro Thr Thr Pro Leu Ala Arg Ala Ala Trp Glu Thr Ala
 1               5                  10                  15

<210> SEQ ID NO 787
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 787

Asp Pro Thr Thr Pro Leu Ala Arg Ala Ala Trp Glu Thr Ala Arg
 1               5                  10                  15

<210> SEQ ID NO 788
<211> LENGTH: 14
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 788

Pro Thr Thr Pro Leu Ala Arg Ala Trp Glu Thr Ala Arg His
 1               5                  10

<210> SEQ ID NO 789
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 789

Tyr Tyr Leu Thr Arg Asp Pro Thr Thr Pro Leu Ala Arg Ala Ala
 1               5                  10                  15

<210> SEQ ID NO 790
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 790

Tyr Leu Thr Arg Asp Pro Thr Thr Pro Leu Ala Arg Ala Ala Trp
 1               5                  10                  15

<210> SEQ ID NO 791
<211> LENGTH: 15
<212> TYPE: PRT
<213> ORGANISM: Artificial Sequence
<220> FEATURE:
<223> OTHER INFORMATION: Description of Artificial Sequence: Synthetic -continued

```
      Peptides

<400> SEQUENCE: 791

Leu Thr Arg Asp Pro Thr Thr Pro Leu Ala Arg Ala Ala Trp Glu
 1               5                  10                  15

<210> SEQ ID NO 792
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 792

Thr Arg Asp Pro Thr Thr Pro Leu Ala Arg Ala Ala Trp Glu Thr
 1               5                  10                  15

<210> SEQ ID NO 793
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 793

Arg Asp Pro Thr Thr Pro Leu Ala Arg Ala Ala Trp Glu Thr Val
 1               5                  10                  15

<210> SEQ ID NO 794
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 794

Asp Pro Thr Thr Pro Leu Ala Arg Ala Ala Trp Glu Thr Val Arg
 1               5                  10                  15

<210> SEQ ID NO 795
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 795

Pro Thr Thr Pro Leu Ala Arg Ala Ala Trp Glu Thr Val Arg His
 1               5                  10                  15

<210> SEQ ID NO 796
<211> LENGTH: 67
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 796

Met Ser Thr Asn Pro Lys Pro Gln Arg Lys Thr Lys Arg Asn Thr Asn
 1               5                  10                  15

Arg Arg Pro Gln Asp Val Lys Phe Pro Gly Gly Gly Gln Ile Val Gly
                20                  25                  30
```

```
Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
    50                  55                  60

Ile Pro Lys
 65

<210> SEQ ID NO 797
<211> LENGTH: 56
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 797

Val Asn Leu Leu Pro Ala Ile Leu Ser Pro Gly Ala Leu Val Val Gly
  1               5                  10                  15

Val Val Cys Ala Ala Ile Leu Arg Arg His Val Gly Pro Gly Glu Gly
             20                  25                  30

Ala Val Gln Trp Met Asn Arg Leu Ile Ala Phe Ala Ser Arg Gly Asn
            35                  40                  45

His Val Ser Pro Thr His Tyr Val
    50                  55

<210> SEQ ID NO 798
<211> LENGTH: 20
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 798

Ile Lys Gly Gly Arg His Leu Ile Phe Cys His Ser Lys Lys Lys Cys
  1               5                  10                  15

Asp Glu Leu Ala
             20

<210> SEQ ID NO 799
<211> LENGTH: 20
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 799

Thr Val Pro Gln Asp Ala Val Ser Arg Ser Gln Arg Gly Arg Thr
  1               5                  10                  15

Gly Arg Gly Arg
             20

<210> SEQ ID NO 800
<211> LENGTH: 21
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 800

Tyr Leu Val Ala Tyr Gln Ala Thr Val Cys Ala Arg Ala Gln Ala Pro
```

```
                    1               5                  10                   15
Pro Pro Ser Trp Asp
                20

<210> SEQ ID NO 801
<211> LENGTH: 41
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 801

His Leu His Ala Pro Thr Gly Ser Gly Lys Ser Thr Lys Val Pro Ala
 1               5                  10                  15

Ala Tyr Ala Ala Gln Gly Tyr Lys Val Leu Val Leu Asn Pro Ser Val
                20                  25                  30

Ala Ala Thr Leu Gly Phe Gly Ala Tyr
            35                  40

<210> SEQ ID NO 802
<211> LENGTH: 41
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 802

Tyr Leu His Ala Pro Thr Gly Ser Gly Lys Ser Thr Lys Val Pro Val
 1               5                  10                  15

Ala Tyr Ala Ala Gln Gly Tyr Lys Val Leu Val Leu Asn Pro Ser Val
                20                  25                  30

Ala Ala Thr Leu Gly Phe Gly Ala Tyr
            35                  40

<210> SEQ ID NO 803
<211> LENGTH: 37
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 803

Gly Ala Ala Val Gly Ser Ile Gly Leu Gly Lys Val Leu Val Asp Ile
 1               5                  10                  15

Leu Ala Gly Tyr Gly Ala Gly Val Ala Gly Ala Leu Val Ala Phe Lys
                20                  25                  30

Ile Met Ser Gly Glu
            35

<210> SEQ ID NO 804
<211> LENGTH: 37
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 804

Gly Ala Ala Val Gly Ser Ile Gly Leu Gly Lys Val Leu Val Asp Ile
 1               5                  10                  15
```

```
Leu Ala Gly Tyr Gly Ala Gly Val Ala Gly Leu Val Ala Phe Lys
            20                  25                  30

Val Met Ser Gly Glu
        35

<210> SEQ ID NO 805
<211> LENGTH: 37
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 805

Gly Ala Ala Val Gly Ser Ile Gly Leu Gly Lys Val Leu Val Asp Ile
1               5                   10                  15

Leu Ala Gly Tyr Gly Ala Gly Ile Ser Gly Ala Leu Val Ala Phe Lys
            20                  25                  30

Ile Met Ser Gly Glu
        35

<210> SEQ ID NO 806
<211> LENGTH: 16
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 806

Phe Thr Glu Ala Met Thr Arg Tyr Ser Ala Pro Pro Gly Asp Pro Pro
1               5                   10                  15

<210> SEQ ID NO 807
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 807

Ser Ser Met Pro Pro Leu Glu Gly Glu Pro Gly Asp Pro Asp Leu
1               5                   10                  15

<210> SEQ ID NO 808
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 808

Cys Gly Tyr Arg Arg Cys Arg Ala Ser Gly Val Leu Thr Thr Ser
1               5                   10                  15

<210> SEQ ID NO 809
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 809
```

-continued

Pro Val Asn Ser Trp Leu Gly Asn Ile Ile Met Tyr Ala Pro Thr
1               5                   10                  15

<210> SEQ ID NO 810
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 810

Pro Val Asn Ser Trp Leu Gly Asn Ile Ile Gln Tyr Ala Pro Thr
1               5                   10                  15

<210> SEQ ID NO 811
<211> LENGTH: 34
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 811

Ser Gly Met Phe Asp Ser Ser Val Leu Cys Glu Cys Tyr Asp Ala Gly
1               5                   10                  15

Cys Ala Trp Tyr Glu Leu Thr Pro Ala Glu Thr Thr Val Arg Leu Arg
            20                  25                  30

Ala Tyr

<210> SEQ ID NO 812
<211> LENGTH: 34
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 812

Ser Gly Met Phe Asp Ser Ser Val Leu Cys Glu Cys Tyr Asp Ala Gly
1               5                   10                  15

Cys Ala Trp Tyr Glu Leu Thr Pro Ala Glu Thr Ser Val Arg Leu Arg
            20                  25                  30

Ala Tyr

<210> SEQ ID NO 813
<211> LENGTH: 34
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 813

Ser Gly Met Phe Asp Ser Val Val Leu Cys Glu Cys Tyr Asp Ala Gly
1               5                   10                  15

Ala Ala Trp Tyr Glu Leu Thr Pro Ala Glu Thr Thr Val Arg Leu Arg
            20                  25                  30

Ala Tyr

<210> SEQ ID NO 814
<211> LENGTH: 34
<212> TYPE: PRT
<213> ORGANISM: Artificial Sequence

```
<220> FEATURE:
<223> OTHER INFORMATION: Description of Artificial Sequence:  Synthetic
      Peptides

<400> SEQUENCE: 814

Ser Gly Met Phe Asp Ser Val Val Leu Cys Glu Cys Tyr Asp Ala Gly
 1               5                  10                  15

Ala Ala Trp Tyr Glu Leu Thr Pro Ala Glu Thr Ser Val Arg Leu Arg
            20                  25                  30

Ala Tyr

<210> SEQ ID NO 815
<211> LENGTH: 34
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 815

Phe Trp Ala Lys His Met Trp Asn Phe Ile Ser Gly Ile Gln Tyr Leu
 1               5                  10                  15

Ala Gly Leu Ser Thr Leu Pro Gly Asn Pro Ala Ile Ala Ser Leu Met
            20                  25                  30

Ala Phe

<210> SEQ ID NO 816
<211> LENGTH: 16
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 816

Gly Glu Val Gln Val Val Ser Thr Ala Thr Gln Ser Phe Leu Ala Thr
 1               5                  10                  15

<210> SEQ ID NO 817
<211> LENGTH: 16
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 817

Gly Glu Val Gln Val Leu Ser Thr Val Thr Gln Ser Phe Leu Gly Thr
 1               5                  10                  15

<210> SEQ ID NO 818
<211> LENGTH: 16
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 818

Phe Thr Asp Asn Ser Ser Pro Pro Ala Val Pro Gln Thr Phe Gln Val
 1               5                  10                  15

<210> SEQ ID NO 819
<211> LENGTH: 16
<212> TYPE: PRT
```

```
<213> ORGANISM: Artificial Sequence
<220> FEATURE:
<223> OTHER INFORMATION: Description of Artificial Sequence: Synthetic
      Peptides

<400> SEQUENCE: 819

Phe Ser Asp Asn Ser Thr Pro Pro Ala Val Pro Gln Thr Tyr Gln Val
 1               5                  10                  15

<210> SEQ ID NO 820
<211> LENGTH: 16
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 820

Asn Ala Val Ala Tyr Tyr Arg Gly Leu Asp Val Ser Val Ile Pro Thr
 1               5                  10                  15

<210> SEQ ID NO 821
<211> LENGTH: 56
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 821

Val Asn Leu Leu Pro Gly Ile Leu Ser Pro Gly Ala Leu Val Val Gly
 1               5                  10                  15

Val Ile Cys Ala Ala Ile Leu Arg Arg His Val Gly Pro Gly Glu Gly
            20                  25                  30

Ala Val Gln Trp Met Asn Arg Leu Ile Ala Phe Ala Ser Arg Gly Asn
        35                  40                  45

His Val Ala Pro Thr His Tyr Val
    50                  55

<210> SEQ ID NO 822
<211> LENGTH: 33
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 822

Thr Thr Ile Leu Gly Ile Gly Thr Val Leu Asp Gln Ala Glu Thr Ala
 1               5                  10                  15

Gly Ala Arg Leu Val Val Leu Ala Thr Ala Thr Pro Pro Gly Ser Val
            20                  25                  30

Thr

<210> SEQ ID NO 823
<211> LENGTH: 33
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 823

Thr Ser Ile Leu Gly Ile Gly Thr Val Leu Asp Gln Ala Glu Thr Ala
 1               5                  10                  15
```

Gly Ala Arg Leu Val Val Leu Ala Thr Ala Thr Pro Pro Gly Ser Val
            20                  25                  30

Thr

<210> SEQ ID NO 824
<211> LENGTH: 33
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 824

Thr Ser Ile Leu Gly Ile Gly Thr Val Leu Asp Gln Ala Glu Thr Ala
 1               5                  10                  15

Gly Val Arg Leu Thr Val Leu Ala Thr Ala Thr Pro Pro Gly Ser Val
            20                  25                  30

Thr

<210> SEQ ID NO 825
<211> LENGTH: 33
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 825

Thr Thr Ile Leu Gly Ile Gly Thr Val Leu Asp Gln Ala Glu Thr Ala
 1               5                  10                  15

Gly Val Arg Leu Thr Val Leu Ala Thr Ala Thr Pro Pro Gly Ser Val
            20                  25                  30

Thr

<210> SEQ ID NO 826
<211> LENGTH: 34
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 826

Phe Trp Ala Lys His Met Trp Asn Phe Ile Ser Gly Ile Gln Tyr Leu
 1               5                  10                  15

Ala Gly Leu Ser Thr Leu Pro Gly Asn Pro Ala Val Ala Ser Met Met
            20                  25                  30

Ala Phe

<210> SEQ ID NO 827
<211> LENGTH: 18
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 827

Val Phe Thr Gly Leu Thr His Ile Asp Ala His Phe Leu Ser Gln Thr
 1               5                  10                  15

Lys Gln

```
<210> SEQ ID NO 828
<211> LENGTH: 18
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 828

Val Val Cys Cys Ser Met Ser Tyr Thr Trp Thr Gly Ala Leu Ile Thr
 1               5                  10                  15

Pro Cys

<210> SEQ ID NO 829
<211> LENGTH: 18
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 829

Val Val Cys Cys Ser Met Ser Tyr Ser Trp Thr Gly Ala Leu Ile Thr
 1               5                  10                  15

Pro Cys

<210> SEQ ID NO 830
<211> LENGTH: 17
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 830

Val Leu Thr Ser Met Leu Thr Asp Pro Ser His Ile Thr Ala Glu Thr
 1               5                  10                  15

Ala

<210> SEQ ID NO 831
<211> LENGTH: 17
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 831

Val Leu Thr Ser Met Leu Thr Asp Pro Ser His Ile Thr Ala Glu Ala
 1               5                  10                  15

Ala

<210> SEQ ID NO 832
<211> LENGTH: 19
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 832

Ala Ser Ser Ser Ala Ser Gln Leu Ser Ala Pro Ser Leu Arg Ala Thr
 1               5                  10                  15

Cys Thr Thr
```

```
<210> SEQ ID NO 833
<211> LENGTH: 19
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 833

Leu Thr Pro Pro His Ser Ala Arg Ser Lys Phe Gly Tyr Gly Ala Lys
 1               5                  10                  15

Asp Val Arg

<210> SEQ ID NO 834
<211> LENGTH: 19
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 834

Leu Thr Pro Pro His Ser Ala Asp Ser Lys Phe Gly Tyr Gly Ala Lys
 1               5                  10                  15

Asp Val Arg

<210> SEQ ID NO 835
<211> LENGTH: 19
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 835

Leu Thr Pro Pro His Ser Ala Lys Ser Lys Tyr Gly Tyr Gly Ala Lys
 1               5                  10                  15

Glu Val Arg

<210> SEQ ID NO 836
<211> LENGTH: 19
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 836

Leu Thr Pro Pro His Ser Ala Arg Ser Lys Tyr Gly Tyr Gly Ala Lys
 1               5                  10                  15

Glu Val Arg

<210> SEQ ID NO 837
<211> LENGTH: 17
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 837

Pro Met Gly Phe Ser Tyr Asp Thr Arg Cys Phe Asp Ser Thr Val Thr
 1               5                  10                  15
```

-continued

Glu

<210> SEQ ID NO 838
<211> LENGTH: 17
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 838

Pro Met Gly Phe Ala Tyr Asp Thr Arg Cys Phe Asp Ser Thr Val Thr
 1               5                  10                  15

Glu

<210> SEQ ID NO 839
<211> LENGTH: 16
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 839

Thr Gly Asp Phe Asp Ser Val Ile Asp Cys Asn Thr Cys Val Thr Gln
 1               5                  10                  15

<210> SEQ ID NO 840
<211> LENGTH: 16
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 840

Thr Gly Asp Phe Asp Ser Val Ile Asp Cys Asn Val Ala Val Thr Gln
 1               5                  10                  15

<210> SEQ ID NO 841
<211> LENGTH: 16
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 841

Asn Thr Pro Gly Leu Pro Val Cys Gln Asp His Leu Glu Phe Trp Glu
 1               5                  10                  15

<210> SEQ ID NO 842
<211> LENGTH: 21
<212> TYPE: PRT
<213> ORGANISM: Artificial Sequence
<220> FEATURE:
<221> NAME/KEY: modified_res
<222> LOCATION: (14)
<223> OTHER INFORMATION: xaa = can be any naturally occurring amino acid
<220> FEATURE:
<223> OTHER INFORMATION: Description of Artificial Sequence:  Synthetic
      Peptides

<400> SEQUENCE: 842

Tyr Leu Val Ala Tyr Gln Ala Thr Val Cys Ala Arg Ala Xaa Ala Pro
 1               5                  10                  15

Pro Pro Ser Trp Asp

-continued

```
                20

<210> SEQ ID NO 843
<211> LENGTH: 19
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 843

Leu Glu Asp Arg Asp Arg Ser Glu Leu Ser Pro Leu Leu Leu Ser Thr
 1               5                  10                  15

Thr Glu Trp

<210> SEQ ID NO 844
<211> LENGTH: 19
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 844

Leu Glu Asp Arg Asp Arg Ser Gln Leu Ser Pro Leu Leu His Ser Thr
 1               5                  10                  15

Thr Glu Trp

<210> SEQ ID NO 845
<211> LENGTH: 19
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 845

Ala Ser Ser Ser Ala Ser Gln Leu Ser Ala Pro Ser Leu Lys Ala Thr
 1               5                  10                  15

Cys Thr Thr

<210> SEQ ID NO 846
<211> LENGTH: 18
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 846

Pro Glu Tyr Asp Leu Glu Leu Ile Thr Ser Cys Ser Ser Asn Val Ser
 1               5                  10                  15

Val Ala

<210> SEQ ID NO 847
<211> LENGTH: 20
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 847

Val Cys Gly Pro Val Tyr Cys Phe Thr Pro Ser Pro Val Val Val Gly
 1               5                  10                  15
```

```
Thr Thr Asp Arg
            20

<210> SEQ ID NO 848
<211> LENGTH: 18
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 848

Gly Trp Ala Gly Trp Leu Leu Ser Pro Arg Gly Ser Arg Pro Ser Trp
  1               5                  10                  15

Gly Pro

<210> SEQ ID NO 849
<211> LENGTH: 17
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 849

Leu Leu Phe Leu Leu Leu Ala Asp Ala Arg Val Cys Ala Cys Leu Trp
  1               5                  10                  15

Met

<210> SEQ ID NO 850
<211> LENGTH: 16
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 850

Ser Gly His Arg Met Ala Trp Asp Met Met Asn Trp Ser Pro Thr
  1               5                  10                  15

<210> SEQ ID NO 851
<211> LENGTH: 16
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 851

Thr Gly His Arg Met Ala Trp Asp Met Met Met Asn Trp Ser Pro Thr
  1               5                  10                  15

<210> SEQ ID NO 852
<211> LENGTH: 30
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 852

Ile Thr Tyr Ser Thr Tyr Gly Lys Phe Leu Ala Asp Gly Gly Cys Ser
  1               5                  10                  15

Gly Gly Ala Tyr Asp Ile Ile Ile Cys Asp Glu Cys His Ser
```

```
                20                  25                  30
```

<210> SEQ ID NO 853
<211> LENGTH: 37
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 853

```
Ala Arg Ala Leu Ala His Gly Val Arg Val Leu Glu Asp Gly Val Asn
  1               5                  10                  15

Tyr Ala Thr Gly Asn Leu Pro Gly Cys Ser Phe Ser Ile Phe Leu Leu
                20                  25                  30

Ala Leu Leu Ser Cys
                35
```

<210> SEQ ID NO 854
<211> LENGTH: 36
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 854

```
Asp Pro Arg Arg Arg Ser Arg Asn Leu Gly Lys Val Ile Asp Thr Leu
  1               5                  10                  15

Thr Cys Gly Phe Ala Asp Leu Met Gly Tyr Ile Pro Leu Val Gly Ala
                20                  25                  30

Pro Leu Gly Gly
                35
```

<210> SEQ ID NO 855
<211> LENGTH: 36
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 855

```
Asp Pro Arg His Arg Ser Arg Asn Val Gly Lys Val Ile Asp Thr Leu
  1               5                  10                  15

Thr Cys Gly Phe Ala Asp Leu Met Gly Tyr Ile Pro Val Val Gly Ala
                20                  25                  30

Pro Leu Gly Gly
                35
```

<210> SEQ ID NO 856
<211> LENGTH: 32
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 856

```
Val Asp Tyr Pro Tyr Arg Leu Trp His Tyr Pro Cys Thr Val Asn Phe
  1               5                  10                  15

Thr Ile Phe Lys Val Arg Met Tyr Val Gly Gly Val Glu His Arg Leu
                20                  25                  30
```

<210> SEQ ID NO 857
<211> LENGTH: 32
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 857

Val Asp Tyr Pro Tyr Arg Leu Trp His Tyr Pro Cys Thr Val Asn Tyr
 1               5                  10                  15

Thr Ile Phe Lys Ile Arg Met Tyr Val Gly Gly Val Glu His Arg Leu
            20                  25                  30

<210> SEQ ID NO 858
<211> LENGTH: 28
<212> TYPE: PRT
<213> ORGANISM: Artificial Sequence
<220> FEATURE:
<221> NAME/KEY: modified_res
<222> LOCATION: (1)
<223> OTHER INFORMATION: xaa = can be any naturally occurring amino acid
<220> FEATURE:
<223> OTHER INFORMATION: Description of Artificial Sequence: Synthetic
      Peptides

<400> SEQUENCE: 858

Xaa Gly Gly Arg Lys Pro Ala Arg Leu Ile Val Phe Pro Asp Leu Gly
 1               5                  10                  15

Val Arg Val Cys Glu Lys Met Ala Leu Tyr Asp Val
            20                  25

<210> SEQ ID NO 859
<211> LENGTH: 28
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 859

Lys Gly Gly Lys Lys Ala Ala Arg Leu Ile Val Tyr Pro Asp Leu Gly
 1               5                  10                  15

Val Arg Val Cys Glu Lys Met Ala Leu Tyr Asp Val
            20                  25

<210> SEQ ID NO 860
<211> LENGTH: 23
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 860

Ile Gln Leu Ile Asn Thr Asn Gly Ser Trp His Ile Asn Arg Thr Ala
 1               5                  10                  15

Leu Asn Cys Asn Asp Ser Leu
            20

<210> SEQ ID NO 861
<211> LENGTH: 23
<212> TYPE: PRT
<213> ORGANISM: Artificial Sequence
<220> FEATURE:
<223> OTHER INFORMATION: Description of Artificial Sequence: Synthetic -continued

```
      Peptides

<400> SEQUENCE: 861

Ile Gln Leu Val Asn Thr Asn Gly Ser Trp His Ile Asn Arg Thr Ala
1               5                   10                  15

Leu Asn Cys Asn Asp Ser Leu
            20

<210> SEQ ID NO 862
<211> LENGTH: 23
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 862

Leu Pro Ala Leu Ser Thr Gly Leu Ile His Leu His Gln Asn Ile Val
1               5                   10                  15

Asp Val Gln Tyr Leu Tyr Gly
            20

<210> SEQ ID NO 863
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 863

Asn Thr Asn Gly Ser Trp His Ile Asn Arg Thr Ala Leu Asn Cys
1               5                   10                  15

<210> SEQ ID NO 864
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 864

Asn Gly Ser Trp His Ile Asn Arg Thr Ala Leu Asn Cys Asn Asp
1               5                   10                  15

<210> SEQ ID NO 865
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 865

Ser Trp His Ile Asn Arg Thr Ala Leu Asn Cys Asn Asp Ser Leu
1               5                   10                  15

<210> SEQ ID NO 866
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 866
```

Asp Ala Gly Cys Ala Trp Tyr Glu Leu Thr Pro Ala Glu Thr Ser
1               5                  10                  15

<210> SEQ ID NO 867
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 867

Ala Gly Cys Ala Trp Tyr Glu Leu Thr Pro Ala Glu Thr Ser Val
1               5                  10                  15

<210> SEQ ID NO 868
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 868

Cys Ala Trp Tyr Glu Leu Thr Pro Ala Glu Thr Ser Val Arg Leu
1               5                  10                  15

<210> SEQ ID NO 869
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 869

Trp Tyr Glu Leu Thr Pro Ala Glu Thr Ser Val Arg Leu Arg Ala
1               5                  10                  15

<210> SEQ ID NO 870
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 870

Ala Gly Ala Ala Trp Tyr Glu Leu Thr Pro Ala Glu Thr Thr Val
1               5                  10                  15

<210> SEQ ID NO 871
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 871

Ala Ala Trp Tyr Glu Leu Thr Pro Ala Glu Thr Thr Val Arg Leu
1               5                  10                  15

<210> SEQ ID NO 872
<211> LENGTH: 15
<212> TYPE: PRT
<213> ORGANISM: Artificial Sequence

```
<220> FEATURE:
<223> OTHER INFORMATION: Description of Artificial Sequence: Synthetic
      Peptide

<400> SEQUENCE: 872

Gly Ser Ile Gly Leu Gly Lys Val Leu Val Asp Ile Leu Ala Gly
 1               5                  10                  15

<210> SEQ ID NO 873
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 873

Ile Gly Leu Gly Lys Val Leu Val Asp Ile Leu Ala Gly Tyr Ala
 1               5                  10                  15

<210> SEQ ID NO 874
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 874

Ile Gly Leu Gly Lys Val Leu Val Asp Ile Leu Ala Gly Tyr Ala
 1               5                  10                  15

<210> SEQ ID NO 875
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 875

Leu Val Asp Ile Leu Ala Gly Tyr Gly Ala Gly Val Ala Gly Ala
 1               5                  10                  15

<210> SEQ ID NO 876
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 876

Thr Arg Val Pro Tyr Phe Val Arg Ala Gln Gly Leu Ile Arg Ala
 1               5                  10                  15

<210> SEQ ID NO 877
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 877

Thr Ala Tyr Ser Gln Gln Thr Arg Gly Leu Leu Gly Cys Ile Ile
 1               5                  10                  15
```

```
<210> SEQ ID NO 878
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 878

Thr Ala Tyr Ser Gln Gln Thr Arg Gly Leu Leu Gly Cys Ile Val
 1               5                  10                  15

<210> SEQ ID NO 879
<211> LENGTH: 19
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 879

Pro Glu Tyr Asp Glu Leu Glu Leu Ile Thr Ser Cys Ser Ser Asn Val
 1               5                  10                  15

Ser Val Ala

<210> SEQ ID NO 880
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 880

Val Cys Gly Pro Val Tyr Cys Phe Thr Pro Ser Pro Val Val Val Gly
 1               5                  10                  15

Thr Thr Asp Arg
             20

<210> SEQ ID NO 881
<211> LENGTH: 19
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 881

Gly Trp Ala Gly Trp Leu Leu Ser Pro Arg Gly Ser Pro Arg Pro Ser
 1               5                  10                  15

Trp Gly Pro

<210> SEQ ID NO 882
<211> LENGTH: 18
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 882

Val Val Cys Cys Ser Met Ser Tyr Thr Trp Thr Gly Ala Leu Ile Thr
 1               5                  10                  15

Pro Cys
```

```
<210> SEQ ID NO 883
<211> LENGTH: 17
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 883

Leu Leu Phe Leu Leu Leu Ala Asp Ala Arg Val Cys Ala Cys Leu Trp
 1               5                  10                  15

Met

<210> SEQ ID NO 884
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 884

Gly Val Leu Phe Gly Leu Ala Tyr Phe Ser Met Val Gly Asn Trp
 1               5                  10                  15

<210> SEQ ID NO 885
<211> LENGTH: 21
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 885

Tyr Leu Val Ala Tyr Gln Ala Thr Val Cys Ala Arg Ala Gln Ala Pro
 1               5                  10                  15

Pro Pro Ser Trp Asp
            20

<210> SEQ ID NO 886
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 886

Asp Ile Leu Ala Gly Tyr Gly Ala Gly Val Ala Gly Ala Leu Val
 1               5                  10                  15

<210> SEQ ID NO 887
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 887

Ile Leu Ala Gly Tyr Gly Ala Gly Val Ala Gly Ala Leu Val Ala
 1               5                  10                  15

<210> SEQ ID NO 888
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      Peptide

<400> SEQUENCE: 888

Leu Ala Gly Tyr Gly Ala Gly Val Ala Gly Ala Leu Val Ala Phe
 1               5                  10                  15

<210> SEQ ID NO 889
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 889

Ala Gly Tyr Gly Ala Gly Val Ala Gly Ala Leu Val Ala Phe Lys
 1               5                  10                  15

<210> SEQ ID NO 890
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 890

Gly Tyr Gly Ala Gly Val Ala Gly Ala Leu Val Ala Lys Phe Ile
 1               5                  10                  15

<210> SEQ ID NO 891
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 891

Glu Thr Ala Gly Val Arg Leu Thr Val Leu Ala Thr Ala Thr Thr
 1               5                  10                  15

<210> SEQ ID NO 892
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 892

Ala Gly Val Arg Leu Thr Val Leu Ala Thr Ala Thr Pro Pro Gly
 1               5                  10                  15

<210> SEQ ID NO 893
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 893

Val Arg Leu Thr Val Leu Ala Thr Ala Thr Pro Pro Gly Ser Val
 1               5                  10                  15
```

-continued

<210> SEQ ID NO 894
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 894

Ala Gly Ile Ser Gly Ala Leu Val Ala Phe Lys Ile Met Ser Gly
 1               5                  10                  15

<210> SEQ ID NO 895
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 895

Val Asn Leu Leu Pro Ala Ile Leu Ser Pro Gly Ala Leu Val Val
 1               5                  10                  15

<210> SEQ ID NO 896
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 896

His Ala Gly Leu Arg Asp Leu Ala Val Ala Val Glu Pro Val Val
 1               5                  10                  15

<210> SEQ ID NO 897
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 897

Thr Thr Leu Leu Phe Asn Ile Leu Gly Gly Trp Val Ala Ala Gln
 1               5                  10                  15

<210> SEQ ID NO 898
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 898

Val Met Gly Ser Ser Tyr Gly Phe Gln Tyr Ser Pro Gly Gln Arg
 1               5                  10                  15

<210> SEQ ID NO 899
<211> LENGTH: 17
<212> TYPE: PRT
<213> ORGANISM: Artificial Sequence
<220> FEATURE:
<223> OTHER INFORMATION: Description of Artificial Sequence: Synthetic
      Peptide

```
<400> SEQUENCE: 899

Val Leu Thr Ser Met Leu Thr Asp Pro Ser His Ile Thr Ala Glu Thr
 1               5                   10                  15

Ala

<210> SEQ ID NO 900
<211> LENGTH: 17
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 900

Val Leu Thr Ser Met Leu Thr Asp Pro Ser His Ile Thr Ala Glu Ala
 1               5                   10                  15

Ala

<210> SEQ ID NO 901
<211> LENGTH: 16
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 901

Gly Glu Val Gln Val Val Ser Thr Ala Thr Gln Ser Phe Leu Ala Thr
 1               5                   10                  15

<210> SEQ ID NO 902
<211> LENGTH: 16
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 902

Gly Glu Val Gln Val Leu Ser Thr Val Thr Gln Ser Phe Leu Gly Thr
 1               5                   10                  15

<210> SEQ ID NO 903
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 903

Ala Gly Ala Ala Trp Tyr Glu Leu Thr Pro Ala Glu Thr Ser Val
 1               5                   10                  15

<210> SEQ ID NO 904
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 904

Ala Ala Trp Tyr Glu Leu Thr Pro Ala Glu Thr Ser Val Arg Leu
 1               5                   10                  15
```

```
<210> SEQ ID NO 905
<211> LENGTH: 21
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 905

Tyr Leu Val Ala Tyr Gln Ala Thr Val Cys Ala Arg Ala Lys Ala Pro
 1               5                  10                  15

Pro Pro Ser Trp Asp
            20

<210> SEQ ID NO 906
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 906

Gln Thr Val Asp Phe Ser Leu Asp Pro Thr Phe Thr Ile Glu Thr
 1               5                  10                  15

<210> SEQ ID NO 907
<211> LENGTH: 18
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 907

Val Phe Thr Gly Leu Thr His Ile Asp Ala His Phe Leu Ser Gln Thr
 1               5                  10                  15

Lys Gln

<210> SEQ ID NO 908
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 908

Gly Val Leu Ala Gly Leu Ala Tyr Tyr Ser Met Val Gly Asn Trp
 1               5                  10                  15

<210> SEQ ID NO 909
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 909

Tyr Tyr Leu Thr Arg Asp Pro Thr Thr Pro Leu Ala Arg Ala Ala
 1               5                  10                  15

<210> SEQ ID NO 910
<211> LENGTH: 15
```

<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 910

Ser Gly Lys Ser Thr Lys Val Pro Val Ala Tyr Ala Ala Gln Gly
 1               5                  10                  15

<210> SEQ ID NO 911
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 911

Lys Ser Thr Lys Val Pro Val Ala Tyr Ala Ala Gln Gly Tyr Lys
 1               5                  10                  15

<210> SEQ ID NO 912
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 912

Thr Lys Val Pro Val Ala Tyr Ala Ala Gln Gly Tyr Lys Val Leu
 1               5                  10                  15

<210> SEQ ID NO 913
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 913

Val Pro Val Ala Tyr Ala Ala Gln Gly Tyr Lys Val Leu Val Leu
 1               5                  10                  15

<210> SEQ ID NO 914
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 914

Val Ala Tyr Ala Ala Gln Gly Tyr Lys Val Leu Val Leu Asn Pro
 1               5                  10                  15

<210> SEQ ID NO 915
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 915

Thr Ile Leu Gly Ile Gly Thr Val Leu Asp Gln Ala Glu Thr Ala

-continued

```
                1               5                  10                 15
```

<210> SEQ ID NO 916
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 916

```
Leu Gly Ile Gly Thr Val Leu Asp Gln Ala Glu Thr Ala Gly Ala
 1               5                  10                  15
```

<210> SEQ ID NO 917
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 917

```
Ala Phe Cys Ser Ala Met Tyr Val Gly Asp Leu Cys Gly Ser Val
 1               5                  10                  15
```

<210> SEQ ID NO 918
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 918

```
Ala Phe Cys Ser Ala Leu Tyr Val Gly Asp Leu Cys Gly Ser Val
 1               5                  10                  15
```

<210> SEQ ID NO 919
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 919

```
Pro Ala Leu Ser Thr Gly Leu Leu His Leu His Gln Asn Ile Val
 1               5                  10                  15
```

<210> SEQ ID NO 920
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 920

```
Ser Gly Met Phe Asp Ser Val Val Leu Cys Glu Cys Tyr Asp Ala
 1               5                  10                  15
```

<210> SEQ ID NO 921
<211> LENGTH: 15
<212> TYPE: PRT
<213> ORGANISM: Artificial Sequence
<220> FEATURE:
<223> OTHER INFORMATION: Description of Artificial Sequence: Synthetic

```
                             -continued
        Peptide

<400> SEQUENCE: 921

Met Phe Asp Ser Val Val Leu Cys Glu Cys Tyr Asp Ala Gly Ala
 1               5                  10                  15

<210> SEQ ID NO 922
<211> LENGTH: 15
<212> TYPE: PRT
<213> ORGANISM: Artificial Sequence
<220> FEATURE:
<223> OTHER INFORMATION: Description of Artificial Sequence:  Synthetic
        Peptide

<400> SEQUENCE: 922

Asp Ser Val Val Leu Cys Glu Cys Tyr Asp Ala Gly Ala Ala Trp
 1               5                  10                  15

<210> SEQ ID NO 923
<211> LENGTH: 15
<212> TYPE: PRT
<213> ORGANISM: Artificial Sequence
<220> FEATURE:
<223> OTHER INFORMATION: Description of Artificial Sequence:  Synthetic
        Peptide

<400> SEQUENCE: 923

Val Val Leu Cys Glu Cys Tyr Asp Ala Gly Ala Ala Trp Tyr Glu
 1               5                  10                  15

<210> SEQ ID NO 924
<211> LENGTH: 15
<212> TYPE: PRT
<213> ORGANISM: Artificial Sequence
<220> FEATURE:
<223> OTHER INFORMATION: Description of Artificial Sequence:  Synthetic
        Peptide

<400> SEQUENCE: 924

Gly Ala Gly Val Ala Gly Ala Leu Val Ala Phe Lys Ile Met Ser
 1               5                  10                  15

<210> SEQ ID NO 925
<211> LENGTH: 15
<212> TYPE: PRT
<213> ORGANISM: Artificial Sequence
<220> FEATURE:
<223> OTHER INFORMATION: Description of Artificial Sequence:  Synthetic
        Peptide

<400> SEQUENCE: 925

Gly Val Ala Gly Ala Leu Val Ala Phe Lys Ile Met Ser Gly Glu
 1               5                  10                  15

<210> SEQ ID NO 926
<211> LENGTH: 15
<212> TYPE: PRT
<213> ORGANISM: Artificial Sequence
<220> FEATURE:
<223> OTHER INFORMATION: Description of Artificial Sequence:  Synthetic
        Peptide

<400> SEQUENCE: 926

Thr Thr Leu Leu Leu Asn Ile Leu Gly Gly Trp Leu Ala Ala Gln
 1               5                  10                  15

<210> SEQ ID NO 927
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 927

Ala Val Arg Thr Lys Leu Lys Leu Thr Pro Leu Pro Ala Ala Ser
  1               5                  10                  15

<210> SEQ ID NO 928
<211> LENGTH: 17
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 928

Pro Met Gly Phe Ser Tyr Asp Thr Arg Cys Phe Asp Ser Thr Val Thr
  1               5                  10                  15

Glu

<210> SEQ ID NO 929
<211> LENGTH: 16
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 929

Asn Thr Pro Gly Leu Pro Val Cys Gln Asp His Leu Glu Phe Trp Glu
  1               5                  10                  15

<210> SEQ ID NO 930
<211> LENGTH: 19
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 930

Leu Glu Asp Arg Asp Arg Ser Glu Leu Ser Pro Leu Leu Leu Ser Thr
  1               5                  10                  15

Thr Glu Trp

<210> SEQ ID NO 931
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 931

Thr Val Pro Gln Asp Ala Val Ser Arg Ser Gln Arg Arg Gly Arg Thr
  1               5                  10                  15

Gly Arg Gly Arg
             20

<210> SEQ ID NO 932
<211> LENGTH: 16
<212> TYPE: PRT
```

```
<213> ORGANISM: Artificial Sequence
<220> FEATURE:
<223> OTHER INFORMATION: Description of Artificial Sequence: Synthetic
      Peptide

<400> SEQUENCE: 932

Phe Thr Glu Ala Met Thr Arg Tyr Ser Ala Pro Pro Gly Asp Pro Pro
 1               5                  10                  15

<210> SEQ ID NO 933
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 933

Leu Pro Gly Cys Ser Phe Ser Ile Phe Leu Leu Ala Leu Leu Ser
 1               5                  10                  15

<210> SEQ ID NO 934
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 934

Met Trp Asn Phe Ile Ser Gly Ile Gln Tyr Leu Ala Gly Leu Ser
 1               5                  10                  15

<210> SEQ ID NO 935
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 935

Val Asp Ile Leu Ala Gly Tyr Gly Ala Gly Ile Ser Gly Ala Leu
 1               5                  10                  15

<210> SEQ ID NO 936
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 936

Ile Leu Ala Gly Tyr Gly Ala Gly Ile Ser Gly Ala Leu Val Ala
 1               5                  10                  15

<210> SEQ ID NO 937
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 937

Ala Gly Tyr Gly Ala Gly Ile Ser Gly Ala Leu Val Ala Phe Lys
 1               5                  10                  15
```

<210> SEQ ID NO 938
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 938

Tyr Gly Ala Gly Ile Ser Gly Ala Leu Val Ala Phe Lys Ile Met
 1               5                  10                  15

<210> SEQ ID NO 939
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 939

Asp Ala Gly Cys Ala Trp Tyr Glu Leu Thr Pro Ala Glu Thr Thr
 1               5                  10                  15

<210> SEQ ID NO 940
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 940

Gly Cys Ala Trp Tyr Glu Leu Thr Pro Ala Glu Thr Thr Val Arg
 1               5                  10                  15

<210> SEQ ID NO 941
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 941

Ala Trp Tyr Glu Leu Thr Pro Ala Glu Thr Thr Val Arg Leu Arg
 1               5                  10                  15

<210> SEQ ID NO 942
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 942

Gly Gln Gly Trp Arg Leu Leu Ala Pro Ile Thr Ala Tyr Ser Gln
 1               5                  10                  15

<210> SEQ ID NO 943
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide -continued

```
<400> SEQUENCE: 943

Gly Cys Ile Val Val Ser Met Thr Gly Arg Asp Lys Thr Gln Val
1               5                   10                  15

<210> SEQ ID NO 944
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 944

Ser Tyr Leu Lys Gly Ser Ser Gly Gly Pro Leu Leu Cys Pro Ser
1               5                   10                  15

<210> SEQ ID NO 945
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 945

Thr Gly Glu Ile Pro Phe Tyr Gly Lys Ala Ile Pro Ile Glu Val
1               5                   10                  15

<210> SEQ ID NO 946
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 946

Phe Phe Thr Trp Leu Asp Gly Val Gln Ile His Arg Tyr Ala Pro
1               5                   10                  15

<210> SEQ ID NO 947
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 947

Asp Leu Pro Gln Ile Ile Glu Arg Leu His Gly Leu Ser Ala Phe
1               5                   10                  15

<210> SEQ ID NO 948
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 948

Asp Leu Pro Gln Ile Ile Gln Arg Leu His Gly Leu Ser Ala Phe
1               5                   10                  15

<210> SEQ ID NO 949
<211> LENGTH: 15
```

<212> TYPE: PRT
<213> ORGANISM: Artificial Sequence
<220> FEATURE:
<223> OTHER INFORMATION: Description of Artificial Sequence: Synthetic
    Peptide

<400> SEQUENCE: 949

Gly Leu Pro Val Ser Ala Leu Arg Gly Arg Glu Ile Leu Leu Gly
 1               5                  10                  15

<210> SEQ ID NO 950
<211> LENGTH: 15
<212> TYPE: PRT
<213> ORGANISM: Artificial Sequence
<220> FEATURE:
<223> OTHER INFORMATION: Description of Artificial Sequence: Synthetic
    Peptide

<400> SEQUENCE: 950

Cys Gly Tyr Arg Arg Cys Arg Ala Ser Gly Val Leu Thr Thr Ser
 1               5                  10                  15

<210> SEQ ID NO 951
<211> LENGTH: 16
<212> TYPE: PRT
<213> ORGANISM: Artificial Sequence
<220> FEATURE:
<223> OTHER INFORMATION: Description of Artificial Sequence: Synthetic
    Peptide

<400> SEQUENCE: 951

Asn Ala Val Ala Tyr Tyr Arg Gly Leu Asp Val Ser Val Ile Pro Thr
 1               5                  10                  15

<210> SEQ ID NO 952
<211> LENGTH: 15
<212> TYPE: PRT
<213> ORGANISM: Artificial Sequence
<220> FEATURE:
<223> OTHER INFORMATION: Description of Artificial Sequence: Synthetic
    Peptide

<400> SEQUENCE: 952

Glu Phe Val Gln Asp Cys Asn Cys Ser Ile Tyr Pro Gly His Val
 1               5                  10                  15

<210> SEQ ID NO 953
<211> LENGTH: 15
<212> TYPE: PRT
<213> ORGANISM: Artificial Sequence
<220> FEATURE:
<223> OTHER INFORMATION: Description of Artificial Sequence: Synthetic
    Peptide

<400> SEQUENCE: 953

Pro Thr Ser Gly Asp Val Val Val Ala Thr Asp Ala Leu Met
 1               5                  10                  15

<210> SEQ ID NO 954
<211> LENGTH: 15
<212> TYPE: PRT
<213> ORGANISM: Artificial Sequence
<220> FEATURE:
<223> OTHER INFORMATION: Description of Artificial Sequence: Synthetic
    Peptide

<400> SEQUENCE: 954

Leu Trp Ala Arg Met Ile Leu Met Thr His Phe Phe Ser Ile Leu

```
                 1               5                  10                 15

<210> SEQ ID NO 955
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 955

Leu Trp Val Arg Met Val Leu Met Thr His Phe Phe Ser Ile Leu
 1               5                  10                 15

<210> SEQ ID NO 956
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 956

Glu Thr Ala Gly Ala Arg Leu Val Val Leu Ala Thr Ala Thr Pro
 1               5                  10                 15

<210> SEQ ID NO 957
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 957

Ala Gly Ala Arg Leu Val Val Leu Ala Thr Ala Thr Pro Pro Gly
 1               5                  10                 15

<210> SEQ ID NO 958
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 958

Ala Arg Leu Val Val Leu Ala Thr Ala Thr Pro Pro Gly Ser Val
 1               5                  10                 15

<210> SEQ ID NO 959
<211> LENGTH: 18
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 959

Val Val Cys Cys Ser Met Ser Tyr Ser Trp Thr Gly Ala Leu Ile Thr
 1               5                  10                 15

Pro Cys

<210> SEQ ID NO 960
<211> LENGTH: 15
<212> TYPE: PRT
<213> ORGANISM: Artificial Sequence
```

-continued

```
<220> FEATURE:
<223> OTHER INFORMATION: Description of Artificial Sequence: Synthetic
      Peptide

<400> SEQUENCE: 960

Ala Ala Gly Leu Arg Asp Leu Ala Val Ala Val Glu Pro Ile Val
 1               5                  10                  15

<210> SEQ ID NO 961
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 961

Ala Val Arg Thr Lys Leu Lys Leu Thr Pro Ile Pro Ala Ala Ser
 1               5                  10                  15

<210> SEQ ID NO 962
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 962

Leu Gly Lys Val Ile Asp Thr Leu Thr Cys Gly Phe Ala
 1               5                  10

<210> SEQ ID NO 963
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 963

Gly Lys Val Ile Asp Thr Leu Thr Cys Gly Phe Ala Asp
 1               5                  10

<210> SEQ ID NO 964
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 964

Thr Cys Gly Phe Ala Asp Leu Met Gly Tyr Ile Pro Leu Val Gly
 1               5                  10                  15

<210> SEQ ID NO 965
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 965

Gly Phe Ala Asp Leu Met Gly Tyr Ile Pro Leu Val Gly Ala Pro
 1               5                  10                  15
```

```
<210> SEQ ID NO 966
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 966

Asp Leu Met Gly Tyr Ile Pro Val Val Gly Ala Pro Leu Gly Gly
 1               5                  10                  15

<210> SEQ ID NO 967
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 967

Cys Gly Phe Ala Asp Leu Met Gly Tyr Ile Pro Val Val Gly Ala
 1               5                  10                  15

<210> SEQ ID NO 968
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 968

Phe Ala Asp Leu Met Gly Tyr Ile Pro Val Val Gly Ala Pro Leu
 1               5                  10                  15

<210> SEQ ID NO 969
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 969

Asp Leu Met Gly Tyr Ile Pro Val Val Gly Ala Pro Leu Gly Gly
 1               5                  10                  15

<210> SEQ ID NO 970
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 970

Leu Ala His Gly Val Arg Val Leu Glu Asp Gly Val Asn Tyr Ala
 1               5                  10                  15

<210> SEQ ID NO 971
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide
```

-continued

```
<400> SEQUENCE: 971

His Gly Val Arg Val Leu Glu Asp Gly Val Asn Tyr Ala Thr Gly
 1               5                  10                  15

<210> SEQ ID NO 972
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 972

Val Arg Val Leu Glu Asp Gly Val Asn Tyr Ala Thr Gly Asn Leu
 1               5                  10                  15

<210> SEQ ID NO 973
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 973

Val Leu Glu Asp Gly Val Asn Tyr Ala Thr Gly Asn Leu Pro Gly
 1               5                  10                  15

<210> SEQ ID NO 974
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 974

Glu Asp Gly Val Asn Tyr Ala Thr Gly Asn Leu Pro Gly Cys Ser
 1               5                  10                  15

<210> SEQ ID NO 975
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 975

Ala Ala Gln Gly Tyr Lys Val Leu Val Leu Asn Pro Ser Val Ala
 1               5                  10                  15

<210> SEQ ID NO 976
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 976

Gln Gly Tyr Lys Val Leu Val Leu Asn Pro Ser Val Ala Ala Thr
 1               5                  10                  15

<210> SEQ ID NO 977
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      Peptide

<400> SEQUENCE: 977

Tyr Lys Val Leu Val Leu Asn Pro Ser Val Ala Ala Thr Leu Gly
 1               5                  10                  15

<210> SEQ ID NO 978
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 978

Val Leu Val Leu Asn Pro Ser Val Ala Ala Thr Leu Gly Phe Gly
 1               5                  10                  15

<210> SEQ ID NO 979
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 979

Ala Val Gln Trp Met Asn Arg Leu Ile Ala Phe Ala Ser Arg Gly
 1               5                  10                  15

<210> SEQ ID NO 980
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 980

Asn Phe Ile Ser Gly Ile Gln Tyr Leu Ala Gly Leu Ser Thr Leu
 1               5                  10                  15

<210> SEQ ID NO 981
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 981

Ile Ser Gly Ile Gln Tyr Leu Ala Gly Leu Ser Thr Leu Pro Gly
 1               5                  10                  15

<210> SEQ ID NO 982
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 982

Gly Ile Gln Tyr Leu Ala Gly Leu Ser Thr Leu Pro Gly Asn Pro
 1               5                  10                  15
```

<210> SEQ ID NO 983
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 983

Gln Tyr Leu Ala Gly Leu Ser Thr Leu Pro Gly Asn Pro Ala Ile
1               5                   10                  15

<210> SEQ ID NO 984
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 984

Leu Ala Gly Leu Ser Thr Leu Pro Gly Asn Pro Ala Ile Ala Ser
1               5                   10                  15

<210> SEQ ID NO 985
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 985

Gly His Ala Val Gly Ile Phe Arg Ala Ala Val Cys Thr Arg Gly
1               5                   10                  15

<210> SEQ ID NO 986
<211> LENGTH: 16
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 986

Thr Gly Asp Phe Asp Ser Val Ile Asp Cys Asn Thr Cys Val Thr Gln
1               5                   10                  15

<210> SEQ ID NO 987
<211> LENGTH: 16
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 987

Thr Gly Asp Phe Asp Ser Val Ile Asp Cys Asn Val Ala Val Thr Gln
1               5                   10                  15

<210> SEQ ID NO 988
<211> LENGTH: 16
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 988

Ser Gly His Arg Met Ala Trp Asp Met Met Asn Trp Ser Pro Thr
1               5                   10                  15

<210> SEQ ID NO 989
<211> LENGTH: 16
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 989

Thr Gly His Arg Met Ala Trp Asp Met Met Asn Trp Ser Pro Thr
1               5                   10                  15

<210> SEQ ID NO 990
<211> LENGTH: 67
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 990

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys
65

<210> SEQ ID NO 991
<211> LENGTH: 56
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 991

Val Asn Leu Leu Pro Ala Ile Leu Ser Pro Gly Ala Leu Val Val Gly
1               5                   10                  15

Val Val Cys Ala Ala Ile Leu Arg Arg His Val Gly Pro Gly Glu Gly
            20                  25                  30

Ala Val Gln Trp Met Asn Arg Leu Ile Ala Phe Ala Ser Arg Gly Asn
        35                  40                  45

His Val Ser Pro Thr His Tyr Val
    50                  55

<210> SEQ ID NO 992
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 992

-continued

```
Ile Lys Gly Gly Arg His Leu Ile Phe Cys His Ser Lys Lys Lys Cys
 1               5                  10                  15

Asp Glu Leu Ala
            20

<210> SEQ ID NO 993
<211> LENGTH: 21
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 993

Tyr Leu Val Ala Tyr Gln Ala Thr Val Cys Ala Arg Ala Gln Ala Pro
 1               5                  10                  15

Pro Pro Ser Trp Asp
            20

<210> SEQ ID NO 994
<211> LENGTH: 41
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 994

Tyr Leu His Ala Pro Thr Gly Ser Gly Lys Ser Thr Lys Val Pro Val
 1               5                  10                  15

Ala Tyr Ala Ala Gln Gly Tyr Lys Val Leu Val Leu Asn Pro Ser Val
            20                  25                  30

Ala Ala Thr Leu Gly Phe Gly Ala Tyr
            35                  40

<210> SEQ ID NO 995
<211> LENGTH: 37
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 995

Gly Ala Ala Val Gly Ser Ile Gly Leu Gly Lys Val Leu Val Asp Ile
 1               5                  10                  15

Leu Ala Gly Tyr Gly Ala Gly Val Ala Gly Ala Leu Val Ala Phe Lys
            20                  25                  30

Ile Met Ser Gly Glu
        35

<210> SEQ ID NO 996
<211> LENGTH: 37
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 996

Gly Ala Ala Val Gly Ser Ile Gly Leu Gly Lys Val Leu Val Asp Ile
 1               5                  10                  15

Leu Ala Gly Tyr Gly Ala Gly Ile Ser Gly Ala Leu Val Ala Phe Lys
            20                  25                  30
```

```
              20                  25                  30

Ile Met Ser Gly Glu
        35

<210> SEQ ID NO 997
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 997

Cys Gly Tyr Arg Arg Cys Arg Ala Ser Gly Val Leu Thr Thr Ser
 1               5                  10                  15

<210> SEQ ID NO 998
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 998

Pro Val Asn Ser Trp Leu Gly Asn Ile Ile Met Tyr Ala Pro Thr
 1               5                  10                  15

<210> SEQ ID NO 999
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 999

Pro Val Asn Ser Trp Leu Gly Asn Ile Ile Gln Tyr Ala Pro Thr
 1               5                  10                  15

<210> SEQ ID NO 1000
<211> LENGTH: 34
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1000

Ser Gly Met Phe Asp Ser Ser Val Leu Cys Glu Cys Tyr Asp Ala Gly
 1               5                  10                  15

Cys Ala Trp Tyr Glu Leu Thr Pro Ala Glu Thr Ser Val Arg Leu Arg
            20                  25                  30

Ala Tyr

<210> SEQ ID NO 1001
<211> LENGTH: 34
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1001

Ser Gly Met Phe Asp Ser Val Val Leu Cys Glu Cys Tyr Asp Ala Gly
 1               5                  10                  15
```

```
Ala Ala Trp Tyr Glu Leu Thr Pro Ala Glu Thr Thr Val Arg Leu Arg
            20                  25                  30

Ala Tyr

<210> SEQ ID NO 1002
<211> LENGTH: 34
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 1002

Phe Trp Ala Lys His Met Trp Asn Phe Ile Ser Gly Ile Gln Tyr Leu
  1               5                  10                  15

Ala Gly Leu Ser Thr Leu Pro Gly Asn Pro Ala Ile Ala Ser Leu Met
            20                  25                  30

Ala Phe

<210> SEQ ID NO 1003
<211> LENGTH: 16
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 1003

Gly Glu Val Gln Val Val Ser Thr Ala Thr Gln Ser Phe Leu Ala Thr
  1               5                  10                  15

<210> SEQ ID NO 1004
<211> LENGTH: 16
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 1004

Gly Glu Val Gln Val Leu Ser Thr Val Thr Gln Ser Phe Leu Gly Thr
  1               5                  10                  15

<210> SEQ ID NO 1005
<211> LENGTH: 16
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 1005

Phe Ser Asp Asn Ser Thr Pro Pro Ala Val Pro Gln Thr Tyr Gln Val
  1               5                  10                  15

<210> SEQ ID NO 1006
<211> LENGTH: 56
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 1006

Val Asn Leu Leu Pro Gly Ile Leu Ser Pro Gly Ala Leu Val Val Gly
```

```
                 1               5                  10                 15
Val Ile Cys Ala Ala Ile Leu Arg Arg His Val Gly Pro Gly Glu Gly
                    20                  25                  30
Ala Val Gln Trp Met Asn Arg Leu Ile Ala Phe Ala Ser Arg Gly Asn
            35                  40                  45
His Val Ala Pro Thr His Tyr Val
        50                  55

<210> SEQ ID NO 1007
<211> LENGTH: 34
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1007

Phe Trp Ala Lys His Met Trp Asn Phe Ile Ser Gly Ile Gln Tyr Leu
 1               5                  10                  15
Ala Gly Leu Ser Thr Leu Pro Gly Asn Pro Ala Val Ala Ser Met Met
            20                  25                  30
Ala Phe

<210> SEQ ID NO 1008
<211> LENGTH: 18
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1008

Val Val Cys Cys Ser Met Ser Tyr Thr Trp Thr Gly Ala Leu Ile Thr
 1               5                  10                  15
Pro Cys

<210> SEQ ID NO 1009
<211> LENGTH: 18
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1009

Val Val Cys Cys Ser Met Ser Tyr Ser Trp Thr Gly Ala Leu Ile Thr
 1               5                  10                  15
Pro Cys

<210> SEQ ID NO 1010
<211> LENGTH: 19
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1010

Leu Thr Pro Pro His Ser Ala Lys Ser Lys Phe Gly Tyr Gly Ala Lys
 1               5                  10                  15
Asp Val Arg
```

```
<210> SEQ ID NO 1011
<211> LENGTH: 19
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1011

Leu Thr Pro Pro His Ser Ala Lys Ser Lys Tyr Gly Tyr Gly Ala Lys
  1               5                  10                  15

Glu Val Arg

<210> SEQ ID NO 1012
<211> LENGTH: 19
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1012

Leu Thr Pro Pro His Ser Ala Arg Ser Lys Tyr Gly Tyr Gly Ala Lys
  1               5                  10                  15

Glu Val Arg

<210> SEQ ID NO 1013
<211> LENGTH: 16
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1013

Thr Gly Asp Phe Asp Ser Val Ile Asp Cys Asn Val Ala Val Thr Gln
  1               5                  10                  15

<210> SEQ ID NO 1014
<211> LENGTH: 21
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1014

Tyr Leu Val Ala Tyr Gln Ala Thr Val Cys Ala Arg Ala Lys Ala Pro
  1               5                  10                  15

Pro Pro Ser Trp Asp
             20

<210> SEQ ID NO 1015
<211> LENGTH: 19
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1015

Leu Glu Asp Arg Asp Arg Ser Glu Leu Ser Pro Leu Leu Leu Ser Thr
  1               5                  10                  15

Thr Glu Trp
```

```
<210> SEQ ID NO 1016
<211> LENGTH: 19
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1016

Leu Glu Asp Arg Asp Arg Ser Gln Leu Ser Pro Leu Leu His Ser Thr
 1               5                  10                  15

Thr Glu Trp

<210> SEQ ID NO 1017
<211> LENGTH: 18
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1017

Pro Glu Tyr Asp Leu Glu Leu Ile Thr Ser Cys Ser Ser Asn Val Ser
 1               5                  10                  15

Val Ala

<210> SEQ ID NO 1018
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1018

Val Cys Gly Pro Val Tyr Cys Phe Thr Pro Ser Pro Val Val Val Gly
 1               5                  10                  15

Thr Thr Asp Arg
            20

<210> SEQ ID NO 1019
<211> LENGTH: 17
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1019

Leu Leu Phe Leu Leu Leu Ala Asp Ala Arg Val Cys Ala Cys Leu Trp
 1               5                  10                  15

Met

<210> SEQ ID NO 1020
<211> LENGTH: 16
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1020

Ser Gly His Arg Met Ala Trp Asp Met Met Asn Trp Ser Pro Thr
 1               5                  10                  15
```

```
<210> SEQ ID NO 1021
<211> LENGTH: 16
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1021

Thr Gly His Arg Met Ala Trp Asp Met Met Asn Trp Ser Pro Thr
 1               5                  10                  15

<210> SEQ ID NO 1022
<211> LENGTH: 30
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1022

Ile Thr Tyr Ser Thr Tyr Gly Lys Phe Leu Ala Asp Gly Gly Cys Ser
 1               5                  10                  15

Gly Gly Ala Tyr Asp Ile Ile Ile Cys Asp Glu Cys His Ser
            20                  25                  30

<210> SEQ ID NO 1023
<211> LENGTH: 37
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1023

Ala Arg Ala Leu Ala His Gly Val Arg Val Leu Glu Asp Gly Val Asn
 1               5                  10                  15

Tyr Ala Thr Gly Asn Leu Pro Gly Cys Ser Phe Ser Ile Phe Leu Leu
            20                  25                  30

Ala Leu Leu Ser Cys
        35

<210> SEQ ID NO 1024
<211> LENGTH: 36
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1024

Asp Pro Arg His Arg Ser Arg Asn Val Gly Lys Val Ile Asp Thr Leu
 1               5                  10                  15

Thr Cys Gly Phe Ala Asp Leu Met Gly Tyr Ile Pro Val Val Gly Ala
            20                  25                  30

Pro Leu Gly Gly
        35

<210> SEQ ID NO 1025
<211> LENGTH: 32
<212> TYPE: PRT
<213> ORGANISM: Artificial Sequence
<220> FEATURE:
<223> OTHER INFORMATION: Description of Artificial Sequence: Synthetic
      Peptide
```

-continued

```
<400> SEQUENCE: 1025

Val Asp Tyr Pro Tyr Arg Leu Trp His Tyr Pro Cys Thr Val Asn Phe
1               5                   10                  15

Thr Ile Phe Lys Val Arg Met Tyr Val Gly Gly Val Glu His Arg Leu
            20                  25                  30

<210> SEQ ID NO 1026
<211> LENGTH: 32
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1026

Val Asp Tyr Pro Tyr Arg Leu Trp His Tyr Pro Cys Thr Val Asn Tyr
1               5                   10                  15

Thr Ile Phe Lys Ile Arg Met Tyr Val Gly Gly Val Glu His Arg Leu
            20                  25                  30

<210> SEQ ID NO 1027
<211> LENGTH: 28
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1027

Lys Gly Gly Arg Lys Pro Ala Arg Leu Ile Val Phe Pro Asp Leu Gly
1               5                   10                  15

Val Arg Val Cys Glu Lys Met Ala Leu Tyr Asp Val
            20                  25

<210> SEQ ID NO 1028
<211> LENGTH: 28
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1028

Lys Gly Gly Lys Lys Ala Ala Arg Leu Ile Val Tyr Pro Asp Leu Gly
1               5                   10                  15

Val Arg Val Cys Glu Lys Met Ala Leu Tyr Asp Val
            20                  25

<210> SEQ ID NO 1029
<211> LENGTH: 23
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1029

Ile Gln Leu Ile Asn Thr Asn Gly Ser Trp His Ile Asn Arg Thr Ala
1               5                   10                  15

Leu Asn Cys Asn Asp Ser Leu
            20

<210> SEQ ID NO 1030
<211> LENGTH: 23
```

```
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1030

Ile Gln Leu Val Asn Thr Asn Gly Ser Trp His Ile Asn Arg Thr Ala
 1               5                  10                  15

Leu Asn Cys Asn Asp Ser Leu
            20

<210> SEQ ID NO 1031
<211> LENGTH: 23
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1031

Leu Pro Ala Leu Ser Thr Gly Leu Ile His Leu His Gln Asn Ile Val
 1               5                  10                  15

Asp Tyr Gln Tyr Leu Tyr Gly
            20

<210> SEQ ID NO 1032
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 1032

Arg Pro Met Thr Tyr Lys Ala Ala Leu
 1               5

<210> SEQ ID NO 1033
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 1033

Leu Pro Cys Val Leu Trp Pro Val Leu
 1               5

<210> SEQ ID NO 1034
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1034

Met Trp Asn Phe Ile Ser Gly Ile Gln Tyr Leu Ala Gly Leu Ser Thr
 1               5                  10                  15

Leu Pro Gly Asn
            20

<210> SEQ ID NO 1035
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1035

His Met Trp Asn Phe Ile Ser Gly Ile
  1               5

<210> SEQ ID NO 1036
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1036

Asn Phe Ile Ser Gly Ile Gln Tyr Leu Ala Gly Leu Ser Thr Leu Pro
  1               5                  10                  15

Gly Asn Pro Ala
            20

<210> SEQ ID NO 1037
<211> LENGTH: 23
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1037

His Met Trp Asn Phe Ile Ser Gly Ile Gln Tyr Leu Ala Gly Leu Ser
  1               5                  10                  15

Thr Leu Pro Gly Asn Pro Ala
            20

<210> SEQ ID NO 1038
<211> LENGTH: 26
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1038

Ile Gly Leu Gly Lys Val Leu Val Asp Ile Leu Ala Gly Tyr Gly Ala
  1               5                  10                  15

Gly Val Ala Gly Ala Leu Val Ala Phe Lys
            20                  25

<210> SEQ ID NO 1039
<211> LENGTH: 16
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1039

Ala Ala Trp Tyr Glu Leu Thr Pro Ala Glu Thr Thr Val Arg Leu Arg
  1               5                  10                  15

<210> SEQ ID NO 1040
<211> LENGTH: 20
```

-continued

```
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1040

Asp Tyr Pro Tyr Arg Leu Trp His Tyr Pro Cys Thr Val Asn Tyr Thr
 1               5                  10                  15

Ile Phe Lys Ile
            20

<210> SEQ ID NO 1041
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1041

Asp Tyr Pro Tyr Arg Leu Trp His Tyr Pro Cys Thr Val Asn Phe Thr
 1               5                  10                  15

Ile Phe Lys Ile
            20

<210> SEQ ID NO 1042
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1042

Ala Tyr Ser Gln Gln Thr Arg Gly Leu Leu
 1               5                  10

<210> SEQ ID NO 1043
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1043

Thr Ala Tyr Ser Gln Gln Thr Arg Gly Leu Leu Gly
 1               5                  10

<210> SEQ ID NO 1044
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1044

Ser Met Ser Tyr Thr Trp Thr Gly Ala Leu Ile Thr Pro
 1               5                  10

<210> SEQ ID NO 1045
<211> LENGTH: 10
<212> TYPE: PRT
<213> ORGANISM: Artificial Sequence
<220> FEATURE:
```

```
<223> OTHER INFORMATION: Description of Artificial Sequence:  Synthetic
      Peptide

<400> SEQUENCE: 1045

Ser Pro Gly Ala Leu Val Val Gly Val Ile
 1               5                   10

<210> SEQ ID NO 1046
<211> LENGTH: 8
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 1046

Leu Pro Arg Arg Gly Pro Arg Leu
 1               5

<210> SEQ ID NO 1047
<211> LENGTH: 19
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 1047

Thr Asn Pro Lys Pro Gln Arg Lys Thr Lys Arg Asn Thr Asn Arg Arg
 1               5                   10                  15

Pro Gln Asp

<210> SEQ ID NO 1048
<211> LENGTH: 11
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 1048

Pro Gln Arg Lys Thr Lys Arg Asn Thr Asn Arg
 1               5                   10

<210> SEQ ID NO 1049
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 1049

Gln Arg Lys Thr Lys Arg Asn Thr Asn
 1               5

<210> SEQ ID NO 1050
<211> LENGTH: 8
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 1050

Gln Arg Lys Thr Lys Arg Asn Thr
 1               5
```

<210> SEQ ID NO 1051
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1051

Arg Lys Thr Lys Arg Asn Thr Asn Arg
 1               5

<210> SEQ ID NO 1052
<211> LENGTH: 21
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1052

Lys Gly Gly Arg Lys Pro Ala Arg Leu Ile Val Phe Pro Asp Leu Gly
 1               5                  10                  15

Val Arg Val Cys Glu
            20

<210> SEQ ID NO 1053
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1053

Ala Arg Leu Ile Val Phe Pro Asp Leu
 1               5

<210> SEQ ID NO 1054
<211> LENGTH: 26
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1054

Ile Gly Leu Gly Lys Val Leu Val Asp Ile Leu Ala Gly Tyr Gly Ala
 1               5                  10                  15

Gly Val Ala Gly Ala Leu Val Ala Phe Lys
            20                  25

<210> SEQ ID NO 1055
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1055

Gly Ser Ile Gly Leu Gly Lys Val Leu Val Asp Ile Leu Ala Gly
 1               5                  10                  15

<210> SEQ ID NO 1056

```
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1056

Ile Gly Leu Gly Lys Val Leu Val Asp Ile Leu Ala Gly Tyr Gly
 1               5                  10                  15

<210> SEQ ID NO 1057
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1057

Leu Gly Lys Val Leu Val Asp Ile Leu Ala Gly Tyr Gly Ala Gly
 1               5                  10                  15

<210> SEQ ID NO 1058
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1058

Leu Val Asp Ile Leu Ala Gly Tyr Gly Ala Gly Val Ala Gly Ala
 1               5                  10                  15

<210> SEQ ID NO 1059
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1059

Asp Ile Leu Ala Gly Tyr Gly Ala Gly Val Ala Gly Ala Leu Val
 1               5                  10                  15

<210> SEQ ID NO 1060
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1060

Leu Ala Gly Tyr Gly Ala Gly Val Ala Gly Ala Leu Val Ala Phe
 1               5                  10                  15

<210> SEQ ID NO 1061
<211> LENGTH: 16
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1061
```

```
Ala Ala Trp Tyr Glu Leu Thr Pro Ala Glu Thr Thr Val Arg Leu Arg
 1               5                  10                  15
```

<210> SEQ ID NO 1062
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1062

```
Ala Gly Ala Ala Trp Tyr Glu Leu Thr Pro Ala Glu Thr Thr Val
 1               5                  10                  15
```

<210> SEQ ID NO 1063
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1063

```
Ala Ala Trp Tyr Glu Leu Thr Pro Ala Glu Thr Thr Val Arg Leu
 1               5                  10                  15
```

<210> SEQ ID NO 1064
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1064

```
Thr Ala Tyr Ser Gln Gln Thr Arg Gly Leu Leu Gly
 1               5                  10
```

<210> SEQ ID NO 1065
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1065

```
Thr Ala Tyr Ser Gln Gln Thr Arg Gly Leu Leu Gly Cys Ile Val
 1               5                  10                  15
```

<210> SEQ ID NO 1066
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1066

```
Ser Met Ser Tyr Thr Trp Thr Gly Ala Leu Ile Thr Pro
 1               5                  10
```

<210> SEQ ID NO 1067
<211> LENGTH: 18
<212> TYPE: PRT
<213> ORGANISM: Artificial Sequence
<220> FEATURE:

```
<223> OTHER INFORMATION: Description of Artificial Sequence: Synthetic
      Peptide

<400> SEQUENCE: 1067

Val Val Cys Cys Ser Met Ser Tyr Thr Trp Thr Gly Ala Leu Ile Thr
1               5                  10                  15

Pro Cys

<210> SEQ ID NO 1068
<211> LENGTH: 32
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1068

Val Asp Tyr Pro Tyr Arg Leu Trp His Tyr Pro Cys Thr Val Asn Phe
1               5                  10                  15

Thr Ile Phe Lys Val Arg Met Tyr Val Gly Gly Val Glu His Arg Leu
            20                  25                  30

<210> SEQ ID NO 1069
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1069

Asp Tyr Pro Tyr Arg Leu Trp His Tyr Pro Cys Thr Val Asn Phe
1               5                  10                  15

<210> SEQ ID NO 1070
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1070

Tyr Pro Tyr Arg Leu Trp His Tyr Pro Cys Thr Val Asn Phe Thr
1               5                  10                  15

<210> SEQ ID NO 1071
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1071

Leu Trp His Tyr Pro Cys Thr Val Asn Phe Thr Ile Phe Lys Val
1               5                  10                  15

<210> SEQ ID NO 1072
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1072
```

Thr Val Asn Phe Thr Ile Phe Lys Val Arg Met Tyr Val Gly Gly
1               5                   10                  15

<210> SEQ ID NO 1073
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1073

Thr Ile Phe Lys Val Arg Met Tyr Val Gly Gly Val Glu His Arg
1               5                   10                  15

<210> SEQ ID NO 1074
<211> LENGTH: 32
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1074

Val Asp Tyr Pro Tyr Arg Leu Trp His Tyr Pro Cys Thr Val Asn Tyr
1               5                   10                  15

Thr Ile Phe Lys Ile Arg Met Tyr Val Gly Gly Val Glu His Arg Leu
            20                  25                  30

<210> SEQ ID NO 1075
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1075

Asp Tyr Pro Tyr Arg Leu Trp His Tyr Pro Cys Thr Val Asn Tyr Thr
1               5                   10                  15

Ile Phe Lys Ile
            20

<210> SEQ ID NO 1076
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1076

Asp Tyr Pro Tyr Arg Leu Trp His Tyr Pro Cys Thr Val Asn Tyr
1               5                   10                  15

<210> SEQ ID NO 1077
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1077

Leu Trp His Tyr Pro Cys Thr Val Asn Tyr Thr Ile Phe Lys Ile
1               5                   10                  15

```
<210> SEQ ID NO 1078
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1078

Thr Val Asn Tyr Thr Ile Phe Lys Ile Arg Met Tyr Val Gly Gly
 1               5                  10                  15

<210> SEQ ID NO 1079
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1079

Thr Ile Phe Lys Ile Arg Met Tyr Val Gly Gly Val Glu His Arg
 1               5                  10                  15

<210> SEQ ID NO 1080
<211> LENGTH: 11
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1080

Arg Met Tyr Val Gly Gly Val Glu His Arg Leu
 1               5                  10

<210> SEQ ID NO 1081
<211> LENGTH: 23
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1081

His Met Trp Asn Phe Ile Ser Gly Ile Gln Tyr Leu Ala Gly Leu Ser
 1               5                  10                  15

Thr Leu Pro Gly Asn Pro Ala
                20

<210> SEQ ID NO 1082
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1082

Asn Phe Ile Ser Gly Ile Gln Tyr Leu Ala Gly Leu Ser Thr Leu Pro
 1               5                  10                  15

Gly Asn Pro Ala
            20

<210> SEQ ID NO 1083
```

-continued

```
<211> LENGTH: 20
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 1083

Met Trp Asn Phe Ile Ser Gly Ile Gln Tyr Leu Ala Gly Leu Ser Thr
 1               5                  10                  15

Leu Pro Gly Asn
            20

<210> SEQ ID NO 1084
<211> LENGTH: 29
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1084

Lys Phe Pro Gly Gly Gly Gln Ile Val Gly Gly Val Tyr Leu Leu Pro
 1               5                  10                  15

Arg Arg Gly Pro Arg Leu Gly Val Arg Ala Thr Arg Lys
            20                  25

<210> SEQ ID NO 1085
<211> LENGTH: 22
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1085

Lys Phe Pro Gly Gly Gly Gln Ile Val Gly Gly Val Tyr Leu Leu Pro
 1               5                  10                  15

Arg Arg Gly Pro Arg Leu
            20

<210> SEQ ID NO 1086
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1086

Tyr Leu Leu Pro Arg Arg Gly Pro Arg Leu
 1               5                  10

<210> SEQ ID NO 1087
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1087

Leu Pro Arg Arg Gly Pro Arg Leu
 1               5

<210> SEQ ID NO 1088
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1088

Gly Pro Arg Leu Gly Val Arg Ala Thr
 1               5

<210> SEQ ID NO 1089
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1089

Arg Leu Gly Val Arg Ala Thr Arg Lys
 1               5

<210> SEQ ID NO 1090
<211> LENGTH: 14
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1090

Gly Tyr Lys Val Leu Val Leu Asn Pro Ser Val Ala Ala Thr
 1               5                  10

<210> SEQ ID NO 1091
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1091

Ala Tyr Ala Ala Gln Gly Tyr Lys Val Leu
 1               5                  10

<210> SEQ ID NO 1092
<211> LENGTH: 19
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1092

Ala Tyr Ala Ala Gln Gly Tyr Lys Val Leu Val Leu Asn Pro Ser Val
 1               5                  10                  15

Ala Ala Thr

<210> SEQ ID NO 1093
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide
```

-continued

```
<400> SEQUENCE: 1093

Asp Leu Met Gly Tyr Ile Pro Ala Val
 1               5

<210> SEQ ID NO 1094
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1094

Gly Tyr Ile Pro Leu Val Gly Ala Pro Leu
 1               5                  10

<210> SEQ ID NO 1095
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1095

Asp Leu Met Gly Tyr Ile Pro Leu Val Gly Ala Pro Leu
 1               5                  10

<210> SEQ ID NO 1096
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1096

Cys Ile Asn Gly Val Cys Trp Thr Val
 1               5

<210> SEQ ID NO 1097
<211> LENGTH: 16
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1097

Gly Glu Val Gln Val Val Ser Thr Ala Thr Gln Ser Phe Leu Ala Thr
 1               5                  10                  15

<210> SEQ ID NO 1098
<211> LENGTH: 25
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1098

Gly Glu Val Gln Val Val Ser Thr Ala Thr Gln Ser Phe Leu Ala Thr
 1               5                  10                  15

Cys Ile Asn Gly Val Cys Trp Thr Val
            20                  25
```

```
<210> SEQ ID NO 1099
<211> LENGTH: 23
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1099

His Met Trp Asn Phe Ile Ser Gly Ile Gln Tyr Leu Ala Gly Leu Ser
 1               5                  10                  15

Thr Leu Pro Gly Asn Pro Ala
            20

<210> SEQ ID NO 1100
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1100

Met Trp Asn Phe Ile Ser Gly Ile Gln Tyr Leu Ala Gly Leu Ser Thr
 1               5                  10                  15

Leu Pro Gly Asn
            20

<210> SEQ ID NO 1101
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1101

Asn Phe Ile Ser Gly Ile Gln Tyr Leu Ala Gly Leu Ser Thr Leu Pro
 1               5                  10                  15

Gly Asn Pro Ala
            20

<210> SEQ ID NO 1102
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1102

Gln Tyr Leu Ala Gly Leu Ser Thr Leu
 1               5

<210> SEQ ID NO 1103
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1103

His Met Trp Asn Phe Ile Ser Gly Ile
 1               5
```

```
<210> SEQ ID NO 1104
<211> LENGTH: 32
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1104

Val Asp Tyr Pro Tyr Arg Leu Trp His Tyr Pro Cys Thr Val Asn Phe
 1               5                  10                  15

Thr Ile Phe Lys Val Arg Met Tyr Val Gly Gly Val Glu His Arg Leu
            20                  25                  30

<210> SEQ ID NO 1105
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1105

Asp Tyr Pro Tyr Arg Leu Trp His Tyr Pro Cys Thr Val Asn Phe Thr
 1               5                  10                  15

Ile Phe Lys Ile
            20

<210> SEQ ID NO 1106
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1106

Asp Tyr Pro Tyr Arg Leu Trp His Tyr Pro Cys Thr Val Asn Phe Thr
 1               5                  10                  15

Ile Phe Lys Val
            20

<210> SEQ ID NO 1107
<211> LENGTH: 32
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1107

Val Asp Tyr Pro Tyr Arg Leu Trp His Tyr Pro Cys Thr Val Asn Tyr
 1               5                  10                  15

Thr Ile Phe Lys Ile Arg Met Tyr Val Gly Gly Val Glu His Arg Leu
            20                  25                  30

<210> SEQ ID NO 1108
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1108

Asp Tyr Pro Tyr Arg Leu Trp His Tyr Pro Cys Thr Val Asn Tyr Thr
```

```
                1               5              10              15

Ile Phe Lys Ile
            20

<210> SEQ ID NO 1109
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1109

Asp Tyr Pro Tyr Arg Leu Trp His Tyr
1               5

<210> SEQ ID NO 1110
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1110

Thr Val Asn Tyr Thr Ile Phe Lys Ile
1               5

<210> SEQ ID NO 1111
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1111

Thr Ile Asn Tyr Thr Ile Phe Lys
1               5

<210> SEQ ID NO 1112
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1112

Thr Val Asn Phe Thr Ile Phe Lys Val
1               5

<210> SEQ ID NO 1113
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1113

His Tyr Pro Cys Thr Val Asn Tyr Thr Ile
1               5                   10

<210> SEQ ID NO 1114
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      Peptide

<400> SEQUENCE: 1114

His Tyr Pro Cys Thr Val Asn Phe Thr Ile
1               5                   10

<210> SEQ ID NO 1115
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1115

Arg Met Tyr Val Gly Gly Val Glu His Arg
1               5                   10

<210> SEQ ID NO 1116
<211> LENGTH: 16
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1116

Ala Ala Trp Tyr Glu Leu Thr Pro Ala Glu Thr Thr Val Arg Leu Arg
1               5                   10                  15

<210> SEQ ID NO 1117
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1117

Thr Pro Ala Glu Thr Thr Val Arg Leu
1               5

<210> SEQ ID NO 1118
<211> LENGTH: 23
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1118

Gly Trp Arg Leu Leu Ala Pro Ile Thr Ala Tyr Ser Gln Gln Thr Arg
1               5                   10                  15

Gly Leu Leu Gly Cys Ile Val
            20

<210> SEQ ID NO 1119
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1119
```

```
Thr Ala Tyr Ser Gln Gln Thr Arg Gly Leu Leu Gly Cys Ile Val
 1               5                   10                  15
```

<210> SEQ ID NO 1120
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1120

```
Thr Ala Tyr Ser Gln Gln Thr Arg Gly Leu Leu Gly
 1               5                   10
```

<210> SEQ ID NO 1121
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1121

```
Gly Gln Gly Trp Arg Leu Leu Ala Pro Ile Thr Ala Tyr Ser Gln
 1               5                   10                  15
```

<210> SEQ ID NO 1122
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1122

```
Arg Leu Leu Ala Pro Ile Thr Ala Tyr
 1               5
```

<210> SEQ ID NO 1123
<211> LENGTH: 25
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1123

```
Gly Gln Gly Trp Arg Leu Leu Ala Pro Ile Thr Ala Tyr Ser Gln Gln
 1               5                   10                  15

Thr Arg Gly Leu Leu Gly Cys Ile Val
            20                  25
```

<210> SEQ ID NO 1124
<211> LENGTH: 22
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1124

```
Gly Gln Gly Trp Arg Leu Leu Ala Pro Ile Thr Ala Tyr Ser Gln Gln
 1               5                   10                  15

Thr Arg Gly Leu Leu Gly
            20
```

```
<210> SEQ ID NO 1125
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1125

Ala Tyr Ser Gln Gln Thr Arg Gly Leu Leu
 1               5                  10

<210> SEQ ID NO 1126
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1126

Ala Tyr Ser Gln Gln Thr Arg Gly Leu
 1               5

<210> SEQ ID NO 1127
<211> LENGTH: 26
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1127

Ile Gly Leu Gly Lys Val Leu Val Asp Ile Leu Ala Gly Tyr Gly Ala
 1               5                  10                  15

Gly Val Ala Gly Ala Leu Val Ala Phe Lys
             20                  25

<210> SEQ ID NO 1128
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1128

Ile Leu Ala Gly Tyr Gly Ala Gly Val
 1               5

<210> SEQ ID NO 1129
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1129

Val Ala Gly Ala Leu Val Ala Phe Lys
 1               5

<210> SEQ ID NO 1130
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      Peptide

<400> SEQUENCE: 1130

Gly Tyr Gly Ala Gly Val Ala Gly Ala Leu
 1               5                  10

<210> SEQ ID NO 1131
<211> LENGTH: 18
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1131

Val Val Cys Cys Ser Met Ser Tyr Thr Trp Thr Gly Ala Leu Ile Thr
 1               5                  10                  15

Pro Cys

<210> SEQ ID NO 1132
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1132

Ser Met Ser Tyr Thr Trp Thr Gly Ala Leu Ile Thr Pro
 1               5                  10

<210> SEQ ID NO 1133
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1133

Ser Met Ser Tyr Thr Trp Thr Gly Ala Leu
 1               5                  10

<210> SEQ ID NO 1134
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1134

Ser Tyr Thr Trp Thr Gly Ala Leu Ile
 1               5

<210> SEQ ID NO 1135
<211> LENGTH: 16
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1135

Phe Thr Asp Asn Ser Ser Pro Pro Ala Val Pro Gln Thr Phe Gln Val
```

```
                1               5                  10                 15
```

<210> SEQ ID NO 1136
<211> LENGTH: 19
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1136

```
Leu Glu Asp Arg Asp Arg Ser Glu Leu Ser Pro Leu Leu Leu Ser Thr
  1               5                  10                 15
Thr Glu Trp
```

<210> SEQ ID NO 1137
<211> LENGTH: 16
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1137

```
Leu Glu Asp Arg Asp Arg Ser Glu Leu Ser Pro Leu Leu Leu Ser Thr
  1               5                  10                 15
```

<210> SEQ ID NO 1138
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1138

```
Arg Ser Glu Leu Ser Pro Leu Leu Leu
  1               5
```

<210> SEQ ID NO 1139
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1139

```
Glu Leu Ser Pro Leu Leu Leu Ser Thr
  1               5
```

<210> SEQ ID NO 1140
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1140

```
Asp Arg Asp Arg Ser Glu Leu Ser Pro Leu
  1               5                  10
```

<210> SEQ ID NO 1141
<211> LENGTH: 9
<212> TYPE: PRT
<213> ORGANISM: Artificial Sequence

```
<220> FEATURE:
<223> OTHER INFORMATION: Description of Artificial Sequence: Synthetic
      Peptide

<400> SEQUENCE: 1141

Leu Glu Asp Arg Asp Arg Ser Glu Leu
 1               5

<210> SEQ ID NO 1142
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1142

Leu Glu Asp Arg Asp Arg Ser Glu Leu
 1               5

<210> SEQ ID NO 1143
<211> LENGTH: 21
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1143

Tyr Leu Val Ala Tyr Gln Ala Thr Val Cys Ala Arg Ala Gln Ala Pro
 1               5                  10                  15

Pro Pro Ser Trp Asp
            20

<210> SEQ ID NO 1144
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1144

Tyr Leu Val Ala Tyr Gln Ala Thr Val
 1               5

<210> SEQ ID NO 1145
<211> LENGTH: 17
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1145

Met Ser Thr Asn Pro Lys Pro Gln Arg Lys Thr Lys Arg Asn Thr Asn
 1               5                  10                  15

Arg

<210> SEQ ID NO 1146
<211> LENGTH: 11
<212> TYPE: PRT
<213> ORGANISM: Artificial Sequence
<220> FEATURE:
<223> OTHER INFORMATION: Description of Artificial Sequence: Synthetic
      Peptide
```

```
<400> SEQUENCE: 1146

Pro Gln Arg Lys Thr Lys Arg Asn Thr Asn Arg
  1               5                  10

<210> SEQ ID NO 1147
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1147

Gln Arg Lys Thr Lys Arg Asn Thr Asn
  1               5

<210> SEQ ID NO 1148
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1148

Arg Lys Thr Lys Arg Asn Thr Asn Arg
  1               5

<210> SEQ ID NO 1149
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1149

Met Ser Thr Asn Pro Lys Pro Gln Arg
  1               5

<210> SEQ ID NO 1150
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1150

Met Ser Thr Asn Pro Lys Pro Gln Lys
  1               5

<210> SEQ ID NO 1151
<211> LENGTH: 21
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1151

Leu Ile Asn Thr Asn Gly Ser Trp His Ile Asn Arg Thr Ala Leu Asn
  1               5                  10                  15

Cys Asn Asp Ser Leu
            20
```

```
<210> SEQ ID NO 1152
<211> LENGTH: 17
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1152

Asn Gly Ser Trp His Ile Asn Arg Thr Ala Leu Asn Cys Asn Asp Ser
 1               5                  10                  15

Leu

<210> SEQ ID NO 1153
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1153

Leu Ile Asn Thr Asn Gly Ser Trp His Ile
 1               5                  10

<210> SEQ ID NO 1154
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1154

Arg Thr Ala Leu Asn Cys Asn Asp Ser Leu
 1               5                  10

<210> SEQ ID NO 1155
<211> LENGTH: 16
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1155

Leu Ile Asn Thr Asn Gly Ser Trp His Ile Asn Arg Thr Ala Leu Asn
 1               5                  10                  15

<210> SEQ ID NO 1156
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1156

Ser Trp His Ile Asn Arg Thr Ala Leu Asn
 1               5                  10

<210> SEQ ID NO 1157
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide
```

```
<400> SEQUENCE: 1157

Thr Thr Ile Leu Gly Ile Gly Thr Val Leu Asp Gln Ala Glu Thr
 1               5                  10                  15

<210> SEQ ID NO 1158
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1158

Thr Thr Ile Leu Gly Ile Gly Thr Val
 1               5

<210> SEQ ID NO 1159
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1159

Thr Ile Leu Gly Ile Gly Thr Val Leu
 1               5

<210> SEQ ID NO 1160
<211> LENGTH: 18
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1160

Phe Asp Ser Ser Val Leu Cys Glu Cys Tyr Asp Ala Gly Ala Ala Trp
 1               5                  10                  15

Tyr Glu

<210> SEQ ID NO 1161
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1161

Phe Asp Ser Ser Val Leu Cys Glu Cys Tyr Asp Ala Gly Cys Ala
 1               5                  10                  15

<210> SEQ ID NO 1162
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1162

Val Leu Cys Glu Cys Tyr Asp Ala Gly Ala
 1               5                  10
```

<210> SEQ ID NO 1163
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1163

Val Val Leu Cys Glu Cys Tyr Asp Ala Gly Ala Ala Trp Tyr Glu
 1               5                  10                  15

<210> SEQ ID NO 1164
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1164

Ala Arg Leu Ile Val Phe Pro Asp Leu Gly Val Arg Val Cys Glu Lys
 1               5                  10                  15

Met Ala Leu Tyr
            20

<210> SEQ ID NO 1165
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1165

Ala Arg Leu Ile Val Phe Pro Asp Leu
 1               5

<210> SEQ ID NO 1166
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1166

Arg Leu Ile Val Phe Pro Asp Leu Gly Val
 1               5                  10

<210> SEQ ID NO 1167
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1167

Arg Val Cys Glu Lys Met Ala Leu Tyr
 1               5

<210> SEQ ID NO 1168
<211> LENGTH: 15
<212> TYPE: PRT
<213> ORGANISM: Artificial Sequence
<220> FEATURE:
<223> OTHER INFORMATION: Description of Artificial Sequence: Synthetic -continued

```
      Peptide

<400> SEQUENCE: 1168

Ala Phe Cys Ser Ala Met Tyr Val Gly Asp Leu Cys Gly Ser Val
1               5                   10                  15

<210> SEQ ID NO 1169
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1169

Gly Val Leu Phe Gly Leu Ala Tyr Phe Ser Met Val Gly Asn Trp
1               5                   10                  15

<210> SEQ ID NO 1170
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1170

Thr Arg Val Pro Tyr Phe Val Arg Ala Gln Gly Leu Ile Arg Ala
1               5                   10                  15

<210> SEQ ID NO 1171
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1171

Thr Thr Leu Leu Phe Asn Ile Leu Gly Gly Trp Val Ala Ala Gln
1               5                   10                  15

<210> SEQ ID NO 1172
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1172

Leu Leu Phe Asn Ile Leu Gly Gly Trp Val
1               5                   10
```

METHOD FOR ISOLATING HEPATITIS C VIRUS PEPTIDES

This application is a national phase application under 35 U.S.C. §371 of International Application No. PCT/EP2003/009482 filed 27 Aug. 2003, which claims priority to Austrian Application No. A 1376/2002 filed 13 Sep. 2002, International Application No. PCT/EP03/02005 filed 27 Feb. 2003, and European Patent Application No. 03450171.8 filed 11 Jul. 2003, the contents of all of which applications are incorporated herein by reference in their entirety.

The Sequence Listing is submitted on one compact disc (Copy 1), together with a duplicate thereof (Copy 2), each created on Aug. 18, 2005, and each containing one 344 kb file entitled "SONN059SEQ.txt." The material contained on the compact disc is specifically incorporated herein by reference.

The present invention relates to a method for isolating HCV-peptides, especially for isolating HCV T cell epitopes which have a binding capacity to a MHC/HLA molecule.

The immune system is a complex network of inter-related cell types and molecules, which has evolved in order to protect multicellular organisms from infectious microorganisms. It can be divided into the evolutionary older innate (or natural) immunity and adaptive (or acquired) immunity. The innate immune system recognizes patterns, which are usually common and essential for pathogens. For this limited number of molecular structures germ-line encoded receptors have evolved. By contrast, cells of the adaptive immune system—B and T lymphocytes—can recognize a huge variety of antigenic structures. The receptors, termed according to the cell types expressing them, B cell receptor (BCR, its soluble versions are called antibodies) and T cell receptor (TCR, only cell-surface associated forms) are generated by somatic recombination and show a clonal distribution. Thus, initially there is only small number of cells with a certain specificity. Upon antigen encounter these cells start to divide (clonal expansion) to generate an effector population able to cope with the antigen. After elimination of antigen a specialized sub-population of cells specifically recognizing this antigen remains as immunological memory. Taken together the adaptive immune system is slow (compared to innate immunity), however specific and it improves upon repeated exposure to a given pathogen/antigen.

T cells have a central role in adaptive immunity. Their receptors (TCRs) recognize "major histocompatibility complex" (MHC or HLA):peptide complexes on the surface of cells. These peptides are called T cell epitopes and represent degradation products of antigens. There are two major classes of T cells: CD8-positive cytotoxic T cells (CTL) are restricted to MHC class I. CD4-positive helper T cells (HTL) are restricted to MHC class II. HTL are essential for many features of adaptive immunity: activation of so called "professional antigen-presenting cells" (APCs), immunoglobulin (Ig) class switch, the germinal center reaction and Ig affinity maturation, activation of CTL, immunological memory, regulation of the immune response and others.

MHC molecules collect peptides inside the cell and present them on the cell surface to TCRs of T cells. There are two major classes of MHC, class I recognized by CD8-positive CTL and class II recognized by CD4-positive HTL.

MHC class I molecules consist of a membrane-anchored alpha-chain of 45 kDa and the non-covalently attached b2-microglobulin (b2m) of 12 kDA. Resolution of the 3-dimensional structure by X-ray crystallography (Stern and Wiley 1994) revealed that the alpha-chain possesses a cleft, which is closed at both ends and accommodates peptides from 8 to 11 amino acids length. Class I molecules are ubiquitously expressed, and the peptides they present originate from cytoplasmic proteins. These are degraded by the proteasome, and the resulting peptides are actively transported into the endoplasmatic reticulum (ER). There, with the help of several chaperones, MHC:peptide complexes are formed and transported to the cell surface (Heemels 1995). Thus, MHC class I mirrors the proteome of a cell on its surface and allows T cells to recognize intracellular pathogens or malignant cells.

MHC class II molecules consist of two membrane-anchored proteins (alpha- and beta-chain) of 35 kDa and 30 kDa, respectively. These together form a cleft, open at both ends, which can accommodate peptides of variable length, usually from 12 to 25 amino acids. Despite these differences, class I and II molecules share surprising structural similarity (Stern and Wiley 1994). Class II molecules are only expressed on professional APC including dendritic cells (DC), B-cells and macrophages/monocytes. These cells are specialized in taking up and processing antigens in the endosomal pathway. Immediately after their biosynthesis, class II molecules are complexed by the so-called invariant chain (Ii), which prevents binding of peptides in the ER. When vesicles containing class II:Ii complexes fuse with endosomes containing degradation products of exogenous antigen, Ii is degraded until the MHC binding cleft is only complexed by the so-called CLIP peptide. The latter is with the help of chaperones like HLA-DM exchanged by antigenic peptides (Villadangos 2000). Finally, MHC:peptide complexes are again presented on the surface of APCs, which interact in numerous ways with HTL.

Being both polygenic and extremely polymorphic, the MHC system is highly complex. For the class I alpha-chain in humans there are three gene loci termed HLA-A, -B and -C. Likewise, there are three class II alpha-chain loci (DRA, DQA, DPA); for class II beta-chain loci the situation is even more complex as there are four different DR beta-chains (DRB1,2,3,5) plus DQB and DPB. Except the monomorphic DR alpha-chain DRA, each gene locus is present in many different alleles (dozens to hundreds) in the population (Klein 1986). Different alleles have largely distinct binding specificities for peptides. Alleles are designated, for example, HLA-A*0201 or HLA-DRB1*0401 or HLA-DPA*0101/DPB*0401.

T cell epitopes have been identified by a variety of approaches (Van den Eynde 1997). T cell lines and clones have for instance been used to screen cDNA expression libraries for instance in the context of COS cells transfected with the appropriate HLA-molecule. Alternatively, biochemical approaches have been pursued. The latter involved elution of natural ligands from MHC molecules on the surface of target cells, the separation of these peptides by several chromatography steps, analysis of their reactivity with lymphocytes in epitope reconstitution assays and sequencing by mass spectrometry (Wölfel et al. 1994, Cox et al. 1994).

Recently the advent of highly sensitive cytokine detection assays like the IFN-gamma ELIspot allowed using lymphocytes directly ex vivo for screening of overlapping synthetic peptides (Maecker 2001, Kern 2000, Tobery 2001). Primarily, Kern et al. (1999&2000) used arrays of pools of overlapping 9mer peptides to map CD8+ T cell epitopes in vitro. Later, Tobery et al., 2001 modified this approach and demonstrated that pools containing as many as 64 20mer peptides may be used to screen for both CD8+ and CD4+ T cell epitopes in mice. Both these methods were based on the monitoring of antigen-specific response by measuring INFgamma production either by intracellular staining (Kern et al 2000) or in ELIspot assay (Tobery et al., 2001). By use of mixtures of 15-mers the CD4+ T cell responses are approximately equal to those detected when whole soluble protein was used as an antigen, while—not surprising—the CD8+ T cell responses are significantly higher than the often negligible responses detected with soluble protein stimulation. Furthermore, the CD8+ T cell responses to a mixture of 15 amino acid peptides are similar to those obtained with a mix of 8-12 amino acid peptides, selected to represent known MHC class I minimal epitopes. Most probably peptidases associated with the cell membrane are responsible for "clipping" peptides to optimal length under these circumstances (Maecker et al, 2001).

An interesting alternative is to screen synthetic combinatorial peptide libraries with specific lymphocytes. For instance, a decapeptide library consisting of 200 mixtures arranged in a positional scanning format, has been successfully used for identification of peptide ligands that stimulate clonotypic populations of T cells (Wilson, et al., J. Immunol., 1999, 163:6424-6434).

Many T cell epitopes have been identified by so called "Reverse immunological approaches" Rammensee 1999). In this case the protein giving rise to a potential T cell epitope is known, and its primary sequence is scanned for HLA binding motifs. Typically dozens to hundreds of candidate peptides or even a full set of overlapping peptides are synthesized and tested for binding to HLA molecules. Usually, the best binders are selected for further characterization with regard to their reactivity with T cells. This can for instance be done by priming T cells in vitro or in vivo with the help of HLA transgenic mice.

Hepatitis C Virus (HCV) is a member of the flaviviridiae chronically infecting about 170 million people worldwide. There are at least 6 HCV genotypes and more than 50 subtypes have been described. In America, Europe and Japan genotypes 1, 2 and 3 are most common. The geographic distribution of HCV genotypes varies greatly with genotype 1a being predominant in the USA and parts of Western Europe, whereas 1b predominates in Southern and Central Europe (Bellentani 2000).

HCV is transmitted through the parenteral or percutan route, and replicates in hepatocytes. About 15% of patients experience acute self-limited hepatitis associated with viral clearance and recovery. About 80% of infected persons become chronic carriers. Infection often persists asymptomatically with slow progression for years, however ultimately HCV is a major cause of cirrhosis, end-stage liver disease and liver cancer (Liang 2000). Strength and quality of both HTL and CTL responses determine whether patients recover (spontaneously or as a consequence of therapy) or develop chronic infection (Liang 2000).

Standard therapy of HCV comprises a combination of pegylated interferon-alpha and the antiviral ribavirin. Virologic responses are, depending on the genotype, achieved in about 50% of HCV patients. The low tolerability and the considerable side effects of this therapy clearly necessitate novel therapeutic intervention including therapeutic vaccines (Cornberg 2002). However, presently the detailed understanding of which epitopes in which MHC combination lead to successful immune responses is lacking (Ward 2002). Therefore, a comprehensive analysis of the T-cell response against the entire HCV is required for development of therapeutic epitope-based vaccines.

The HCV virion contains a 9.5-kilobase positive single-strand RNA genome encoding a large single polyprotein of about 3000 amino acids. The latter is processed to at least 10 proteins by both host and HCV-encoded proteolytic activities (Liang 2000). Importantly, the HCV RNA-dependent RNA polymerase is error prone giving rise to the evolution of viral quasispecies and contributing to immune-escape variants (Farci 2000).

It is an object of the present invention to provide a method for screening HCV-peptides for specific MHC molecules, preferably for delivering suitable and specific HCV T cell epitopes selected from a variety of HCV-peptides having unknown specificity for a given MHC molecule and thereby to provide efficient means for preventing and combatting HCV infections.

Therefore the present invention provides a method for isolating HCV-peptides which have a binding capacity to a MHC/HLA molecule or a complex comprising said HCV-peptide and said MHC/HLA molecule which method comprises the following steps:

providing a pool of HCV-peptides, said pool containing HCV-peptides which bind to said MHC/HLA molecule and HCV-peptides which do not bind to said MHC/HLA molecule, contacting said MHC/HLA molecule with said pool of HCV-peptides whereby a HCV-peptide which has a binding capacity to said MHC/HLA molecule binds to said MHC/HLA molecule and a complex comprising said HCV-peptide and said MHC/HLA molecule is formed, detecting and optionally separating said complex from the HCV-peptides which do not bind to said MHC/HLA molecule and optionally isolating and characterising the HCV-peptide from said complex.

The present invention also provides a method for isolating HCV T cell epitopes which have a binding capacity to a MHC/HLA molecule or a complex comprising said epitope and said MHC/HLA molecule which method comprises the following steps:

providing a pool of HCV-peptides, said pool containing HCV-peptides which bind to a MHC/HLA molecule and HCV-peptides which do not bind to said MHC/HLA molecule, contacting said MHC/HLA molecule with said pool of HCV-peptides whereby a HCV-peptide which has a binding capacity to said MHC/HLA molecule binds to said MHC/HLA molecule and a complex comprising said HCV-peptide and said MHC/HLA molecule is formed, detecting and optionally separating said complex from the HCV-peptides which do not bind to said MHC/HLA molecule, optionally isolating and characterising the HCV-peptide from said complex, assaying said optionally isolated HCV-peptide or said complex in a T cell assay for T cell activation capacity and providing the optionally isolated HCV-peptide with a T cell activation capacity as HCV T cell epitope or as complex.

The method according to the present invention enables a screening system for screening binding capacity to specific MHC/HLA molecules. Identifying MHC binding molecules is an important tool for molecular characterisation of pathogens, tumors, etc. It is therefore possible with the present invention to screen a variety (a "pool") of potential HCV-peptides as ligands at once for their functional affinity towards MHC molecules. Binding affinity towards MHC molecules is also a necessary prerequisite for HCV-peptides intended to be used as T cell epitopes, although not a sufficient one. Suitable HCV T cell epitope candidates have also to be screened and assayed with respect to their T cell activation capacity. The combination of the screening method for binding according to the present invention with a suitable T cell assay therefore provides the method for isolating HCV T cell epitopes according to the present invention wherein such T cell epitopes are identifiable out of a pool of potential HCV-peptides using an MHC binding assay.

In contrast to the prior art, where such assays have always been performed on ligands with known binding/MHC specificity, the methods according to the present invention provide such assays as a screening tool for pools with ligands of unknown specificity. In the prior art such assays have been typically performed on individual single ligands, to test their binding affinity to MHC/HLA molecules. In Kwok et al. (2001) pools of maximally up to 5 overlapping synthetic peptides were used to generate MHC class II tetramers; the latter were then used to stain PBMC for T cells specific for particular MHC class II:peptide complexes which were generated in the binding reaction with the pools of 5 peptides. However, an increase in the number of ligands per pool in such an approach was not regarded as being possible, both for sensitivity and specificity reasons (Novak et al. 2001). A problem with regard to specificity would be the generation of MHC tetramers with more then one binder per tetramer, if more than one binder would be present in the pool. This would preclude staining of T cells, which is used for identification of epitopes in the approach described in the prior art. In strong contrast to that the approach according to the present invention allows the identification of more than on binder out of highly complex mixtures containing more than one binder.

The nature of the pool to be screened with the present invention is not critical: the pools may contain any naturally or not naturally occurring HCV-peptide which a) binds specifically to MHC/HLA molecules and/or b) may be specifically recognized by T cells. The binding properties of the set of HCV-peptides of the pool with respect to MHC molecules is not known; therefore, usually binders and at least a non-binder for a given MHC molecule are contained in the pool. The pool therefore comprises at least ten different HCV-peptides. Practically, pools are used according to the present invention containing significantly more different HCV-peptide species, e.g. 20 or more, 100 or more, 1.000 or more or 10.000 or more. It is also possible to screen larger libraries (with e.g. more than $10^6$, more than $10^8$ or even more than $10^{10}$ different HCV-peptide species). This, however, is mainly dependent on the availability of such HCV-peptide libraries.

Preferred pools of ligands to be used in the method according to the present invention are selected from the group consisting of a pool of peptides, especially overlapping peptides, a pool of protein fragments, a pool of modified peptides, a pool obtained from antigen-presenting cells, preferably in the form of total lysates or fractions thereof, especially fractions eluted from the surface or the MHC/HLA molecules of these cells, a pool comprised of fragments of cells, especially HCV containing cells, tumor cells or tissues, especially from liver, a pool comprised of peptide libraries, pools of (poly)-peptides generated from recombinant DNA libraries, especially derived from pathogens or (liver) tumor cells, a pool of proteins and/or protein fragments from HCV or mixtures thereof.

The HCV-peptides of the pools may be derived from natural sources (in native and/or derivatised form) but also be produced synthetically (e.g. by chemical synthesis or by recombinant technology). If (poly)peptide ligands are provided in the pools, those peptides are preferably generated by peptide synthesizers or by recombinant technology. According to a preferred embodiment, a pool of (poly) peptides may be generated from recombinant DNA libraries, e.g. derived from HCV or HCV containing (tumor) cells, by in vitro translation (e.g. by ribosome display) or by expression through heterologous hosts like *E. coli* or others.

The nature of the specific MHC molecules (of course also MHC-like molecules are encompassed by this term) to be selected for the present methods is again not critical. Therefore, these molecules may be selected in principle from any species, especially primates like humans (HLA, see below), chimpanzees, other mammals, e.g. maquaques, rabbits, cats, dogs or rodents like mice, rats, guinea pigs and others, agriculturally important animals like cattle, horses, sheep and fish, although human (or "humanized") molecules are of course preferred for providing vaccines for humans. For providing vaccines for specific animals, especially agriculturally important animals, like cattle, horses, sheep and fish, the use of MHC molecules being specific for these animals is preferred.

Preferred HLA molecules therefore comprise Class I molecules derived from the HLA-A, -B or -C loci, especially A1, A2, A3, A24, A11, A23, A29, A30, A68; B7, B8, B15, B16, B27, B35, B40, B44, B46, B51, B52, B53; Cw3, Cw4, Cw6, Cw7; Class II molecules derived from the HLA-DP, -DQ or -DR loci, especially DR1, DR2, DR3, DR4, DR7, DR8, DR9, DR11, DR12, DR13, DR51, DR52, DR53; DP2, DP3, DP4; DQ1, DQ3, DQ5, DQ6; and non-classical MHC/HLA and MHC/HLA-like molecules, which can specifically bind ligands, especially HLA-E, HLA-G, MICA, MICB, Qa1, Qa2, T10, T18, T22, M3 and members of the CD1 family.

According to a preferred embodiment, the methods according to the present invention is characterised in that said MHC/HLA molecules are selected from HLA class I molecules, HLA class II molecules, non classical MHC/HLA and MHC/HLA-like molecules or mixtures thereof, or mixtures thereof.

Preferably, the optional characterising step of the HCV-peptides of the complex is performed by using a method selected from the group consisting of mass spectroscopy, polypeptide sequencing, binding assays, especially SDS-stability assays, identification of ligands by determination of their retention factors by chromatography, especially HPLC, or other spectroscopic techniques, especially violet (UV), infra-red (IR), nuclear magnetic resonance (NMR), circular dichroism (CD) or electron spin resonance (ESR), or combinations thereof.

According to a preferred embodiment the method of the present invention is characterised in that it is combined with a cytokine secretion assay, preferably with an Elispot assay, an intracellular cytokine staining, FACS or an ELISA (enzyme-linked immunoassays) (see e.g. Current Protocols in Immunology).

Preferred T cell assays comprise the mixing and incubation of said complex with isolated T cells and subsequent measuring cytokine secretion or proliferation of said isolated T cells and/or the measuring up-regulation of activation markers, especially CD69, CD38, or down-regulation of surface markers, especially CD3, CD8 or TCR and/or the measuring up-/down-regulation of mRNAs involved in T cell activation, especially by real-time RT-PCR (see e.g. Current Protocols in Immunology, Current Protocols in Molecular Biology).

Further preferred T cell assays are selected from T cell assays measuring phosphorylation/de-phosphorylation of components downstream of the T cell receptor, especially p56 lck, ITAMS of the TCR and the zeta chain, ZAP70, LAT, SLP-76, fyn, and lyn, T cell assays measuring intracellular $Ca^{++}$ concentration or activation of $Ca^{++}$-dependent proteins, T cell assays measuring formation of immunological synapses, T cell assays measuring release of effector molecules, especially perforin, granzymes or granulolysin or combinations of such T cell assays (see e.g. Current Protocols in Immunology, Current Protocols in Cell Biology).

In order to identify the molecular determinants of immune-protection against HCV a specific method of epitope capturing was applied using synthetic peptides representing the conserved parts of HCV genotypes 1, 2 and 3. Focusing on conserved regions ensures broad applicability of the epitopes. Moreover, these regions probably cannot easily be mutated by the virus, thus minimizing the danger of evolution of immune-escape variants.

With the methods of the present invention novel HCV-epitopes are detected. According to a further aspect, the present invention therefore also provides HCV T cell epitopes identifiable by a method according to the present invention, said T cell epitopes preferably being selected from the group consisting of polypeptides comprising the peptides A120-A124, B25-B30, B46-B48, B84-B92, C106, C113-C114, 1627, 1628, 1629, 1604 according to Table 1 or 2. These peptides are novel ligands for at least HLA-DRB1*0101, *0401, *0404, *0701 and thus covering at least 45-55% of major populations (see Tab. 2).

Preferred polypeptides are selected from the group comprising the peptides 1630, C97, 1547, B94-B98, A272-A276 according to Table 1 or 2. These peptides are novel ligands for at least HLA-DRB1*0101, *0401, *0701 and thus covering at least 40-50% of major populations (see Tab. 2).

Preferred polypeptides are selected from the group comprising the peptides B120, B122, C108, C134, C152 according to Table 1 or 2. These peptides are novel ligands for at least HLA-DRB1*0101, *0404, *0701 and thus covering at least 45% of major populations (see Tab. 2).

Preferred polypeptides are selected from the group comprising the peptides 1606, 1607, 1577, 1578 according to Table 1 or 2. These peptides are novel ligands for at least HLA-DRB1*0401, *0404, *0701 and thus covering at least 45% of major populations (see Tab. 2).

Preferred polypeptides are selected from the group comprising the peptides B50-52, 1623, C130 according to Table 1 or 2. These peptides are novel ligands for at least HLA-DRB1*0101, *0401, *0404 and thus covering at least 40% of major populations (see Tab. 2).

Preferred polypeptides are selected from the group comprising the peptides 1603, C96 according to Table 1 or 2. These peptides are novel ligands for at least HLA-DRB1*0101, *0701 and thus covering at least 40% of major populations (see Tab. 2).

Preferred polypeptides are selected from the group comprising the peptides C191 according to Table 1, being a novel ligand for at least HLA-DRB1*0401, *0701 and thus covering at least 40% of major populations (see Tab. 2).

Preferred polypeptides are selected from the group comprising the peptides A216-A224, A242-A244, C92-C93 according to Table 1 or 2. These peptides are novel ligands for at least HLA-DRB1*0101, *0401 and thus covering at least 35% of major populations (see Tab. 2).

Preferred polypeptides are selected from the group comprising the peptide A174 according to Table 1 or 2, being a novel ligand for at least HLA-DRB1*0404, *0701 and thus covering at least 25-30% of major populations (see Tab. 2).

Preferred polypeptides are selected from the group comprising the peptides B32-B38, B100-B102, C135 according to Table 1 or 2. These peptides are novel ligands for at least HLA-DRB1*0101, *0404 and thus covering at least 20-25% of major populations (see Tab. 2).

Preferred polypeptides are selected from the group comprising the peptide C162 according to Table 1 or 2, being a novel ligand for at least HLA-DRB1*0401, *0404 and thus covering at least 20-25% of major populations (see Tab. 2).

Preferred polypeptides are selected from the group comprising the peptides 1618, 1622, 1624, 1546, 1556 according to Table 1 or 2. These peptides are novel ligands for at least HLA-DRB1*0701 and thus covering at least 25% of major populations (see Tab. 2).

Preferred polypeptides are selected from the group comprising the peptides A114, B58, B112-B118, B18-B22, C112, C116, C122, C127, C144, C159-C160, C174, 1558, 1581 according to Table 1 or 2. These peptides are novel ligands for at least HLA-DRB1*0101 and thus covering at least 20% of major populations (see Tab. 2).

Preferred polypeptides are selected from the group comprising the peptide C95, being a novel ligand for at least HLA-DRB1*0401 and thus covering at least 20% of major populations (see Tab. 2).

Preferred polypeptides are selected from the group comprising the peptides C129, C157-C158, A254-A258, 1605, C109, C161 according to Table 1 or 2. These peptides comprising novel ligands for at least HLA-DRB1*0404 and thus covering at least 5% of major populations (see Tab. 2).

Preferred polypeptides are selected from the group comprising the peptides 1547, 1555, 1558, 1559, 1560, 1563, 1592, 1604, 1605, 1616, 1621, 1623, 1625, 1627, 1630, 1649, 1650, 1651, 1652, 1654, 1655, 1656 according to Table 1 or 2, these peptides displaying immunogenicity in HLA-DRB1*0401 transgenic mice (see Example II) and thus representing or containing a confirmed HLA class II T-cell epitope binding to at least HLA-DRB1*0401 (see Tab. 3).

Preferred polypeptides are selected from the group comprising the peptides 1545, 1552, 1555, 1558, 1559, 1560, 1577, 1592, 1604, 1605, 1615, 1617, 1621, 1627, 1631, 1632, 1641, 1647, 1650, 1651, 1652, 1653, 1654, 1655 according to Table 1 or 2, these peptides displaying immunogenicity in HLA-A*0201 transgenic mice (see Example II) and thus representing or containing a confirmed HLA class I T-cell epitope binding to at least HLA-A*0201 (see Tab. 3).

Preferred polypeptides which are shown to be HLA-B*0702 epitopes with T-cell activating capacity are selected from the group consisting of polypeptides 1506, 1526, 1547, 1552, 1553, 1555, 1558, 1562, 1563, 1565, 1577, 1578, 1580, 1587, 1592, 1604, 1605, 1621, 1623, 1624, 1627, 1628, 1647, 1650, 1651, 1843 with sequence LPRRGPRL (SEQ ID NO:163) (contained in 1506) and 1838 with sequence SPGALVVGVI (SEQ ID NO:164) (contained in 1587) as minimal HLA-B*0702 epitopes.

Peptides 1526, 1565, 1631 are also shown to be immunogenic in HLA-DRB1*0401 transgenic mice contain known class II epitopes. Peptides 1526, 1553, 1565, 1587, 1623, 1630 are also shown to be immunogenic in HLA-A*0201 transgenic mice contain known A2 epitopes.

Preferred polypeptides are selected from the group comprising the peptides listed in tables 3, 5 and the bold peptides in 7 ("hotspots").

The preferred polypeptides mentioned above also include all fragments containing the minimal sequence of the epitope, i.e. the 8- or 9-mer being necessary for binding to MHC/HLA molecules.

Preferably, the epitopes or peptides according to the present invention further comprises 1 to 30, preferably 2 to 10, especially 2 to 6, naturally occurring amino acid residues at the N-terminus, the C-terminus or at the N- and C-terminus. For the purposes of the present invention the term "naturally occurring" amino acid residue relates to amino acid residues present in the naturally occurring protein at the specific position, relative to the epitope or peptide. For example, for the HLA-A2 epitope with the amino acid sequence HMWNFISGI (SEQ ID NO:192) contained within peptide ID 1565 (Tab. 1), the naturally occurring amino acid residue at the N-terminus is –K; the three naturally occurring amino acid residues at the C-terminus are –QYL. A "non-naturally occurring" amino acid residue is therefore any amino acid residue being different as the amino acid residue at the specific position relative to the epitope or peptide.

According to a preferred embodiment of the present invention, the present epitopes or peptides further comprise non-naturally occurring amino acid(s), preferably 1 to 1000, more preferred 2 to 100, especially 2 to 20 non-naturally occurring amino acid residues, especially at the N-terminus, the C-terminus or at the N- and C-terminus. Also combinations of non-naturally and naturally occurring amino acid residues are possible under this specific preferred embodiment. The present epitope may also contain modified amino acids (i.e. amino acid residues being different from the 20 "classical" amino acids, such as D-amino acids or S—S bindings of Cys) as additional amino acid residues or in replacement of a naturally occurring amino acid residue.

It is clear that also epitopes or peptides derived from the present epitopes or peptides by amino acid exchanges improving, conserving or at least not significantly impeding the T cell activating capability of the epitopes are covered by the epitopes or peptides according to the present invention. Therefore, the present epitopes or peptides also cover epitopes or peptides, which do not contain the original sequence as derived from a specific strain of HCV, but trigger the same or preferably an improved T cell response. These epitopes are referred to as "heteroclitic". These include any epitope, which can trigger the same T cells as the original epitope and has preferably a more potent activation capacity of T cells preferably in vivo or also in vitro. Also the respective homologous epitopes from other strains of HCV are encompassed by the present invention.

Heteroclitic epitopes can be obtained by rational design i.e. taking into account the contribution of individual residues to binding to MHC/HLA as for instance described by Ramensee et al. 1999 or Sturniolo et al. 1999, combined with a systematic exchange of residues potentially interacting with the TCR and testing the resulting sequences with T cells directed against the original epitope. Such a design is possible for a skilled man in the art without much experimentation.

Another possibility includes the screening of peptide libraries with T cells directed against the original epitope. A preferred way is the positional scanning of synthetic peptide libraries. Such approaches have been described in detail for instance by Blake et al 1996 and Hemmer et al. 1999 and the references given therein.

As an alternative to epitopes represented by the cognate HCV derived amino acid sequence or heteroclitic epitopes, also substances mimicking these epitopes e.g. "peptidemimetica" or "retro-inverso-peptides" can be applied.

Another aspect of the design of improved epitopes is their formulation or modification with substances increasing their capacity to stimulate T cells. These include T helper cell epitopes, lipids or liposomes or preferred modifications as described in WO 01/78767.

Another way to increase the T cell stimulating capacity of epitopes is their formulation with immune stimulating substances for instance cytokines or chemokines like interleukin-2, -7, -2, -18, class I and II interferons (IFN), especially IFN-gamma, GM-CSF, TNF-alpha, flt3-ligand and others.

According to a further aspect, the present invention is drawn to the use of a HCV epitope or HCV peptide according to the present invention for the preparation of a HLA restricted vaccine for treating or preventing hepatitis C virus (HCV) infections.

The invention also encompasses the use of an epitope according to the present invention for the preparation of a vaccine for treating or preventing preventing hepatitis C virus (HCV) infections.

Consequently, the present invention also encompasses a vaccine for treating or preventing hepatitis C virus (HCV) infections comprising an epitope according to the present invention.

Furthermore, also a HLA specific vaccine for treating or preventing hepatitis C virus (HCV) infections comprising the epitopes or peptides according to the present invention is an aspect of the present invention.

Preferably, such a vaccine further comprises an immunomodulating substance, preferably selected from the group consisting of polycationic substances, especially polycationic polypeptides, immunomodulating nucleic acids, especially deoxyinosine and/or deoxyuracile containing oligodeoxynucleotides, or mixtures thereof.

Preferably the vaccine further comprises a polycationic polymer, preferably a polycationic peptide, especially polyarginine, polylysine or an antimicrobial peptide.

The polycationic compound(s) to be used according to the present invention may be any polycationic compound, which shows the characteristic effect according to the WO 97/30721. Preferred polycationic compounds are selected from basic polypeptides, organic polycations, basic polyaminoacids or mixtures thereof. These polyaminoacids should have a chain length of at least 4 amino acid residues. Especially preferred are substances containing peptidic bounds, like polylysine, polyarginine and polypeptides containing more than 20%, especially more than 50% of basic amino acids in a range of more than 8, especially more than 20, amino acid residues or mixtures thereof. Other preferred polycations and their pharmaceutical compositions are described in WO 97/30721 (e.g. polyethyleneimine) and WO 99/38528. Preferably these polypeptides contain between 20 and 500 amino acid residues, especially between 30 and 200 residues.

These polycationic compounds may be produced chemically or recombinantly or may be derived from natural sources.

Cationic (poly)peptides may also be polycationic antibacterial microbial peptides. These (poly)peptides may be of prokaryotic or animal or plant origin or may be produced chemically or recombinantly. Peptides may also belong to the class of defensines. Such host defense peptides or defensines are also a preferred form of the polycationic polymer according to the present invention. Generally, a compound allowing as an end product activation (or down-regulation) of the adaptive immune system, preferably mediated by APCs (including dendritic cells) is used as polycationic polymer.

Especially preferred for use as polycationic substance in the present invention are cathelicidin derived antimicrobial peptides or derivatives thereof (WO 02/13857), incorporated herein by reference), especially antimicrobial peptides derived from mammal cathelicidin, preferably from human, bovine or mouse, or neuroactive compounds, such as (human) growth hormone (as described e.g. in WO01/24822).

Polycationic compounds derived from natural sources include HIV-REV or HIV-TAT (derived cationic peptides, antennapedia peptides, chitosan or other derivatives of chitin) or other peptides derived from these peptides or proteins by biochemical or recombinant production. Other preferred polycationic compounds are cathelin or related or derived substances from cathelin, especially mouse, bovine or especially human cathelins and/or cathelicidins. Related or derived cathelin substances contain the whole or parts of the cathelin sequence with at least 15-20 amino acid residues. Derivations may include the substitution or modification of the natural amino acids by amino acids, which are not among the 20 standard amino acids. Moreover, further cationic residues may be introduced into such cathelin molecules. These cathelin molecules are preferred to be combined with the antigen/vaccine composition according to the present invention. However, these cathelin molecules surprisingly have turned out to be also effective as an adjuvant for a antigen without the addition of further adjuvants. It is therefore possible to use such cathelin molecules as efficient adjuvants in vaccine formulations with or without further immunactivating substances.

Another preferred polycationic substance to be used according to the present invention is a synthetic peptide containing at least 2 KLK-motifs separated by a linker of 3 to 7 hydrophobic amino acids, especially L (WO 02/32451, incorporated herein by reference).

The immunomodulating (or:immunogenic) nucleic acids to be used according to the present invention can be of synthetic, prokaryotic and eukaryotic origin. In the case of eukaryotic origin, DNA should be derived from, based on the phylogenetic tree, less developed species (e.g. insects, but also others). In a preferred embodiment of the invention the immunogenic oligodeoxynucleotide (ODN) is a synthetically produced DNA-molecule or mixtures of such molecules. Derivatives or modifications of ODNs such as thiophosphate substituted analogues (thiophosphate residues substitute for phosphate) as for example described in US patents U.S. Pat. No. 5,723,335 and U.S. Pat. No. 5,663,153, and other derivatives and modifications, which preferably stabilize the immunostimulatory composition(s) but do not change their immunological properties, are also included. A preferred sequence motif is a six base DNA motif containing an (unmethylated) CpG dinucleotide flanked by two 5' purines and two 3' pyrimidines (5'-Pur-Pur-C-G-Pyr-Pyr-3'). The CpG motifs contained in the ODNs according to the present invention are more common in microbial than higher vertebrate DNA and display differences in the pattern of methylation. Surprisingly, sequences stimulating mouse APCs are not very efficient for human cells. Preferred palindromic or non-palindromic ODNs to be used according to the present invention are disclosed e.g. in Austrian Patent applications A 1973/2000, A 805/2001, EP 0 468 520 A2, WO 96/02555, WO 98/16247, WO 98/18810, WO 98/37919, WO 98/40100, WO 98/52581, WO 98/52962, WO 99/51259 and WO 99/56755 all incorporated herein by reference. Apart from stimulating the immune system certain ODNs are neutralizing some immune responses. These sequences are also included in the current invention, for example for applications for the treatment of autoimmune diseases. ODNs/DNAs may be produced chemically or recombinantly or may be derived from natural sources. Preferred natural sources are insects.

Alternatively, also nucleic acids based on inosine and cytidine (as e.g. described in the WO 01/93903) or deoxynucleic acids containing deoxy-inosine and/or deoxyuridine residues (described in WO 01/93905 and PCT/EP 02/05448, incorporated herein by reference) may preferably be used as immunostimulatory nucleic acids for the present invention.

Of course, also mixtures of different immunogenic nucleic acids may be used according to the present invention.

Preferably, the present vaccine further comprises a pharmaceutically acceptable carrier.

According to a further preferred embodiment, the present vaccine comprises an epitope or peptide which is provided in a form selected from peptides, peptide analogues, proteins, naked DNA, RNA, viral vectors, virus-like particles, recombinant/chimeric viruses, recombinant bacteria or dendritic cells pulsed with protein/peptide/RNA or transfected with DNA comprising the epitopes or peptides.

According to a further aspect, the present invention is drawn to T cells, a T cell clone or a population (preparation) of T cells specifically recognizing any HCV epitope or peptide according to the present invention, especially a HCV epitope as described above. A preferred application of such T cells is their expansion in vitro and use for therapy of patients e.g. by adoptive transfer. Therefore, the present invention also provides the use of T cells, a T cell clone or a population (preparation) of T cells for the preparation of a composition for the therapy of HCV patients.

Such T cells (clones or lines) according to the present invention, specifically those recognizing the aforementioned HCV peptides are also useful for identification of heteroclitic epitopes, which are distinct from the originally identified epitopes but trigger the same T cells.

Such cells, compositions or vaccines according to the present invention are administered to the individuals in an effective amount.

According to a further aspect, the present invention also relates to the use of the peptides with formulae QRKTKRNTN (SEQ ID NO:167), QRKTKRNT (SEQ ID NO:166), or 1615, 1616, 1617 in particular 9meric peptides derived from the latter 3 peptides with formulae SAKSKFGYG (SEQ ID NO:193), SAKSKYGYG (SEQ ID NO:194), or SARSKYGYG (SEQ ID NO:195) as HLA-B*08 epitopes, especially for the preparation of a pharmaceutical preparation for a HLA-B*08 specific vaccine; the use of the peptides with the formulae RKTKRNTNR (SEQ ID NO:170) as HLA-B*2705 epitope, especially for the preparation of a pharmaceutical preparation for a HLA-B*2705 specific vaccine; and the use of the peptides with the formulae ARLIVFPDL (SEQ ID NO:1053) as HLA-B*2705 and HLA-B*2709 specific vaccine. Further, it also relates to the use of the hotspot epitopes selected from the group of peptides 1835, 84EX, 87EX, 89EX, 1426, 1650, 1836, 1846, 1651, 1800, 1799, C114, 1827, C112, C114EX, 1827EX, 1798, 1604, 1829, 1579, 1624, 1848, 1547, A1A7, A122EX, A122, 1825, A241, B8B38, C70EX, C92, C97, C106, and C134 according to table 7 for the preparation of a vaccine comprising synthetic peptides, recombinant protein and/or DNA constitutes of such epitopes.

In particular, two or more epitope hotspots can be combined, with or without linker sequences. Preferred linker sequences consist for instance of 3 to 5 glycine, or alanine or lysine residues. This may be achieved by peptide synthesis, However, combination of hotspots may result in quite long polypeptides. In this case, cloning DNA encoding for such constructs and expressing and purifying the corresponding recombinant protein is an alternative. Such recombinant proteins can be used as antigens, which in combination with the right adjuvant (IC31, pR, . . . ) can elicit T-cell responses against all the epitopes they harbor. At the same time, such artificial polypeptides are devoid of the activities (enzymatic, toxic, immuno-suppressive, . . . ), the natural HCV antigens may possess.

There are several other ways of delivering T-cell epitope hotspots or combinations thereof. These include: recombinant viral vectors like vaccinia virus, canary pox virus, adenovirus; self-replicating RNA vectors; "naked DNA" vaccination with plasmids encoding the hotspots or combination thereof; recombinant bacteria (e.g. *Salmonella*); dendritic cells pulsed with synthetic peptides, or recombinant protein, or RNA or transfected with DNA, each encoding T-cell epitope hotspots or combinations thereof.

The invention will be explained in more detail by way of the following examples and drawing figures, to which, however it is not limited.

FIG. 1 shows 40 peptide mixtures each containing up to 20 HCV derived 15- to 23mer peptides.

FIG. 2 shows the Epitope Capture approach using peptide pools and empty DRB1*0401 molecules.

FIG. 3 shows the Epitope Capture approach using peptide pools and empty DRB1*0404 molecules.

FIG. 4 shows binding of individual peptides to DRB1*0401.

FIG. 5 shows binding of individual peptides to DRB1*0404.

FIG. 6 shows binding of individual peptides to DRB1*0101.

FIG. 7 shows peptides binding to DRB1*0701.

EXAMPLES

Figure 8:
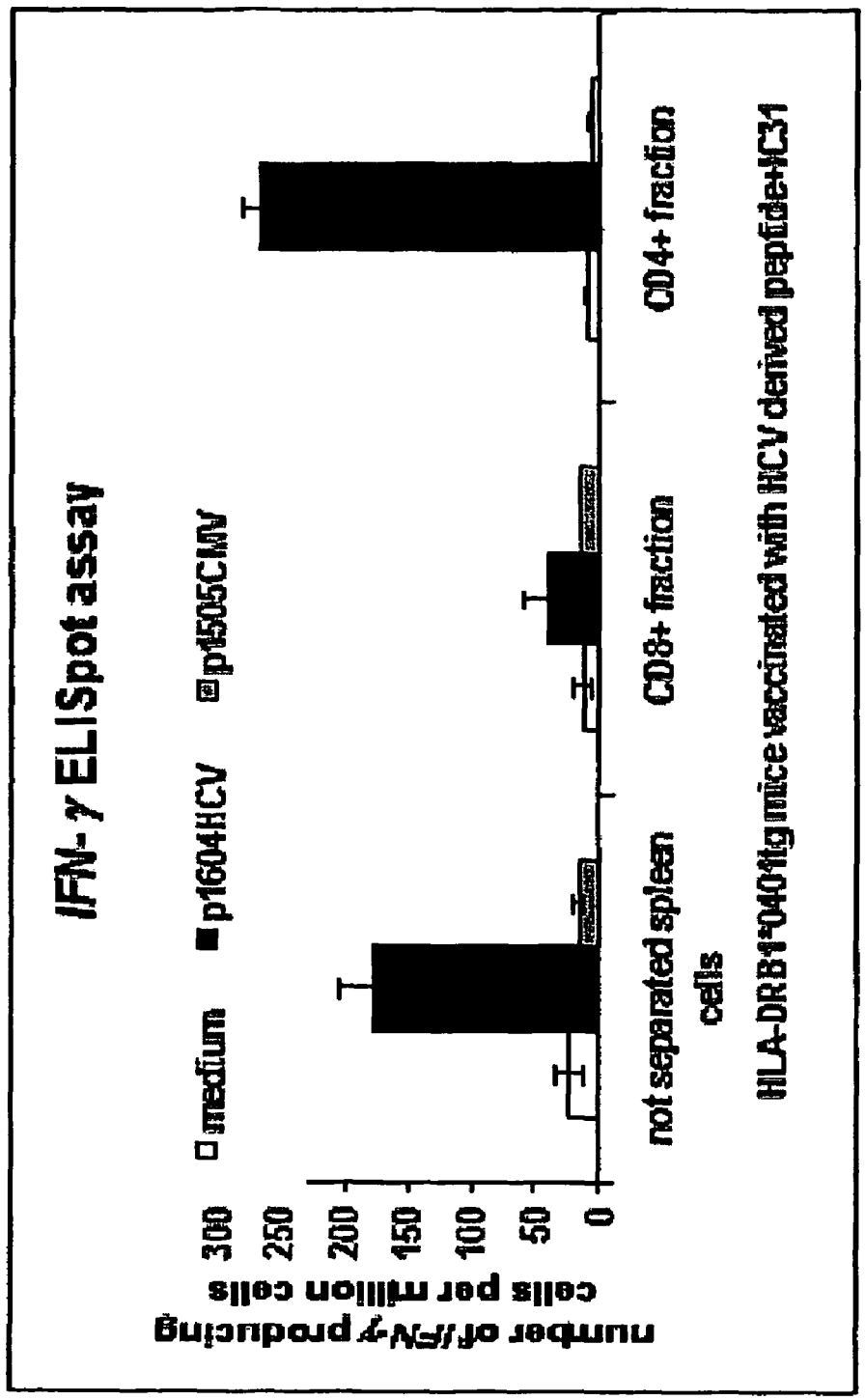
FIG. 8 shows mouse IFN-gamma ELIspot with splenocytes or separated CD8+ or CD4+ cells from HLA-DRB1*0401 tg mice vaccinated with Ipep1604+IC31.

General description of the examples:

The present examples show the performance of the present invention on a specific pathogen hepatitis C virus (HCV).

In the first part the method according to the present invention was applied, which is based on the use of "empty HLA molecules". These molecules were incubated with mixtures of potential HCV derived peptide ligands, screening for specific binding events. The possibility to use highly complex mixtures allows a very quick identification of the few binders out of hundreds or even thousands of potential ligands. This is demonstrated by using HLA-DRB1*0101, -DRB1*0401, -DRB1*0404, -DRB1*0701 molecules and pools of overlapping 15- to 23mers. Importantly, this analysis using multiple different HLA-alleles allows identifying promiscuous ligands capable of binding to more than one HLA allele. Promiscuous T-cell epitopes are particularly valuable components of epitope-based vaccines. They enable treating a higher portion of a population than epitopes restricted to one HLA allele.

The same process can be applied for class I molecules and peptides of appropriate length i.e. 8 to 11-mers. The ligand-pools can be synthetic overlapping peptides. Another possibility is to digest the antigen in question enzymatically or non-enzymatically. The latter achieved by alkali-hydrolysis generates all potential degradation products and has been successfully used to identify T cell epitopes (Gavin 1993). Enzymatic digestions can be done with proteases. One rational way would further be to use proteases involved in the natural antigen-processing pathway like the proteasome for class I restricted epitopes (Heemels 1995) or cathepsins for class II restricted epitopes (Villadangos 2000). Ligand pools could also be composed of naturally occurring ligands obtained for instance by lysis of or elution from cells carrying the respective epitope. In this regard it is important to note that also non-peptide ligands like for instance glycolipids can be applied. It is known that nonclassical class I molecules, which can be encoded by the MHC (e.g. HLA-G, HLA-E, MICA, MICB) or outside the MHC (e.g. CD1 family) can present various non-peptide ligands to lymphocytes (Kronenberg 1999). Use of recombinant "empty" nonclassical class I molecules would allow binding reactions and identification of binders in similar manner as described here.

After rapid identification of ligands capable of binding to HLA molecules the process according to the present invention also offers ways to characterize directly specific T cell responses against these binders. One possibility is to directly use the isolated HLA:ligand complex in a so called "synthetic T cell assay". The latter involves antigen-specific re-stimulation of T cells by the HLA:ligand complex together with a second signal providing co-stimulation like activation of CD28 by an activating antibody. This assay can be done in an ELIspot readout.

Another possibility is the immunization of HLA-transgenic mice to prove immunogenicity of ligands identified by the Epitope Capture approach as demonstrated in Example II.

Materials & Methods

Peptides

In order to identify conserved regions between HCV genotypes 1, 2 and 3, about 90 full genomes publicly available through Genebank were aligned. In total, 43% of the coding region of HCV was found to be conserved in at least 80% of clinical isolates. In cases, where at a certain position consistently two distinct amino acids (eg. arginine or lysine) were found, both variants were considered for analysis. Altogether 148 conserved regions, longer than 8 amino acids were identified. Conserved region were spanned by ~500 fifteen amino acid residue (15mer) peptides, each peptide overlapping its precursor by 14 out of 15 amino acids. Conserved regions between 8 and 14 amino acids long were covered by further 80 (non-overlapping) 15mers. 15mers were synthesized using standard F-moc chemistry in parallel (288 at a time) on a Syro II synthesizer (Multisyntech, Witten, Germany). Each fourth 15mer was checked by mass spectrometry. 15mers were applied for experiments without further purification. In addition 63 peptides of 16-xx aa were synthesized using standard F-moc chemistry on an ABI 433A synthesizer (Applied Biosystems, Weiterstadt, Germany) and purified by RP-HPLC (Biocut 700E, Applied Biosystems, Langen, Germany) using a C18 column (either ODS ACU from YMC or 218TP, Vydac). Purity and identity were characterized by MALDI-TOF on a Reflex III mass-spectrometer (Bruker, Bremen, Germany). Peptides were solubilized in 100% DMSO at ~10 mg/ml (~5 mM). Stocks of peptide pools (20 peptides each) were made in 100% DMSO at a final concentration of 0.5 mg/ml (~0.25 mM) for each peptide. All peptides used in the present invention are listed in Table 1. Peptides YAR (YARFQSQTTLKQKT (SEQ ID NO:196)), HA (PKYVKQNTLKLAT (SEQ ID NO:197)), P1 (GYKVLVLNPSVAAT (SEQ ID NO:198)), P2(HMWNFISGIQYLAGLSTLPGNPA (SEQ ID NO:199)), P3(KFPGGGQIVGVYLLPRRRGPRL (SEQ ID NO:200)), P4 (DLMGYIPAV (SEQ ID NO:201)) and CLIP (KLPKPPKPVSKMRMATPLLMQALPM (SEQ ID NO:202)) were used as control peptides in binding assays.

Epitope Capture and Peptide Binding Assay

Soluble HLA class II DRA1*0101/DRB1*0101/Ii, DRA1*0101/DRB1*0401/Ii, DRA1*0101/DRB1*0404/Ii and DRA1*0101/DRB1*0701/Ii molecules were expressed in SC-2 cells and purified as described in Aichinger et al., 1997. In peptide binding reactions soluble DRB1*0101, DRB1*0401, DRB1*0404 molecules were used in a concentration of ~0.5 µM, and each single peptide was added in 10-fold molar excess (5 µM) if not mentioned differently. The concentration of DMSO in the binding reaction did not exceed 4%. The reaction was performed in PBS buffer (pH 7.4) at room temperature for 48 hours in the presence of a protease inhibitor cocktail (Roche) and 0.1% octyl-beta-D-glucopyranoside (Sigma). Peptide binding was evaluated in an SDS-stability assay (Gorga et al., 1987): trimeric HLA class II alpha:beta:peptide complexes are resistant to SDS and consequently appear as ~60 kDa band in SDS-PAGE Western blot analysis. Individual HLA class II alpha- and beta-chains not stabilized by bound peptide migrate as ~35 kDa and ~25 kDa bands, respectively. Briefly, HLA-peptide complexes were treated with 1% SDS at room temperature and resolved by SDS-PAGE run with 20 mA for approximately 2.5 hours at room temperature. Protein was transferred onto PVDF membrane by electroblotting, and stained with anti-alpha-chain TAL.1B5 or/and beta-chain MEM136 antibodies. For detection of Western-blot signals ECL solutions (Amersham) were used. For DRB1*0101 molecules HA and P1 peptides were used as controls for evaluation of strong binding, P2 peptide for intermediate binding and YAR as a negative control. For DRB1*0401 the strongest binding controls were YAR and HA peptides, while P1 and P2 served as an intermediate and weak binder, respectively. In the case of DRB1*0404 molecules P1 and P2 peptides were used to estimate strong binding, YAR peptide to control intermediate binding and HA peptide as an negative control. The binding affinities to DRB1*0701 were test by a peptide-competition assay (Reay et al., 1992). Briefly, binding of the biotinylated CLIP peptide with high affinity (reference peptide) has been used for monitoring of HLA: peptide complex formation. A testing peptide added to the binding reaction at an equimolar concentration to CLIP peptide could compete out CLIP when its affinity is higher or inhibit binding for 50% if its affinity is equal to affinity of CLIP. In the case of lower affinity peptides they should be added in excess to the reference peptide to compete for occupancy of HLA binding grove. The values of the concentration of competitor peptides required for 50% inhibition of reference peptide (biotinylated CLIP) binding ($IC_{50}$) can be used for evaluation of peptide binding affinities. Alternatively, comparing of the amount of reference peptide bound to HLA molecules in the presence or absence of competitor peptide one can determine the binding activity of the peptide of interest. In the present peptide-competition assay conditions of peptide binding were similar to described above. DRB1*0701 molecules were used in a concentration of ~0.5 µM and biotinylated CLIP was added to all samples in the final concentration of 2 µM. Competitor peptides were added in three different concentrations: 2 nM, 20 µM and 200 µM. Binding reaction was performed in PBS buffer (pH 7.4) for 18 hours at 37° C. The amount of biotinylated CLIP associated with soluble DRB1*0701 molecules was determined by ELISA. Briefly, MaxiSorp 96-well plates (Nunc, Denmark) were coated with mouse anti-DR antibody L243 by overnight incubation with 50 µl of 10 µg/ml dilution in PBS at 4° C. Non-specific binding to wells a was blocked by incubation with T-PBS containing 3% of BSA for 2 hours at 37° C. and binding reactions were then "captured" for 2 hours at room temperature. Following extensive washing, HLA-assosiated peptide complexes were detected using alkaline phosphatase-streptavidin (Dako) and Sigma 104 phosphatase substrate. A microplate reader (VICTOR) was used to monitor optical density at 405 nm. Non-biotinylated CLIP, P1 and P2 peptides were used as positive controls to evaluate strong binding. Peptide P3 and P4 served as a weakly binding and non-binding control, respectively.

Immunization of HLA-Transgenic Mice

Immunogenicity of synthetic HCV-derived peptides was tested in HLA-DRB1*0401- and HLA-A*0201-transgenic mice as follows: Groups of 3 mice (female, 8 weeks of age) were injected subcutaneously into the flank (in total 100 µg of peptide +30 µg oligodinucleotide CpI (Purimex, Göttingen, Germany) per mouse). One week after the vaccination, spleens were removed and the splenocytes were activated ex vivo with the peptide used for vaccination and an irrelevant negative control peptide to determine IFN-gamma-producing specific cells (mouse ELISpot assay).

Mouse splenocyte ELIspot assay for single cell IFN-gamma release ELISpot plates (MAHA S4510, Millipore, Germany) were rinsed with PBS (200 µl/well), coated with anti-mouse IFN-gamma mAb (clone R46A2; 100 µl/well of 5 µg/ml in 0.1 M NaHCO$_3$, pH 9.2-9.5) and incubated overnight at 4° C. Plates were washed four times with PBS/0.1% Tween 20 and incubated with PBS/1% BSA (200 µl/well) at room temperature for 2 h to block nonspecific binding. Spleen cells from vaccinated mice were prepared and plated at 1×10$^6$-3×10$^5$ cells/well and incubated overnight at 37° C./5% CO$_2$ either in the presence of the immunizing antigen (peptide), control peptides or with medium alone. Subsequently, plates were washed four times and incubated with biotinylated anti-mouse IFN-gamma mAb (clone AN18.17.24, 100 µl/well of 2 µg/ml in PBS/1% BSA) for 2 h at 37° C. After washing, streptavidin-peroxidase (Roche Diagnostics, Vienna, Austria) was added (⅕₀₀₀ in PBS, 100 µl/well) and plates were incubated at room temperature for 2 additional hours. Subsequently, substrate was added to the washed plates (100 µl/well of a mixture of 10 ml 100 mM Tris pH 7.5 supplemented with 200 µl of 40 mg/ml DAB stock containing 50 µl of 80 mg/ml NiCl$_2$ stock and 5 µl of 30% H$_2$O$_2$). The reaction was stopped after 20-30 minutes by washing the plates with tap water. Dried plates were evaluated with an ELISpot reader (BIOREADER 2000, BioSys, Karben, Germany).

IFN-Gamma ELIspot with Human PBMC

PBMC from HCV RNA-negativ therapy responders or subjects spontaneously recovered were collected and HLA-typed serologically. Whole blood was collected in ACD Vacutainer tubes (Becton Dickinson Europe, Erembodegem, Germany). PBMC were isolated on Lymphoprep (Nycomed Pharma AS, Oslo, Norway) using Leuco-sep tubes (Greiner, Frickenhausen, Germany), washed 3× with PBS (Invitrogen Life Technologies (formerly GIBCOBRL), Carlsbad, Calif., USA) and resuspended at a concentration of 2×10⁷/ml in freezing medium consisting of 4 parts RPMI 1640 supplemented with 1 mM sodium pyruvate, 2 mM L-glutamine, 0.1 mM non-essential amino acids, 50 μM 2-mercaptoethanol (all from Invitrogen Life Technologies), 9 parts foetal bovine serum (FCS; from PAA, Linz, Austria) and 1 part DMSO (SIGMA, Deisenhofen, Germany). PBMC were stored over night in 1° C. freezing containers (Nalgene Nunc International, Rochester, N.Y., USA) at −80° C. and then transferred into liquid nitrogen. The ELIspot assay was essentially done as described (Lalvani et al.). Briefly, Multi Screen 96-well filtration plates MAIP S4510 (Millipore, Bedford, Mass.) were coated with 10 μg/ml (0,75 μg/well) anti-human IFN-g monoclonal antibody (Mab) B140 (Bender Med Systems, Vienna, Austria) over night at 4° C. Plates were washed 2 times with PBS (Invitrogen Life Technologies) and blocked with ELIspot medium (RPMI 1640 supplemented with 1 mM sodium pyruvate, 2 mM L-glutamine, 0.1 mM non-essential amino acids, 50 μM 2-mercaptoethanol (all from Invitrogen Life Technologies) and 10% human serum type AB (PAA, Linz, Austria). Cryo-preserved PBMC were thawed quickly in a 37° C. water bath, washed 1× with ELISPOT medium and incubated overnight (37° C., 5% CO₂). The next day cells were plated at 200,000 PBMC/well and co-cultivated with either individual peptides (10 μg/ml) or peptide pools (each peptide at a final concentration of 5 μg/ml) for 20 hrs. After removing cells and washing 6 times with wash buffer (PBS; 0,1% Tween 20 from SIGMA), 100 μl of a 1:10000 dilution (0.015 μg/well) of the biotinylated anti-human IFN-γ MAb B308-BT2 (Bender Med Systems), was added for an incubation of 2 hrs at 37° C. or alternatively for over night at 4° C. After washing, Streptavidin-alkaline phosphatase (DAKO, Glostrup, Denmark) was added at 1.2 μg/ml for 1 hr at 37° C. The assay was developed by addition of 100 μl/well BCIP/NBT alkaline phosphatase substrate (SIGMA).

In Vitro Priming of Human PBMCs

Human PBMCs are repeatedly stimulated with antigen (peptide or peptide mixture) in the presence of IL-2 and IL-7. This leads to the selective oligoclonal expansion of antigen-specific T cells. Responses against individual epitopes can be assessed for instance by IFN-γ ELIspot assays. Freshly thawed PBMCs were cultured in 6 well plates (2-4×10⁶/mL viable cells) in RPMI-1640 (GibcoBRL), 1% non-essential amino acids (GibcoBRL, cat# 11140-035), 1% Penicillin (10,000 U/ml)-Streptomycin (10, 000 μg/ml) (GibcoBRL, cat#15140-122), 1% L-Glutamine (GibcoBRL), 0.1% beta-mercapto-ethanol (GibcoBRL), 1% Na-pyruvate (GibcoBRL), plus 10% Human AB serum (PAA, Linz, Austria). Peptides (10 μM each) were added to each well. rhIL-7 (Strathmann Biotech) was added at 10 ng/mL final concentration. 20-30 U/mL rhIL-2 (Strathmann Biotech) were added on day 4. On day 10, all cells were removed from plates, washed once in media (as above), and counted. For the next cycle of in vitro priming, viable cells were co-cultivated with autologous gamma irradiated (1.2 gray/min, for 20 minutes) PBMC as feeders (plated at 100,000 per well) and peptides, rh-IL-2 as described above. ELIspot was done as described above, except that 200,000 responder cells (pre-stimulated for 2 rounds of in vitro priming) were used together with 60,000 autologous irradiated responder cells.

Example I

Rapid Identification of Promiscuous HLA-Binding Peptides from Hcv by Measuring Peptide Pools Arrayed in Matrix Format To span conserved regions within the HCV polyprotein more than 640 peptides were synthesized (Table 1). For rapid identification of HLA ligands and novel T-cell epitopes, 40 peptide pools each containing 20 single peptides were prepared. The pools were constructed in a way that each peptide was present in 2 pools (matrix format). This allows identification of reactive peptides at the cross-over points of row- and column mixtures (FIG. 1 HCV peptide matrix).

TABLE 1

Synthetic peptides derived from conserved regions of HCV

| PEPTIDE ID | SEQ ID | PEPTIDE |
|---|---|---|
| A1 | 203 | MSTNPKPQRKTKRNT |
| A2 | 204 | STNPKPQRKTKRNTN |
| A3 | 205 | TNPKPQRKTKRNTNR |
| A4 | 206 | NPKPQRKTKRNTNRR |
| A5 | 207 | PKPQRKTKRNTNRRP |
| A6 | 208 | KPQRKTKRNTNRRPQ |
| A7 | 209 | PQRKTKRNTNRRPQD |
| A8 | 210 | QRKTKRNTNRRPQDV |
| A9 | 211 | RKTKRNTNRRPQDVK |
| A10 | 212 | KTKRNTNRRPQDVKF |
| A11 | 213 | TKRNTNRRPQDVKFP |
| A12 | 214 | KRNTNRRPQDVKFPG |
| A13 | 215 | RNTNRRPQDVKFPGG |
| A14 | 216 | NTNRRPQDVKFPGGG |
| A15 | 217 | TNRRPQDVKFPGGGQ |
| A16 | 218 | NRRPQDVKFPGGGQI |
| A17 | 219 | RRPQDVKFPGGGQIV |
| A18 | 220 | RPQDVKFPGGGQIVG |
| A19 | 221 | PQDVKFPGGGQIVGG |
| A20 | 222 | QDVKFPGGGQIVGGV |
| A21 | 223 | DVKFPGGGQIVGGVY |
| A22 | 224 | VKFPGGGQIVGGVYL |
| A23 | 225 | KFPGGGQIVGGVYLL |
| A24 | 226 | FPGGGQIVGGVYLLP |
| A25 | 227 | PGGGQIVGGVYLLPR |
| A26 | 228 | GGGQIVGGVYLLPRR |
| A27 | 229 | GGQIVGGVYLLPRRG |

TABLE 1-continued

| | | |
|---|---|---|
| A28 | 230 | GQIVGGVYLLPRRGP |
| A29 | 231 | QIVGGVYLLPRRGPR |
| A30 | 232 | IVGGVYLLPRRGPRL |
| A31 | 233 | VGGVYLLPRRGPRLG |
| A32 | 234 | GGVYLLPRRGPRLGV |
| A33 | 235 | GVYLLPRRGPRLGVR |
| A34 | 236 | VYLLPRRGPRLGVRA |
| A35 | 237 | YLPRRGPRLGVRAT |
| A36 | 238 | LLPRRGPRLGVRATR |
| A37 | 239 | LPRRGPRLGVRATRK |
| A38 | 240 | PRRGPRLGVRATRKT |
| A39 | 241 | RRGPRLGVRATRKTS |
| A40 | 242 | RGPRLGVRATRKTSE |
| A41 | 243 | GPPWGVRATRKTSER |
| A42 | 244 | PRLGVRATRKTSERS |
| A43 | 245 | RLGVRATRKTSERSQ |
| A44 | 246 | LGVRATRKTSERSQP |
| A45 | 247 | GVRATRKTSERSQPR |
| A46 | 248 | VRATRKTSERSQPRG |
| A47 | 249 | RATRKTSERSQPRGR |
| A48 | 250 | ATRKTSERSQPRGRR |
| A49 | 251 | TRKTSERSQPRGRRQ |
| A50 | 252 | RKTSERSQPRGRRQP |
| A51 | 253 | KTSERSQPRGRRQPI |
| A52 | 254 | TSERSQPRGRRQPIP |
| A53 | 255 | SERSQPRGRRQPIPK |
| A54 | 256 | DPRRRSRNLGKVIDT |
| A55 | 257 | PRRRSRNLGKVIDTL |
| A56 | 258 | RRRSRNLGKVIDTLT |
| A57 | 259 | RRSRNLGKVIDTLTC |
| A58 | 260 | RSRNLGKVIDTLTCG |
| A59 | 261 | SRNLGKVIDTLTCGF |
| A60 | 262 | RNLGKVIDTLTCGFA |
| A61 | 263 | NLGKVIDTLTCGFAD |
| A62 | 264 | LGKVIDTLTCGFADL |
| A63 | 265 | GKVIDTLTCGFADLM |
| A64 | 266 | KVIDTLTCGFADLMG |
| A65 | 267 | VIDTLTCGFADLMGY |
| A66 | 268 | IDTLTCGFADLMGYI |
| A67 | 269 | DTLTCGFADLMGYIP |
| A68 | 270 | TLTCCFADLMGYIPL |
| A69 | 271 | LTCGFADLMGYIPLV |
| A70 | 272 | TCGFADLMGYIPLVG |
| A71 | 273 | CGFADLMGYIPLVGA |
| A72 | 274 | GFADLMGYIPLVGAP |
| A73 | 275 | FADLMGYIPLVGAPL |
| A74 | 276 | ADLMGYIPLVGAPLG |
| A75 | 277 | DLMGYIPLVGAPLGG |
| A76 | 278 | DPRHRSRNVGKVIDT |
| A77 | 279 | PRHRSRNVGKVIDTL |
| A78 | 280 | RHRSRNVGKIDTLT |
| B41 | 281 | CECYDAGAAWYELTP |
| B42 | 282 | ECYDAGAAWYELTPA |
| B43 | 283 | CYDAGAAWYELTPAE |
| B44 | 284 | YDAGAAWYELTPAET |
| B45 | 285 | DAGAAWYELTPAETT |
| B46 | 286 | AGAAWYELTPAETTV |
| B47 | 287 | GAAWYELTIPAETTV |
| B48 | 288 | AAWYELTPAETTVRL |
| B49 | 289 | DAGAAWYELTPAETS |
| B50 | 290 | AGAAWYELTPAETSV |
| B51 | 291 | GAAWYELTPAETSVR |
| B52 | 292 | AAWYELTPAETSVRL |
| B53 | 293 | FWAKHMWNFISGIQY |
| B54 | 294 | WAKHMWNFISGIQYL |
| B55 | 295 | AKHMWNFISGIQYLA |
| B56 | 296 | KHMWNFISGIQYLAG |
| B57 | 297 | HMWNFISGIQYLAGL |
| B58 | 298 | MWNFISGIQYLAGLS |
| B59 | 299 | WNFISGIQYLAGLST |
| B60 | 300 | NFISGIQYLAGLSTL |
| B61 | 301 | FISGIQYLAGLSTLP |
| B62 | 302 | ISGIQYLAGLSTLPG |
| B63 | 303 | SGIQYLAGLSTLPGN |
| B64 | 304 | GIQYLAGLSTLPGNP |
| B65 | 305 | IQYLAGLSTLPGNPA |
| B66 | 306 | QYLAGLSTLPGNPAI |
| B67 | 307 | YLAGLSTLPGNPAIA |
| B68 | 308 | LAGLSTLPGNPAIAS |

TABLE 1-continued

| | | |
|---|---|---|
| B69 | 309 | AGLSTLPGNPAIASI |
| B70 | 310 | GLSTLPGNPAIASLM |
| B71 | 311 | LSTLPGNPAIASLMA |
| B72 | 312 | STLPGNPAIASLMAF |
| B73 | 313 | QYLAGLSTLPGNPAV |
| B74 | 314 | YLAGLSTLPGNPAVA |
| B75 | 315 | LAGLSTLPGNPAVAS |
| B76 | 316 | AGLSTLPGNPAVASM |
| B77 | 317 | GLSTLPGNPAVASMM |
| B78 | 318 | LSTLPGNPAVASMMA |
| B79 | 319 | STLPGNPAVASMMAF |
| B80 | 320 | GAAVGSIGLGKVLVD |
| B81 | 321 | AAVGSIGLGKVLVDI |
| B82 | 322 | AVGSIGLGKVLVDIL |
| B83 | 323 | VGSIGLGKVLVDILA |
| B84 | 324 | GSIGLGKVLVDILAG |
| B85 | 325 | SIGLGKVLVDILAGY |
| B86 | 326 | IGLGKVLVDILAGYG |
| B87 | 327 | GLGKVLVDILAGYGA |
| B88 | 328 | LGKVLVDILAGYGAG |
| B89 | 329 | GKVLVDILAGYGAGV |
| B90 | 330 | KVLVDILAGYGAGVA |
| B91 | 331 | VLVDILAGYGAGVAG |
| B92 | 332 | LVDILAGYGAGVAGA |
| B93 | 333 | VDILAGYGAGVAGAL |
| B94 | 334 | DILAGYGAGVAGALV |
| B95 | 335 | ILAGYGAGVAGALVA |
| B96 | 336 | LAGYGAGVAGALVAF |
| B97 | 337 | AGYGAGVAGALVAFK |
| B98 | 338 | GYGAGVAGALVAFKI |
| B99 | 339 | YGAGVAGALVAFKIM |
| B100 | 340 | GAGVAGALVAFKIMS |
| B101 | 341 | AGVAGALVAFKIMSG |
| B102 | 342 | GVAGALVAFKIMSGE |
| B103 | 343 | GYGAGVAGALVAFKV |
| B104 | 344 | YGAGVAGALVAFKVM |
| B105 | 345 | GAGVAGALVAFKVMS |
| B106 | 346 | AGVAGALVAFKVMSG |
| B107 | 347 | GVAGALVAFKVMSGE |
| B108 | 348 | GKVLVDILAGYGAGI |
| B109 | 349 | KVLVDILAGYGAGIS |
| B110 | 350 | VLVDILAGYGAGISG |
| B111 | 351 | LVDILAGYGAGISGA |
| B112 | 352 | VDILAGYGAGISGAL |
| B113 | 353 | DILAGYGAGISGALV |
| B114 | 354 | ILAGYGAGISGALVA |
| B115 | 355 | LAGYGAGISGALVAF |
| B116 | 356 | AGYGAGISGALVAFK |
| B117 | 357 | GYGAGISGALVAFKI |
| B118 | 358 | YGAGISGALVAFKIM |
| B119 | 359 | GAGISGALVAFKIMS |
| A79 | 360 | HRSRNVGKVIDTLTC |
| A80 | 361 | RSRNVGKVIDTLTCG |
| A81 | 362 | SRNVGKVIDTLTCGF |
| A82 | 363 | RNVGKVIDTLTCGFA |
| A83 | 364 | NVGKVIDTLTCGFAD |
| A84 | 365 | VGKVIDTLTCGFADL |
| A85 | 366 | TLTCGFADLMGYIPV |
| A86 | 367 | LTCGFADLMGYIPVV |
| A87 | 368 | TCGFADLMGYIPVVG |
| A88 | 369 | CGFADLMGYIPVVGA |
| A89 | 370 | GFADLMGYIPVVGAP |
| A90 | 371 | FADLMGYIPVVGAPL |
| A91 | 372 | ADLMGYIPVVCAPLG |
| A92 | 373 | DLMGYIPVVGAPLGG |
| A93 | 374 | ARALAHGVRVLEDGV |
| A94 | 375 | RALAHGVRVLEDGVN |
| A95 | 376 | ALAHGVRVLEDGVNY |
| A96 | 377 | LAHGVRVLEDGVNYA |
| A97 | 378 | AHGVRVLEDGVNYAT |
| A98 | 379 | HGVRVLEDGVNYATG |
| A99 | 380 | GVRVLEDGVNYATGN |
| A100 | 381 | VRVLEDGVNYATGNL |
| A101 | 382 | RVLEDGVNYATGNLP |
| A102 | 383 | VLEDGVNYATGNLPG |
| A103 | 384 | LEDGVNYATGNLPGC |
| A104 | 385 | EDGVNYATGNLPGCS |
| A105 | 386 | DGVNYATGNLPGCSF |
| A106 | 387 | GVNYATGNLPGCSES |

TABLE 1-continued

| | | |
|---|---|---|
| A107 | 388 | VNYATGNLPGCSFSI |
| A108 | 389 | NYATGNLPGCSFSIF |
| A109 | 390 | YATGNLPGCSFSIFL |
| A110 | 391 | ATGNLPGCSFSIFLL |
| A111 | 392 | TGNLPGCSFSIFLLA |
| A112 | 393 | GNLPGCSFSIFLLAL |
| A113 | 394 | NLPGCSFSIFLLALL |
| A114 | 395 | LPGCSFSIFLLALLS |
| A115 | 396 | PGCSFSIFLLALLSC |
| A116 | 397 | IQLINTNGSWHINRT |
| A117 | 398 | QLINTNGSWHINRTA |
| A118 | 399 | LINTNGSWHINRTAL |
| A119 | 400 | INTNGSWINRTALN |
| A120 | 401 | NTNGSWHINRTALNC |
| A121 | 402 | TNGSWHINRTALNCN |
| A122 | 403 | NGSWHINRTALNCND |
| A123 | 404 | GSWHINRTALNCNDS |
| A124 | 405 | SWHINRTALNCNDSL |
| A125 | 406 | IQLVNTNGSWHINRT |
| A126 | 407 | QLVNTNGSWHINRTA |
| A127 | 408 | LVNTNGSWHINRTAL |
| A128 | 409 | VNTNGSWHINRTALN |
| A129 | 410 | VDYPYRLWHYPCTVN |
| A130 | 411 | DYPYRLWHYPCTVNF |
| A131 | 412 | YPYRLWHYPCTVNFT |
| A132 | 413 | PYRLWHYPCTVNFTI |
| A133 | 414 | YRLWHYPCTVNFTIF |
| A134 | 415 | RLWHYPCTVNFTIFK |
| A135 | 416 | LWHYPCTVNFTIFKV |
| A136 | 417 | WHYPCTVNFTIFKVR |
| A137 | 418 | HYPCTVNFTIFKVRM |
| A138 | 419 | YPCTVNFTIFKVRMY |
| A139 | 420 | PCTVNFTIFKVRMYV |
| A140 | 421 | CTVNFTIFKVRMYVG |
| A141 | 422 | TVNFTIFKVRMYVGG |
| A142 | 423 | VNFTIFKVRMYVGGV |
| A143 | 424 | NFTIFKVRMYVGGVE |
| A144 | 425 | FTIFKVRMYVGGVEH |
| A145 | 426 | TIFKVRMYVGGVEHR |
| A146 | 427 | IFKVRMYVGGVEHRL |
| A147 | 428 | DYPYRLWHYPCTVNY |
| A148 | 429 | YPYRLWHYPCTVNYT |
| A149 | 430 | PYRLWHYPCTVNYTI |
| A150 | 431 | YRLWHYPCTVNYTIF |
| A151 | 432 | RLWHYPCTVNYTIFK |
| A152 | 433 | LWHYPCTVNYTIFKI |
| A153 | 434 | WHYPCTVNYTIFKIR |
| A154 | 435 | HYPCTVNYTIFKIRM |
| A155 | 436 | YPCTVNYTIFKIRMY |
| A156 | 437 | PCTVNYTIFKIRMYV |
| B120 | 438 | AGISGALVAFKIMSG |
| B121 | 439 | GISGALVAFKIMSGE |
| B122 | 440 | VNLLPAILSPGALVV |
| B123 | 441 | NLLPAILSPGALVVG |
| B124 | 442 | LLPAILSPGALVVGV |
| C1 | 443 | LPAILSPGALVVGVV |
| C2 | 444 | PAILSPGALVVGVVC |
| C3 | 445 | AILSPGALVVGVVCA |
| C4 | 446 | ILSPGALVVGVVCAA |
| C5 | 447 | LSPGALVVGVVCAAI |
| C6 | 448 | SPGALVVGVVCAAIL |
| C7 | 449 | PGALVVGVVCAAILR |
| C8 | 450 | GALVVGV0AAILRR |
| C9 | 451 | ALVVGVVCAAILRRH |
| C10 | 452 | LVVGVVCAAILRRHV |
| C11 | 453 | VVGVVCAAILRRHVG |
| C12 | 454 | VGVVCAAILRRHVGP |
| C13 | 455 | GVVCAAILRRHVGPG |
| C14 | 456 | VVCAAILRRHVGPGE |
| C15 | 457 | VCAAILRRHVGPGEG |
| C16 | 458 | CAAILRRHVGPGEGA |
| C17 | 459 | AAILRRHVGPGEGAV |
| C18 | 460 | AILRRHVGPGEGAVQ |
| C19 | 461 | ILRRHVGPGEGAVQW |
| C20 | 462 | LRRHVGPGEGAVQWM |
| C21 | 463 | RRHVGPGEGAVQWMN |
| C22 | 464 | RHVGPGEGAVQWMNR |
| C23 | 465 | HVGPGEGAVQWMNRL |
| C24 | 466 | VGPGEGAVQWMNRLI |

TABLE 1-continued

| | | |
|---|---|---|
| C25 | 467 | GPGEGAVQWMNRLIA |
| C26 | 468 | PGEGAVQWMNRLIAF |
| C27 | 469 | GEGAVQWMNRLIAFA |
| C28 | 470 | EGAVQWMNRLIAFAS |
| C29 | 471 | GAVQWMNRLIAFASR |
| C30 | 472 | AVQWMNRLIAFASRG |
| C31 | 473 | VQWMNRLIAFASRGN |
| C32 | 474 | QWMNRLIAFASRGNH |
| C33 | 475 | WMNRLIAFASRGNHV |
| C34 | 476 | MNRLAFASRGNHVS |
| C35 | 477 | NRLIAFASRGNHVSP |
| C36 | 478 | RLIAFASRGNHVSPT |
| C37 | 479 | LIAFASRGNHVSPTH |
| C38 | 480 | IAFASRGNHVSPTHY |
| C39 | 481 | AFASRGNHVSPTHYV |
| C40 | 482 | VNLLPGILSPGALVV |
| C41 | 483 | NLLPGILSPGALVVG |
| C42 | 484 | LLPGILSPGALVVGV |
| C43 | 485 | LPGILSPGALVVGVI |
| C44 | 486 | PGILSPGALVVGVIC |
| C45 | 487 | GILSPGALVVGVICA |
| C46 | 488 | ILSPGALVVGVICAA |
| C47 | 489 | LSPGALVVGVICAAI |
| C48 | 490 | SPGALVVGVICAAIL |
| C49 | 491 | PGALVVGVICAAILR |
| C50 | 492 | GALVVGVICAAILRR |
| C51 | 493 | ALVVGVICAAILRRH |
| C52 | 494 | LVVGVICAAILRRHV |
| C53 | 495 | VVGVI0AAILRRHVG |
| C54 | 496 | VGVI0AAILRRHVGP |
| C55 | 497 | GVICAAILRRHVGPG |
| C56 | 498 | VICAAILRRHVGPGE |
| C57 | 499 | CAAILRRHVGPGEG |
| C58 | 500 | MNRLIAFASRGNHVA |
| C59 | 501 | NRLIAFASRGNHVAP |
| C60 | 502 | RLIAFASRGNHVAPT |
| C61 | 503 | LIAFASRGNHVAPTH |
| C62 | 504 | IAFASRGNHVAPTHY |
| C63 | 505 | AFASRGNHVAPTHYV |
| C64 | 506 | KGGRKPARLIVFPDL |
| C65 | 507 | GGRKPARLIVFPDLG |
| C66 | 508 | GRKPARLIVFPDLGV |
| C67 | 509 | RKPARLIVFPDLGVR |
| C68 | 510 | KPARLIVFPDLGVRV |
| C69 | 511 | PARLIVFPDLGVRVC |
| C70 | 512 | ARLIVFPDLGVRVCE |
| C71 | 513 | RLIVFPDLGVRVCEK |
| C72 | 514 | LIVFPDLGVRVCEKM |
| C73 | 515 | IVFPDLGVRVCEKMA |
| C74 | 516 | VFPDLGVRVCEKMAL |
| A157 | 517 | CTVNYTIFKIRMYVG |
| A158 | 518 | TVNYTIFKIRMYVGG |
| A159 | 519 | VNYTIFKIRMYVGGV |
| A160 | 520 | NYTIFKIRMYVGGVE |
| A161 | 521 | YTIFKIRMYVGGVEH |
| A162 | 522 | TIFKIRMYVGGVEHR |
| A163 | 523 | IFKIRMYVGGVEHRL |
| A164 | 524 | LPALSTGLIHLHQNI |
| A165 | 525 | PALSTGIHLHQNIV |
| A166 | 526 | ALSTGLIHLHQNIVD |
| A167 | 527 | LSTGIHLHQNIVDV |
| A165 | 528 | STGLIHLHQNIVDVQ |
| A169 | 529 | TQLIHLHQNIVDVQY |
| A170 | 530 | GLIHLHQNIVDVQYL |
| A171 | 531 | LIHLHQNIVDVQYLY |
| A172 | 532 | IHLHQNIVDVQYLYG |
| A173 | 533 | LPALSTGLLHLHQNI |
| A174 | 534 | PALSTGLLHLHQNIV |
| A175 | 535 | ALSTGLLHLHQNIVD |
| A176 | 536 | LSTGLLHLHQNIVDV |
| A177 | 537 | STGLLHLHQNIVDVQ |
| A178 | 538 | TGLLHLHQNIVDVQY |
| A179 | 539 | GLLHLHQNIVDVQYM |
| A180 | 540 | LLHLHQNIVDVQYMY |
| A181 | 541 | LHLHQNIVDVQYMYG |
| A182 | 542 | HLHAPTGSGKSTKVP |
| A183 | 543 | LHAPTGSGKSTKVPA |
| A184 | 544 | HAPTGSGKSTKVPAA |
| A185 | 545 | APTGSGKSTKVPAAY |

TABLE 1-continued

| | | |
|---|---|---|
| A186 | 546 | PTGSGKSTKVPAAYA |
| A187 | 547 | TGSGKSTKVPAAYAA |
| A188 | 548 | GSGKSTKVPAAYAAQ |
| A189 | 549 | SGKSTKVPAAYAAQG |
| A190 | 550 | GKSTKVPAAYAAQGY |
| A191 | 551 | KSTKVPAAYAAQGYK |
| A192 | 552 | STKVPAAYAAQGYKV |
| A193 | 553 | TKVPAAYAAQGYKVL |
| A194 | 554 | KVPAAYAAQGYKVLV |
| A195 | 555 | VPAAYAAQGYKVLVL |
| A196 | 556 | PAAYAAQGYKVLVLN |
| A197 | 557 | AAYAAQGYKVLVLNP |
| A198 | 558 | AYAAQGYKVLVLNPS |
| A199 | 559 | YAAQGYKVLVLNPSV |
| A200 | 560 | AAQGYKVLVLNPSVA |
| A201 | 561 | AQGYKVLVLNPSVAA |
| A202 | 562 | QGYKVLVLNPSVAAT |
| A203 | 563 | GYKVLVLNPSVAATL |
| A204 | 564 | YKVLVLNPSVAATLG |
| A205 | 565 | KVLVLNPSVAATLGF |
| A206 | 566 | VLVLNPSVAATLGFG |
| A207 | 567 | LVLNPSVAATLGFGA |
| A208 | 568 | VLNPSVAATLGFGAY |
| A209 | 569 | YLHAPTGSGKSTKVP |
| A210 | 570 | LHAPTGSGKSTKVPV |
| A211 | 571 | HAPTGSGKSTKVPVA |
| A212 | 572 | APTGSGKSTKVPVAY |
| A213 | 573 | PTGSGKSTKVPVAYA |
| A214 | 574 | TGSGKSTKVPVAYAA |
| A215 | 575 | GSGKSTKVPVAYAAQ |
| A216 | 576 | SGKSTKVPVAYAAQG |
| A217 | 577 | GKSTKVPVAYAAQGY |
| A218 | 578 | KSTKVPVAYAAQGYK |
| A219 | 579 | STKVPVAYAAQGTKV |
| A220 | 580 | TKVPVAYAAQGYKVL |
| A221 | 581 | KVPVAYAAQGYKVLV |
| A222 | 582 | VPVAYAAQGYKVLVL |
| A223 | 583 | PVAYAAQGYKVLVLN |
| A224 | 584 | VAYAAQGYKVLVLNP |
| A225 | 585 | ITSTYGKFLADGGC |
| A226 | 586 | TYSTYGKFLADGGCS |
| A227 | 587 | YSTYGKFLADGCCSG |
| A228 | 588 | STYGKFLADGGCSGG |
| A229 | 589 | TYGKFLADGGCSGGA |
| A230 | 590 | YGKFLADGGCSGGAY |
| A231 | 591 | GKFLADGGCSGGAYD |
| A232 | 592 | KFLADGGCSGGAYDI |
| A233 | 593 | FLADGGCSGGAYDII |
| A234 | 594 | LADGGCSGGAYDIII |
| C75 | 595 | FPDLGVRVCEKMALY |
| C76 | 596 | PDLGVRVCEKMALYD |
| C77 | 597 | DLGVRVCEKMALYDV |
| C78 | 598 | KGGKKAARLIVYPDL |
| C79 | 599 | GGKKAARLIVYPDLG |
| C80 | 600 | GKKAARLIVYPDLGV |
| C81 | 601 | KKAARLIVYPDLGVR |
| C82 | 602 | KAARLIVYPDLGVRV |
| C83 | 603 | AARLIVYPDLGVRVC |
| C84 | 604 | ARLIVYPDLGVRVCE |
| C85 | 605 | RLIVYPDLGVRVCEK |
| C86 | 606 | LIVYPDLGVRVCEKM |
| C87 | 607 | IVPDLGVRVCEKMA |
| C88 | 608 | VYPDLGVRVCEKMAL |
| C89 | 609 | YPDLGVRVCEKMALY |
| C90 | 610 | AQPGYPWPLYGNEGL |
| C91 | 611 | GQPGYPWPLYGNEGL |
| C92 | 612 | AFCSAMYVGDLCGSV |
| C93 | 613 | AFCSALYVGDLCGSV |
| C94 | 614 | ETVQDCNCSIYPGHV |
| C95 | 615 | EFVQDCNCSIYPGHV |
| C96 | 616 | GVLAGLAYYSMVGNW |
| C97 | 617 | GVLFGLAYFSMVGNW |
| C98 | 618 | DQRPYCWHYAPRPCG |
| C99 | 619 | DQRPYCWYPPRPCG |
| C100 | 620 | TCPTDCFRKHPEATY |
| C101 | 621 | YTKCGSGPWLTPRCL |
| C102 | 622 | LNAACNWTRGERCDL |
| C103 | 623 | LNAACNFTRGERCDL |
| C104 | 624 | IAQAEAALENLVVLN |

TABLE 1-continued

| | | |
|---|---|---|
| C105 | 625 | IAQAEAALEKLVVLH |
| C106 | 626 | TRVPYFVRAQGLIRA |
| C107 | 627 | TRVPYFVRAHGLIRA |
| C108 | 628 | HAGLRDLAVAVEPVV |
| C109 | 629 | AAGLRDLAVAVEPIV |
| C110 | 630 | ITWGADTAACGDIIL |
| C111 | 631 | ITWGAETAACGDIIL |
| C112 | 632 | GQGWRLLAPITAYSQ |
| C113 | 633 | TAYSQQTRGLLGCII |
| C114 | 634 | TAYSQQTRGLLGCIV |
| C115 | 635 | GCIITSLTGRDKNQV |
| C116 | 636 | GCIVVSMTGRDKTQV |
| C117 | 637 | VNGVCWTVYHGAGSK |
| C118 | 638 | KGPITQMYTNVDQDL |
| C119 | 639 | KGPITQMYSSAEQDL |
| C120 | 640 | GDSRGSLLSPRPVSY |
| C121 | 641 | GDSRGALLSPRPVSY |
| C122 | 642 | SYLKGSSGGPLLCPS |
| C123 | 643 | SYLKGSSGGPVLCPS |
| C124 | 644 | GHAVGIFRAAVCTRG |
| C125 | 645 | GVDPNIRTGVRTITT |
| C126 | 646 | VPHPNIEEVALSNTG |
| C127 | 647 | TGEIPFYGKAIPIEV |
| C128 | 648 | TGEIPFYGKAIPLEV |
| C129 | 649 | PTSGDVVVATDALM |
| C130 | 650 | QTVDFSLDPTFTIET |
| C131 | 651 | TLHGPTPLLYRLGAV |
| C132 | 652 | VQNEVTLTHPITKYI |
| C133 | 653 | LYREFDEMEECASHL |
| C134 | 654 | TTLLFNILGGWVAAQ |
| C135 | 655 | TTLLNILGGWLAAQ |
| C136 | 656 | PSAASAFVGAGIAGA |
| C137 | 657 | PSAATGFVVSGLAGA |
| C138 | 658 | TPCSGSWLRDVWDWI |
| C139 | 659 | VAAEEYVEVTRVGDF |
| C140 | 660 | VAAEEYAEVTRHGDF |
| C141 | 661 | FFTEVDGVRLHRYAP |
| C142 | 662 | FFTELDGVRLHRYAP |
| C143 | 663 | FFTWVDGVQIHRYAP |
| C144 | 664 | FFTWLDGVQIHRYAP |
| C145 | 665 | YLVGSQLPCEPEPDV |
| C146 | 666 | YLVGSQLPCDPEPDV |
| C147 | 667 | LPTWARPDYNPPLLE |
| C148 | 668 | ASLRQKKVTFDRLQV |
| C149 | 669 | ASLRAKKVTFDRLQV |
| C150 | 670 | HIRSVWKDLLEDTET |
| C151 | 671 | IDTTIMAKNEVFCVQ |
| C152 | 672 | VMGSSYGFQYSPGQR |
| C153 | 673 | DCTMLVCGDDLVVIC |
| A235 | 674 | ADGGCSGGAYDIIIC |
| A236 | 675 | DGGCSGGAYDIIICD |
| A237 | 676 | GGCSGGAYDIIICDE |
| A238 | 677 | GCSGGAYDIIICDEC |
| A239 | 678 | CSGGAYDIIICDECH |
| A240 | 679 | SGGAYDIIICDECHS |
| A241 | 680 | TTILGIGTVLDQAET |
| A242 | 681 | TILGIGTVLDQAETA |
| A243 | 682 | ILGIGTVLDQAETAG |
| A244 | 683 | LGIGTVLDQAETAGA |
| A245 | 684 | GIGTVLDQAETAGAR |
| A246 | 685 | IGTVLDQAETAGARL |
| A247 | 686 | GTVLDQAETAGARLV |
| A248 | 687 | TVLDQAETAGARLVV |
| A249 | 688 | VLDQAETAGARLVVL |
| A250 | 689 | LDQAETACARLVVLA |
| A251 | 690 | DQAETAGARLVVLAT |
| A252 | 691 | QAETAGARLVVLATA |
| A253 | 692 | AETAGARLVVLATAT |
| A254 | 693 | ETAGARLVVLATATP |
| A255 | 694 | TAGARLVVLATATPP |
| A256 | 695 | AGARLVVLATATPPG |
| A257 | 696 | GARLVVLATATPPGS |
| A258 | 697 | ARLVVLATATPPGSV |
| A259 | 698 | RLVVLATATPPGSVT |
| A260 | 699 | TSILGIGTVLDQAET |
| A261 | 700 | SILGIGTVLDQAETA |
| A262 | 701 | LGIGTVLDQAETAGV |
| A263 | 702 | GIGTVLDQAETAGVR |
| A264 | 703 | IGTVLDQAETAGVRL |

TABLE 1-continued

| | | |
|---|---|---|
| A265 | 704 | GTVLDQAETAGVRLT |
| A266 | 705 | TVLDQAETAGVRLTV |
| A267 | 706 | VLDQAETAGVRLTVL |
| A268 | 707 | LDQAETAGVRLTVLA |
| A269 | 708 | DQAETAGVRLTVLAT |
| A270 | 709 | QAETAGVRLTVLATA |
| A271 | 710 | AETAGVRLTVLATAT |
| A272 | 711 | ETAGVRLTVLATATP |
| A273 | 712 | TAGVRLTVLATATPP |
| A274 | 713 | AGVRLTVLATATPPG |
| A275 | 714 | GVRLTVLATATPPGS |
| A276 | 715 | VRLTVLATATPPGSV |
| B5 | 716 | SGMFDSSVLCECYDA |
| B6 | 717 | GMFDSSVLCECYDAG |
| B7 | 718 | MFDSSVLCECYDAGC |
| B8 | 719 | FDSSVLCECDAGCA |
| B9 | 720 | DSSVLCECYDAGCAW |
| B10 | 721 | SSVLCECYDAGCAWY |
| B11 | 722 | SVLCECYDAGCAWYE |
| B12 | 723 | VLCECYDAGCAWYEL |
| B13 | 724 | LCECYDAGCAWYELT |
| B14 | 725 | CECYDAGCAWYELTP |
| B15 | 726 | ECYDAGCAWYELTA |
| B16 | 727 | CYDAGCAWYELTPAE |
| B17 | 728 | YDAGCAWYELTPAET |
| B18 | 729 | DAGCAWYELTPAETT |
| B19 | 730 | AGCAWYELTPAETTV |
| B20 | 731 | CCAWYELTPAETTVR |
| B21 | 732 | CAWYELTPAETTVRL |
| B22 | 733 | AWYELTPAETTVRLR |
| B23 | 734 | WYELTPAETTVRLRA |
| B24 | 735 | YELTPAETTVRLRAY |
| B25 | 736 | DAGCAWYELTPAETS |
| B26 | 737 | AGCAWYELTPAETSV |
| B27 | 738 | GCAWYELTPAETSVR |
| B28 | 739 | CAWYELTPAETSVRL |
| B29 | 740 | AWYELTPAETSVRLR |
| B30 | 741 | WYELTPAETSVRLRA |
| B31 | 742 | GMFDSVVLCECYDAG |
| B32 | 743 | SGMFDSVVLCECYDA |
| B33 | 744 | GMFDSVVLCECYDAG |
| B34 | 745 | MFDSVVLCECYDAGA |
| B35 | 746 | FDSVVLCECYDAGAA |
| B36 | 747 | DSVVLCECYDAGAAW |
| B37 | 748 | SVVLCECYDAGAAWY |
| B38 | 749 | VVLCECYDAGAAWYE |
| B39 | 750 | VLCECYDAGAAWYEL |
| B40 | 751 | LCECYDAGAAWYELT |
| C154 | 752 | DCTMLVNGDDLWIC |
| C155 | 753 | DPTMLVCGDDLVVIC |
| C156 | 754 | DPTMLVNGDDLWIC |
| C157 | 755 | LWARMILMTHFFSIL |
| C158 | 756 | LWVRMVLMTHFFSIL |
| C159 | 757 | DLPQIIERLHGLSAF |
| C160 | 758 | DLPQIIQRLHGLSAF |
| C161 | 759 | AVRTKLKLTPIPAAS |
| C162 | 760 | AVRTKLKLTPLPAAS |
| C163 | 761 | SGGDIYHSLSRARPR |
| C164 | 762 | SGGDIYHSVSRARPR |
| C165 | 763 | WGENETDVLLLNNTR |
| C166 | 764 | GENETDVLLLNNTRP |
| C167 | 765 | WFGCTWMNSTGFTKT |
| C168 | 766 | FGCTWMNSTGFTKTC |
| C169 | 767 | GCTWMNSTGFTKTCG |
| C170 | 768 | GLPVSARRGREILLG |
| C171 | 769 | LPVSARRGREILLGP |
| C172 | 770 | PVSARRGREILLGPA |
| C173 | 771 | VSARRGREILLGPAD |
| C174 | 772 | GLPVSALRGREILLG |
| C175 | 773 | LPVSALRGREILLGP |
| C176 | 774 | PVSALRGREILLGPA |
| C177 | 775 | VSALRGREILLGPAD |
| C178 | 776 | PDREVLYREFDEMEE |
| C179 | 777 | DREVLYREFDEMEEC |
| C180 | 778 | REVLYREFDEMEECA |
| C181 | 779 | EVLYREFDEMEECAS |
| C182 | 780 | VLYREFDEMEECASH |
| C183 | 781 | LYREFDEMEECASHL |
| C184 | 782 | YYLTRDPTTPLARAA |

TABLE 1-continued

| Peptide ID | SEQ ID NO: | Sequence |
|---|---|---|
| C185 | 783 | YLTRDPTTPLARAAW |
| C186 | 784 | LTRDPTTPLARAAWE |
| C187 | 785 | TRDPTTPLARAAWET |
| C188 | 786 | RDPTTPLARAAWETA |
| C189 | 787 | DPTTPLARAAWETAR |
| C190 | 788 | PTTPLARAWETARH |
| C191 | 789 | YYLTRDPTTPLARAA |
| C192 | 790 | YLTRDPTTPLARAAW |
| C193 | 791 | LTRDPTTPLARAAWE |
| C194 | 792 | TRDPTTPLARAAWET |
| C195 | 793 | RDPTTPLARAAWETV |
| C196 | 794 | DPTTPLARAAWETVR |
| C197 | 795 | PTTPLARAAWETVRH |

| Peptide ID (Ipep) | SEQ ID NO: | Sequence |
|---|---|---|
| 1506 | 796 | MSTNPKPQRKTKRNTNRRPQDVKFPGGGQIVGGVYLLPRRGPRLGVRATRKTSERSQPRGRRQPIPK |
| 1526 | 797 | VNLLPAILSPGALVVGVVCAAILRRHVGPGEGAVQWMNRLIAFASRGNHVSPTHYV |
| 1545 | 798 | IKGGRHLTFCHSKKKCDELA |
| 1546 | 799 | TVPQDAVSRSQRRGRTGRGR |
| 1547 | 800 | YLVAYQATVCARAQAPPPSWD |
| 1551 | 801 | HLHAPTGSGKSTKVPAAYAAQGYKVLVLNPSVAATLGFGAY |
| 1552 | 802 | YLHAPTGSGKSTKVPAYAAQGYKVLVLNPSVAATLGFGAY |
| 1553 | 803 | GAAVGSICLGKVLVDILAGYGAGVAGALVAFKIMSGE |
| 1554 | 804 | GAAVGSIGLGKVLVDILAGYGAGVAGALVAFKVMSGE |
| 1555 | 805 | GAAVGSIGLGKVLVDILAGYGAGISGALVAFKIMSGE |
| 1556 | 806 | FTEAMTRYSAPPGDPP |
| 1557 | 807 | SSMPPLEGEPGDPDL |
| 1558 | 808 | CGYRRCRASGVLTTS |
| 1559 | 809 | PVNSWLGNIIMYAPT |
| 1560 | 810 | PVNSWLGNIIQYAPT |
| 1561 | 811 | SGMFDSSVLCECYDAGCAWYELTPAETTVRLRAY |
| 1562 | 812 | SGMFDSSVLCECYDAGCAWYELTPAETSVRLRAY |
| 1563 | 813 | SGMFDSVVLCECYDAGAAWYELTPAETTVRLRAY |
| 1564 | 814 | SGMFDSVVLCECYDAGAAWYELTPAETSVRLRAY |
| 1565 | 815 | FWAKHMWNFISGIQYLAGLSTLPGNPAIASLMAF |
| 1577 | 816 | GEVQVVSTATQSFLAT |
| 1578 | 817 | GEVQVLSTVTQSFLGT |
| 1579 | 818 | FTDNSSPPAVPQTFQV |
| 1580 | 819 | FSDNSTPPAVPQTYQV |
| 1581 | 820 | NAVAYYRGLDVSVIPT |
| 1587 | 821 | VNLLPGILSPGALVVGVICAAILRRHVGPGEGAVQWMNRLIAFASRGNHVAPTHYV |
| 1588 | 822 | TTILGIGTVLDQAETAGARLVVLATATPPGSVT |
| 1589 | 823 | TSILGIGTVLDQAETAGARLVVLATATPPGSVT |
| 1590 | 824 | TSILGIGTVLDQAETAGVRLTVLATATPPGSVT |
| 1591 | 825 | TTILGIGTVLDQAETAGVRLTVLATATPPGSVT |
| 1592 | 826 | FWAKHMWNFISGIQYLAGLSTLPGNPAVASMMAF |
| 1603 | 827 | VFTGLTHIDAHFLSQTKQ |
| 1604 | 828 | VVCCSMSYTWTGALITPC |
| 1605 | 829 | VVCCSMSYSWTGALITPC |
| 1606 | 830 | VLTSMLTDPSHITAETA |
| 1607 | 831 | VLTSMLTDPSHITAEAA |
| 1613 | 832 | ASSSASQLSAPSLRATCTT |
| 1614 | 833 | LTPPHSARSKFGYGAKDVR |
| 1615 | 834 | LTPPHSADSKFGYGAKDVR |
| 1616 | 835 | LTPPHSAKSKYGYGAKEVR |
| 1617 | 836 | LTPPHSARSKYGYGAKEVR |
| 1618 | 837 | PMGFSYDTRCFDSTVTE |
| 1619 | 838 | PMGFAYDTRCFDSTVTE |
| 1620 | 839 | TGDFDSVIDCNTCVTQ |
| 1621 | 840 | TGDFDSVIDCNVAVTQ |
| 1622 | 841 | NTPGLPVCQDHLEFWE |
| 1623 | 842 | YLVAYQATVCARAXAPPPSWD |
| 1624 | 843 | LEDRDRSELSPLLLSTTEW |
| 1625 | 844 | LEDRDRSQLSPLLHSTTEW |
| 1626 | 845 | ASSSASQLSAPSLKATCTT |
| 1627 | 846 | PEYDLELITSCSSNVSVA |
| 1628 | 847 | VCGPVYCFTPSPVVVGTTDR |
| 1629 | 848 | GWAGWLLSPRGSRPSWGP |
| 1630 | 849 | LLFLLLADARVCACLWM |
| 1631 | 850 | SGHRMAWDMMMNWSPT |
| 1632 | 851 | TGHRMAWDMMMNWSPT |
| 1641 | 852 | ITYSTYGKFLADGGCSGGAYDIIICDECHS |
| 1647 | 853 | ARALAHGVRVLEDGVNYATGNLPGCSFSIFLLALLSC |
| 1648 | 854 | DPRRRSRNLGKVIDTLTCGFADLMGYIPLVGAPLGG |
| 1649 | 855 | DPRHRSRNVGKVIDTLTCGFADLMGYIPVVGAPLGG |

TABLE 1-continued

| | | |
|---|---|---|
| 1650 | 856 | VDYPYRLWHYPCTVNFTIFKVRMYVGGVEHRL |
| 1651 | 857 | VDYPYRLWHYPCTVNYTIFKIRMYVGGVEHRL |
| 1652 | 858 | XGGRKPARLIVFPDLGVRVCEKMALYDV |
| 1653 | 859 | KGGKKAARLIVYPDLGVRVCEKMALYDV |
| 1654 | 860 | IQLINTNGSWHINRTALNCNDSL |
| 1655 | 861 | IQLVNTNGSWHINRTALNCNDSL |
| 1656 | 862 | LPALSTGLIHLHQNIVDVQYLYG |

For epitope capture, each peptide pool was incubated with soluble recombinant HLA-class II molecules and specific binding was assessed by an SDS-stability assay. The results using the HLA molecules DRB1*0401, DRB1*0404 and DRB1*0101 are shown in FIGS. 2 and 3 respectively: 28 peptide pools were found which bind to DRB1*0401 molecules: no. 1, 2, 6, 7, 8, 9, 10, 11, 12, 13, 14, 16, 17, 18, 19, 20 from "row" pools and no. 23, 25, 26, 27, 29, 30, 31, 34, 36, 38, 39 and 40 from "column" pools (FIG. 2). 35 peptide pools out of 40 tested were positive in binding to DRB1*0404 molecules (FIG. 3), while all peptide pools showed binding activity to DRB1*0101 molecules. By finding the intersections of reactive pools in the array, potential individual binders were determined and re-checked for binding affinity individually.

All individually confirmed peptides are summarized in Table 2. Binding to DRB1*0401 is shown in FIG. 4: 54 individual peptides were identified as ligands of this HLA-type. Often several overlapping 15mers in a row bound to HLA allowing identification of their core binding regions. Peptide differing only by one or two amino acids representing variants (see Table 1) usually bound both to soluble HLA class II molecules. Such "duplicates" were considered to represent the same epitope. Thus, 31 ligands capable to bind to DRB1*0401 were identified, including 11 previously known class II epitopes. From the latter, however, only two (A202-A206 and B60-B68) had been known to be restricted to DR4 (see Table 2). 20 ligands are candidates for novel epitopes. For DRB1*0404, 64 binders designated as 28 potential epitopes were determined, 4 of them belong to already known epitopes (FIG. 5, Table 2). For DRB1*0101, 83 peptides representing 44 potential epitopes were identified (FIG. 6, Table 2). Of those, 7 had been described previously but with different HLA restriction.

All individually confirmed peptides binding to at least one of the 3 above mentioned HLA types were also tested for affinity to DRB1*0701 molecules in a peptide-competition assay (FIG. 7, Table 2). Here, 50 ligands were identified. Of those, 7 correspond to already known class II epitopes, but only one was described as DRB1*0701 epitope (A202-A206).

TABLE 2

HCV derived peptides binding to soluble HLA class II molecules. About 400 15- to 23-mer peptides derived from conserved regions of HCV were analyzed by the Epitope Capture Method using pools of up to 20 peptides arrayed in matrix format (see FIG. 1) and four different HLA class II molecules. Specific binding was confirmed for individual peptides.

| ID | SEQ ID NO: | Peptide Sequences | Binding to DRB1 *0101 | *0401 | *0404 | *0701 | Known/new potential epitope, HLA coverage |
|---|---|---|---|---|---|---|---|
| A120 | 863 | NTNGSWHINRTALNC | * | | | nb | |
| A122 | 864 | NGSWHINRTALNCND | * | | * | * | new DRB1*0101, |
| A124 | 865 | SWHINRTALNCNDSL | * | | | | *0404, *0701: 45-55% |
| B25 | 866 | DAGCAWYELTPAETS | *** | * | *** | | |
| B26 | 867 | AGCAWYELTPAETSV | *** | *** | *** | nb | new DRB1*0101, |
| B28 | 868 | CAWYELTPAETSVRL | *** | ** | *** | * | *0404, *0701: 45- |
| B30 | 869 | WYELTPAETSVRLRA | ** | * | ** | nb | 55% |
| B46 | 870 | AGAAWYELTPAETTV | *** | | *** | nb | new DRB1*0101, |
| B48 | 871 | AAWYELTPAETTVRL | *** | | *** | ** | *0404, *0701: 45-55% |
| B84 | 872 | GSIGLGKVLVDILAG | * | * | * | | |
| B86 | 873 | IGLGKVLVDILAGYA | * | ** | * | ** | new DRB1*0101, |
| B88 | 874 | LGKVLVDILAGYGAG | * | ** | * | | *0404, *0701: 45- |

TABLE 2-continued

HCV derived peptides binding to soluble HLA class II
molecules. About 400 15- to 23-mer peptides derived from
conserved regions of HCV were analyzed by the Epitope Capture
Method using pools of up to 20 peptides arrayed in matrix format
(see FIG. 1) and four different HLA class II molecules.
Specific binding was confirmed for individual peptides.

| ID | SEQ ID NO: | Peptide Sequences | Binding to DRB1 *0101 | *0401 | *0404 | *0701 | Known/new potential epitope, HLA coverage |
|---|---|---|---|---|---|---|---|
| B92 | 875 | LVDILAGYGAGVAGA | * | nb | | | 55% |
| C106 | 876 | TRVPYFVRAQGLIRA | * | * | * | * | new DRB1*0101, *0404, *0701: 45-55% |
| C113 | 877 | TAYSQQTRGLLGCII | *** | * | | | new DRB1*0101, |
| C114 | 878 | TAYSQQTRGLLGCIV | *** | * | * | * | *0404, *0701: 45-55% |
| 1627 | 879 | PEYDELELITSCSSNVSVA | *** | | *** | ** | new DRB1*0101, *0404, *0701: 45-55% |
| 1628 | 880 | VCGPVYCFTPSPVVVGTTDR | *** | ** | * | * | new DRB1*0101, *0404, *0701: 45-55% |
| 1629 | 881 | GWAGWLLSPRGSPRPSWGP | * | * | ** | * | new DRB1*0101, *0404, *0701: 45-55% |
| 1604 | 882 | VVCCSMSYTWTGALITPC | * | | ** | *** | new DRB1*0101, *0404, *0701: 45-55% |
| 1630 | 883 | LLFLLLADARVCACLWM | * | | nb | *** | new DRB1*0101, *0701: 40-50% |
| C97 | 884 | GVLFGLAYFSMVGNW | ** | ** | nb | ** | new DRB1*0101, *0701: 40-50% |
| 1547 | 885 | YLVAYQATVCARAQAPPPSWD | *** | | NB | ** | new DRB1*0101, *0701: 40-50% |
| B94 | 886 | DILAGYGAGVAGALV | * | nb | nb | nb | |
| B95 | 887 | ILAGYGAGVAGALVA | * | nb | nb | | new DRB1*0101, |
| B96 | 888 | LAGYCAGVAGALVAF | ** | ** | nb | * | *0404, *0701: 40-50% |
| B97 | 889 | AGYGAGVAGALVAFK | * | nb | nb | | |
| B98 | 890 | GYGAGVACALVAKFI | * | nb | nb | nb | |
| A272 | 891 | ETAGVRLTVLATATT | * | * | nb | | |
| A274 | 892 | AGVRLTVLATATPPG | * | nb | | nb | new DRB1*0101, |
| A276 | 893 | VRLTVLATATPPGSV | | nb | | * | *0404, *0701: 40-50% |
| B120 | 894 | AGISGALVAFKIMSG | * | nb | * | *** | new DRB1*0101, *0404, *0701: ~45 |
| B122 | 895 | VNLLPAILSPGALVV | * | nb | * | * | new DRB1*0101, *0404, *0701: ~45 |
| C108 | 896 | HAGLRDLAVAVEPVV | * | nb | * | * | new DRB1*0101, *0404, *0701: ~45 |
| C134 | 897 | TTLLFNILGGWVAAQ | * | nb | * | ** | new DRB1*0101, *0404, *0701: ~45 |
| C152 | 898 | VMGSSYGFQYSPGQR | * | nb | * | * | new DRB1*0101, |

TABLE 2-continued

HCV derived peptides binding to soluble HLA class II molecules. About 400 15- to 23-mer peptides derived from conserved regions of HCV were analyzed by the Epitope Capture Method using pools of up to 20 peptides arrayed in matrix format (see FIG. 1) and four different HLA class II molecules. Specific binding was confirmed for individual peptides.

| SEQ ID ID | NO: | Peptide Sequences | Binding to DRB1 *0101 | *0401 | *0404 | *0701 | Known/new potential epitope, HLA coverage |
|---|---|---|---|---|---|---|---|
| | | | | | | | *0404, *0701: ~45 |
| 1606 | 899 | VLTSMLTDPSHITAETA | nb | *** | ** | ** | new DRB1*0401, *0404, *0701: ~45 |
| 1607 | 900 | VLTSMLTDPSHITAEAA | nb | *** | ** | * | new DRB1*0401, *0404, *0701: ~45 |
| 1577 | 901 | GEVQVVSTATQSFLAT | nb | * | *** | *** | new DRB1*0401, *0404, *0701: ~45 |
| 1578 | 902 | GEVQVLSTVTQSFLGT | nb | * | *** | *** | new DRB1*0401, *0404, *0701: ~45 |
| B50 | 903 | AGAAWYELTPAETSV | *** | *** | *** | | new DRB1*0101, |
| B52 | 904 | AAWYELTPAETSVRL | *** | *** | *** | nb | *0401, *0404: ~40 |
| 1623 | 905 | YLVAYQATVCARAKAPPPSWD | * | | ** | | new DRB1*0101, *0401, *0404: ~40 |
| C130 | 906 | QTVDFSLDPTFTIET | ** | *** | ** | nb | new DRB1*0101, *0401, *0404: ~40 |
| 1603 | 907 | VFTGLTHIDAHFLSQTKQ | *** | nb | nb | * | new DRB1*0101, *0701: ~40 |
| C96 | 908 | GVLAGLAYYSMVGNW | ** | nb | nb | * | new DRB1*0101, *0701: ~40 |
| C191 | 909 | YYLTRDPTTPLARAA | nb | *** | nb | | new DRB1*0401, *0701: ~40 |
| A216 | 910 | SGKSTKVPVAYAAQG | nb | * | nb | nb | |
| A218 | 911 | KSTKVPVAYAAQGYK | nb | * | nb | | new DRB1*0101, |
| A220 | 912 | TKVPVAYAAQGYKVL | * | ** | nb | | *0401 ~35 |
| A222 | 913 | VPVAYAAQGYKVLVL | * | nb | nb | nb | |
| A224 | 914 | VAYAAQGYKVLVLNP | * | nb | nb | | |
| A242 | 915 | TILGIGTVLDQAETA | nb | nb | * | | new DRB1*0101, |
| A244 | 916 | LGIGTVLDQAETAGA | * | * | nb | nb | *0401: ~35 |
| C92 | 917 | AFCSAMYVGDLCGSV | * | ** | nb | nb | new DRB1*0101, |
| C93 | 918 | AFCSALYVGDLCGSV | * | * | nb | | *0401: ~35 |
| A174 | 919 | PALSTGLLHLHQNIV | | nb | * | * | new DRB1*0404, *0701: ~25-30 |
| B32 | 920 | SGMFDSVVLCECYDA | * | nb | *** | | |
| B34 | 921 | MFDSVVLCECYDAGA | * | nb | *** | nb | new DRB1*0101, |
| B36 | 922 | DSVVLCECYDAGAAW | * | nb | *** | | *0404: ~20-25 |
| B38 | 923 | VVLCECYDAGAAWYE | nb | nb | * | nb | |
| B100 | 924 | GAGVAGALVAFKIMS | ** | nb | ** | | new DRB1*0101, |
| B102 | 925 | GVAGALVAFKIMSGE | *** | nb | *** | | *0404: ~20-25 |

TABLE 2-continued

HCV derived peptides binding to soluble HLA class II molecules. About 400 15- to 23-mer peptides derived from conserved regions of HCV were analyzed by the Epitope Capture Method using pools of up to 20 peptides arrayed in matrix format (see FIG. 1) and four different HLA class II molecules. Specific binding was confirmed for individual peptides.

| ID | SEQ ID NO: | Peptide Sequences | Binding to DRB1 *0101 | *0401 | *0404 | *0701 | Known/new potential epitope, HLA coverage |
|---|---|---|---|---|---|---|---|
| C135 | 926 | TTLLLNILGGWLAAQ | ** | nb | * |  | new DRB1*0101, *0404: ~20-25 |
| C162 | 927 | AVRTKLKLTPLPAAS | nb | * | * | nb | new DRB1*0401, *0404: ~20-25 |
| 1618 | 928 | PMGFSYDTRCFDSTVTE | nb | nb |  | ** | new DRB1*0701: ~25 |
| 1622 | 929 | NTPGLPVCQDHLEFWE | nb | nb |  | *** | new DRB1*0701: ~25 |
| 1624 | 930 | LEDRDRSELSPLLLSTTEW | nb | nb |  | * | new DRB1*0701: ~25 |
| 1546 | 931 | TVPQDAVSRSQRRGRTGRGR | nb | nb | nb | * | new DRB1*0701: ~25 |
| 1556 | 932 | FTEAMTRYSAPPGDPP | nb | nb | nb | * | new DRB1*0701: ~25 |
| A114 | 933 | LPGCSFSIFLLALLS | ** | nb | nb | nb | new DRB1*0101: ~20 |
| B58 | 934 | MWNFISGIQYLAGLS | * | nb | nb |  | new DRB1*0101: ~20 |
| B112 | 935 | VDILAGYGAGISGAL | * |  |  |  |  |
| B114 | 936 | ILAGYGAGISGALVA | *** |  |  |  | new DRB1*0101: ~20 |
| B116 | 937 | AGYGAGISGALVAFK | *** |  | nb | nb |  |
| B118 | 938 | YGAGISGALVAFKIM | *** |  | nb |  |  |
| B18 | 939 | DAGCAWYELTPAETT | *** |  | nb | nb |  |
| B20 | 940 | GCAWYELTPAETTVR | *** | nb |  |  | new DRB1*0101: ~20 |
| B22 | 941 | AWYELTPAETTVRLR | ** |  | nb | nb |  |
| C112 | 942 | GQGWRLLAPITAYSQ | ** | nb |  |  | new DRB1*0101: ~20 |
| C116 | 943 | GCIVVSMTGRDKTQV | * | nb | nb |  | new DRB1*0101: ~20 |
| C122 | 944 | SYLKGSSGGPLLCPS | * | nb | nb |  | new DRB1*0101: ~20 |
| C127 | 945 | TGEIPFYGKAIPIEV | * | nb |  |  | new DRB1*0101: ~20 |
| C144 | 946 | FFTWLDGVQIHRYAP | ** | nb | nb |  | new DRB1*0101: ~20 |
| C159 | 947 | DLPQIIERLHGLSAF | * | nb | nb | nb | new DRB1*0101: ~20 |
| C160 | 948 | DLPQIIQRLHGLSAF | * | nb |  |  |  |
| C174 | 949 | GLPVSALRGREILLG | * | nb | nb |  | new DRB1*0101: ~20 |
| 1558 | 950 | CGYRRCRASGVLTTS | *** |  | nb | nb | new DRB1*0101: ~20 |
| 1581 | 951 | NAVAYYRGLDVSVIPT | ** | nb | nb | nb | new DRB1*0101: ~20 |
| C95 | 952 | EFVQDCNCSIYPGHV | nb | ** | nb | nb | new DRB1*0401: ~20 |
| C129 | 953 | PTSGDVVVVATDALM | nb | nb | ** |  | new DRB1*0404: ~5 |
| C157 | 954 | LWARMILMTHFESIL | nb | nb | * | nb | new DRB1*0404: ~5 |
| C158 | 955 | LWVRMVLMTHFFSIL |  | nb | * |  |  |
| A254 | 956 | ETAGARLVVLATATP | nb | nb | * |  |  |
| A256 | 957 | AGARLVVLATATPPG | nb | nb | * |  | new DRB1*0404: ~5 |

TABLE 2-continued

HCV derived peptides binding to soluble HLA class II molecules. About 400 15- to 23-mer peptides derived from conserved regions of HCV were analyzed by the Epitope Capture Method using pools of up to 20 peptides arrayed in matrix format (see FIG. 1) and four different HLA class II molecules. Specific binding was confirmed for individual peptides.

| ID | SEQ ID NO: | Peptide Sequences | Binding to DRB1 *0101 | *0401 | *0404 | *0701 | Known/new potential epitope, HLA coverage |
|---|---|---|---|---|---|---|---|
| A258 | 958 | ARLVVLATATPPGSV | nb | nb | ** | | |
| 1605 | 959 | VVCCSMSYSWTGALITPC | nb | nb | * | nb | new DRB1*0404: ~5 |
| C109 | 960 | AAGLRDLAVAVEPIV | | nb | * | | new DRB1*0404: ~5 |
| C161 | 961 | AVRTKLKLTPIPAAS | | | * | | new DRB1*0404: ~5 |
| A60 | 962 | LGKVIDTLTCGFA | ** | nb | nb | ** | known DR4, DR8, DR15 |
| A61 | 963 | GKVIDTLTCGFAD | ** | | | | new DR*0101, 0701 |
| A70 | 964 | TCGFADLMGYIPLVG | * | nb | nb | | |
| A72 | 965 | GFADLMGYIPLVGAP | *** | * | ** | | known class II |
| A74 | 966 | DLMGYIPVVGAPLGG | *** | | *** | ** | DR*0101, 0404, 0701 |
| A88 | 967 | CGFADLMGYIPVVGA | ** | | ** | * | |
| A90 | 968 | FADLMGYIPVVGAPL | *** | | *** | | known class II |
| A92 | 969 | DLMGYIPVVGAPLGG | *** | | *** | *** | DR*0101, 0404, 0701 |
| A96 | 970 | LAHGVRVLEDGVNYA | nb | *** | nb | | |
| A98 | 971 | HGVRVLEDGVNYATG | nb | *** | *** | ** | known DR11 |
| A100 | 972 | VRVLEDGVNYATGNL | nb | *** | *** | * | new DR*0401, |
| A102 | 973 | VLEDGVNYATGNLPG | nb | | * | | 0404, 0701 |
| A104 | 974 | EDGVNYATGNLPGCS | nb | * | nb | nb | |
| A200 | 975 | AAQGYKVLVLNPSVA | | nb | *** | ** | |
| A202 | 976 | QGYKVLVLNPSVAAT | *** | *** | *** | *** | known DRB1*0401, |
| A204 | 977 | YKVLVLNPSVAATLG | *** | *** | *** | *** | 0701, DR11, DR15 |
| A206 | 978 | VLVLNPSVAATLGFG | *** | *** | *** | *** | new DR*0101 |
| C30 | 979 | AVQWMNRLIAFASRG | * | | nb | | known DR11, DQ5, also DR*0101 |
| B60 | 980 | NFISGIQYLAGLSTL | ** | | nb | 8 | |
| B62 | 981 | ISGIQYLAGLSTLPG | *** | | *** | ** | |
| B64 | 982 | GIQYLAGLSTLPGNP | *** | | *** | ** | know DR#0401, |
| B66 | 983 | QYLAGLSTLPGNPAI | * | | *** | ** | 1101 |
| B68 | 984 | LAGLSTLPGNPAIAS | * | | *** | ** | new 0101, 0404, 0701 |
| C124 | 985 | GHAVGIFRAAVCTRG | ** | * | nb | ** | known DR*0101, 0401, 0701 |
| 1620 | 986 | TGDFDSVIDCNTCVTQ | nb | nb | * | | new DR*0404 |
| 1621 | 987 | TGDFDSVIDCNVAVTQ | * | | nb | nb | known DR13, 11so DR*0101, 0401 |

TABLE 2-continued

HCV derived peptides binding to soluble HLA class II molecules. About 400 15- to 23-mer peptides derived from conserved regions of HCV were analyzed by the Epitope Capture Method using pools of up to 20 peptides arrayed in matrix format (see FIG. 1) and four different HLA class II molecules. Specific binding was confirmed for individual peptides.

| ID | SEQ ID NO: | Peptide Sequences | Binding to DRB1 *0101 | *0401 | *0404 | *0701 | Known/new potential epitope, HLA coverage |
|---|---|---|---|---|---|---|---|
| 1631 | 988 | SGHRMAWDMMMNWSPT | nb | | | nb | known class II, also DR*0401 |
| 1632 | 989 | TGHRMAWDMMMNWSPT | nb | * | | | known class II, also DR*0401 |

\*\*\* strong binding
\*\* intermediate binding
\* weak binding
nb no binding
Boldface peptide IDs indicates HLA-ligands with confirmed immunogenicity in HLA-transgenic mice
Boldface peptide sequences indicate putative core binding regions based on prediction algorithms as described in the test.
[1]) immunogenic in DRB1 *0401 transgenic mice.

Some of the highly promiscuous peptides and/or with computer algorithm (SYFPEITHI (SEQ ID NO:203), TEPITOPE (SEQ ID NO:204))-predicted affinities were checked for binding to soluble HLA-DRB1*1101 molecules in a peptide-competition assay as it is described for HLA-DRB1*0701. Several known DR11 epitopes were used as controls and were confirmed to bind HLA-DRB1*1101 molecules in vitro. Among newly identified HLA-DRB1*1101 binders, there are peptides with IDs A120, A122, A141, C114, C134, 1426, 1628, 1629 of high affinity, 5 peptides with IDs C106, C135, 1578, 1547, 1604 of moderate affinity and 4 peptides with IDs B46, B48, B86, B96 of weak affinity ligands.

In summary eight novel ligands binding at least to HLA-DRB1*0101, *0401, *0404, *0701 and *1101 (Tab. 2: peptide Ids A120, A122, A141, 1604, 1547, 1628, 1629, and Tab. 6: peptide ID 1426); novel 10 ligands binding at least to HLA-DRB1*0101, *0401, *0404 and *0701 (Tab. 2: peptide IDs A120-A124, B25-B30, B46-B48, B84-B92, C106, C113-C114, 1627, 1628, 1629, 1604); 5 novel ligands binding at least to HLA-DRB1*0101, *0401 and *0701, 5 novel ligands binding at least to HLA-DRB1*0101, *0404 and *0701, 4 novel ligands binding at least to HLA-DRB1*0401, *0404 and *0701, 3 novel ligands binding at least to HLA-DRB1*0101, *0401 and *0404, 2 novel ligands binding at least to HLA-DRB1*0101 and *07.01, 1 novel ligand binding at least to HLA-DRB1*0401 and *0701, 3 novel ligands binding at least to HLA-DRB1*0101, *0401, 1 novel ligand binding at least to HLA-DRB1*0404 and *0701, 4 novel ligand binding at least to HLA-DRB1*0101 and *0404, 5 novel ligands binding at least to HLA-DRB1*0701, 13 novel ligands binding at least to HLA-DRB1*0101, 1 novel ligand binding at least to HLA-DRB1*0401, and 6 novel ligands binding at least to HLA-DRB1*0404.

Moreover, 12 known HLA class II epitopes were confirmed, in several cases binding to alleles not reported yet was demonstrated (Tab. 2, last group).

Having established physical binding too HLA class II it is straightforward to verify immunogenicity for a given ligand: for instance peptide IDs A120-A124, B46-B48, 1627, 1604, 1630, 1547, 1623, B112-118, 1558, all binding to one or more HLA class II alleles were also shown to be immunogenic in HLA-DRB1*0401 transgenic mice (see Example II).

To determine the optimal epitope within a longer polypeptide, mice can be vaccinated with a longer polypeptide incorporating the candidate epitope sequences. Generation of specific CD4+ T cell responses against naturally processed and presented epitopes can then be assayed by re-stimulation of murine splenocytes or lymph node cells with overlapping 15-mers and IFN-gamma ELIspot. Final confirmation/validation of the newly identified HLA-ligands can be achieved by testing these peptides with T-cells from humans. Ideally, these comprise therapy responders or subjects spontaneously recovered from infection.

Example II

Immunogenicity of HCV-Derived Peptides in HLA-Transgenic Mice

Synthetic HCV-derived peptides (from conserved regions) were investigated for immunogenicity in HLA-transgenic mice: 36 of 68 peptides tested were found to induce peptide-specific IFN-gamma-producing cells in vaccination experiments. As summarized in Table 3, some peptides were either immunogenic (+, less than 100 peptide-specific cells among a million splenocytes) or even strongly immunogenic (++, more than 100 peptide-specific cells among a million splenocytes) in DR4- and/or A*0201-transgenic mice.

TABLE 3

| Ipep | DRB1*0401 | A*0201 | B*0702 | SEQ ID NO | Sequence |
|---|---|---|---|---|---|
| 1506 | | | + | 990 | MSTNPKPQRKTKRNTNRRPQDVKFPGGGQIVGGVYLLPRRGPRLGVRATRKTSERSQPRGRRQPIPK |
| 1526 | + | + | + | 991 | VNLLPAILSPGALVVGVVCAAILRRHVGPGEGAVQWMNRLIAFASRGNHVSPTHYV |
| 1545 | | | + | 992 | IKGGRHLIFCHSKKKCDELA |
| 1547 | ++ | | +++ | 993 | YLVAYQATVCARAQAPPPSWD |
| 1552 | | + | + | 994 | YLHAPTGSGKSTKVPVAYAAQGYKVLVLNPSVAATLGFGAY |
| 1553 | | + | + | 995 | GAAVGSIGLGKVLVDILAGYGAGVAGALVAFKIMSGE |
| 1555 | + | + | + | 996 | GAAVGSIGLGKVLVDILAGYGAGISGALVAFKIMSGE |
| 1558 | ++ | + | ++ | 997 | CGYRRCRASGVLTTS |
| 1559 | + | ++ | | 998 | PVNSWLGNIIMYAPT |
| 1560 | + | ++ | | 999 | PVNSWLGNIIQYAPT |
| 1562 | | | + | 1000 | SGMFDSSVLCECYDAGCAWYELTPAETSVRLRAY |
| 1563 | + | | + | 1001 | SGMFDSVVLCECYDAGAAWYELTPAETTVRLRAY |
| 1565 | ++ | ++ | + | 1002 | FWAKHMWNFISGIQYLAGLSTLPGNPAIASLMAF |
| 1577 | | + | + | 1003 | GEVQVVSTATQSFLAT |
| 1578 | | | + | 1004 | GEVQVLSTVTQSFLGT |
| 1580 | | | + | 1005 | FSDNSTPPAVPQTYQV |
| 1587 | | + | + | 1006 | VNLLPGILSPGALVVGVICAAILRRHVGPGEGAVQWMNRLIAFASRGNHVAPTHYV |
| 1592 | ++ | ++ | + | 1007 | FWAKHMWNFISGIQYLAGLSTLPGNPAVASMMAF |
| 1604 | ++ | ++ | ++ | 1008 | VVCCSMSYTWTGALITPC |
| 1605 | + | + | + | 1009 | VVCCSMSYSWTGALITPC |
| 1615 | | + | | 1010 | LTPPHSAKSKFGYGAKDVR |
| 1616 | + | | | 1011 | LTPPHSAKSKYGYGAKEVR |
| 1617 | | + | | 1012 | LTPPHSARSKYGYGAKEVR |
| 1621 | + | + | + | 1013 | TGDFDSVIDCNVAVTQ |
| 1623 | + | + | + | 1014 | YLVAYQATVCARAKAPPPSWD |
| 1624 | | | + | 1015 | LEDRDRSELSPLLLSTTEW |
| 1625 | + | | | 1016 | LEDRDRSQLSPLLHSTTEW |
| 1627 | + | + | ++ | 1017 | PEYDLELITSCSSNVSVA |
| 1628 | | | ++ | 1018 | VCGPVYCFTPSPVVVGTTDR |
| 1630 | ++ | ++ | | 1019 | LLFLLLADARVCACLWM |
| 1631 | + | + | | 1020 | SGHRMAWDMMMNWSPT |
| 1632 | | + | | 1021 | TGHRMAWDMMMNWSPT |
| 1641 | | + | | 1022 | ITYSTYGKFLADGGCSGGAYDIIICDECHS |
| 1647 | | + | | 1023 | ARALAHGVRVLEDGVNYATGNLPGCSFSIFLLALLSC |
| 1649 | + | | | 1024 | DPRHRSRNVGKVIDTLTCGFADLMGYIPVVGAPLGG |
| 1650 | ++ | ++ | + | 1025 | VDYPYRLWHYPCTVNFTIFKVRMYVGGVEHRL |
| 1651 | ++ | ++ | + | 1026 | VDYPYRLWHYPCTVNYTIFKIRMYVGGVEHRL |
| 1652 | ++ | + | | 1027 | KGGRKPARLIVFPDLGVRVCEKMALYDV |

TABLE 3-continued

| Ipep | DRB1*0401 | A*0201 | B*0702 | SEQ ID NO | Sequence |
|------|-----------|--------|--------|-----------|----------|
| 1653 |           | +      |        | 1028      | KGGKKAARLIVYPDLGVRVCEKMALYDV |
| 1654 | ++        | +      |        | 1029      | IQLINTNGSWHINRTALNCNDSL |
| 1655 | ++        | +      |        | 1030      | IQLVNTNGSWHINRTALNCNDSL |
| 1656 | +         |        |        | 1031      | LPALSTGLIHLHQNIVDYQYLYG |

Peptide 1526, 1565, 1631, also shown to be immunogenic in HLA-DRB1*0401 transgenic mice contain known class II epitopes. Peptide IDs 1526, 1553, 1565, 1587, 1623, 1630 also shown to be immunogenic in HLA-A*0201 transgenic mice contain known A2epitopes.

For further characterizing the novel epitopes provided herewith, one may define the exact HLA restriction of these epitopes and the minimal epitopes within the sequences recognized by T cells. Both can be done by a variety of well-established approaches known to the one skilled in the art (Current Protocols in Immunology, John Wiley & Sons, Inc.).

First, publicly available programs can be used to predict T cell epitopes on the basis of binding motifs. These include for instance: http://bimas.dcrt.nih.gov/molbio/hla_bind/ (Parker et al. 1994), http://134.2.96.221/scripts/MHC-Server.dll/home.htm (Rammensee at al. 1999), http://mypage.ihost.com/usinet.hamme76/(Sturniolo et al. 1999). The latter prediction algorithm offers the possibility to identify promiscuous T helper-epitopes, i.e. peptides that bind to several HLA class II molecules. These predictions can be verified by testing of binding of the peptide to the respective HLA.

A way of quickly discerning whether the response towards a peptide is class I or class II restricted is to repeat the ELIspot assay with pure CD4+ or CD8+ T cell effector populations. This can for instance be achieved by isolation of the respective subset by means of magnetic cell sorting. Pure CD8+ T cells can also be tested in ELIspot assays together with artificial antigen-presenting-cells, expressing only one HLA molecule of interest. One example are HLA-A*0201 positive T2 cells (174CEM.T2, Nijman et al., 1993). Alternatively, one can use ELIspot assays with whole PBMCs in the presence of monoclonal antibodies specifically blocking either the CD4+ or CD8+ T cell sub-population. Exact HLA restriction can be determined in a similar way, using blocking monoclonal antibodies specific for a certain allele. For example the response against an HLA-A24 restricted epitope can be specifically blocked by addition of an HLA-A24 specific monoclonal antibody.

For definition of the minimal epitopes within the peptide sequences recognized by T cells, one can test overlapping and truncated peptides (e.g. 8-, 9-, 10-mers) with splenocytes from immunized transgenic mice or T-cells from humans recognizing the respective epitope.

Example III

HLA Restriction of Immunogenic HCV-Derived Peptides Investigated in Transgenic Mice Groups of 5 mice (HLA-A*0201-, HLA-DRB1*0401- and HLA-B*0702 transgenic mice, male, 8-14 weeks of age) were injected subcutaneous into the hind footpads with 100 µg of peptide +IC31 per mouse (50 µg per footpad). (PCT/EP01/12041, WO 02/32451 A1 and PCT/EP01/06433, WO 01/93905 A1; IC31 is a combination of the immunizer disclosed in WO 01/93905 and WO 02/32451).

6 days after vaccination single cell suspension of pooled spleens were prepared and additionally pure fractions of CD8+ in the case of A2 and B7 tg mice (CD8+ fraction for B7 mice containing 97% of CD8 and 1.5% of CD4 cells and for A2 tg mice 83% of CD8 and 8% of CD4 cells) and CD4+ for DR4tg mice (CD4+ fraction for DR4tg mice containing 98% of CD4 cells and 0.2% of CD8 cells) were separated from the spleen cell suspension using MACS separating kit (Miltenyi, Germany). All cells (not separated cells, positive and corresponding negative fractions) were re-stimulated ex vivo with relevant peptide (for instance Ipep1604) and irrelevant peptides as negative control (known HLA-DRB1*0401 CMV-derived epitope Ipep 1505, HLA-B*0702 HIV-derived epitope Ipep 1787, or HLA-A*0201 tyrosinase-derived epitope Ipep1124) to detect INF-γ producing cells in ELISpot assay.

Figure 9:
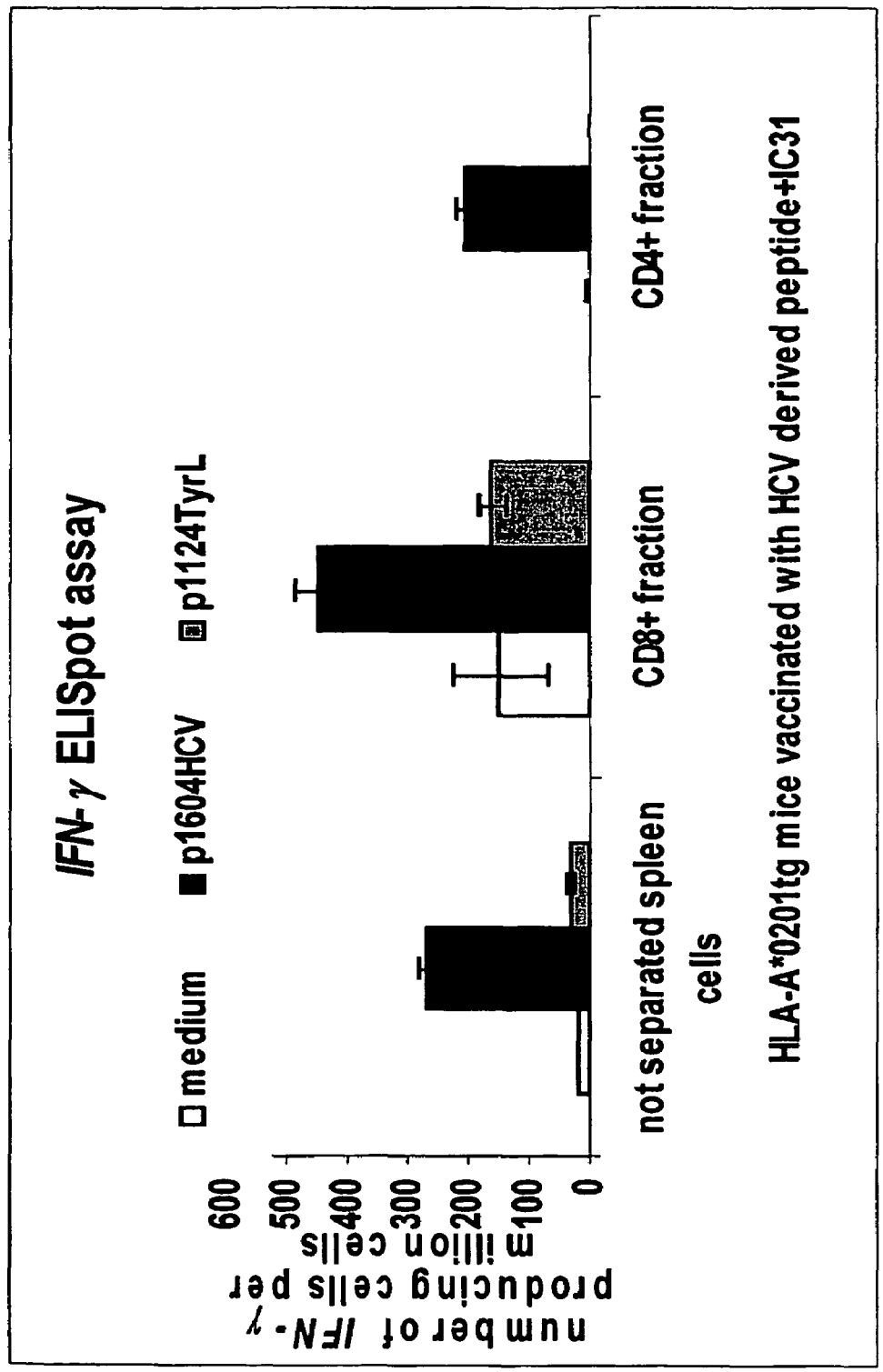
FIG. 9 shows mouse IFN-gamma ELIspot with splenocytes or separated CD8+ or CD4+ cells from HLA-A*0201 tg mice vaccinated with Ipep1604+IC31.
Figure 10:
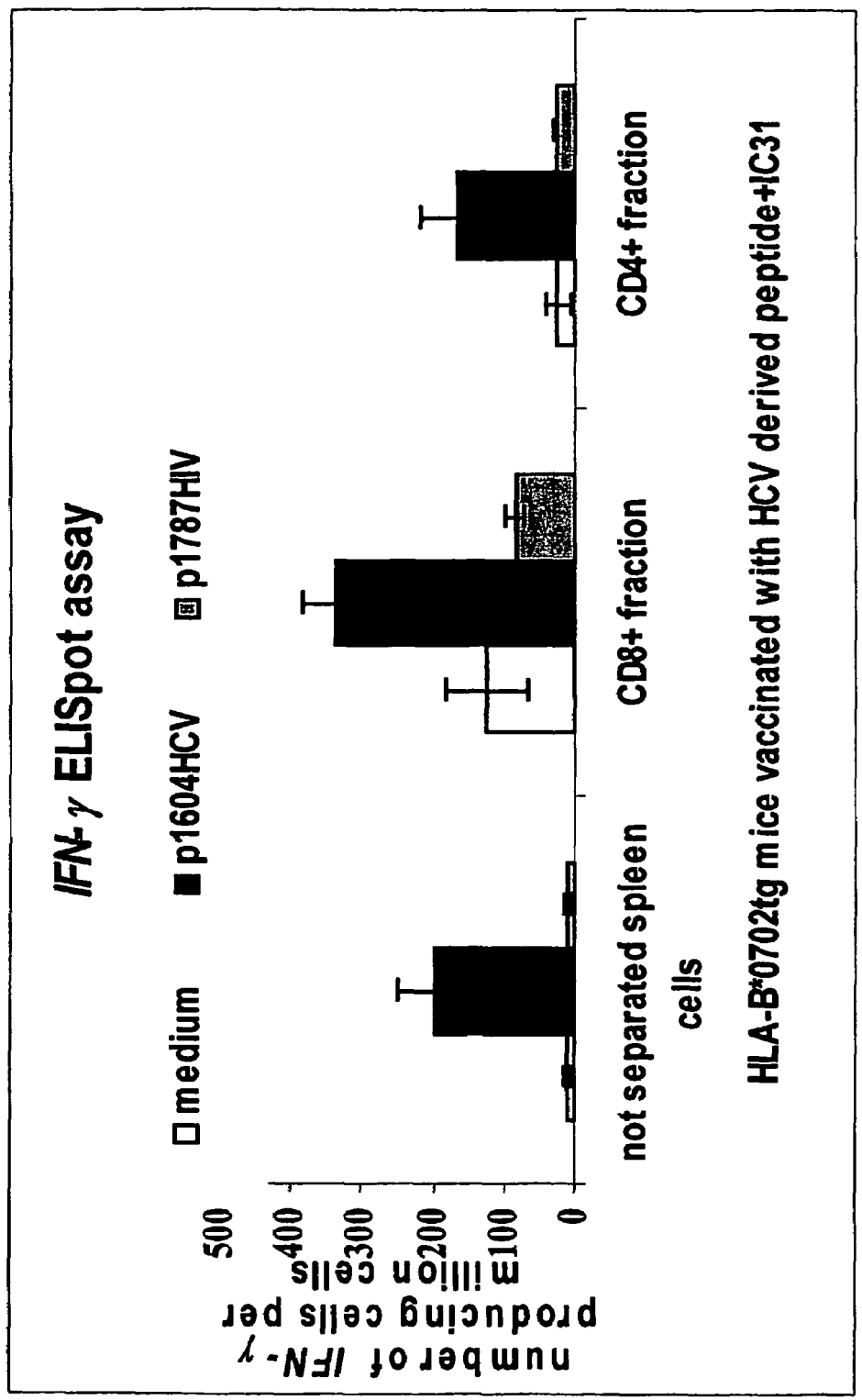
FIG. 10 shows mouse IFN-gamma ELIspot with splenocytes or separated CD8+ or CD4+ cells from HLA-B*0702 tg mice vaccinated with Ipep1604+IC31.

As an example shown in FIG. 8-10 the Ipep1604 (VVCCSMSYTWTGALITPC (SEQ ID NO:30), in combination with immunizer IC31) was able to induce high numbers of specific INF-γ producing T cells in all three transgenic class I and II mouse strains. This was shown not only with whole spleen derived cells but also with enriched fractions of CD8+ cells correspondingly for A2 and B7 and CD4+ cells for DR4tg mice. Similar, albeit weaker responses were seen with Ipep1605 (VVCCSMSYSWT-GALITPC (SEQ ID NO:126)), a sequence variant with a serine instead of a threonine.

Thus, Ipep1604 contains class I epitopes for HLA-A*0201 and HLA-B*0702 and a class II epitope for HLA-DRB1*0401 molecules.

As shown in Tables 2 and 6, Ipep 1604 binds to class II molecules in a promiscuous manner. Thus, it contains further epitopes, at least for HLA-DRB1*0101, DRB1*0404, DRB1*0701 and DRB1*1101.

Other peptides were analysed in a similar way: Ipeps 1605, 1623, 1547, 1558, 1559, 1560, 1565, 1592, 1650, 1654 and 1655 were confirmed to contain human HLA-DRB1*0401 epitopes. Again, for most of these epitopes binding is not limited to HLA-DRB1*0401 as shown in Tables 2 and 6.

Ipeps 1565, 1605 and 1650 were confirmed to contain human HLA-A*0201 epitopes.

Ipeps 1506, 1587 were confirmed to contain human HLA-B*0702 epitopes.

Ipep 1843 with sequence LPRRGPRL (SEQ ID NO:1046) was shown to be the HLA-B*0702 minimal epitope contained in 1506:

FIG. 10 shows mouse IFN-gamma ELIspot with splenocytes or separated CD8+ or CD4+ cells from HLA-A*0702 transgenic mice vaccinated with Ipep1506+IC31 or Ipep1835+IC31.

FIG. 10 A) and B) shows that after a single vaccination with either Ipep 1506+IC31 or Ipep1835+IC31, upon restimulation with overlapping 15mers, the 15mers A30 to A37 (see Tab.1) react. The common sequence of these 15mers is LPRRGPRL (SEQ ID NO:1046) (Ipep 1843, see Tab.4).

FIG. 10 C) confirms these findings: after a single vaccination with either Ipep1506+IC31 or Ipep14835+IC31, significant interferon-gamma induction against Ipep14843 can be detected. In both cases Ipep 1790 an HIV NEF-derived HLA-B*0702 epitope (sequence RPMTYKAAL (SEQ ID NO:1032)) was used as negative control for restimulation.

Ipep 1838 with sequence SPGALVVGVI (SEQ ID NO:1045) (see Tab.4) was shown to be an HLA-B*0702 minimal epitope contained in 1587: In the case of Ipep14587 a different approach was taken: the sequence of Ipep14587 was inspected for HLA-B*0702 binding motifs and a couple of short peptides were synthesized accordingly. These were tested in a competition-type peptide binding assay using soluble HLA-B*0702 and the FITC-labelled reference peptide LPCVLWPVL (SEQ ID NO:1033), which is a known HLA-B*0702 epitope derived from EBV (Stuber et al., 1995). Peptide Ipep14838 showed ~30% competition when used in 80-fold molar excess for 48 h at 37° C. Thus it is likely to present the minimal HLA-B*0702 epitope contained in Ipep 1587.

Example IV

Identification and Confirmation of Novel HCV Peptides Reactive in IFN-Gamma ELIspot with Human PBMC from HCV Therapy Responders or Patients with Spontaneous Recovery 40 peptide mixtures in matrix format (FIG. 1) containing synthetic peptides derived from conserved regions of HCV (Table 1) were screened in IFN-gamma ELIspot using PBMC from more than 50 individuals who were either responders to interferon/ribavirin standard therapy, or, who had spontaneously cleared HCV (i.e. all subjects were HCV antibody positive, but HCV-RNA negative). PBMC from such individuals are supposed to contain the relevant T-cell populations responsible for clearing HCV. Thus, peptides discovered or confirmed by using these PBMC are likely to represent the structural determinants of immune protection against/clearance of HCV. Based on the results from this primary matrix-screen, a number of peptides were chosen for individual re-testing in IFN-gamma ELIspot using PBMC from selected donors. In addition, several new peptides incorporating sequences from overlapping reactive peptides or avoiding critical residues like cystein were synthesized. These are summarized in Table 4.

TABLE 4 additional peptides derived from conserved regions of HCV.

| Peptide ID | Peptide sequence (1 amino acid code) | SEQ ID NO: |
|---|---|---|
| 1006 | MWNFISGIQYLAGLSTLPGN | 1034 |
| 1334 | HMWNFISGI | 1035 |

TABLE 4-continued additional peptides derived from conserved regions of HCV.

| Peptide ID | Peptide sequence (1 amino acid code) | SEQ ID NO: |
|---|---|---|
| 1425 | NFISGIQYLAGLSTLPGNPA | 1036 |
| 1426 | HMWNFISGIQYLAGLSTLPGNPA | 1037 |
| 1798 | IGLGKVLVDILAGYGAGVAGALVAFK | 1038 |
| 1799 | AAWYELTPAETTVRLR | 1039 |
| 1800 | DYPYRLWHYPCTVNYTIFKI | 1040 |
| 1836 | DYPYRLWHYPCTVNFTIFKI | 1041 |
| 1801 | AYSQQTRGLL | 1042 |
| 1827 | TAYSQQTRGLLG | 1043 |
| 1829 | SMSYTWTGALITP | 1044 |
| 1838 | SPGALVVGVI | 1045 |
| 1843 | LPRRGPRL | 1046 |

Results of the secondary screening with individual peptides are summarized in Table 5. Altogether ~20% of subjects (G05, G18, H02, H03, H04, H10, H12, H19, H32, H38) showed a significant IFN-gamma T-cell response against one ore more of the peptides. In some cases the observed number of ELIspots was clearly elevated, but not statistically significant above background. In these cases, PBMC (donors H03, H10, H33, H38) were stimulated with the respective peptides in vitro (2 rounds of in vitro priming, see Material & Methods) in order to increase the peptide specific response. Several peptides were confirmed in this way, results are again summarized in Table 5.

Peptides A3-A7 represent overlapping 15mers spanning the sequence TNPKPQRKTKRNTNRRPQD (SEQ ID NO:1047). Since they all react with PBMC from donor H03, the minimal sequence of the epitope is located within the sequence PQRKTKRNTNR (SEQ ID NO:1048). Prediction algorithms indicate that QRKTKRNTN (SEQ ID NO:1049) and QRKTKRNT (SEQ ID NO:1050) represent ligands of HLA-B*08, whereas RKTKRNTNR (SEQ ID NO:1051) most probably binds to HLA-B*2705.

Peptides C64-C70 represent overlapping 15mers spanning the sequence KGGRKPARLIVFPDLGVRVCE (SEQ ID NO:1052). C64 and C70 react with PBMC from donor H32 and H38, respectively. The minimal sequence of the epitope is therefore located within the sequence ARLIVF-PDL (SEQ ID NO:1053). Prediction algorithms indicate that ARLIVFPDL (SEQ ID NO:1053) represents a ligand of HLA- HLA-B*2705 and HLA-B*2709.

TABLE 5

Summary of HCV peptides reactive with PBMC. Numbers represent peptide-specific IFN-gamma secreting T-cells/$10^6$ PBMC calculated from ELIspot results (duplicate determinations); values >8 (>3x over background) were regarded statistically significant. Donors H32 and H33 are spontaneously recovered patients.

| Peptide ID | Donors reactive directly ex vivo in IFN-gamma ELIspot with HCV-derived peptides | | | | | | | | | | ...reactive after 2 rounds of in vitro stimulation | | | |
|---|---|---|---|---|---|---|---|---|---|---|---|---|---|---|
| | G05 | G18 | H02 | H03 | H04 | H10 | H12 | H19 | H32 SPR | H38 | H03 | H10 | H33 SPR | H38 |
| 1557 | | | | 20 | | | | | | | 75 | | | |
| 1577 | | | 15 | 30 | | | | | | | | | 165 | |
| 1579 | | | 45 | 35 | | | | | | | 75 | | | |
| 1605 | | | | 25 | | | | | | | | | | |
| 1615 | | | | 30 | | | | | | | 325 | | | |
| 1624 | 30 | | 55 | 30 | | | 420 | | | | | | | |
| 1628 | | | 40 | 45 | | 25 | | | | 20 | | | | 100 |
| 1629 | | | 30 | 70 | | 15 | | | | | | | | |
| 1798 | | | | 25 | | | | | | | | 115 | | |
| 1799 | | | | | | 20 | | | | | | 90 | | |
| 1800 | | | | | | | | | | 35 | | 95 | | |
| 1801 | | | | | | | 20 | | | 20 | | | | |
| A3 | | | | | | | | | | | 80 | | | |
| A4 | | | 15 | | | | | | | | | | | |
| A5 | | | | | | | | | | | | 110 | | |
| A7 | | | | | | | | | | | | 70 | | |
| A78 | | | | 25 | | | | | | | | | | |
| A170 | | | | 35 | | | | | | | | | | |
| A212 | | | | 60 | | | | | | | | | | |
| A241 | | | | 35 | | | | | | | | | | |
| B08 | | | | 55 | | | | | | | | | | |
| B38 | | | | | | | | | 30 | | | | | |
| B76 | | | | 35 | | | | | | | | | | |
| C64 | | | | | | | | | 30 | | | | | |
| C70 | | | | | | | | | | 20 | | | | |
| C92 | | | | 25 | | | | | | | | | | |
| C94 | | | | 25 | | | | | | | | | | |
| C97 | | | | 35 | | | | | | | | | | |
| C98 | | | | 70 | | | | | | | | | | |
| C100 | | 60 | | 70 | | | | | | | | | | |
| C101 | | | | 50 | | | | | | | | | | |
| C102 | | | 20 | | | | | | | | | | | |
| C106 | | | | 45 | | | | | | | | | | |
| C112 | | | | 20 | | | | | | | | | | |
| C118 | | | 35 | | | | | | | | | | | |
| C120 | | | 25 | 45 | | | | | | | 105 | | | |
| C134 | | | 20 | | | | | | | | | | | |
| C138 | | | | | | | | | | | | 30 | | |

TABLE 5-continued

Summary of HCV peptides reactive with PBMC.
Numbers represent peptide-specific IFN-gamma secreting T-cells/10^6 PBMC calculated from ELIspot results (duplicate determinations); values >8 (>3x over background) were regarded statistically significant. Donors H32 and H33 are spontaneously recovered patients.

| | | | | | |
|---|---|---|---|---|---|
| B08 | | 55 | | | |
| B38 | | | 30 | | |
| B76 | | 35 | | | |
| C64 | | | 30 | | |
| C70 | | | | 20 | |
| C92 | | 25 | | | |
| C94 | | 25 | | | |
| C97 | | 35 | | | |
| C98 | | 70 | | | |
| C100 | 60 | 70 | | | |
| C101 | | 50 | | | |
| C102 | 20 | | | | |
| C106 | | 45 | | | |
| C112 | | 20 | | | |
| C118 | 35 | | | | |
| C120 | 25 | 45 | | 105 | |

Example V

Binding of HCV Derived Peptides to HLA class II Molecules

In addition to the peptides listed in Table 1, several new peptides incorporating sequences from overlapping reactive peptides or avoiding critical residues like cystein were synthesized (Table 4). These were retested for their affinities to class II soluble HLA molecules, and results were compared to those obtained with the original (Table 6).

TABLE 6

Binding of selected HCV-derived peptides and their 15-mer counterparts to soluble HLA class II molecules ("+++" strong affinity, "++" intermediate affinity, "+" weak affinity, "-" no affinity, "nd" not done; core binding motifs are underlined)

| Peptide ID SEQ ID NO: | HLA-DRB1* | Peptide sequences | Binding to soluble 0101 | 0401 | 0404 | 0701 | 1101 |
|---|---|---|---|---|---|---|---|
| 1054 | 1798 | IG<u>LGKVLVDILAG</u><u>YGAGVAGALV</u>AFK | - | - | + | ++ | +/- |
| 1055 | B84 | GSIG<u>LGKVLVDILAG</u> | + | + | + | | - |
| 1056 | B86 | IG<u>LGKVLVDILAG</u>YG | + | ++ | + | + | +/- |
| 1057 | B88 | <u>LGKVLVDILAG</u>YGAG | + | ++ | + | | |
| 1058 | B92 | LVDILAGYGAGVAGA | + | - | | | |
| 1059 | B94 | DILAG<u>YGAGVAGALV</u> | + | - | - | - | |
| 1060 | B96 | LAG<u>YGAGVAGALV</u>AF | ++ | ++ | - | +/- | +/- |
| 1061 | 1799 | AA<u>WYELTPAETT</u>VRLR | +++ | + | + | - | +/- |
| 1062 | B46 | AGAA<u>WYELTPAETT</u>V | +++ | +++ | +++ | - | +/- |
| 1063 | B48 | AA<u>WYELTPAETT</u>VRL | +++ | +++ | +++ | - | +/- |
| 1064 | 1827 | <u>TAYSQQTRGLLG</u> | ++ | - | +/- | + | + |
| 1065 | C114 | <u>TAYSQQTRGLLG</u>CIV | +++ | +/- | +/- | + | ++ |
| 1066 | 1829 | SM<u>SYTWTGALITP</u> | + | - | - | + | +/- |
| 1067 | 1604 | VVCCSM<u>SYTWTGALITP</u>C | + | + | ++ | ++ | + |
| 1068 | 1650 | V<u>DYPYRLWHYPC</u><u>TVNFTIFKVR</u><u>MYVGGVEHR</u>L | | | | | |

TABLE 6-continued

Binding of selected HCV-derived peptides and their 15-mer counterparts to soluble HLA class II molecules ("+++" strong affinity, "++" intermediate affinity, "+" weak affinity, "-" no affinity, "nd" not done; core binding motifs are underlined)

| Peptide ID<br>SEQ<br>NO: | HLA-DRB1*<br> | Peptide sequences | Binding to soluble | | | | |
|---|---|---|---|---|---|---|---|
| | | | 0101 | 0401 | 0404 | 0701 | 1101 |
| 1069 | A130 | D<u>YPYRLWHY</u>PCTVNF | + | ++ | +/- | | |
| 1070 | A131 | YPYRLWHYPCTVNFT | - | | | | |
| 1071 | A135 | LWH<u>YPCTVNFTIFKV</u> | - | - | | ++ | |
| 1072 | A141 | TVN<u>FTIFKVRMY</u>VGG | - | - | +/- | | ++ |
| 1073 | A145 | TIFKVRMYVGGVEHR | +/- | - | | | |
| 1074 | 1651 | VDYPYRLWHYPCTVNYTIFKIRMYVGGVEHRL | | | | | |
| 1075 | 1800 | DYPYRLWH<u>YPCTVNYTIFKI</u> | - | - | +/- | ++ | - |
| 1076 | A147 | DYPYRLWHYPCTVNY | - | - | | | |
| 1077 | A152 | LWHYPCTVNYTIFKI | - | - | | | |
| 1078 | A158 | TVNYTIFKIRMYVGG | - | - | +/- | | |
| 1079 | A162 | TIFKIRMYVGGVEHR | +/- | - | | | |
| 1080 | 1817 | RMYVGGVEHRL | - | - | +/- | | |
| 1081 | 1426 | HMWNFISGIQYLAGLSTLPGNPA | + | + | ++ | ++ | + |
| 1082 | 1425 | NFISGIQYLAGLSTLPGNPA | ++ | ++ | ++ | nd | nd |
| 1083 | 1006 | MWNFISGIQYLAGLSTLPGN | ++ | + | ++ | nd | nd |

Abolished affinities to DRB1*0101 and DRB1*0401 molecules in the case of peptide 1798 in comparison with its shorter counterparts (B84-B96) is probably due to the long sequence (26 amino acids) which can have a secondary structure that prevents binding. It is to be expected that in vivo, upon proteolytic cleavage, peptide 1798 will give rise to two shorter class II epitopes. Removed cystein (C) residues in peptides 1827 and 1829 (derivatives of peptides C114 and 1604, respectively) seem to be crucial for binding to DRB1*0401 molecules but do not essentially change affinities to other tested DR subtypes.

Example VI

Identification and Characterization of HCV-Epitope hotspots

Here a T-cell epitope hotspot (thereafter referred to as "hotspot") is defined as a short peptide sequence at least comprising more than one T-cell epitope. For example, two or more epitopes may be located shortly after each other (shortly being defined as less than 5-10 amino acids), or directly after each other, or partially or even fully overlapping. Hotspots may contain only class I or class II epitopes, or a combination of both. Epitopes in hotspots may have different HLA restrictions.

Due to the highly complex and selective pathways of class I and class II antigen processing, referred to in the introduction, T-cell epitopes cannot be easily predicted within the sequence of a polypeptide. Though widely used, computer algorithms for T-cell epitope prediction have a high rate of both false-negatives and false-positives.

Thus, as even individual T-cell epitopes are not obvious within the sequence of a polypeptide, the same is even more the case for hotspots. Several radically different experimental approaches are combined according to the present invention for T-cell epitope identification, including epitope capture, HLA-transgenic animals and in vitro stimulation of human mononuclear cells. All three approaches are systematically applied on overlapping peptides spanning the antigen of interest, enabling comprehensive identification of epitopes (refer to CMV Epitope Capture patent). Upon such a comprehensive analysis, not limited to a particular HLA allele, but rather unravelling all possibly targeted epitopes within a population, epitope hotspots may become apparent. Within an antigen, only few if any sequences show characteristics of hotspots. Thus the identification of a hotspot is always a surprising event.

T-cell epitope hotspots offer important advantages: Hotspots can activate and can be recognized by different T-cell clones of a subject. Hotspots (when comprising epitopes with different HLA restriction) can interact with T-cells from different non HLA-matched individuals.

Epitope-based vaccines, so far have aimed at selected prevalent HLA-alleles, for instance HLA-A2, which is expressed in about half of Caucasians. Since other alleles are less frequent, epitope-based vaccines with broad worldwide population coverage will have to comprise many different epitopes. The number of chemical entities (for instance peptides) of a vaccine is limited by constraints originating from manufacturing, formulation and product stability.

Hotspots enable such epitope-based vaccines with broad worldwide population coverage, as they provide a potentially high number of epitopes by a limited number of peptides.

TABLE 7

T-cell epitope hotspots in conserved regions of HCV. Hotspots (incl. some variations) are shown in bold, epitopes contained within the hotspots in normal font. Peptide number and sequence, as well as HLA-class I and class II coverage are given. Source data refers to Examples and Tables within this specification, or literature references.

| peptide ID | peptide sequence | | Class I | class II | source data |
|---|---|---|---|---|---|
| 1835 | KFPGGGQIVGGVYLLPRRGPRLGVRATRK | (SEQ ID NO: 1084) | A2, A3, B7 | DR11 | Example III, VI |
| 83 | KFPGGGQIVGGVYLLPRRGPRL | (SEQ ID NO: 1085) | A2   B7 | DR11 | Example VI |
| 1051 | YLLPRRGPRL | (SEQ ID NO: 1086) | A2 | | Bategay 1995 |
| 1843 | LPRRGPRL | (SEQ ID NO: 1087) | B7 | | Example III |
| | GPRLGVRAT | (SEQ ID NO: 1088) | B7 | | Koziel 1993 |
| | RLGVRATRK | (SEQ ID NO: 1089) | A3 | | Chang 1999 |
| 84 | GYKVLVLNPSVAAT | (SEQ ID NO: 1090) | | DR1,4,7,11 | Tab.2: A200-A206 |
| | AYAAQGYKVL | (SEQ ID NO: 1091) | A24 | | prediction |
| 84EX | AYAAQGYKVLVLNPSVAAT | (SEQ ID NO: 1092) | A24 | DR1,4,7,11 | Example VI |
| 87 | DLMGYIPAV | (SEQ ID NO: 1093) | A2 | | Sarobe 1998 |
| | GYIPLVGAPL | (SEQ ID NO: 1094) | A24 | | prediction |
| 87EX | DLMGYIPLVGAPL | (SEQ ID NO: 1095) | A2,A24 | | Example VI |
| 89 | CINGVCWTV | (SEQ ID NO: 1096) | A2 | | Koziel 1995 |
| 1577 | GEVQVVSTATQSFLAT | (SEQ ID NO: 1097) | | DR 4, 7 | Tab.2 |
| 89EX | GEVQVVSTATQSFLATCINGVCWTV | (SEQ ID NO: 1098) | A2 | DR 4, 7 | Example VI |
| 1426 | HMWNFISGIQYLAGLSTLPGNPA | (SEQ ID NO: 1099) | A2 | DR1,4,7,11 | Example VII |
| 1006 | MWNFISGIQYLAGLSTLPGN | (SEQ ID NO: 1100) | | | Example VII |
| 1425 | NFISGIQYLAGLSTLPGNPA | (SEQ ID NO: 1101) | | | Example VII |
| | QYLAGLSTL | (SEQ ID NO: 1102) | A24 | | prediction |
| 1334 | HMWNFISGI | (SEQ ID NO: 1103) | A2 | | Wentworth 1996 |
| 1650 | VDYPYRLWHYPCTVNFTIFKVRMYVGGVEHRL | (SEQ ID NO: 1104) | Cw7,A2,A24, A11 ,A3 | DR1,4,7,11 | Tab. 2,3,6 Example III |
| 1836 | DYPYRLWHYPCTVNFTIFKI | (SEQ ID NO: 1105) | Cw7,A2;A24, A11 | DR1,4,7,11 | Tab. 2,3,6 |
| 1846 | DYPYRLWHYPCTVNFTIFKV | (SEQ ID NO: 1106) | Cw7,A2;A24, A11 | DR1,4,7,11 | Tab. 2,3,6 Example III |
| 1651 | VDYPYRLWHYPCTVNYTIFKIRMYVGGVEHRL | (SEQ ID NO: 1107) | | | Tab. 2,3,6 |
| 1800 | DYPYRLWHYPCTVNYTIFKI | (SEQ ID NO: 1108) | Cw7,A24,A11 | DR7 | Tab. 2,5,6 |
| 1754 | DYPYRLWHY | (SEQ ID NO: 1109) | Cw7 | | Lauer 2002 |
| 1815 | TVNYTIFKI | (SEQ ID NO: 1110) | A11 | | prediction |
| 1816 | TINYTIFK | (SEQ ID NO: 1111) | A11 | | Koziel 1995 |
| | TVNFTIFKV | (SEQ ID NO: 1112) | A11 | | prediction |
| | HYPCTVNYTI | (SEQ ID NO: 1113) | A24 | | prediction |

TABLE 7-continued

T-cell epitope hotspots in conserved regions of HCV.
Hotspots (incl. some variations) are shown in bold, epitopes
contained within the hotspots in normal font. Peptide number and
sequence, as well as HLA-class I and class II coverage are
given. Source data refers to Examples and Tables within this
specification, or literature references.

| peptide ID | peptide sequence | | Class I | class II | source data |
|---|---|---|---|---|---|
|  | HYPCTVNFTI | (SEQ ID NO: 1114) | A24 |  | prediction |
|  | RMYVGGVEHR | (SEQ ID NO: 1115) | A3 |  | Chang 1999 |
| 1799 | AAWYELTPAETTVRLR | (SEQ ID NO: 1116) | B7? B35 | DR1, 4 | Tab. 2,5,6 |
| 1818 | TPAETTVRL | (SEQ ID NO: 1117) | B7? B35 |  | Ibe 1998 |
| 1827EX | GWRLLAPITAYSQQTRGLLGCIV | (SEQ ID NO: 1118) | A2,A3,A24, B8 | DR1,4,7,11 | Example VI |
| C114 | TAYSQQTRGLLGCIV | (SEQ ID NO: 1119) | A24, B8? | DR1,4,7,11 | Tab. 2, 6 |
| 1827 | TAYSQQTRGLLG | (SEQ ID NO: 1120) | A24, B8 | DR1, 7,11 | Tab. 6 |
| C112 | GQGWRLLAPITAYSQ | (SEQ ID NO: 1121) | A3?,A2?, | DR1 | Tab.2, 5 |
|  | RLLAPITAY | (SEQ ID NO: 1122) | A3 |  | prediction |
| C114EX | GQGWRLLAPITAYSQQTRGLLGCIV | (SEQ ID NO: 1123) | A24,A3?,A2?, B8? | DR1,4,7,11 | Tab. 2, 5, 6 |
| 1827EX | GQGWRLLAPITAYSQQTRGLLG | (SEQ ID NO: 1124) | A24,A3?,A2?, B8? | DR1, 7,11 | Tab. 2, 5, 6 |
| 1801 | AYSQQTRGLL | (SEQ ID NO: 1125) | A24 |  | Tab. 5 |
| 1819 | AYSQQTRGL | (SEQ ID NO: 1126) | A24 |  | Kurokohchi 2001 |
| 1798 | IGLGKVLVDILAGYGAGVAGALVAFK | (SEQ ID NO: 1127) | A2,24,3,11 | DR1,4,7 | Tab. 2,3,5,6 |
| 1820 | ILAGYGAGV | (SEQ ID NO: 1128) | A2 |  | Bategay 1995 |
| 1821 | VAGALVAFK | (SEQ ID NO: 1129) | A3,11 |  | Chang 1999 |
|  | GYGAGVAGAL | (SEQ ID NO: 1130) | A24 |  | prediction |
| 1604 | VVCCSMSYTWTGALITPC | (SEQ ID NO: 1131) | A2,A24,B7 | DR1,4,7,11 | Tab. 2,3,6 |
| 1829 | SMSYTWTGALITP | (SEQ ID NO: 1132) | A2,A24,B7, | DR1,7,11 | Tab. 6 |
|  | SMSYTWTGAL | (SEQ ID NO: 1133) | A2,B7 |  | prediction |
|  | SYTWTGALI | (SEQ ID NO: 1134) | A24 |  | prediction |
| 1579 | FTDNSSPPAVPQTFQV | (SEQ ID NO: 1135) | A1,2;B7,51 | **DR53 = B4*01 | Tab. 5** |
| 1624 | LEDRDRSELSPLLLSTTEW | (SEQ ID NO: 1136) | A1,2,3,26 B8,27,4402,60 | DR7 | Tab. 2,3,5 |
| 1848 | LEDRDRSELSPLLLST | (SEQ ID NO: 1137) | A1,2,3,26, B8,27,4402,60 | DR7 | Example VI |
|  | RSELSPLLL | (SEQ ID NO: 1138) | A1 |  | prediction |
|  | ELSPLLLST | (SEQ ID NO: 1139) | A2,A3 |  | prediction |
|  | DRDRSELSPL | (SEQ ID NO: 1140) | A26,B27 |  | prediction |
|  | LEDRDRSEL | (SEQ ID NO: 1141) | B08,B4402 |  | prediction |
| 1824 | LEDRDRSEL | (SEQ ID NO:1142) | B60 |  | Wong 2001 |
| 1547 | YLVAYQATVCARAQAPPPSWD | (SEQ ID NO: 1143) | A2 | DR1,4,7,11 | Tab. 2,3 |
| 1822 | YLVAYQATV | (SEQ ID NO: 1144) | A2 |  | Wentworth 1996 |
| A1A7 | MSTNPKPQRKTKRNTNR | (SEQ ID NO: 1145) | A11,B08,B27 |  | Tab. 5 |

TABLE 7-continued

T-cell epitope hotspots in conserved regions of HCV.
Hotspots (incl. some variations) are shown in bold, epitopes
contained within the hotspots in normal font. Peptide number and
sequence, as well as HLA-class I and class II coverage are
given. Source data refers to Examples and Tables within this
specification, or literature references.

| peptide ID | peptide sequence | Class I | | class II | source data |
|---|---|---|---|---|---|
| A3A7 | PQRKTKRNTNR | (SEQ ID NO: 1146) | B08,527 | | Tab.5 |
| | QRKTKRNTN | (SEQ ID NO: 1147) | B08 | | prediction |
| | RKTKRNTNR | (SEQ ID NO: 1148) | B2705 | | prediction |
| | MSTNPKPQR | (SEQ ID NO: 1149) | A11 | | prediction |
| | MSTNPKPQK | (SEQ ID NO: 1150) | A11 | | Wong 1998 |
| A122EX | LINTNGSWHINRTALNCNDSL | (SEQ ID NO: 1151) | A2,2,3,B8 | DR1,4,7,11 | Tab. 2,3 |
| A122 | NGSWHINRTALNCNDSL | (SEQ ID NO: 1152) | A2 | DR1,4,7,11 | Tab. 2,3 |
| | LINTNGSWHI | (SEQ ID NO: 1153) | A2,3 | | prediction |
| | RTALNCNDSL | (SEQ ID NO: 1154) | A2 | | prediction |
| 1825 | LINTNGSWHINRTALN | (SEQ ID NO: 1155) | A2,3,B8 | | prediction |
| 1826 | SWHINRTALN | (SEQ ID NO: 1156) | B8 | | prediction |
| A241 | TTILGIGTVLDQAET | (SEQ ID NO: 1157) | A2,A3 | DR1, 4 | Tab. 2,5 |
| | TTILGIGTV | (SEQ ID NO: 1158) | A2 | | prediction |
| | TILGIGTVL | (SEQ ID NO: 1159) | A3 | | prediction |
| B8B38 | FDSSVLCECYDAGAAWYE | (SEQ ID NO: 1160) | A1,2,3,26 | | Tab. 5 |
| B8 | FDSSVLCECYDAGCA | (SEQ ID NO: 1161) | A3,A26 | | Tab.5 |
| | VLCECYDAGA | (SEQ ID NO: 1162) | A2 | | prediction |
| B38 | VVLCECYDAGAAWYE | (SEQ ID NO: 1163) | A1 | | Tab. 5 |
| C70EX | ARLIVFPDLGVRVCEKMALY | (SEQ ID NO: 1164) | A2,A3,B27 | | Tab. 5 |
| C64-C70 | ARLIVFPDL | (SEQ ID NO: 1165) | B*2705?, *2709? | | Tab.5 |
| 1831 | RLIVFPDLGV | (SEQ ID NO: 1166) | A2 | | Gruener 2000 |
| 1832 | RVCEKMALY | (SEQ ID NO: 11670) | A3 | | Wong 1998 |
| C92 | AFCSAMYVGDLCGSV | (SEQ ID NO: 1168) | A2,B51 | DR1,4 | Tab.2,5 |
| C97 | GVLFGLAYFSMVGNW | (SEQ ID NO: 1169) | A2,3,26, B2705,51 | DR1,4,7 | Tab.5 |
| C106 | TRVPYFVRAQGLIRA | (SEQ ID NO: 1170) | A3,24, B7,B8,B2705 | DR1,4,7 | Tab.2,5 |
| C134 | TTLLFNILGGWVAAQ | (SEQ ID NO: 1171) | A2 | DR1,7,11 | Tab.2,5 |
| 1823 | LLFNILGGWV | (SEQ ID NO: 1172) | A2 | | Bategay 1995 |

Example VII

HCV Epitope Hotspot Ipep 1426 Contains at Least HLA-A*201 and Several Promiscuous Class II T-Cell Epitopes The major objective of this experiment was to compare the immunogenicity of the "hotspot" Ipep 1426, which contains at least one HLA-A*0201 epitope (Ipep 1334) and 2 promiscuous class II epitopes (Ipeps 1006 and 1425), to the individual epitopes. To this end peripheral blood mononuclear cells (PBMC) from several healthy HLA-typed blood donors were stimulated in vitro either with 1426 or a mixture of 1334, 1006, 1425. Three rounds of stimulation were performed resulting in oligoclonal T cell lines. Then, responses against all four peptides were assessed by interferon-gamma (IFN-γ) ELIspot analysis.

Peptide 426, induces T cell responses similarly well as individual epitopes comprised within its sequence. In particular CD8 positive T cells directed against the HLA-A*0201 restricted epitope 1334 were successfully generated.

TABLE 8 peptide induced IFN-γ secretion of oligoclonal T cell lines. Lines were generated from two HLA-typed healthy individuals by 3 rounds of in vitro priming with either peptide 1426 or a mixture of peptides 1006 + 1425 + 1334. The reactivity of CD4 and CD8 positive T cells in these lines was assessed by IFN-γ ELIspot ("+++" very strong, "++" strong, "+" significant, "−" no IFN-gamma secretion).

| | Donor HLA | | | |
|---|---|---|---|---|
| | A*0201, A*03, B7, B60; DRB1*1501, −B1*1302 | | A*0206, A*01, B27, B50; DRB1*0401, −B1*1402 | |
| Peptide ID | line raised against 1426 | line raised against 1006 + 1425 + 1334 | line raised against 1426 | line raised against 1006 + 1425 + 1334 |
| 1006 | ++ | ++ | ++ | ++ |
| 1425 | +++ | +++ | +++ | ++ |
| 1334 | + | + | − | − |
| 1006 + 1425 + 1334 | ++ | ++ | ++ | ++ |
| 1426 | +++ | +++ | +++ | ++ |
| 84 (HCV derived negative control) | − | − | − | − |

REFERENCES

Aichinger G et al., 1997. J. Biol. Chem. 272: 29127-29136.
Ausubel F M et al. (editors), 2001. Current Protocols in Molecular Biology, Volumes 1-4, John Wiley and Sons (publishers).
Battegay et al. 1995, J. Virol. 69:2452
Bellentani S et al., Microbes Infect. 2000 November;2(14): 1757-63.
Bonifacino J S et al. (editors), 2001. Current Protocols in Cell Biology, Volumes 1-2, John Wiley and Sons (publishers).
Chang et al. 1999, J. Immunol. 162:1156
Cornberg M et al., Curr Gastroenterol Rep. 2002 February; 4(1):23-30.
Cox A L et al., 1994. Science 264: 716-719
Coligan J E et al. (editors), 2001. Current Protocols in Immunology, Volumes 1-4, John Wiley and sons (publishers).
Farci P et al., Semin Liver Dis. 2000; 20(1):103-26 Gavin M A et al., 1993. J Immunol. 151: 3971-80
Gorga, J C et al., 1987. J. Biol. Chem. 262: 16087-16094.
Gruener et al. 2000, J. Infect. Dis. 181:1528
Heemels, M T et al, 1995. Annu. Rev. Biochem. 64: 463-491
Ibe et al. 1998, J General Virol. 79:1735
Kern F et al, 2000. Eur J Immun 30: 1676-1682
Kern F et al, 1999. J Virol 73(10): 8179-8184
Klein, J, 1986. Natural History of the MHC, John Wiley and Sons (publishers)
Koziel et al. 1995, J. Clin. Invest. 96:2311
Kronenberg M et al., 1999. Immunol Today 20: 515-21.
Kurokohchi 2001, J. Hepatology 34:930
Kwok W W et al., 2001. Trends Immunol 22(11): 583-588.
Lalvani A et al., 1997. J. Exp. Med. 186 (6): 859-865.
Lamonaca et al 1999, Hepatology 30:1088
Lauer et al. 2002, J. Virol. 76:6104
Liang T J et al., Ann Intern Med. 2000 Feb. 15; 132(4):296-305.
Maecker H T et al, 2001. J Immunol Methods 255: 27-40
Nijman H W et al, 1993. Eur. J. Immunol., 6, 1215-9
Novak N et al., 2001. J. Immunol. 166: 6665-6670.
Parker, K C et al., 1994. J. Immunol. 152: 163.
Rammensee, H G et al., 1999. Immunogenetics 50: 213-219
Sarobe et al. 1998, J. Clin. Invest. 102:1239
Stern L J et al., 1994. Structure 2: 245-251
Stuber et al., 1995, Int. Immunology 7: 653
Sturniolo T et al., 1999. Nature Biotechnology 17: 555-562.
Tobery W T et al., 2001. J Immunol Methods 254: 59-66.
Valli A et al., 1993. J. Clin. Invest. 91: 616-628
Van den Eynde B J, et al., 1997. Curr Opin Immunol. 5: 684-93
Villadangos J A et al., 2000. Immunity 12: 233-239
Ward S et al., Clin Exp Immunol. 2002 May;128(2):195-203.
Wentworth et al. 1996, Int Immunol. 8:651
Wilson D B et al., 1999. J. Immunol. 163: 6424-6434.
Wong et al. 1998, J. Immunol 16:1479
Wong et al. 2001, J. Virol. 75:1229

---

The invention claimed is:

1. A method for isolating Hepatitis C Virus peptides (HPs) or isolating HCV T cell epitopes which have a binding capacity to a purified, recombinant MHC/HLA molecule or a complex comprising the HCV-peptide or HCV T cell epitope and the purified, recombinant MHC/HLA molecule, the method comprising:

providing a pool comprising at least 10 HCV peptides, the pool containing HCV-peptides which bind to the purified, recombinant MHC/HLA molecule (binding HCV peptides) and HCV-peptides which do not bind to the purified, recombinant MHC/HLA molecule (non-binding HCV peptides);

contacting the purified, recombinant MHC/HLA molecule with the pool of HCV-peptides whereby a binding HCV-peptide binds to the purified, recombinant MHC/HLA molecule and a complex comprising the HCV-peptide and the purified, recombinant MHC/HLA molecule is formed;

detecting the complex and, optionally, separating the complex from non-binding HCV peptides;

optionally isolating and characterizing the binding HCV peptides from the complex;

assaying the complex or the optionally isolated binding HCV peptides in a T cell assay for T cell activation capacity; and identifying optionally isolated binding HCV peptides with T cell activation capacity as a T cell epitope or the complex.

2. The method of claim 1, further comprising separating the complex from the HCV-peptides which do not bind to the purified, recombinant MHC/HLA molecule.

3. The method of claim 1, further comprising isolating and characterizing the HCV-peptide from the complex.

4. The method of claim 1, further defined as a method for isolating HPs.

5. The method of claim 1, further comprising isolating and characterizing the HCV-peptide from the complex before assaying the HCV-peptide.

6. The method of claim 1, wherein the pool of peptides is further defined as a pool of overlapping peptides, a pool of protein fragments, a pool of modified peptides, a pool obtained from antigen-presenting cells, a pool comprised of fragments of cells, a pool comprised of peptide libraries, a pool of (poly)-peptides generated from a recombinant DNA library, a pool of proteins and/or protein fragments from HCV, or a combination of any of these.

7. The method of claim 6, wherein the pool is obtained from a total lysate or fraction of antigen-presenting cells.

8. The method of claim 7, wherein the pool is obtained from a fraction eluted from surface or MHC/HLA molecules of the antigen-presenting cells.

9. The method of claim 6, wherein the pool is comprised of fragments of HCV-containing cells, tumor cells, or tissue cells.

10. The method of claim 9, wherein the pool is comprised of fragments from liver cells.

11. The method of claim 6, wherein the pool is generated from a recombinant DNA library derived from pathogens or tumor cells.

12. The method of claim 1, wherein the purified, recombinant MHC/HLA molecules are HLA class I molecules, HLA class II molecules, non classical MIHC/HLA molecules, MHC/HLA-like molecules or a mixture thereof.

13. The method of claim 1, wherein the characterizing of the HCV-peptides of the complex comprises at least one of mass spectroscopy, polypeptide sequencing, a binding assay, identification of HCV-peptides by determination of their retention factors by chromatography, or a spectroscopic technique.

14. The method of claim 13, wherein the characterizing of the HCV-peptides of the complex comprises a binding assay, further defined as an SDS-stability assay.

15. The method of claim 13, wherein the characterizing of the HCV-peptides of the complex comprises identification of HCV-peptides by determination of their retention factors by HPLC.

16. The method of claim 13, wherein the characterizing of the HCV-peptides of the complex comprises violet (UV) spectroscopy, infra-red (IR) spectroscopy, nuclear magnetic resonance (NMR) spectroscopy, circular dichroism (CD) spectroscopy, or electron spin resonance (ESR) spectroscopy.

17. The method of claim 1, further comprising performing a cytokine secretion assay.

18. The method of claim 17, wherein the cytokine secretion assay is an Elispot assay, intracellular cytokine staining, FACS, or an ELISA.

19. The method of claim 1, wherein the T cell assay comprises the mixing and incubation of the complex with isolated T cells and subsequent measuring cytokine secretion or proliferation of the isolated T cells.

20. The method of claim 1, wherein the T cell assay comprises measuring up-regulation of an activation marker.

21. The method of claim 20, wherein the activation marker is CD69 or CD38.

22. The method of claim 20, wherein the T cell assay comprises measuring down-regulation of a surface marker.

23. The method of claim 22, wherein the surface marker is CD3, CD8 or TCR.

24. The method of claim 1, wherein the T cell assay comprises measuring up-/down-regulation of mRNAs involved in T cell activation.

25. The method of claim 24, further defined as comprising real-time RT-PCR.

26. The method of claim 1, wherein the T cell assay is a T cell assay measuring phosphorylation/de-phosphorylation of components downstream of the T cell receptor, T cell assay measuring intracellular $Ca^{++}$ concentration or activation of $Ca^{++}$-dependent proteins, T cell assay measuring formation of immunological synapses, or T cell assay measuring release of effector molecules.

27. The method of claim 26, wherein the T cell assay measures phosphorylation/de-phosphorylation of p56, lck, ITAMS of the TCR and the zeta chain, ZAP70, LAT, SLP-76, fyn, or lyn.

28. The method of claim 26, wherein the T cell assay measures release of perforin, a granzyme, or granulolysin.

29. A method for preparing an immunogenic composition comprising Hepatitis C Virus peptides (HPs) or isolated HCV T cell epitopes which have a binding capacity to a MHC/HLA molecule or a complex comprising the HCV-peptide or HCV T cell epitope and the MHC/HLA molecule, comprising:

providing a pool comprising at least 10 HCV peptides, the pool containing HCV-peptides which bind to the MHC/HLA molecule (binding HCV peptides) and HCV-peptides which do not bind to the MHC/HLA molecule (non-binding HCV peptides);

contacting the MHC/HLA molecule with the pool of HCV-peptides whereby a binding HCV-peptide binds to the MHC/HLA molecule and a complex comprising the HCV-peptide and the MHC/HLA molecule is formed;

detecting the complex and, optionally, separating the complex from non-binding HCV peptides;

optionally isolating and characterizing the binding HCV peptides from the complex; assaying the complex or the optionally isolated binding HCV peptides in a T cell assay for T cell activation capacity;

identifying optionally isolated binding HCV peptides with T cell activation capacity as a T cell epitope or the complex; and formulating the peptide or epitope in an immunogenic composition.

30. A method for inducing an immune response directed against Hepatitis C Virus with an immunogenic composition comprising Hepatitis C Virus peptides (HPs) or isolated HCV T cell epitopes which have a binding capacity to a MHC/HLA molecule or a complex comprising the HCV-peptide or HCV T cell epitope and the MHC/HLA molecule, comprising:

providing a pool comprising at least 10 HCV peptides, the pool containing HCV-peptides which bind to the MHC/HLA molecule (binding HCV peptides) and HCV-peptides which do not bind to the MHC/HLA molecule (non-binding HCV peptides);

contacting the MHC/HLA molecule with the pool of HCV-peptides whereby a binding HCV-peptide binds to the MHC/HLA molecule and a complex comprising the HCV-peptide and the MHC/HLA molecule is formed;

detecting the complex and, optionally, separating the complex from non-binding HCV peptides;

optionally isolating and characterizing the binding HCV peptides from the complex; assaying the complex or the optionally isolated binding HCV peptides in a T cell assay for T cell activation capacity;

identifying optionally isolated binding HCV peptides with T cell activation capacity as a T cell epitope or the complex;

formulating the peptide or epitope in an immunogenic composition; and administering the immunogenic composition to a subject, wherein an immune response specific for Hepatitis C Virus is induced.

31. The method of claim 30, wherein the subject is a human.

* * * * *

UNITED STATES PATENT AND TRADEMARK OFFICE
CERTIFICATE OF CORRECTION

| | |
|---|---|
| PATENT NO. | : 7,378,234 B2 |
| APPLICATION NO. | : 10/512885 |
| DATED | : May 27, 2008 |
| INVENTOR(S) | : Michael Buschle et al. |

It is certified that error appears in the above-identified patent and that said Letters Patent is hereby corrected as shown below:

Title page, item (87) PCT Pub. Date, line 2, delete "May 25, 2004" and insert --March 25, 2004-- therefor.

In claim 12, column 485, line 42, delete "MIHC" and insert --MHC-- therefor.

Signed and Sealed this

Fifth Day of August, 2008

JON W. DUDAS
*Director of the United States Patent and Trademark Office*